United States Patent
Kamtekar et al.

(10) Patent No.: US 9,296,999 B2
(45) Date of Patent: *Mar. 29, 2016

(54) RECOMBINANT POLYMERASES WITH INCREASED PHOTOTOLERANCE

(71) Applicant: Pacific Biosciences of California, Inc., Menlo Park, CA (US)

(72) Inventors: Satwik Kamtekar, Redwood City, CA (US); Lei Jia, North Potomac, MD (US); Walter Lee, Campbell, CA (US); Erik Miller, San Francisco, CA (US); Pranav Patel, Fremont, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/533,571

(22) Filed: Nov. 5, 2014

(65) Prior Publication Data

US 2015/0218535 A1 Aug. 6, 2015

Related U.S. Application Data

(63) Continuation of application No. 13/756,113, filed on Jan. 31, 2013, now Pat. No. 8,906,660.

(60) Provisional application No. 61/593,569, filed on Feb. 1, 2012.

(51) Int. Cl.
C12N 9/12 (2006.01)
C12P 19/34 (2006.01)
C12Q 1/68 (2006.01)

(52) U.S. Cl.
CPC ............... *C12N 9/1252* (2013.01); *C12P 19/34* (2013.01); *C12Q 1/6869* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,001,050 A | 3/1991 | Blanco et al. |
| 5,198,543 A | 3/1993 | Blanco et al. |
| 5,576,204 A | 11/1996 | Blanco et al. |
| 6,917,726 B2 | 7/2005 | Levene et al. |
| 7,041,812 B2 | 5/2006 | Kumar et al. |
| 7,056,661 B2 | 6/2006 | Korlach et al. |
| 8,133,672 B2 | 3/2012 | Bjornson et al. |
| 8,257,954 B2 | 9/2012 | Clark et al. |
| 8,343,746 B2 | 1/2013 | Rank et al. |
| 8,389,676 B2 | 3/2013 | Christians |
| 8,420,366 B2 | 4/2013 | Clark et al. |
| 2003/0044781 A1 | 3/2003 | Korlach et al. |
| 2004/0259082 A1 | 12/2004 | Williams |
| 2007/0072196 A1 | 3/2007 | Xu et al. |
| 2007/0196846 A1 | 8/2007 | Hanzel et al. |
| 2008/0032301 A1 | 2/2008 | Rank et al. |
| 2009/0286245 A1 | 11/2009 | Bjornson et al. |
| 2010/0075332 A1 | 3/2010 | Patel et al. |
| 2010/0093555 A1 | 4/2010 | Bjornson et al. |
| 2010/0260465 A1 | 10/2010 | Hanzel et al. |
| 2010/0261185 A1 | 10/2010 | Nikiforov |
| 2010/0261247 A1 | 10/2010 | Hanzel et al. |
| 2011/0014612 A1 | 1/2011 | Hendricks et al. |
| 2011/0165652 A1 | 7/2011 | Hardin et al. |
| 2012/0034602 A1 | 2/2012 | Emigetas |
| 2013/0040365 A1 | 2/2013 | Vander Horn et al. |
| 2013/0273526 A1 | 10/2013 | Brandis et al. |
| 2014/0094374 A1 | 4/2014 | Kamtekar et al. |
| 2014/0094375 A1 | 4/2014 | Kamtekar et al. |

FOREIGN PATENT DOCUMENTS

WO    WO 02/086088 A2    10/2002

OTHER PUBLICATIONS

Alba (2001) "Protein Family Review: Replicative DNA Polymerases" Genome Biology 2(1): reviews 3002.1-3002.4.
Augustin et al. (2001) "Progress towards single-molecule sequencing: enzymatic synthesis of nucleotide-specifically labeled DNA" J. Biotechnol. 86:289-301.
Berman et al. (2007) "Structures of phi29 DNA polymerase complexed with substrate: The mechanism of translocation in B-family polymerases" EMBO J. 26:3494-3505.
Burgers et al. (2001) "Eukaryotic DNA polymerases: proposal for a revised nomenclature" J Biol Chem. 276(47): 43487-90.
De Vega et al. (2010) "Improvement of ψ29 DNA polymerase amplification performance by fusion of DNA binding motifs", PNAS, 107(38):16506-16511.
Eid et al. (2009) "Real-time DNA sequencing from single polymerase molecules," Science 323:133-138.
Gardner and Jack (1999) "Determinants of nucleotide sugar recognition in an archaeon DNA polymerase," Nucleic Acids Research 27(12):2545-2553.
Gardner et al. (2004) "Comparative Kinetics of Nucleotide Analog Incorporation by Vent DNA Polymerase," J. Biol. Chem. 279(12):11834-11842.
Giller et al. (2003) "Incorporation of reporter molecule-labeled nucleotides by DNA polymerases. I. Chemical synthesis of various reporter group-labeled 2'-deoxyribonucleoside-5'-triphosphates," Nucleic Acids Res., 31(10):2630-2635.

(Continued)

*Primary Examiner* — Suzanne M Noakes
*Assistant Examiner* — Jae W Lee
(74) *Attorney, Agent, or Firm* — Monicia Elrod-Erickson

(57) ABSTRACT

Provided are compositions comprising recombinant DNA polymerases that include amino acid substitutions, insertions, deletions, and/or exogenous features that confer modified properties upon the polymerase for enhanced single molecule sequencing. Such properties include increased resistance to photodamage, and can also include enhanced metal ion coordination, reduced exonuclease activity, reduced reaction rates at one or more steps of the polymerase kinetic cycle, decreased branching fraction, altered cofactor selectivity, increased yield, increased thermostability, increased accuracy, increased speed, increased readlength, and the like. Also provided are nucleic acids which encode the polymerases with the aforementioned phenotypes, as well as methods of using such polymerases to make a DNA or to sequence a DNA template.

19 Claims, 39 Drawing Sheets

(56) References Cited

OTHER PUBLICATIONS

Hübscher et al. (2002) "Eukaryotic DNA Polymerases," Annual Review of Biochemistry, 71:133-163.
Johnson (1986) "Rapid kinetic analysis of mechanochemical adenosinetriphosphatases" Methods Enzymol. 134:677-705.
Kamtekar et al. (2004) "Insights into strand displacement and processivity from the crystal structure of the protein-primed DNA polymerase of bacteriophage Φ29" Mol. Cell 16(4): 609-618.
Kamtekar et al. (2006) "The phi29 DNA polymerase:protein-primer structure suggests a model for the initiation to elongation transition," EMBO J. 25(6):1335-1343.
Korlach et al (2010) "Real-Time DNA Sequencing from Single Polymerase Molecules," Methods in Enzymology vol. 472, Chapter 20, pp. 431-455.
Korlach et al. (2008) "Long, processive enzymatic DNA synthesis using 100% dye-labeled terminal phosphate-linked nucleotides," Nucleosides, Nucleotides and Nucleic Acids 27:1072-1083.
Korlach et al. (2008) "Selective aluminum passivation for targeted immobilization of single DNA polymerase molecules in zero-mode waveguide nanostructures," PNAS, 105(4):1176-1181.
Levene et al. (2003) "Zero-mode waveguides for single-molecule analysis at high concentrations" Science 299:682-686.
Meijer et al. (2001) "Φ29 Family of Phages" Microbiology and Molecular Biology Reviews, 65(2):261-287.
Méndez et al.(1994) "Primer-terminus stabilization at the phi 29 DNA polymerase active site. Mutational analysis of conserved motif TX$_2$GR" J Biol Chem. Nov. 25;269(47):30030-30038.
Patel et al. (1991) "Pre-steady-state kinetic analysis of processive DNA replication including complete characterization of an exonuclease-deficient mutant" Biochemistry 30(2):511-525.
Pinard et al. (2006) "Assessment of whole genome amplification-induced bias through high-throughput, massively parallel whole genome sequencing" BMC Genomics 7:216.
Ried et al. (1992) "Simultaneous visualization of seven different DNA probes by in situ hybridization using combinatorial fluorescence and digital imaging microscopy," PNAS, 89:1388-1392.
Silander and Saarela (2008) "Whole Genome Amplification with Phi29 DNA Polymerase to Enable Genetic or Genomic Analysis of Samples of Low DNA Yield" Methods in Molecular Biology 439:1-18.
Steitz (1999) "DNA polymerases: structural diversity and common mechanisms" J Biol Chem 274(25):17395-17398.
Tonon et al. (2000) "Spectral karyotyping combined with locus-specific FISH simultaneously defines genes and chromosomes involved in chromosomal translocations" Genes Chromosom. Cancer 27:418-423.
Truniger et al. (2005) "Involvement of the "linker" region between the exonuclease and polymerization domains of phi29 DNA polymerase in DNA and TP binding" Gene, 348:89-99.
Tsai and Johnson (2006) "A new paradigm for DNA polymerase specificity," Biochemistry 45(32):9675-9687.
Yu et al. (1994) "Cyanine dye dUTP analogs for enzymatic labeling of DNA probes," Nucleic Acids Res. 22(15):3226-3232.
Zhu et al. (1994) "Directly labeled DNA probes using fluorescent nucleotides with different length linkers" Nucleic Acids Res., 22(16):3418-3422.
Zhu and Waggoner (1997) "Molecular mechanism controlling the incorporation of fluorescent nucleotides into DNA by PCR" Cytometry, 28:206-211.
Bernad, et al. (1990) "The highly conserved amino acid sequence motif Tyr-Gly-Asp-Thr-Asp-Ser in alpha-like DNA polymerases is required by phage phi 29 DNA polymerase for protein-primed initiation and polymerization." *Proc. Natl. Acad. Sci. U S A*, 87(12): 4610-4614.
Bernad, et al. (1990) "Site-directed mutagenesis of the YCDTDS amino acid motif of the Φ29 DNA polymerase." *Gene*, 94: 45-51.
Blasco, et al. (1991) "Characterization and Mapping of the Pyrophosphorolytic Activity of the Phage Φ29 DNA Polymerase." *J. Biol. Chem.*, 266(12): 7904-7909.

```
M2Y    1    MSRKMFSCDFETTTKLDDCRVWAYGYMEIGNLDNYKIGNSLDEFMQWVMEIQADLYFHNL    60
            M RKM+SCDFETTTK++DCRVWAYGYM I +   YKIGNSLDEFM WV+++QADLYFHNL
φ29    4    MPRKMYSCDFETTTKVEDCRVWAYGYMNIEDHSEYKIGNSLDEFMAWVLKVQADLYFHNL    63

M2Y   61    KFDGAFIVNWLEQHGFKWSNEGLPNTYNTIISKMGQWYMIDICFGYKGKRKLHTVIYDSL   120
            KFDGAFI+NWLE++GFKWS +GLPNTYNTIIS+MGQWYMIDIC GYKGKRK+HTVIYDSL
φ29   64    KFDGAFIINWLERNGFKWSADGLPNTYNTIISRMGQWYMIDICLGYKGKRKIHTVIYDSL   123

M2Y  121    KKLPFPVKKIAKDFQLPLLKGDIDYHTERPVGHEITPEEYEYIKNDIEIIARALDIQFKQ   180
            KKLPFPVKKIAKDF+L +LKGDIDYH ERPVG+++ITPEEY YIKNDI+IIA AL IQFKQ
φ29  124    KKLPFPVKKIAKDFKLTVLKGDIDYHKERPVGYKITPEEYAYIKNDIQIIAEALLIQFKQ   183

M2Y  181    GLDRMTAGSDSLKGFKDILSTKKFNKVFPKLSLPMDKEIRKAYRGGFTWLNDKYKEKEIG   240
            GLDRMTAGSDSLKGFKDI++TKKF KVFP LSL +DKE+R AYRGGFTWLND++KEKEIG
φ29  184    GLDRMTAGSDSLKGFKDIITTKKFKKVFPTLSLGLDKEVRYAYRGGFTWLNDRFKEKEIG   243

M2Y  241    EGMVFDVNSLYPSQMYSRPLPYGAPIVFQGKYEKDEQYPLYIQRIRFEFELKEGYIPTIQ   300
            EGMVFDVNSLYP+QMYSR LPYG PIVF+GKY  DE YPL+IQ IR EFELKEGYIPTIQ
φ29  244    EGMVFDVNSLYPAQMYSRLLPYGEPIVFEGKYVWDEDYPLHIQHIRCEFELKEGYIPTIQ   303

M2Y  301    IKKNPFFKGNEYLKNSGVEPVELYLTNVDLELIQEHYELYNVEYIDGFKFREKTGLFKDF   360
            IK++ F+KGNEYLK+SG E  +L+L+NVDLEL++EHY+LYNVEYI G KF+  TGLFKDF
φ29  304    IKRSRFYKGNEYLKSSGGEIADLWLSNVDLELMKEHYDLYNVEYISGLKFKATTGLFKDF   363

M2Y  361    IDKWTYVKTHEEGAKKQLAKLMLNSLYGKFASNPDVTGKVPYLKDDGSLGFRVGDEEYKD   420
            IDKWTY+KT  EGA KQLAKLMLNSLYGKFASNPDVTGKVPYLK++G+LGFR+G+EE KD
φ29  364    IDKWTYIKTTSEGAIKQLAKLMLNSLYGKFASNPDVTGKVPYLKENGALGFRLGEEETKD   423

M2Y  421    PVYTPMGVFITAWARFTTITAAQACYDRIIYCDTDSIHLTGTEVPEIIKDIVDPKKLGYW   480
            PVYTPMGVFITAWAR+TTITAAQACYDRIIYCDTDSIHLTGTE+P++IKDIVDPKKLGYW
φ29  424    PVYTPMGVFITAWARYTTITAAQACYDRIIYCDTDSIHLTGTEIPDVIKDIVDPKKLGYW   483

M2Y  481    AHESTFKRAKYLRQKTYIQDIYVKEVDGKLKECSPDEATTTKFSVKCAGMTDTIKKKVTF   540
            AHESTFKRAKYLRQKTYIQDIY+KEVDGKL E SPD+ T  KFSVKCAGMTD IKK+VTF
φ29  484    AHESTFKRAKYLRQKTYIQDIYMKEVDGKLVEGSPDDYTDIKFSVKCAGMTDKIKKEVTF   543

M2Y  541    DNFAVGFSSMGKPKPVQVNGGVVLVDSVFTIK   572
            +NF VGFS  KPKPVQV GGVVLVD  FTIK
φ29  544    ENFKVGFSRKMKPKPVQVPGGVVLVDDTFTIK   575
```

Fig. 1

| |
|---|
| pET16.Btagco.His10.Phi29.L253A_E375Y_A484E_K512Y_D523T.co.His10co |
| pET16.Btagco.His10co.Phi29.L253A_E375Y_A484E_K512Y_E540K.co.His10co |
| pET16.BtagV7co.His10co.Phi29.Y148I_Y224K_E239G_V250I_L253A_E375Y_A484E_D510K_K512Y_E515K.co.His14co |
| pET16.BtagV7co.His10co.Phi29.D145M_Y224K_E239G_L253A_E375Y_A484E_K512Y.co.His10co |
| pET16.BtagV7co.His10co.Phi29.D145L_Y224K_E239G_L253A_E375Y_A484E_K512Y.co.His10co |
| pET16.BtagV7co.His10co.Phi29.D136R_Y224K_E239G_L253A_E375Y_A484E_D510K_K512Y.co.His10co |
| pET16.BtagV7co.His10co.Phi29.Y224K_E239G_Y250A_L253A_E375Y_A484E_D510K_K512Y_D523Y.co.His10co |
| pET16.BtagV7co.His10co.Phi29.Y148I_Y224K_E239G_V250H_L253A_E375Y_A484E_D510K_K512Y.co.His10co |
| pET16.BtagV7co.His10co.Phi29.Y148I_Y224K_E239G_V250I_L253A_E375Y_A484E_D510K_K512Y_E515F.co.His10co |
| pET16.BtagV7co.His10co.Phi29.L253A_E375Y_A484E_K512Y_576GTGSGA_Maltose_Binding_Fusion_Protein.co |
| pET16.BtagV7co.His10co.Phi29.Y148I_Y224K_E239G_V250I_L253A_E375Y_A484E_D510K_K512Y_576GTGSGA_Maltose_Binding_Fusion_Protein.co |
| pET16.BtagV7co.His10co.Phi29.D66R_D84C_C106S_Y148I_Y224K_E239G_V250I_L253A_E375Y_C448T_A484E_D510K_K512Y.co.His10co |
| pET16.BtagV7co.His10co.Phi29.D66R_C106S_Y148I_Y224K_E239G_V250I_L253A_E375Y_E418C_C448T_A484E_D510K_K512Y.co.His10co |
| pET16.BtagV7co.His10co.Phi29.V19C_D66R_Y148I_Y224K_E239G_V250I_L253A_E375Y_N409C_C448V_A484E_D510K_K512Y.co.His10co |
| pET16.BtagV7co.His10co.Phi29.Y148I_Y224K_E239G_V250I_L253A_E375Y_A484E_E508R_D510K_K512Y_D523Y.co.His10co |
| pET16.BtagV7co.His10co.Phi29.Y148I_Y224K_E239G_V250I_L253A_E375Y_A484E_E508K_D510K_K512Y_D523Y.co.His10co |
| pET16.BtagV7co.His10co.Phi29.Y148I_Y224K_E239G_L253A_A256G_E375Y_R261Q_E375Y_A484E_D510K_K512Y.co.His10co |
| pET16.BtagV7co.His10co.Phi29.Y148I_Y224K_E239G_L253A_E375Y_Y482A_A484A_A484E_D510K_K512Y.co.His10co |
| pET11.Phi29.Y148I_E239G_L253H_E375Y_A437Y_A484E_D510K_K512Y_E515P.co.His10co.GGGSGGGSGGGS.BtagV7co |
| pET11.Phi29.Y148I_E239G_L253H_E375Y_A437G_A484E_D510K_K512Y_E515Q.co.His10co.GGGSGGGSGGGS.BtagV7co |
| pET11.Phi29.Y148I_E239G_L253H_E375Y_A437G_A484E_D510K_K512Y.co.His10co.GGGSGGGSGGGS.BtagV7co |
| pET16.Phi29.D34N_D84E_V222I_Y224K_L253A_E375Y_A484E_D510K_K512Y_G516C_Y521A_D523T_M554G.co.Nhe.His10co |
| pET16.Phi29.C22V_Y148I_Y224K_E239G_V250I_L253A_E375Y_A481E_D507Y_K509Y.co.His10co |
| pET16.Phi29.M2.Y145I_E236G_L250H_E372Y_A434G_A481E_D507Y_K509Y.co.His10co |
| pET16.Phi29.M2.Y145I_E236G_L250H_E372Y_A434G_A481E_D507K_K509Y.co.His10co |
| pET16.Phi29.M2.Y145I_E236G_V247I_L250H_E372Y_A434G_A481E_D507K_K509Y.co.His10co |
| pET16.Phi29.M2.Y145I_E236G_V247I_L250A_E372Y_A434G_A481E_D507K_K509Y.co.His10co |
| pET16.Phi29.Y148I_Y224K_E239G_E241Q_L253H_E375Y_A437G_A484E_D510K_K512Y.co.His10co |

| Construct |
|---|
| pET16.BtagV7co.His10co.Phi29.Y148I_Y224K_E239G_L253H_E375Y_A437G_D469K_A484E_D510K_K512Y.co.His10co |
| pET16.BtagV7co.His10co.Phi29.Y148I_Y224K_E239G_E241Q_L253H_E375Y_A437G_D469K_A484E_D510K_K512Y.co.His10co |
| pET16.BtagV7co.His10co.Phi29.Y148I_Y224K_E239G_E241Q_L253A_V250I_L253A_E375Y_D469K_A484E_D510K_K512Y.co.His10co |
| pET16.BtagV7co.His10co.Phi29.Y148I_K157E_E161D_Y224K_E239G_V250I_V247I_V250I_L328V_Y369H_E375Y_Y449F_A484E_D510K_K512Y_D523T.co.His10co |
| pET16.BtagV7co.His10co.Phi29.Y148I_Y224K_E239G_V247I_V250I_L253A_E375Y_A484E_D510K_K512Y.co.His10co |
| pET16.BtagV7co.His10co.Phi29.H149M_E239G_V250I_L253A_E375Y_A484E_D510K_K512Y.co.His10co |
| pET16.BtagV7co.His10co.Phi29.H149K_E239G_V250I_L253A_E375Y_A484E_D510K_K512Y.co.His10co |
| pET16.BtagV7co.His10co.Phi29.H149D_E239G_V250I_L253A_E375Y_A484E_D510K_K512Y.co.His10co |
| pET16.BtagV7co.His10co.Phi29.H149A_E239G_V250I_L253A_E375Y_A484E_D510K_K512Y.co.His10co |
| pET16.BtagV7co.His10co.Phi29.D147Y_Y224K_E239G_V250I_L253A_E375Y_A484E_D510K_K512Y.co.His10co |
| pET16.BtagV7co.His10co.Phi29.D147A_Y224K_E239G_V250I_L253A_E375Y_A484E_D510K_K512Y.co.His10co |
| pET16.BtagV7co.His10co.Phi29.D147K_Y224K_E239G_V250I_L253A_E375Y_A484E_D510K_K512Y.co.His10co |
| pET16.BtagV7co.His10co.Phi29.D147Q_Y224K_E239G_V250I_L253A_E375Y_A484E_D510K_K512Y.co.His10co |
| pET16.BtagV7co.His10co.Phi29.Y148I_H149M_Y224K_E239G_V250I_L253A_E375Y_A484E_D510K_K512Y.co.His10co |
| pET16.BtagV7co.His10co.Phi29.Q183W_Y224K_E239G_L253A_E375Y_A484E_K512Y.co.His10co |
| pET16.BtagV7co.His10co.Phi29.Y148I_Y224K_E239G_V250I_L253A_E375Y_T440L_A484E_D510K_K512Y.co.His10co |
| pET16.BtagV7co.His10co.Phi29.V141K_L142K_Y148I_Y224K_E239G_L253A_E375Y_T440L_A484E_D510K_K512Y.co.His10co |
| pET16.BtagV7co.His10co.Phi29.Y148I_Y224K_E239G_V250I_L253A_A256S_E375Y_A484E_D510K_K512Y.co.His10co |
| pET16.BtagV7co.His10co.Phi29.Y148I_Y224K_E239G_V250I_L253A_A256T_E375Y_A484E_D510K_K512Y.co.His10co |
| pET16.BtagV7co.His10co.Phi29.Y148I_Y224K_E239G_V250I_L253A_E375Y_A484E_D510K_K512Y.co.His16co |
| pET16.BtagV7co.His10co.M2.L250A_E372Y_A481E_K509Y.co.His10co |
| pET16.BtagV7co.His10co.M2.L250A_E372Y_A481E_K509Y.co |
| pET16.BtagV7co.His10co.Phi29.K205E_Y224K_E239G_V250I_L253A_E375Y_A484E_D510K_K512Y_576_GTGSGA |
| pET16.BtagV7co.His10co.Phi29.Y148I_Y224K_E239G_V250I_L253A_E375Y_A484E_D510K_K512Y_576_GTGSGA |
| pET11.Phi29.Y148I_Y224K_E239G_V250I_L253A_E375Y_A484E_D510K_K512Y.co.His10co.GGGSGGGSGGGSGGGS.BtagV7co |
| pET16.BtagV7co.His10co.Phi29.Y148I_P127V_Y224K_E239G_V250I_L253A_E375Y_A484E_D510K_K512Y_F526L.co.His10co |
| pET16.BtagV7co.His10co.Phi29.Y148I_Y224K_E239G_V250I_L253A_E375Y_A484E_D510A_K512Y.co.His10co |
| pET16.BtagV7co.His10co.Phi29.Y148I_Y224K_E239G_V250I_L253A_E375Y_A484E_D510C_K512Y.co.His10co |
| pET16.BtagV7co.His10co.Phi29.Y148I_Y224K_E239G_V250I_L253A_E375Y_A484E_D510E_K512Y.co.His10co |
| pET16.BtagV7co.His10co.Phi29.Y148I_Y224K_E239G_V250I_L253A_E375Y_A484E_D510F_K512Y.co.His10co |
| pET16.BtagV7co.His10co.Phi29.Y148I_Y224K_E239G_V250I_L253A_E375Y_A484E_D510H_K512Y.co.His10co |

| | |
|---|---|
| pET16.BtagV7co.His10co.Phi29.Y148I_Y224K_E239G_V250I_L253A_E375Y_A484E_D510I_K512Y.co.His10co | |
| pET16.BtagV7co.His10co.Phi29.Y148I_Y224K_E239G_V250I_L253A_E375Y_A484E_D510L_K512Y.co.His10co | |
| pET16.BtagV7co.His10co.Phi29.Y148I_Y224K_E239G_V250I_L253A_E375Y_A484E_D510M_K512Y.co.His10co | |
| pET16.BtagV7co.His10co.Phi29.Y148I_Y224K_E239G_V250I_L253A_E375Y_A484E_D510N_K512Y.co.His10co | |
| pET16.BtagV7co.His10co.Phi29.Y148I_Y224K_E239G_V250I_L253A_E375Y_A484E_D510Q_K512Y.co.His10co | |
| pET16.BtagV7co.His10co.Phi29.Y148I_Y224K_E239G_V250I_L253A_E375Y_A484E_D510R_K512Y.co.His10co | |
| pET16.BtagV7co.His10co.Phi29.Y148I_Y224K_E239G_V250I_L253A_E375Y_A484E_D510S_K512Y.co.His10co | |
| pET16.BtagV7co.His10co.Phi29.Y148I_Y224K_E239G_V250I_L253A_E375Y_A484E_D510T_K512Y.co.His10co | |
| pET16.BtagV7co.His10co.Phi29.Y148I_Y224K_E239G_V250I_L253A_E375Y_A484E_D510Y_K512Y.co.His10co | |
| pET16.BtagV7co.His10co.Phi29.Y148I_Y224K_E239G_V250I_L253A_E375Y_A484E_D510K_K512Y_F526L_V541I.co.His10co | |
| pET16.BtagV7co.His10co.Phi29.Y148I_Y224K_E239G_V250I_L253A_E375Y_A484E_D510K_K512Y_F526L_V528I.co.His10co | |
| pET16.BtagV7co.His10co.Phi29.A68K_Y148I_Y224K_E239G_V250I_L253A_E375Y_A484E_D510K_K512Y_Q560D.co.His10co | |
| pET16.BtagV7co.His10co.Phi29.Y148I_Y224K_E239G_V250I_L253A_E375Y_A484E_D510K_K512Y_L513Y.co.His10co | |
| pET16.BtagV7co.His10co.Phi29.A68S_Y148I_Y224K_E239G_V250I_L253A_E375Y_A484E_D510K_K512Y_Q560E.co.His10co | |
| pET16.BtagV7co.His10co.Phi29.Y148I_Y224K_E239G_V250I_L253A_E375Y_A484E_D510K_K512Y_D520K.co.His10co | |
| pET16.BtagV7co.His10co.Phi29.Y148I_K196R_Y224K_E239G_V250I_L253A_Y369E_A484E_D510K_K512Y.co.His10co | |
| pET16.BtagV7co.His10co.Phi29.Y148I_K196I_Y224K_E239G_V250I_L253A_E375Y_A484E_D510K_K512Y.co.His10co | |
| pET16.BtagV7co.His10co.Phi29.Y148I_K196Q_Y224K_E239G_V250I_L253A_E375Y_A484E_D510K_K512Y.co.His10co | |
| pET16.BtagV7co.His10co.Phi29.Y148I_K196E_D200R_Y224K_E239G_V250I_L253A_E375Y_A484E_D510K_K512Y.co.His10co | |
| pET16.BtagV7co.His10co.Phi29.Y148I_K206Q_Y224K_E239G_V250I_L253A_E375Y_A484E_D510K_K512Y.co.His10co | |
| pET16.BtagV7co.His10co.Phi29.Y148I_K206Q_Y224K_E239G_V250I_L253A_E375Y_A484E_D510K_K512Y.co.His10co | |
| pET16.BtagV7co.His10co.Phi29.Y148I_Y224K_R223I_E239G_V250I_L253A_E375Y_A484E_D510K_K512Y.co.His10co | |
| pET16.BtagV7co.His10co.Phi29.Y148I_Y224K_R223Q_E239G_V250I_L253A_E375Y_A484E_D510K_K512Y.co.His10co | |
| pET16.BtagV7co.His10co.Phi29.Y148I_Y224K_R223A_E239G_V250I_L253A_E375Y_A484E_D510K_K512Y.co.His10co | |
| pET16.BtagV7co.His10co.Phi29.Y148I_Y224K_E239G_V250I_L253A_E375Y_N396D_A484E_D510K_K512Y.co.His10co | |
| pET16.BtagV7co.His10co.Phi29.Y148I_Y224K_E239G_V250I_L253A_E375Y_N396S_A484E_D510K_K512Y.co.His10co | |
| pET16.BtagV7co.His10co.Phi29.Y148I_Y224K_R227K_E239G_V250I_L253A_E375Y_A484E_D510K_K512Y.co.His10co | |
| pET16.BtagV7co.His10co.Phi29.Y148I_Y224K_R227I_E239G_V250I_L253A_E375Y_A484E_D510K_K512Y.co.His10co | |

Fig. 7 cont'd

| | |
|---|---|
| pET16.BtagV7co.His10co.Phi29.Y148I_Y224K_R227Q_E239G_V250I_L253A_E375Y_A484E_D510K_K512Y.co.His10co |
| pET16.BtagV7co.His10co.Phi29.Y148I_Y224K_E239G_V250I_L253A_E375Y_A484E_D510K_K512Y.co.His10co |
| pET16.BtagV7co.His10co.Phi29.Y148I_Y224K_E239G_V250I_L253A_K305I_E375Y_A484E_D510K_K512Y.co.His10co |
| pET16.BtagV7co.His10co.Phi29.Y148I_Y224K_E239G_V250I_L253A_K305I_E375Y_A484E_D510K_K512Y.co.His10co |
| pET16.BtagV7co.His10co.Phi29.Y148I_Y224K_E239G_V250I_L253A_K305R_E375Y_A484E_D510K_K512Y.co.His10co |
| pET16.BtagV7co.His10co.Phi29.Y148I_Y224K_E239G_V250I_L253A_K305R_E375Y_A484E_D510K_K512Y.co.His10co |
| pET16.BtagV7co.His10co.Phi29.Y148I_Y224K_E239G_V250I_L253A_E375Y_A484E_D510K_K512Y.co.His10co |
| pET16.BtagV7co.His10co.Phi29.Y148I_Y224K_E239G_V250I_L253A_E375Y_A484E_D510K_K512Y_L567M.co.His10co |
| pET16.BtagV7co.His10co.Phi29.Y148I_Y224K_E239G_V250I_L253A_E375Y_A484E_D510K_K512Y_L567A.co.His10co |
| pET16.BtagV7co.His10co.Phi29.Y148I_Y224K_E239G_V250I_L253A_E375Y_A484E_D510K_K512Y_L567E.co.His10co |
| pET16.BtagV7co.His10co.Phi29.F65Y_Y148I_Y224K_E239G_V250I_L253A_E375Y_A484E_D510K_K512Y.co.His10co |
| pET16.BtagV7co.His10co.Phi29.F65Y_Y148I_Y224K_E239G_V250I_L253A_Y369E_E375Y_A484E_D510K_K512Y_576_GTGSGA_696-802topoV_fusion.co |
| pET16.BtagV7co.His10co.Phi29.Y148I_Q183T_Y224K_E239G_V250I_L253A_E375Y_A484E_D510K_K512Y.co.His10co |
| pET16.BtagV7co.His10co.Phi29.Y148I_Y224K_E239G_V250I_L253A_E375Y_S395T_A484E_D510K_K512Y.co.His10co |
| pET16.BtagV7co.His10co.Phi29.Y148I_Y224K_E239G_V250I_L253A_E375Y_A484E_D510K_V559L.co.His10co |
| pET16.BtagV7co.His10co.Phi29.G197S_G78D_Y148I_Y224K_E239G_V250I_L253A_E375Y_A484E_D510K_K512Y.co.His10co |
| pET16.BtagV7co.His10co.Phi29.G197S_G78D_Y148I_G197S_Y224K_E239G_V250I_L253A_E375Y_A484E_D510K_K512Y.co.His10co |
| pET16.BtagV7co.His10co.Phi29.G78D_Y148I_G197S_Y224K_E239G_V250I_L253A_E375Y_A484E_D510K_K512Y.co.His10co |
| pET16.BtagV7co.His10co.Phi29.G78D_N88K_Y148I_G197S_Y224K_E239G_V250I_L253A_E375Y_A484E_D510K_K512Y.co.His10co |
| pET16.BtagV7co.His10co.Phi29.G78D_Y148I_G197D_Y224K_E239G_V250I_L253A_E375Y_A484E_D510K_K512Y.co.His10co |
| pET16.BtagV7co.His10co.Phi29.Y148I_G197E_Y224K_E239G_V250I_L253A_E375Y_A484E_D510K_K512Y.co.His10co |
| pET16.BtagV7co.His10co.Phi29.Y148I_G197K_Y224K_E239G_V250I_L253A_E375Y_A484E_D510K_K512Y.co.His10co |
| pET16.BtagV7co.His10co.Phi29.E14A_Y224K_E239G_V250I_L253A_E375Y_A484E_D510K_K512Y.co.His10co |
| pET16.BtagV7co.His10co.Phi29.E14A_Y148I_T140Y_Y224K_E239G_V250I_L253A_E375Y_A484E_D510K_K512Y.co.His10co |
| pET16.BtagV7co.His10co.Phi29.E14A_T140Y_Y148I_G197A_Y224K_E239G_V250I_L253A_E375Y_A484E_D510K_K512Y.co.His10co |
| pET16.BtagV7co.His10co.Phi29.Y224K_E239G_V250I_L253C_E375Y_A484E_D510K_K512Y.co.His10co |
| pET16.BtagV7co.His10co.Phi29.Y148I_E239G_V250I_L253C_E375Y_A484E_D510K_K512Y.co.His10co |

Fig. 7 cont'd

| Construct |
|---|
| pET16.BtagV7co.His10co.Phi29.Y148I_Y224K_E239G_V250I_L253C_E375Y_A484E_D510K_K512Y_E515K_F526L.co.His10co |
| pET16.BtagV7co.His10co.Phi29.K143R_Y148I_Y224K_E239K_V250I_L253C_E375Y_A484E_D510K_K512Y.co.His10co |
| pET16.BtagV7co.His10co.Phi29.D66R_Y148I_Y224K_E239G_V250I_L253C_E375Y_A484E_K512Y.co.His10co |
| pET16.BtagV7co.His10co.Phi29.N62H_Y148I_Y224K_E239K_V250I_L253A_E375Y_A484E_D510K_K512Y.co.His10co |
| pET16.BtagV7co.His10co.Phi29.N62H_Y148I_S194A_Y224K_E239G_V250I_L253A_E375Y_A484E_D510K_K512Y.co.His10co |
| pET16.BtagV7co.His10co.Phi29.Y148I_S194T_Y224K_E239G_V250I_L253A_E375Y_A484E_D510K_K512Y.co.His10co |
| pET16.BtagV7co.His10co.Phi29.Y148I_S194A_Y224K_E239K_V250I_L253A_E375Y_S388A_A484E_D510K_K512Y.co.His10co |
| pET16.BtagV7co.His10co.Phi29.Y148I_S194A_Y224K_E239G_V250I_L253A_E375Y_S388A_A484E_D510K_K512Y.co.His10co |
| pET16.BtagV7co.His10co.Phi29.Y148I_Y224K_E239G_V250I_L253A_F363Y_E375Y_A484E_D510K_K512Y.co.His10co |
| pET16.BtagV7co.His10co.Phi29.Y148I_I201V_Y224K_E239K_V250I_L253A_E375Y_A484E_D510K_K512Y.co.His10co |
| pET16.BtagV7co.His10co.Phi29.Y148I_I201L_Y224K_E239K_V250I_L253A_E375Y_A484E_D510K_K512Y.co.His10co |
| pET16.BtagV7co.His10co.Phi29.Y148I_I201A_Y224K_E239K_V250I_L253A_E375Y_A484E_D510K_K512Y.co.His10co |
| pET16.BtagV7co.His10co.Phi29.Y148I_I201A_Y224K_E239G_V250I_L253A_E375Y_A484E_D510K_K512Y.co.His10co |
| pET16.BtagV7co.His10co.Phi29.Y148I_I201E_Y224K_E239K_V250I_L253A_E375Y_A484E_D510K_K512Y.co.His10co |
| pET16.BtagV7co.His10co.Phi29.Y148I_Y224K_E239G_V250I_L253A_E375Y_L381I_A484E_D510K_K512Y.co.His10co |
| pET16.BtagV7co.His10co.Phi29.Y148I_Y224K_E239G_V250I_L253A_E375Y_L381A_A484E_D510K_K512Y.co.His10co |
| pET16.BtagV7co.His10co.Phi29.Y148I_Y224K_E239G_V250I_L253A_E375Y_L381F_A484E_D510K_K512Y.co.His10co |
| pET16.BtagV7co.His10co.Phi29.Y148I_Y224K_E239G_V250I_L253A_D365A_E375Y_A484E_D510K_K512Y.co.His10co |
| pET16.BtagV7co.His10co.Phi29.Y148I_Y224K_E239G_V250I_L253A_D365N_E375Y_A484E_D510K_K512Y.co.His10co |
| pET16.BtagV7co.His10co.Phi29.Y148I_Y224K_E239G_V250I_L253A_Y259F_E375Y_A484E_D510K_K512Y.co.His10co |
| pET16.BtagV7co.His10co.Phi29.Y148I_Y224K_E239G_V250I_L253A_K361N_E375Y_A484E_D510K_K512Y.co.His10co |
| pET16.BtagV7co.His10co.Phi29.Y148I_Y224K_E239G_V250I_L253A_K361R_E375Y_A484E_D510K_K512Y.co.His10co |
| pET16.BtagV7co.His10co.Phi29.Y148I_Y224K_E239G_V250I_L253A_K361A_E375Y_A484E_D510K_K512Y.co.His10co |
| pET16.BtagV7co.His10co.Phi29.Y148I_Y224K_E239G_V250I_L253A_K361D_E375Y_A484E_D510K_K512Y.co.His10co |
| pET16.BtagV7co.His10co.Phi29.Y148I_Y224K_E239G_V250I_L253A_Y259K_E375Y_A484E_D510K_K512Y.co.His10co |
| pET16.BtagV7co.His10co.Phi29.Y148I_Y224K_E239G_V250I_L253A_Y259K_E375Y_Y482K_A484E_D510K_K512Y.co.His10co |
| pET16.BtagV7co.His10co.Phi29.Y148I_Y224K_E239G_V250I_L253A_E375Y_Y482R_A484E_D510K_K512Y.co.His10co |
| pET16.BtagV7co.His10co.Phi29.Y148I_Y224K_E239G_V250I_L253A_E375Y_Y482E_A484E_D510K_K512Y.co.His10co |
| pET16.BtagV7co.His10co.Phi29.Y148I_Y224K_E239G_V250I_L253A_E375Y_E466K_A484E_D510K_K512Y.co.His10co |
| pET16.BtagV7co.His10co.Phi29.Y148I_Y224K_E239G_V250I_L253A_E375Y_E466R_A484E_D510K_K512Y.co.His10co |

Fig. 7 cont'd

| Plasmid | Mutations |
|---|---|
| pET16.BtagV7co.His10co.Phi29.Y148I_Y224K_E239G_V250I_L253A_E375Y_E466A_A484E_D510K_K512K.co.His10co | |
| pET16.BtagV7co.His10co.Phi29.Y148I_E161R_Y224K_E239G_V250I_L253A_E375Y_A484E_D510K_K512Y.co.His10co | |
| pET16.BtagV7co.His10co.Phi29.Y148I_E161A_Y224K_E239G_V250I_L253A_E375Y_A484E_D510K_K512Y.co.His10co | |
| pET16.BtagV7co.His10co.Phi29.Y148I_E161K_Y224K_E239G_V250I_L253A_E375Y_A484E_D510K_K512Y.co.His10co | |
| pET16.BtagV7co.His10co.Phi29.Y148I_Y224K_E239G_V250I_L253A_E375Y_N409C_A484E_D510K_K512Y.co.His10co | |
| pET16.BtagV7co.His10co.Phi29.Y148I_Y224K_E239G_V250I_L253A_E375Y_A484E_D510K_K512Y_V568C.co.His10co | |
| pET16.BtagV7co.His10co.Phi29.Y148I_Y224K_E239G_V250I_L253A_E375Y_A484E_D510K_K512Y_V568L.co.His10co | |
| pET16.BtagV7co.His10co.Phi29.Y148I_Y224K_E239G_V250I_L253A_E375Y_A484E_D510K_K512Y_V568M.co.His10co | |
| pET16.BtagV7co.His10co.Phi29.Y148I_Y224K_E239G_V250I_L253A_E375Y_A484E_D510K_K512Y_V568I.co.His10co | |
| pET16.BtagV7co.His10co.Phi29.Y148I_Y224K_E239G_V250I_L253A_E375Y_A484E_D510K_K512Y_V568R.co.His10co | |
| pET16.BtagV7co.His10co.Phi29.Y148I_Y224K_E239G_V250I_L253A_E375Y_A484E_D510K_K512Y_V568E.co.His10co | |
| pET16.BtagV7co.His10co.Phi29.Y148I_Y224K_E239G_V250I_L253A_E375Y_A484E_D510K_K512Y_V568Q.co.His10co | |
| pET16.BtagV7co.His10co.Phi29.Y148I_Y224K_E239G_V250I_L253A_E375Y_N409M_A484E_D510K_K512Y.co.His10co | |
| pET16.BtagV7co.His10co.Phi29.Y148I_Y224K_E239G_V250I_L253A_E375Y_N409L_A484E_D510K_K512Y.co.His10co | |
| pET16.BtagV7co.His10co.Phi29.Y148I_Y224K_E239G_V250I_L253A_E375Y_N409A_A484E_D510K_K512Y.co.His10co | |
| pET16.BtagV7co.His10co.Phi29.Y148I_Y224K_E239G_V250I_L253A_E375Y_N409E_A484E_D510K_K512Y.co.His10co | |
| pET16.BtagV7co.His10co.Phi29.Y148I_Y224K_E239G_V250I_L253A_E375Y_N409R_A484E_D510K_K512Y.co.His10co | |
| pET16.BtagV7co.His10co.Phi29.V19L_Y148I_Y224K_E239G_V250I_L253A_E375Y_A484E_D510K_K512Y.co.His10co | |
| pET16.BtagV7co.His10co.Phi29.V19M_Y148I_Y224K_E239G_V250I_L253A_E375Y_A484E_D510K_K512Y.co.His10co | |
| pET16.BtagV7co.His10co.Phi29.V19L_Y148I_Y224K_E239G_V250I_L253A_E375Y_A484E_D510K_K512Y_V568L.co.His10co | |
| pET16.BtagV7co.His10co.Phi29.Y148I_Y224K_E239G_V250I_L253A_E375Y_A484E_D510K_K512Y_D569E.co.His10co | |
| pET16.BtagV7co.His10co.Phi29.G197A_Y224K_E239G_V250I_L253A_F363Y_E375Y_A484E_D510K_K536R_D569E.co.His10co | |
| pET16.BtagV7co.His10co.Phi29.Y148I_Y224K_E239G_V250I_L253A_E375Y_A484E_D510K_K512Y.co.His10co | |
| pET16.BtagV7co.His10co.Phi29.Y148I_Y224K_E239G_V250I_L253A_E375Y_A484K_D510K_K536R.co.His10co | |
| pET16.BtagV7co.His10co.Phi29.D66R_Y148I_Y224K_E239G_V250I_L253A_E375Y_A484K_D510K_K512Y.co.His10co | |
| pET16.BtagV7co.His10co.Phi29.K143R_Y148I_Y224K_E239G_V250I_L253A_E375Y_A484K_D510K_K512Y.co.His10co | |
| pET16.BtagV7co.His10co.Phi29.Y148I_Y224K_E239G_V250I_L253A_E375Y_A484E_D510K_K512Y_F526Q.co.His10co | |
| pET16.BtagV7co.His10co.Phi29.Y148I_Y224K_E239G_V250I_L253A_E375Y_A484E_D510K_K512Y_E515Q.co.His10co | |
| pET16.BtagV7co.His10co.Phi29.Y148I_Y224K_E239G_V250I_L253A_E375Y_A484E_D510K_K512Y_E525I.co.His10co | |
| pET16.BtagV7co.His10co.Phi29.Y148I_Y224K_E239G_V250I_L253A_E375Y_A484E_D510K_K512Y_K525L.co.His10co | |
| pET16.BtagV7co.His10co.Phi29.Y148I_Y224K_E239G_V250I_L253A_E375Y_A484E_D510K_K512Y_E515Q_K525V.co.His10co | |

Fig. 7 cont'd

| |
|---|
| pET16.BtagV7co.His10co.Phi29.Y148I_Y224K_E239G_V250I_L253A_E375Y_A484E_D510K_K512Y_K525V_F526L.co.His10co |
| pET16.BtagV7co.His10co.Phi29.Y148I_Y224K_E239G_V250I_L253A_E375Y_A484E_D510K_K512Y_K525V_F526Q.co.His10co |
| pET16.BtagV7co.His10co.Phi29.D66R_Y148I_Y224K_E239G_V250I_L253A_E375Y_A484E_D510K_K512Y_K525V.co.His10co |
| pET16.BtagV7co.His10co.Phi29.K143R_Y148I_Y224K_E239G_V250I_L253A_E375Y_A484E_D510K_K512Y_K525V.co.His10co |
| pET16.BtagV7co.His10co.Phi29.Y148I_Y224K_E239G_V250I_L253A_E375Y_A484E_D510K_E515K_K525V.co.His10co |
| pET16.BtagV7co.His10co.Phi29.Y148I_Y224K_E239G_M246A_V250I_L253A_E375Y_A484E_D510K_K512Y.co.His10co |
| pET16.BtagV7co.His10co.Phi29.Y148I_Y224K_E239G_M246I_V250I_L253A_E375Y_A484E_D510K_K512Y.co.His10co |
| pET16.BtagV7co.His10co.Phi29.Y148I_Y224K_E239G_M246V_V250I_L253A_E375Y_A484E_D510K_K512Y.co.His10co |
| pET16.BtagV7co.His10co.Phi29.Y148I_Y224K_E239G_M246D_V250I_L253A_E375Y_A484E_D510K_K512Y.co.His10co |
| pET16.BtagV7co.His10co.Phi29.Y148I_Y224K_E239G_M246T_V250I_L253A_E375Y_A484E_D510K_K512Y.co.His10co |
| pET16.BtagV7co.His10co.Phi29.Y148I_Y224K_E239G_E244K_V250I_L253A_E375Y_A484E_D510K_K512Y.co.His10co |
| pET16.BtagV7co.His10co.Phi29.Y148I_Y224K_E239G_E244R_V250I_L253A_E375Y_A484E_D510K_K512Y.co.His10co |
| pET16.BtagV7co.His10co.Phi29.Y148I_Y224K_E239G_E244Q_V250I_L253A_E375Y_A484E_D510K_K512Y.co.His10co |
| pET16.BtagV7co.His10co.Phi29.Y148I_Y224K_E239G_E241K_V250I_L253A_E375Y_A484E_D510K_K512Y.co.His10co |
| pET16.BtagV7co.His10co.Phi29.Y148I_Y224K_E239G_E241R_V250I_L253A_E375Y_A484E_D510K_K512Y.co.His10co |
| pET16.BtagV7co.His10co.Phi29.Y148I_Y224K_E239G_E241Q_V250I_L253A_E375Y_A484E_D510K_K512Y.co.His10co |
| pET16.BtagV7co.His10co.Phi29.Y148I_Y224K_E239G_V250I_L253A_D362K_E375Y_A484E_D510K_K512Y.co.His10co |
| pET16.BtagV7co.His10co.Phi29.Y148I_Y224K_E239G_V250I_L253A_D362R_E375Y_A484E_D510K_K512Y.co.His10co |
| pET16.BtagV7co.His10co.Phi29.Y148I_Y224K_E239G_V250I_L253A_D362N_E375Y_A484E_D510K_K512Y.co.His10co |
| pET16.BtagV7co.His10co.Phi29.Y148I_Y224K_E239G_V250I_L253A_D365K_E375Y_A484E_D510K_K512Y.co.His10co |
| pET16.BtagV7co.His10co.Phi29.Y148I_Y224K_E239G_V250I_L253A_D365R_E375Y_A484E_D510K_K512Y.co.His10co |
| pET16.BtagV7co.His10co.Phi29.Y148I_Y224K_E239G_V250I_L253A_D365Q_E375Y_A484E_D510K_K512Y.co.His10co |
| pET16.BtagV7co.His10co.Phi29.Y148I_Y224K_E239G_V250I_L253A_E375Y_T465K_A484E_D510K_K512Y.co.His10co |
| pET16.BtagV7co.His10co.Phi29.Y148I_Y224K_E239G_V250I_L253A_E375Y_T465R_A484E_D510K_K512Y.co.His10co |
| pET16.BtagV7co.His10co.Phi29.Y148I_Y224K_E239G_V250I_L253A_E375Y_T465N_A484E_D510K_K512Y.co.His10co |
| pET16.BtagV7co.His10co.Phi29.Y148I_Y224K_E239G_V250I_L253A_E375Y_D469K_A484E_D510K_K512Y.co.His10co |
| pET16.BtagV7co.His10co.Phi29.Y148I_Y224K_E239G_V250I_L253A_E375Y_D469R_A484E_D510K_K512Y.co.His10co |
| pET16.BtagV7co.His10co.Phi29.Y148I_Y224K_E239G_V250I_L253A_E375Y_D469N_A484E_D510K_K512Y.co.His10co |
| pET16.BtagV7co.His10co.Phi29.Y148I_Y224K_E239G_V250I_L253A_E375Y_A484E_D503K_D510K_K512Y.co.His10co |
| pET16.BtagV7co.His10co.Phi29.Y148I_Y224K_E239G_V250I_L253A_E375Y_A484E_D503R_D510K_K512Y.co.His10co |
| pET16.BtagV7co.His10co.Phi29.Y148I_Y224K_E239G_V250I_L253A_E375Y_A484E_D503N_D510K_K512Y.co.His10co |
| pET16.BtagV7co.His10co.Phi29.T140Y_Y148I_Y224K_E239G_M246L_V250I_L253A_E375Y_A484E_D510K_K512Y_E515Q.co.His10co |

| Construct |
|---|
| pET16.BtagV7co.His10co.Phi29.Y148I_Y224K_E239G_L253A_E375Y_T441A_A484E_D510K_K512Y.co.His10co |
| pET16.BtagV7co.His10co.Phi29.T140K_L142K_Y148I_Y224K_E239G_L253A_E375Y_T441A_A484E_D510K_K512Y.co.His10co |
| pET16.BtagV7co.His10co.Phi29.V141K_L142K_Y148I_Y224K_E239K_V250I_L253A_E375Y_T441A_A484E_D510K_K512Y.co.His10co |
| pET16.BtagV7co.His10co.Phi29.V141K_Y148I_Y224K_E239G_V250I_L253A_E375Y_T441A_A484E_E508R_D510K_K512Y.co.His10co |
| pET16.BtagV7co.His10co.Phi29.Y148I_Y224K_T231A_E239G_V250I_L253A_E375Y_A484E_D510K_K512Y.co.His10co |
| pET16.BtagV7co.His10co.Phi29.Y148I_Y224K_T231S_E239G_V250I_L253A_E375Y_A484E_D510K_K512Y.co.His10co |
| pET16.BtagV7co.His10co.Phi29.Y148I_Y224K_T231V_E239G_V250I_L253A_E375Y_A484E_D510K_K512Y.co.His10co |
| pET16.BtagV7co.His10co.Phi29.Y148I_Y224K_T231L_E239G_V250I_L253A_E375Y_A484E_D510K_K512Y.co.His10co |
| pET16.BtagV7co.His10co.Phi29.Y148I_Y224K_E239G_V250I_L253A_E375Y_Y454F_A484E_D510K_K512Y.co.His10co |
| pET16.BtagV7co.His10co.Phi29.Y148I_Y224K_F230Y_E239G_V250I_L253A_E375Y_A484E_D510K_K512Y.co.His10co |
| pET16.BtagV7co.His10co.Phi29.Y148I_Y224K_E239G_V250I_L253A_E375Y_I460V_A484E_D510K_K512Y.co.His10co |
| pET16.BtagV7co.His10co.Phi29.Y148I_Y224K_E239G_V250I_L253A_E375Y_I460L_A484E_D510K_K512Y.co.His10co |
| pET16.BtagV7co.His10co.Phi29.Y148I_Y224K_E239G_V250I_L253A_E375Y_I460F_A484E_D510K_K512Y.co.His10co |
| pET16.BtagV7co.His10co.Phi29.Y148I_Y224K_E239G_V250I_L253A_E375Y_E420M_A484E_D510K_K512Y.co.His10co |
| pET16.BtagV7co.His10co.Phi29.Y148I_Y224K_E239G_V250I_L253A_E375Y_E420K_A484E_D510K_K512Y.co.His10co |
| pET16.BtagV7co.His10co.Phi29.Y148I_Y224K_E239G_V250I_L253A_E375Y_Y439E_A484E_D510K_K512Y.co.His10co |
| pET16.BtagV7co.His10co.Phi29.Y148I_Y224K_E239G_V250I_L253A_E375Y_Y439A_A484E_D510K_K512Y.co.His10co |
| pET16.BtagV7co.His10co.Phi29.Y148I_Y224K_E239G_V250I_L253A_E375Y_Y439K_A484E_D510K_K512Y.co.His10co |
| pET16.BtagV7co.His10co.Phi29.Y148I_Y224K_E239G_V250I_L253A_E375Y_T443K_A484E_D510K_K512Y.co.His10co |
| pET16.BtagV7co.His10co.Phi29.Y148I_Y224K_E239G_V250I_L253A_E375Y_T443E_A484E_D510K_K512Y.co.His10co |
| pET16.BtagV7co.His10co.Phi29.Y148I_Y224K_E239G_V250I_L253A_E375Y_A447L_A484E_D510K_K512Y.co.His10co |
| pET16.BtagV7co.His10co.Phi29.Y148I_Y224K_E239G_V250I_L253A_E375Y_A447K_A484E_D510K_K512Y.co.His10co |
| pET16.BtagV7co.His10co.Phi29.Y148I_Y224K_E239G_V250I_L253A_E375Y_A447E_A484E_D510K_K512Y.co.His10co |
| pET16.BtagV7co.His10co.Phi29.Y148I_Y224K_E239G_V250I_L253A_E375Y_I442L_A484E_D510K_K512Y.co.His10co |
| pET16.BtagV7co.His10co.Phi29.Y148I_Y224K_E239G_V250I_L253A_E375Y_I442V_A484E_D510K_K512Y.co.His10co |
| pET16.BtagV7co.His10co.Phi29.Y148I_Y224K_E239G_V250I_L253A_E375Y_I442A_A484E_D510K_K512Y.co.His10co |
| pET16.BtagV7co.His10co.Phi29.Y148I_Y224K_E239G_V250I_L253A_E272Q_E375Y_A484E_D510K_K512Y.co.His10co |
| pET16.BtagV7co.His10co.Phi29.Y148I_Y224K_E239G_V250I_L253A_L328V_E375Y_A484E_D510K_K512Y.co.His10co |
| pET16.BtagV7co.His10co.Phi29.Y148I_Y224K_E239G_V250I_L253A_E272Q_L328V_E375Y_A484E_D510K_K512Y.co.His10co |
| pET16.BtagV7co.His10co.Phi29.Y148I_Y224K_E239G_V250I_L253H_E375Y_A437G_A484E_D510K_K512Y.co.His10co |
| pET16.BtagV7co.His10co.Phi29.Y148I_Y224K_E239G_V250I_L253A_E375Y_A437G_A484E_D510K_K512Y.co.His10co |

Fig. 7 cont'd

| |
|---|
| pET16.BtagV7co.His10co.Phi29.Y148I_Y224K_E239G_V250I_L253H_E375Y_A437G_A484E_D510K_K512Y.co.His10co |
| pET16.BtagV7co.His10co.Phi29.Y148I_Y224K_E239G_V250I_L253A_E375Y_A437T_T440R_A484E_D510K_K512Y.co.His10co |
| pET16.BtagV7co.His10co.Phi29.K131R_Y148I_Y224K_E239G_V250I_L253A_E375Y_A484E_D510K_K512Y.co.His10co |
| pET16.BtagV7co.His10co.Phi29.K131Q_Y148I_Y224K_E239G_V250I_L253A_E375Y_A484E_D510K_K512Y.co.His10co |
| pET16.BtagV7co.His10co.Phi29.K131E_Y148I_Y224K_E239G_V250I_L253A_E375Y_Y405E_A484E_D510K_K512Y.co.His10co |
| pET16.BtagV7co.His10co.Phi29.Y148I_Y224K_E239G_V250I_L253A_E375Y_Y405S_A484E_D510K_K512Y.co.His10co |
| pET16.BtagV7co.His10co.Phi29.Y148I_Y224K_E239G_V250I_L253A_E375Y_Y405L_A484E_D510K_K512Y.co.His10co |
| pET16.BtagV7co.His10co.Phi29.N77H_Y148I_Y224K_E239G_V250I_L253A_E375Y_A484E_D510K_K512Y.co.His10co |
| pET16.BtagV7co.His10co.Phi29.Y148I_Y224R_E239G_V250I_L253A_E375Y_A484E_D510K_K512Y.co.His10co |
| pET16.BtagV7co.His10co.Phi29.Y148I_E221D_Y224K_E239G_V250I_L253A_E375Y_A484E_D510K_K512Y.co.His10co |
| pET16.BtagV7co.His10co.Phi29.Y148I_E221D_Y224K_E239G_V250I_L253A_E375Y_A484E_D510K_K512C.co.His10co |
| pET16.BtagV7co.His10co.Phi29.Y148I_E221Q_Y224K_E239G_V250I_L253A_E375Y_A484E_D510K_K512Y.co.His10co |
| pET16.BtagV7co.His10co.Phi29.K135C_Y148I_Y224K_E239G_V250I_L253A_E375Y_A484E_D510K_K512Y.co.His10co |
| pET16.BtagV7co.His10co.Phi29.C106S_K135C_Y148I_Y224K_E239G_V250I_L253A_E375Y_C448V_A484E_D510K_K512Y.co.His10co |
| pET16.BtagV7co.His10co.Phi29.C106S_Y148I_Y224K_E239G_V250I_L253A_E375Y_C448S_A484E_D510K_K512Y.co.His10co |
| pET16.BtagV7co.His10co.Phi29.C106S_Y148I_Y224K_E239G_V250I_L253A_E375Y_A484E_D510K_K512C.co.His10co |
| pET16.BtagV7co.His10co.Phi29.C106S_Y148I_Y224K_E239G_V250I_L253A_E375Y_K478C_A484E_D510K_K512Y.co.His10co |
| pET16.BtagV7co.His10co.Phi29.C106S_Y148I_Y224K_E239G_V250I_L253A_E375Y_P477C_A484E_D510K_K512Y.co.His10co |
| pET16.BtagV7co.His10co.Phi29.Y148I_Y224K_E239G_V250I_L253A_E375Y_P477C_A484E_D510K_K512Y.co.His10co |
| pET16.BtagV7co.His10co.Phi29.Y148I_Y224K_E239G_V250I_L253A_T368F_E375Y_A484E_D510K_K512Y.co.His10co |
| pET16.BtagV7co.His10co.Phi29.Y148I_Y224K_E239G_V250I_L253A_E375Y_A484E_D510C_K512Y.co.His10co |
| pET16.BtagV7co.His10co.Phi29.Y148I_Y224K_E239G_V250I_L253A_E375Y_A484E_D510K_K512Y_D523T.co.His10co |
| pET16.BtagV7co.His10co.Phi29.Y148I_Y224K_E239G_V250I_L253A_E375Y_N387V_A484E_D510K_K512Y.co.His10co |
| pET16.BtagV7co.His10co.Phi29.Y148I_Y224K_E239G_V250I_L253A_E375Y_N387T_A484E_D510K_K512Y.co.His10co |
| pET16.BtagV7co.His10co.Phi29.Y148I_Y224K_E239G_V250I_L253A_E375Y_N387L_A484E_D510K_K512Y.co.His10co |
| pET16.BtagV7co.His10co.Phi29.Y148I_Y224K_E239G_V250I_L253A_E375Y_W367Y_A484E_D510K_K512Y.co.His10co |
| pET16.BtagV7co.His10co.Phi29.Y148I_Y224K_E239G_V250I_L253A_E375Y_W367F_A484E_D510K_K512Y.co.His10co |
| pET16.BtagV7co.His10co.Phi29.Y148I_Y224K_E239G_V250I_L253A_E375Y_W367L_A484E_D510K_K512Y.co.His10co |
| pET16.BtagV7co.His10co.Phi29.Y148I_Y224K_E239G_V250I_L253A_E375Y_A444G_A484E_D510K_K512Y_E515K.co.His10co |
| pET16.BtagV7co.His10co.Phi29.Y148I_Y224K_E239G_V250I_L253A_E375Y_A444S_A484E_D510K_K512Y.co.His10co |
| pET16.BtagV7co.His10co.Phi29.Y148I_Y224K_E239G_V250I_L253A_E375Y_A444V_A484E_D510K_K512Y.co.His10co |

Fig. 7 cont'd

| Plasmid |
|---|
| pET16.BtaqV7co.His10co.Phi29.Y148I_Y224K_E239G_V250I_L253A_E375Y_A444L_A484E_D510K_K512Y.co.His10co |
| pET16.BtaqV7co.His10co.Phi29.Y148I_Y224K_E239G_V250I_L253A_V331L_E375Y_A484E_D510K_K512Y.co.His10co |
| pET16.BtaqV7co.His10co.Phi29.Y148I_Y224K_E239G_V250I_L253A_E375Y_A484E_D510K_K512Y_V514K.co.His10co |
| pET16.BtaqV7co.His10co.Phi29.Y148I_Y224K_E239G_V250I_L253A_E375Y_A484E_D510K_K512Y_V514E.co.His10co |
| pET16.BtaqV7co.His10co.Phi29.Y148I_Y224K_E239G_V250I_L253A_E375Y_A484E_D510K_K512Y_V514D_E515K.co.His10co |
| pET16.BtaqV7co.His10co.Phi29.Y148I_Y224K_E239G_V250I_L253A_E375Y_A484E_D510K_K512Y_V514E_E515K.co.His10co |
| pET16.BtaqV7co.His10co.Phi29.Y148I_Y224K_E239G_V250I_L253A_E375Y_A484E_D510K_K512Y_V514C_E515K.co.His10co |
| pET16.BtaqV7co.His10co.Phi29.Y148I_Y224K_E239G_V250I_L253A_E375Y_A484E_D510K_K512Y_V514C.co.His10co |
| pET16.BtaqV7co.His10co.Phi29.Y148I_Y224K_E239G_V250I_L253A_E375Y_A484E_D510K_K512Y_V514Q_E515K.co.His10co |
| pET16.BtaqV7co.His10co.Phi29.Y148I_Y224K_E239G_V250I_L253A_E375Y_A484E_D510K_K512Y_V514Y_E515K.co.His10co |
| pET16.BtaqV7co.His10co.Phi29.Y148I_Y224K_E239G_V250I_L253A_E375Y_A484E_D510K_K512Y_V514K_E515K.co.His10co |
| pET16.BtaqV7co.His10co.Phi29.Y148I_Y224K_E239G_V250I_L253A_E375Y_A484E_D510K_K512Y_V514K_E515P.co.His10co |
| pET16.BtaqV7co.His10co.Phi29.Y148I_Y224K_E239G_V250I_L253A_E375Y_A484E_D510K_K512Y_V514D_E515P.co.His10co |
| pET16.BtaqV7co.His10co.CTerm_His10co.Phi29.Y148I_Y224K_E239G_V250I_L253A_A256G_E375Y_A484E_D510K_K512Y_F526L.co.His10co |
| pET16.BtaqV7co.His10co.Phi29.Y148I_Y224K_C106S_Y148I_Y224K_E239G_V250I_L253A_E375Y_P477C_A484E_D510K_K512Y.co.His10co |
| pET16.BtaqV7co.His10co.Phi29.Y224K_E239G_L253A_E375Y_A437S_T440V_A484E_D510K_K512Y_F526L.co.Nhe.His10co |
| pET16.BtaqV7co.His10co.Phi29.Y224K_E239G_V250M_L253A_E375Y_A437G_T440V_A484E_D510K_K512Y_F526L.co.Nhe.His10co |
| pET16.BtaqV7co.His10co.Phi29.Y224K_E239G_V250M_L253A_E375Y_T440Q_A484E_D510K_K512Y_F526L.co.Nhe.His10co |
| pET16.BtaqV7co.His10co.Phi29.Y224K_E239G_V250Q_L253N_E375Y_T440V_A484E_D510K_K512Y_F526L.co.Nhe.His10co |
| pET16.BtaqV7co.His10co.Phi29.I202L_L253A_A324V_E375Y_A484E_D510K_K512Y_M554G.co.Nhe.His10co |
| pET16.BtaqV7co.His10co.Phi29.A164E_R236K_L253A_E375Y_A484E_D510K_K512Y_M554G.co.Nhe.His10co |
| pET16.BtaqV7co.His10co.Phi29.T140P_K157E_R236K_F237Y_L253A_W277K_E375Y_A484E_D510K_K512Y_G516C_Y521A_D523T_M554G.co.Nhe.His10co |
| pET16.BtaqV7co.His10co.Phi29.S36D_Y224K_L253A_W277K_E375Y_A484E_D510K_K512Y_G516C_R552S_M554G.co.Nhe.His10co |
| pET16.BtaqV7co.His10co.Phi29.S36D_V222I_Y224K_L253A_E375Y_A484E_D510K_K512Y_M554G.co.Nhe.His10co |
| pET16.BtaqV7co.His10co.Phi29.K157E_V222I_Y224K_L253A_A324V_E375Y_A484E_D510K_K512Y_M554G.co.Nhe.His10co |
| pET16.BtaqV7co.His10co.Phi29.D84E_T140P_A164E_V222I_Y224K_F237Y_L253A_W277K_H284Y_M336I_L351F_E375Y_A484E_D510K_K512Y_M554G.co.Nhe.His10co |
| pET16.BtaqV7co.His10co.Phi29.D84E_L253A_A324V_E375Y_A484E_D510K_K512Y_M336I_L351F_E375Y_A484E_D510K_K512Y_M554G.co.Nhe.His10co |
| pET16.BtaqV7co.His10co.Phi29.D84E_K157E_Y224K_R236K_L253A_L351F_E375Y_A484E_D510K_K512Y_M554G.co.Nhe.His10co |
| pET16.BtaqV7co.His10co.Phi29.V222I_Y224K_F237Y_L253A_S307N_L351F_E375Y_A484E_D510K_K512Y_M554G.co.Nhe.His10co |
| pET16.BtaqV7co.His10co.Phi29.T140P_K157E_Y224K_F237Y_L253A_S307N_A324V_E375Y_A484E_D510K_K512Y_M554G.co.Nhe.His10co |
| pET16.BtaqV7co.His10co.Phi29.N31E_V222I_Y224K_R236K_L253A_E375Y_A484E_D510K_K512Y_G516C_Y521A_M554G.co.Nhe.His10co |
| pET16.BtaqV7co.His10co.Phi29.N62D_L253A_E375Y_R552S_M554G.co.Nhe.His10co |
| pET16.BtaqV7co.His10co.Phi29.K157E_A164E_Y224K_L253A_W277K_H284Y_M336I_L351F_E375Y_A484E_D510K_K512Y_M554G.co.Nhe.His10co |

- pET16.BtagV7co.His10co.Phi29.K157E_V222I_L253A_E375Y_P397T_A484E_D510K_K512Y_M554G.co.Nhe.His10co
- pET16.BtagV7co.Phi29.S36D_K157E_I202L_V222I_L253A_W277K_L351F_E375Y_A484E_D510K_K512Y_M554G.co.Nhe.His10co
- pET16.BtagV7co.His10co.Phi29.K157E_V222I_Y224K_L253A_W277K_H284Y_M336I_L351F_E375Y_A484E_D510K_K512Y_R552S_M554G.co.Nhe.His10co
- pET16.BtagV7co.His10co.Phi29.Y148I_Y224K_E239G_V250I_L253A_E375Y_A484E_D510K_K512Y_V566C.co.His10co
- pET16.BtagV7co.His10co.Phi29.Y148I_Y224K_D235E_E239G_V250I_L253A_E375Y_T441A_C448T_A484E_D510K_K512Y_E515Q.co.His10co
- pET16.BtagV7co.His10co.Phi29.Y148I_S194A_Y224K_D235E_E239G_V250I_L253A_E375Y_T441A_C448T_A484E_D510K_K512Y_E515Q.co.His10co
- pET16.BtagV7co.His10co.Phi29.Y148I_S194A_Y224K_D235E_E239G_V250I_L253A_E375Y_T441A_C448T_A484E_D510K_K512Y_E515Q.co.His10co
- pET16.BtagV7co.His10co.Phi29.Y148I_S194A_K196R_Y224K_D235E_E239G_V250I_L253A_E375Y_T441A_C448T_A484E_D510K_K512Y_E515Q.co.His10co
- pET16.BtagV7co.His10co.Phi29.Y148I_Y224K_E239G_V250I_L253C_E375Y_A484E_D510K_K512Y_E515Q.co.His10co
- pET16.BtagV7co.His10co.Phi29.V19D_Y148I_Y224K_E239G_V250I_L253A_E375Y_A484E_D510K_K512Y_V568R.co.His10co
- pET16.BtagV7co.His10co.Phi29.V19D_Y148I_Y224K_E239G_V250I_L253A_E375Y_A484E_D510K_K512Y_V568K.co.His10co
- pET16.BtagV7co.His10co.Phi29.V19E_Y148I_Y224K_E239G_V250I_L253A_E375Y_A484E_D510K_K512Y_V568R.co.His10co
- pET16.BtagV7co.His10co.Phi29.V19E_Y148I_Y224K_E239G_V250I_L253A_E375Y_A484E_D510K_K512Y_V568R.co.His10co
- pET16.BtagV7co.His10co.Phi29.K143R_Y148I_Y224K_E239G_V250I_L253A_E375Y_A484E_D510K_K512Y_V568R.co.His10co
- pET16.BtagV7co.His10co.Phi29.D66R_Y148I_Y224K_E239G_V250I_L253A_E375Y_A484E_D510K_K512Y_V568R.co.His10co
- pET16.BtagV7co.His10co.Phi29.Y148I_S194A_Y224K_E239G_V250I_L253A_E375Y_A484E_Y505Q_D510K_K512Y_K525A.co.His10co
- pET16.BtagV7co.His10co.Phi29.Y148I_Y224K_E239G_V250I_L253A_E375Y_A484E_M506A_V514I_G516C_D520E_Y521A_D523T_I524T.co.His10co
- pET16.BtagV7co.His10co.Phi29.Y148I_Y224K_E239G_V250I_L253A_E375Y_A484E_M506A_D510K_V514I_G516C_D520E_Y521A_D523T_I524T.co.His10co
- pET16.BtagV7co.His10co.Phi29.Y148I_Y224K_E239G_V250I_L253A_E375Y_A484E_M506A_K512Y_V514I_G516C_D520E_Y521A_D523T_I524T.co.His10co
- pET16.BtagV7co.His10co.Phi29.Y148I_Y224K_E239G_V250I_L253A_E375Y_A484E_D510K_K512Y_V568R.co.His10co
- pET11.Phi29.Y148I_Y224K_E239G_V250I_L253A_K361R_E375Y_A484E_D510K_K512Y_E508K.co.His10co.GGGSGGGSGGGS.BtagV7co
- pET11.Phi29.Y148I_Y224K_E239G_V250I_L253A_K361R_E375Y_A484E_D510K_K512Y_V568R.co.His10co.GGGSGGGSGGGS.BtagV7co
- pET11.Phi29.S194A_Y224K_E239G_V250I_L253A_E375Y_A484E_E508K_K512Y_L513Y.co.His10co
- pET16.Phi29.Y148I_S194A_Y224K_E239G_V250I_L253A_E375Y_A484E_E508R_K512Y_L513Y.co.His10co
- pET16.Phi29.Y148I_G197E_K205E_Y224K_E239G_V250I_L253A_E375Y_K472A_A484E_D510K_K512Y.co.His10co

| Vector | Construct |
|---|---|
| pET16.BtagV7co.His10co.Phi29.Y148I_G197E_K205E_Y224K_E239G_V250I_L253A_E375Y_K472A_K479Q_A484E_D510K_K512Y_co.His10co |
| pET16.BtagV7co.His10co.Phi29.Y148I_G197E_K205E_Y224K_E239G_V250I_L253A_E375Y_K472A_K479Q_A484E_D510K_K512Y_K536Q_co.His10co |
| pET16.BtagV7co.His10co.Phi29.Y148I_L185I_Y224K_E239G_V250I_L253A_E375Y_A484E_D510K_K512Y_co.His10co |
| pET16.BtagV7co.His10co.Phi29.Y148I_L185M_Y224K_E239G_V250I_L253A_E375Y_A484E_D510K_K512Y_co.His10co |
| pET16.BtagV7co.His10co.Phi29.Y148I_L185A_Y224K_E239G_V250I_L253A_E375Y_A484E_D510K_K512Y_co.His10co |
| pET16.BtagV7co.His10co.Phi29.Y148I_Q183K_Y224K_E239G_V250I_L253A_E375Y_A484E_D510K_K512Y_co.His10co |
| pET16.BtagV7co.His10co.Phi29.Y148I_Q183N_Y224K_E239G_V250I_L253A_E375Y_A484E_D510K_K512Y_co.His10co |
| pET16.BtagV7co.His10co.Phi29.Y148I_Q183F_Y224K_E239G_V250I_L253A_E375Y_A484E_D510K_K512Y_co.His10co |
| pET16.BtagV7co.His10co.Phi29.Y148I_Y224K_E239G_L253H_E375Y_A437G_A484E_D510K_K512Y_E515K_co.His10co |
| pET16.BtagV7co.His10co.Phi29.Y148I_Y224K_E239G_L253H_E375Y_A437G_A484E_D510K_K512Y_E515P_co.His10co |
| pET16.BtagV7co.His10co.Phi29.Y148I_Y224K_E239G_L253H_E375Y_A437G_A484E_D510K_K512Y_co.His10co |
| pET16.BtagV7co.His10co.Phi29.Y148I_Y224K_E239G_L253H_E375Y_A484E_D510K_K512Y_E515Q_co.His10co |
| pET11.Phi29.Y148I_Y224K_D235E_E239G_L253H_E375Y_A437G_A484E_D510K_K512Y_E515Q_co.His10co.GGGSGGGSGGGS.BtagV7co |
| pET11.Phi29.Y148I_Y224K_D235E_E239G_L253H_E375Y_A484E_D510K_K512Y_E515P_co.His10co.GGGSGGGSGGGS.BtagV7co |
| pET11.Phi29.Y148I_Y224K_D235E_E239G_L253C_E375Y_A484E_D510K_K512Y_E515K_co.His10co.GGGSGGGSGGGS.BtagV7co |
| pET16.BtagV7co.His10co.Phi29.K143R_Y148I_Y224K_E239G_L253H_E375Y_A484E_E508K_D510S_K512Y_co.His10co |
| pET16.BtagV7co.His10co.Phi29.N62D_Y148I_Y224K_E239G_L253H_E375Y_A437G_A484E_D510K_K512Y_co.His10co |
| pET16.BtagV7co.His10co.Phi29.Y148I_Y224K_E239G_V250I_L253A_E375Y_A437G_C448I_A484E_D510K_K512Y_K525V_co.His10co |
| pET16.BtagV7co.His10co.Phi29.Y148I_Y224K_E239G_V250I_L253A_E375Y_A437G_C448I_A484E_D510K_K512Y_co.His10co |
| pET11.BtagV7co.His10co.Phi29.Y148I_Y224K_E239G_L253H_E375Y_A437G_A484E_D510K_K512Y_co.His10co.GGGSGGGSGGGS.BtagV7co |
| pET16.BtagV7co.His10co.Phi29.Y148I_Y224K_E239G_V250I_L253A_E375Y_A484E_D510K_K512Y_E515Q_co.His10co |
| pET16.BtagV7co.His10co.Phi29.Y148I_Y224K_E239G_V250I_L253A_E375Y_Y369R_A484E_D510K_K512Y_576GTGSGA_Maltose_Binding_Fusion_Protein.co |
| pET16.BtagV7co.His10co.Phi29.Y148I_Y224K_E239G_V250I_L253A_E375A_T441A_A484E_D510K_K512Y_E515Q_576GTGSGA_Maltose_Binding_Fusion_Protein.co |
| pET16.BtagV7co.His10co.Phi29.Y148I_Y224K_E239G_V250I_L253A_Y254F_E375Y_A484E_D510K_K512Y_co.His10co |
| pET16.BtagV7co.His10co.Phi29.Y148I_Y224K_E239G_V250I_L253A_E375Y_A437G_A484E_D510K_K512Y_co.His10co |

Fig. 7 cont'd

| Plasmid |
|---|
| pET16.BtagV7.co.His10co.Phi29.Y148I_E239G_V250I_L253A_E375Y_Y390F_A484E_D510K_K512Y.co.His10co |
| pET16.BtagV7.co.His10co.Phi29.Y148I_E221D_E239G_V250I_L253A_E375Y_A484E_D510K_K512Y.co.His10co |
| pET16.BtagV7.co.His10co.Phi29.Y148I_E239G_V250I_L253A_E375Y_A484E_D510K_K512Y_Q560E.co.His10co |
| pET16.BtagV7.co.His10co.Phi29.Y38K_Y163D_L253A_E375Y_A484E_K512Y.co.His10co |
| pET16.BtagV7.co.His10co.Phi29.Y38D_Y163K_L253A_E375Y_A484E_K512Y.co.His10co |
| pET16.BtagV7.co.His10co.Phi29.Y38N_Y163N_L253A_E375Y_A484E_K512Y.co.His10co |
| pET16.BtagV7.co.His10co.Phi29.Y165D_L253A_E375Y_A484E_K512Y.co.His10co |
| pET16.BtagV7.co.His10co.Phi29.Y165N_L253A_E375Y_A484E_K512Y.co.His10co |
| pET16.BtagV7.co.His10co.Phi29.Y165K_L253A_E375Y_A484E_K512Y.co.His10co |
| pET16.BtagV7.co.His10co.Phi29.Y156D_L253A_E375Y_A484E_K512Y.co.His10co |
| pET16.BtagV7.co.His10co.Phi29.Y156N_L253A_E375Y_A484E_K512Y.co.His10co |
| pET16.BtagV7.co.His10co.Phi29.Y156K_L253A_E375Y_A484E_K512Y.co.His10co |
| pET16.BtagV7.co.His10co.Phi29.L253A_Y347D_E375Y_A484E_K512Y.co.His10co |
| pET16.BtagV7.co.His10co.Phi29.L253A_Y347N_E375Y_A484E_K512Y.co.His10co |
| pET16.BtagV7.co.His10co.Phi29.Y148I_D235E_E239K_D481E_D507K_K509Y.co.His10co |
| pET16.BtagV7.co.His10co.M2.L250A_E372Y_A481E_V247I_L250A_E372Y_A481E_D507K_K509Y.co.His10co |
| pET16.BtagV7.co.His10co.M2.Y145I_V247I_L250A_E372Y_A481E_D507K_K509Y.co.His10co |
| pET16.BtagV7.co.His10co.M2.Y145I_E236G_V247I_L250A_E372Y_A481E_V250I_L253A_E375Y_C448T_A484E_D510K_K512Y.co.His10co |
| pET16.BtagV7.co.His10co.Phi29.Y148I_S194A_K196R_Y224K_E239G_V250I_L253A_E375Y_A484E_D510K_K512Y.co.His10co |
| pET16.BtagV7.co.His10co.Phi29.Y148I_S194G_Y224K_E239G_V250I_L253A_E375Y_A484E_D510K_K512Y.co.His10co |
| pET16.BtagV7.co.His10co.Phi29.Y148I_S194G_Y224K_E239G_V250I_L253A_E375Y_A484E_D510K_K512Y_F526L.co.His10co |
| pET16.BtagV7.co.His10co.Phi29.Y148I_G197D_Y224K_E239G_V250I_L253A_E375Y_A484E_D510K_K512Y.co.His10co |
| pET16.BtagV7.co.His10co.Phi29.Y148I_G197E_Y224K_E239G_V250I_L253A_K366R_E375Y_A484E_D510K_K512Y.co.His10co |
| pET16.BtagV7.co.His10co.Phi29.Y148I_G197E_Y224K_E239G_V250I_L253A_K366R_E375Y_A484E_D510K_K512Y.co.His10co |
| pET16.BtagV7.co.His10co.Phi29.Y148I_Y224K_E239G_V250I_L253A_K366Q_E375Y_A484E_D510K_K512Y.co.His10co |
| pET16.BtagV7.co.His10co.Phi29.Y148I_Y224K_E239G_V250I_L253A_K366Q_E375Y_A484E_D510K_K512Y.co.His10co |
| pET16.BtagV7.co.His10co.Phi29.Y148I_Y224K_E239G_V250I_L253A_S374E_E375Y_I378K_A484E_D510K_K512Y.co.His10co |
| pET16.BtagV7.co.His10co.M2.L250A_E372Y_A481E_K509Y_E512K.co.His10co |
| pET16.BtagV7.co.His10co.M2.L250A_E372Y_A481E_K509Y_E512K_C513G.co.His10co |
| pET16.BtagV7.co.His10co.M2.L250A_E372Y_A481E_K509Y_E512K_C513G_K512Y_D520E.co.His10co |
| pET16.BtagV7.co.His10co.M2.L250A_E372Y_A481E_V503M_K509Y_K511V_C513G_E517D_A518Y_T520D_T521I.co.His10co |

Fig. 7 cont'd

| Construct |
|---|
| pET16.BtagV7co.His10co.M2.L250A.H370T.E371S.E372Y.K375I.A481E.K509Y.co.His10co |
| pET16.BtagV7co.His10co.M2.L250A.S253A.E372Y.A481E.K509Y.co.His10co |
| pET16.BtagV7co.His10co.Phi29.Y148I.Y224K.D235E.E372Y.A481E.K509Y.co.His10co |
| pET16.BtagV7co.His10co.Phi29.A68S.Y148I.Y224K.E239G.V250I.L253A.E375Y.T441A.A484E.D510K.K512Y.E515Q.co.His10co |
| pET16.BtagV7co.His10co.Phi29.C22A.Y148I.Y224K.E239G.V250I.L253A.E375Y.A484E.D510K.K512Y.Q560E.co.His10co |
| pET16.BtagV7co.His10co.Phi29.K135Q.Y148I.Y224K.E239G.V250I.L253A.E375Y.C448V.A484E.D510K.K512Y.C530V.V566I.co.His10co |
| pET16.BtagV7co.His10co.Phi29.K131E.Y148I.Y224K.E239G.V250I.L253A.E375Y.A484E.D510K.K512Y.co.His10co |
| pET16.BtagV7co.His10co.Phi29.K131E.K135Q.Y148I.Y224K.E239G.V250I.L253A.E375Y.A484E.D510K.K512Y.co.His10co |
| pET16.BtagV7co.His10co.Phi29.K131E.K135Q.Y148I.Y224K.E239G.V250I.L253A.E375Y.T441I.A484E.D510K.K512Y.co.His10co |
| pET16.BtagV7co.His10co.Phi29.K131E.K135Q.Y148I.K205E.Y224K.E239G.V250I.L253A.E375Y.K479Q.A484E.D510K.K512Y.K536Q.K539Q.co.His10co |
| pET16.BtagV7co.His10co.Phi29.K131E.K135Q.Y148I.G197E.K205E.Y224K.E239G.V250I.L253A.E375Y.K479Q.A484E.D510K.K512Y.K536Q.K539Q.co.His10co |
| pET16.BtagV7co.His10co.Phi29.K131E.K135Q.Y148I.G197E.K205E.Y224K.E239G.V250I.L253A.E375Y.K479Q.A484E.D510S.K512Y.K536Q.K539Q.co.His10co |
| pET16.BtagV7co.His10co.Phi29.K131E.K135Q.Y148I.G197E.K205E.Y224K.E239G.V250I.L253A.E484K.D510S.K512Y.co.His10co |
| pET16.BtagV7co.His10co.Phi29.K131E.K135Q.Y148I.G197E.K205E.Y224K.E239G.V250I.L253A.E375Y.A484E.D510K.K512Y.K525V.K536Q.K539Q.co.His10co |
| pET16.BtagV7co.His10co.Phi29.K131E.K135Q.Y148I.S194A.K196R.Y224K.E239G.V250I.L253A.E375Y.T441I.A484E.D510K.K512Y.co.His10co |
| pET16.BtagV7co.His10co.Phi29.K131E.K135Q.Y148I.S194A.K196R.Y224K.E239G.V250I.L253A.E375Y.T441I.A484E.D510K.K512Y.co.His10co |
| pET16.BtagV7co.His10co.Phi29.K131E.K135Q.Y148I.S194A.K196R.Y224K.E239G.V250I.L253A.E375Y.T441I.A484E.D510K.K512Y.co.His10co |
| pET16.BtagV7co.His10co.Phi29.K131E.K135Q.Y148I.S194A.Y224K.E239G.V250I.L253A.E375Y.C448Y.A484E.D510K.K512Y.co.His10co |
| pET16.BtagV7co.His10co.Phi29.M97C.C106S.Y148I.G197E.K205E.Y224K.E239G.V250I.L253A.E375Y.K472A.K479Q.A484E.D510K.K512Y.K536Q.K539Q.BtagV7co |
| pET16.BtagV7co.His10co.Phi29.M97C.K131E.K135Q.Y148I.G197E.K205E.Y224K.E239G.V250I.L253A.E375Y.K472A.K479Q.A484E.D510K.K512Y.K525V.K536Q.K539Q.BtagV7co |
| pET11.Phi29.Y148I.S194A.Y224K.E239G.L253H.E375Y.A437G.A484E.D510K.K512Y.E515P.co.His10co.GGGSGGGSGGGS.BtagV7co |
| pET11.Phi29.Y148I.S194A.Y224K.E239G.L253H.E375Y.A437G.A484E.D510K.K512Y.E515P.co.His10co.GGGSGGGSGGGS.BtagV7co |
| pET11.Phi29.Y148I.Y224K.E239G.V250Q.L253H.E375Y.A437G.A484E.D510K.K512Y.co.His10co.GGGSGGGSGGGS.BtagV7co |
| pET11.Phi29.Y148I.Y224K.E239G.V250M.L253H.E375Y.A437G.A484E.D510K.K512Y.co.His10co.GGGSGGGSGGGS.BtagV7co |
| pET11.Phi29.Y148I.Y224K.E239G.V250L.L253H.E375Y.A437G.A484E.D510K.K512Y.co.His10co.GGGSGGGSGGGS.BtagV7co |

Fig. 7 cont'd pET11.Phi29.Y148I.Y224K.E239G.L253H.Q257L.E375Y.A437G.A484E.D510K.K512Y.co.His10co.GGGSGGGSGGGS.BtagV7co
pET11.Phi29.Y148I.Y224K.E239G.L253H.R261E.E375Y.A437G.A484E.D510K.K512Y.co.His10co.GGGSGGGSGGGS.BtagV7co
pET11.Phi29.Y148I.Y224K.E239G.L253H.Q257E.E375Y.A437G.A484E.D510K.K512Y.co.His10co.GGGSGGGSGGGS.BtagV7co
pET11.Phi29.Y148I.Q183T.Y224K.E239K.L253H.E375Y.A437G.A484E.D510K.K512Y.co.His10co.GGGSGGGSGGGS.BtagV7co
pET11.Phi29.Y148I.Y224K.E239G.L253H.E375Y.N387V.A437G.A484E.D510K.K512Y.co.His10co.GGGSGGGSGGGS.BtagV7co
pET11.Phi29.K143R.Y148I.Y224K.E239G.L253H.E375Y.A437G.A484E.D510K.K512Y.co.His10co.GGGSGGGSGGGS.BtagV7co
pET11.Phi29.Y148I.D235E.Y224K.E239G.L253H.E375Y.A437G.A484E.D510K.K525V.co.His10co.GGGSGGGSGGGS.BtagV7co
pET11.Phi29.C106S.Y148I.D235E.E239G.L253H.E375Y.A437G.A484V.C448V.D510K.K512Y.E515Q.co.His10co.GGGSGGGSGGGS.BtagV7co
pET11.Phi29.C106S.K135S.Y148I.D235E.E239G.L253H.E375Y.A437G.A484V.C448V.D510K.K512Y.E515Q.co.His10co.GGGSGGGSGGGS.BtagV7co
pET11.Phi29.C106S.K135S.Y148I.D235E.E239G.L253H.E375Y.A437G.T441I.C448V.A484V.D510K.K512Y.E515Q.co.His10co.GGGSGGGSGGGS.BtagV7co
pET11.Phi29.C106S.Y148I.D235E.E239G.L253H.E375Y.A437G.C448V.A484V.D510K.K512Y.E515Q.co.His10co.GGGSGGGSGGGS.BtagV7co
pET11.Phi29.C106S.Y148I.D235E.E239G.L253H.E375Y.A437G.T441I.C448V.A484V.D510K.K512Y.E515P.co.His10co.GGGSGGGSGGGS.BtagV7co
pET11.Phi29.C106S.Y148I.D235E.E239G.L253H.E375Y.A437G.C448V.A484V.D510K.K512Y.E515P.co.His10co.GGGSGGGSGGGS.BtagV7co
pET11.Phi29.C106S.K135S.Y148I.D235E.E239G.L253H.E375Y.A437G.C448V.A484V.D510K.K512Y.E515P.co.His10co.GGGSGGGSGGGS.BtagV7co
pET11.Phi29.Y148I.Y224K.D235E.E239G.L253H.E375Y.A437G.A484V.D510K.K512Y.E515Q.co.His10co.GGGSGGGSGGGS.BtagV7co
pET11.Phi29.Y148I.Y224K.D235E.E239G.L253H.E375Y.Q380K.A437G.A484V.Q497K.D510K.K512Y.E515Q.co.His10co.GGGSGGGSGGGS.BtagV7co
pET11.Phi29.D66R.Y148I.Y224K.D235E.E239G.L253H.E375Y.A437G.A484V.Q497K.D510K.K512Y.E515Q.co.His10co.GGGSGGGSGGGS.BtagV7co
pET11.Phi29.N62D.Y148I.Y224K.D235E.E239G.L253H.E375Y.A437G.A484E.D510K.K512Y.E515Q.co.His10co.GGGSGGGSGGGS.BtagV7co
pET11.Phi29.Y148I.Y224K.E239G.V250I.L253A.E375Y.A437G.A484E.D510K.K512Y.E515Q.co.His10co.GGGSGGGSGGGS.BtagV7co
pET11.Phi29.Y148I.Y224K.E239G.V250I.L253A.E375Y.A437G.A484E.D510K.K512Y.E515P.co.His10co.GGGSGGGSGGGS.BtagV7co
pET11.Phi29.Y148I.S194A.K196R.Y224K.E239G.V250I.L253A.Y369R.E375Y.A437G.A484E.D510K.K512Y.E515P.co.His10co.GGGSGGGSGGGS.BtagV7co
pET11.Phi29.Y148I.Y224K.E239G.E241Q.V250I.L253A.E375Y.A437G.D469R.A484E.D510K.K512Y.co.His10co.GGGSGGGSGGGS.BtagV7co
pET11.Phi29.Y148I.Y224K.E239G.E241Q.V250I.L253A.E375Y.A437G.D469R.A484E.D510K.K512Y.co.His10co.GGGSGGGSGGGS.BtagV7co
pET11.Phi29.Y148I.Y224K.E239G.V250I.L253A.E375Y.A437G.A484E.D510K.K512Y.co.His10co.GGGSGGGSGGGS.BtagV7co
pET11.Phi29.Y148I.K131E.Y224K.D235E.E239G.V250I.L253A.E375Y.A437G.A484E.D510K.K512Y.E515Q.co.His10co.GGGSGGGSGGGS.BtagV7co
pET11.Phi29.Y148I.K135Q.Y224K.D235E.E239G.V250I.L253A.E375Y.A437G.A484E.D510K.K512Y.E515Q.co.His10co.GGGSGGGSGGGS.BtagV7co

Fig. 7 cont'd

| Construct |
|---|
| pET11.Phi29.K131E_Y148I_Y224K_D235E_E239G_V250I_L253A_E375Y_A437G_A484E_D510K_K512Y.co.His10co.GGGSGGGSGGGS.BtagV7co |
| pET11.Phi29.K135Q_Y148I_Y224K_D235E_E239G_V250I_L253A_E375Y_A437G_A484E_D510K_K512Y.co.His10co.GGGSGGGSGGGS.BtagV7co |
| pET11.Phi29.Y148I_Y224K_E239G_L253S_E375Y_A437G_A484E_D510K_K512Y.co.His10co.GGGSGGGSGGGS.BtagV7co |
| pET11.Phi29.Y148I_Y224K_D235E_E239G_V250I_L253A_K361R_E375Y_A437G_A484E_D510K_K512Y.co.His10co.GGGSGGGSGGGS.BtagV7co |
| pET11.Phi29.Y148I_Y224K_E239G_V250I_L253A_K361R_E375Y_A437G_A484E_D510K_K512Y.co.His10co.GGGSGGGSGGGS.BtagV7co |
| pET11.Phi29.Y148I_Y224K_D235E_E239G_V250I_L253A.M2.L250A_S253A_E372Y_A434G_A481E_K509Y.co |
| pET11.Phi29.Y148I_Y224K_E239G_V250I_L253A.M2.L250A_S253A_K358R_E372Y_A434G_A481E_K509Y.co |
| pET11.Phi29.Y148I_Y224K_E239G_V250I_L253A_K361R_Y369R_E375Y_A437T_A484E_D510K_K512Y.co.His10co.GGGSGGGSGGGS.BtagV7co |
| pET11.Phi29.C106S_Y148I_Y224K_E239G_V250I_L253A_E375Y_C448V_A484E_K490C_D510K_K512Y.co.His10co |
| pET16.BtagV7co.His10co.Phi29.Y148I_Y224K_E239G_K240E_V250I_L253A_E375Y_A437G_A484E_D510K_K512Y.co.His10co |
| pET16.BtagV7co.His10co.Phi29.Y148I_Y224K_E239G_K240Q_V250I_L253A_E375Y_A437G_A484E_D510K_K512Y.co.His10co |
| pET16.BtagV7co.His10co.Phi29.Y148I_Y224K_E239G_K240S_V250I_L253A_E375Y_A437G_A484E_D510K_K512Y.co.His10co |
| pET16.BtagV7co.His10co.Phi29.Y148I_Y224K_E239G_V250I_L253A_E375Y_A437G_A484E_K490E_D510K_K512Y.co.His10co |
| pET16.BtagV7co.His10co.Phi29.Y148I_Y224K_E239G_V250I_L253A_E375Y_A437G_A484E_K490Q_D510K_K512Y.co.His10co |
| pET16.BtagV7co.His10co.Phi29.Y148I_Y224K_E239G_V250I_L253A_E375Y_A437G_A484E_K490S_D510K_K512Y.co.His10co |
| pET16.BtagV7co.His10co.Phi29.Y148I_Y224K_E239G_V250I_L253A_E375Y_K337G_A437G_A484E_D510K_K512Y.co.His10co |
| pET16.BtagV7co.His10co.Phi29.Y148I_Y224K_E239G_V250I_L253A_E375Y_K337Q_A437G_A484E_D510K_K512Y.co.His10co |
| pET16.BtagV7co.His10co.Phi29.M2.D63R_L250A_S253A_E372Y_A434G_A481E_K509Y.co.His10co |
| pET16.BtagV7co.His10co.Phi29.M2.N59D_L250A_S253A_E372Y_A434G_A481E_K509Y.co.His10co |
| pET16.BtagV7co.His10co.Phi29.M2.K140R_L250A_S253A_E372Y_A434G_A481E_K509Y.co.His10co |
| pET16.BtagV7co.His10co.Phi29.M2.V247I_L250A_S253A_E372Y_A434G_A481E_K509Y.co.His10co |
| pET11.Phi29.K131E_Y148I_Y224K_D235E_E239G_L253H_E375Y_A437G_A484E_D510K_K512Y_E515Q.co.His10co.GGGSGGGSGGGS.BtagV7co |
| pET11.Phi29.K131E_L142K_Y148I_Y224K_D235E_E239G_L253H_E375Y_A437G_A484E_D510K_K512Y_E515Q.co.His10co.GGGSGGGSGGGS.BtagV7co |
| pET11.Phi29.K131E_Y148I_Y224K_D235E_E239G_E241Q_L253H_E375Y_A437G_A484E_D510K_K512Y_E515Q.co.His10co.GGGSGGGSGGGS.BtagV7co |
| pET11.Phi29.K131E_Y148I_Y224K_K205D_D235E_E239G_L253H_E375Y_A437G_A484E_D510K_K512Y_E515Q.co.His10co.GGGSGGGSGGGS.BtagV7co |
| pET11.Phi29.K131E_Y148I_Y224K_D235E_E239G_L253H_Y369R_E375Y_A437G_A484E_D510K_K512Y_E515Q.co.His10co.GGGSGGGSGGGS.BtagV7co |

| Construct |
|---|
| pET11.Phi29.K131E_Y148I_Y224K_D235E_E239G_L253H_E375Y_A437G_C448T_A484E_D510K_K512Y_E515Q.co.His10co.GGGSGGGSGGGS.BtagV7co |
| pET11.Phi29.C106S_K131E_L142K_Y148I_K205D_Y224K_D235E_E239G_E241Q_L253H_K361R_Y369R_E375Y_A437G_C448T_A484E_D510K_K512Y_E515Q.co.His10co.GGGSGGGSGGGS.BtagV7co |
| pET11.Phi29.K131E_Y148I_D235E_E239G_L253H_E375Y_A437G_A484E_D510K_K512Y_E515Q.co.His10co.GGGSGGGSGGGS.BtagV7co |
| pET11.Phi29.K131E_Y148I_D235E_E239G_L253H_E375Y_A437G_A484E_D510K_K512Y_E515Q.co.His10co.GGGSGGGSGGGS.BtagV7co |
| pET11.Phi29.K131E_Y148I_E239G_L253H_E375Y_A437G_A484E_D510K_K512Y_E515Q.co.His10co.GGGSGGGSGGGS.BtagV7co |
| pET11.Phi29.K131E_Y148I_E239G_L253A_E375Y_A437G_A484E_D510K_K512Y.co.His10co.GGGSGGGSGGGS.BtagV7co |
| pET11.Phi29.K131E_Y148I_E239G_L253A_E375Y_A437G_A484E_D510K_K512Y.co.His10co.GGGSGGGSGGGS.BtagV7co |
| pET16.BtagV7co.His10co.Phi29.K131E_Y148I_H149D_Y224K_E239G_V250I_L253A_E375Y_A484E_D510K_K512Y.co.His10co |
| pET16.BtagV7co.His10co.Phi29.K135Q_H149D_Y148I_Y224K_E239G_V250I_L253A_E375Y_A484E_D510K_K512Y.co.His10co |
| pET16.BtagV7co.His10co.Phi29.K131E_K135Q_Y148I_Y224K_E239G_V250I_L253A_E375Y_A484E_D510K_K512Y.co.His10co |
| pET16.BtagV7co.His10co.Phi29.K138E_Y148I_Y224K_E239G_V250I_L253A_E375Y_A484E_D510K_K512Y.co.His10co |
| pET16.BtagV7co.His10co.Phi29.K138Q_Y148I_Y224K_E239G_V250I_L253A_E375Y_A484E_D510K_G511D_K512Y.co.His10co |
| pET16.BtagV7co.His10co.Phi29.K138S_Y148I_Y224K_E239G_V250I_L253A_E375Y_A484E_D510K_G511E_K512Y.co.His10co |
| pET16.BtagV7co.His10co.Phi29.Y148I_Y224K_E239G_V250I_L253A_E375Y_A484E_V509E_D510K_K512Y.co.His10co |
| pET16.BtagV7co.His10co.Phi29.Y148I_Y224K_E239G_V250I_L253A_E375Y_A484E_V509K_D510K_K512Y.co.His10co |
| pET16.BtagV7co.His10co.Phi29.Y148I_Y224K_E239G_V250I_L253A_E375Y_A484E_V509T_D510K_K512Y.co.His10co |
| pET16.BtagV7co.His10co.Phi29.Y148I_Y224K_R236K_E239G_V250I_L253A_E375Y_A484E_D510K_K512Y.co.His10co |
| pET16.BtagV7co.His10co.Phi29.Y148I_Y224K_R236Q_E239G_V250I_L253A_E375Y_A484E_D510K_K512Y.co.His10co |
| pET16.BtagV7co.His10co.Phi29.Y148I_Y224K_R236E_E239G_V250I_L253A_E375Y_A484E_D510K_K512Y.co.His10co |
| pET16.BtagV7co.His10co.Phi29.Y148I_Y224K_R236S_E239G_V250I_L253A_E375Y_K472E_A484E_D510K_K512Y.co.His10co |
| pET16.BtagV7co.His10co.Phi29.Y148I_Y224K_E239G_V250I_L253A_E375Y_K472S_A484E_D510K_K512Y.co.His10co |
| pET16.BtagV7co.His10co.Phi29.Y148I_G197K_Y224K_E239G_V250I_L253A_K366S_E375Y_A484E_D510K_K512Y.co.His10co |
| pET16.BtagV7co.His10co.Phi29.Y148I_G197R_Y224K_E239G_V250I_L253A_K366E_E375Y_A484E_D510K_K512Y.co.His10co |
| pET16.BtagV7co.His10co.Phi29.Y148I_K182Q_Y224K_E239G_V250I_L253A_K366D_E375Y_A484E_D510K_K512Y.co.His10co |
| pET16.BtagV7co.His10co.Phi29.Y148I_K182D_Y224K_E239G_V250I_L253A_E375Y_A484E_D510K_K512Y.co.His10co |
| pET16.BtagV7co.His10co.Phi29.Y148I_K182S_Y224K_E239G_V250I_L253A_E375Y_A484E_D510K_K512Y.co.His10co |
| pET16.BtagV7co.His10co.Phi29.K135D_Y148I_Y224K_E239G_V250I_L253A_E375Y_A484E_D510K_K512Y.co.His10co |

Fig. 7 cont'd

| Plasmid |
|---|
| pET16.BtagV7co.His10co.Phi29.K135N_Y148I_Y224K_E239G_V250I_L253A_E375Y_A484E_D510K_K512Y.co.His10co |
| pET16.BtagV7co.His10co.Phi29.K131D_Y148I_Y224K_E239G_V250I_L253A_E375Y_A484E_D510K_K512Y.co.His10co |
| pET16.BtagV7co.His10co.Phi29.K132N_Y148I_Y224K_E239G_V250I_L253A_E375Y_A484E_D510K_K512Y.co.His10co |
| pET16.BtagV7co.His10co.Phi29.K132D_Y148I_Y224K_E239G_V250I_L253A_E375Y_A484E_D510K_K512Y.co.His10co |
| pET16.BtagV7co.His10co.Phi29.K131E_Y148I_Q183Y_Y224K_E239G_V250I_L253A_E375Y_A484E_D510K_K512Y.co.His10co |
| pET16.BtagV7co.His10co.Phi29.K131E_Y148I_Q180L_Y224K_E239G_V250I_L253A_E375Y_A484E_D510K_K512Y.co.His10co |
| pET16.BtagV7co.His10co.Phi29.K131E_Y148I_Q180N_Y224K_E239G_V250I_L253A_E375Y_A437G_A484E_D510K_K512Y.co.His10co |
| pET16.BtagV7co.His10co.Phi29.K131E_Y148I_Y224K_E239G_V250I_L253A_E375Y_A437G_A484E_D510K_K512Y.co.His10co |
| pET16.BtagV7co.His10co.Phi29.K131E_Y148I_K135Q_Y224K_E239G_V250I_L253A_E375Y_A437G_A484E_D510K_K512Y.co.His10co.GGGSGGGSGGGS.BtagV7co |
| pET11.Phi29.K131E_Y148I_K135Q_Y148I_Y224K_E239G_V250I_L253A_E375Y_A437G_A484E_E508K_D510S_K512Y_E515Q_F526L.co.His10co.GGGSGGGSGGGS.BtagV7co |
| pET11.Phi29.K131E_Y148I_Y224K_E239G_V250I_L253A_E375Y_A437G_A484E_E508R_D510S_K512Y_E515P_F526L.co.His10co.GGGSGGGSGGGS.BtagV7co |
| pET11.Phi29.Y148I_Y224K_E239G_L253H_E375Y_A437G_A484E_D510K_K512Y_E515P_F526L.co.His10co.GGGSGGGSGGGS.BtagV7co |
| pET11.Phi29.Y148I_Y224K_E239G_L253H_E375Y_A437G_A484E_D510K_K512Y_E515P_F526L.co.His10co.GGGSGGGSGGGS.BtagV7co |
| pET11.Phi29.Y148I_G197D_Y224K_E239G_L253H_K366R_E375Y_A437G_A484E_E508K_D510K_K512Y_E515P_F526L.co.His10co.GGGSGGGSGGGS.BtagV7co |
| pET11.Phi29.C106S_Y148I_Y224K_D235E_E239G_V250I_A437G_A484E_E375Y_N387L_A437G_A484E_D510K_K512Y_E515P.co.His10co.GGGSGGGSGGGS.BtagV7co |
| pET11.Phi29.C106S_Y148I_Y224K_D235E_E239G_V250I_L253A_E375Y_N387L_A437G_C448I_A484E_D510K_K512Y_E515P.co.His10co.GGGSGGGSGGGS.BtagV7co |
| pET11.Phi29.C106S_Y148I_Y224K_D235E_E239G_V250I_L253A_E375Y_A437G_C448I_A484E_D510K_K512Y_K525A.co.His10co.GGGSGGGSGGGS.BtagV7co |
| pET11.Phi29.C225_Y148I_Y224K_D235E_E239G_V250I_L253A_E375Y_A437G_C448I_A484E_D510K_K512Y_K525A.co.His10co.GGGSGGGSGGGS.BtagV7co |
| pET11.Phi29.C22A_Y148I_Y224K_D235E_E239G_V250I_L253A_E375Y_A437G_C448V_A484E_D510K_K512Y_E515P_K525A.co.His10co.GGGSGGGSGGGS.BtagV7co |
| pET11.Phi29.C22T_Y148I_Y224K_D235E_E239G_V250I_L253A_E375Y_A437G_C448V_A484E_D510K_K512Y.co.His10co.GGGSGGGSGGGS.BtagV7co |
| pET11.Phi29.C106S_Y148I_Y224K_D235E_E239G_V250I_L253A_E375Y_A437G_C448V_A484E_D510K_K512Y.co.GGGSGGGSGGGS.BtagV7co |
| pET11.Phi29.C106S_Y148I_Y224K_D235E_E239G_V250I_L253A_E375Y_A437G_C448V_A484E_D510K_K512Y_C530A.co.His10co.GGGSGGGSGGGS.BtagV7co |
| pET11.Phi29.C106S_Y148I_Y224K_D235E_E239G_V250I_L253A_E375Y_A437G_C448V_A484E_D510K_K512Y_C530T.co.His10co.GGGSGGGSGGGS.BtagV7co |
| pET11.Phi29.F69Y_K131E_Y148I_Y224K_D235E_E239G_V250I_L253A_E375Y_A437G_C448V_A484E_D510K_K512Y_F572Y.co.His10co.GGGSGGGSGGGS.BtagV7co |
| pET11.Phi29.C106S_Y148I_Y224K_D235E_E239G_V250I_L253A_E375Y_A437G_C448V_A484E_D510K_K512Y_C530S_F572Y.co.His10co.GGGSGGGSGGGS.BtagV7co |

| Construct |
|---|
| pET11.Phi29.K131E_Y148I_Y224K_D235E_E239G_V250I_L253A_E375Y_A437G_A484E_D510K_K512Y_A531S.co.GGGSGGGSGGGS.BtagV7co |
| pET11.Phi29.K131E_Y148I_Y224K_D235E_E239G_V250I_L253A_E375Y_A437G_A484E_D510K_K512Y_A531G.co.His10co.GGGSGGGSGGGS.BtagV7co |
| pET11.Phi29.K131E_Y148I_Y224K_D235E_E239G_V250I_L253A_E375Y_A437G_A484E_D510K_K512Y_A531T.co.His10co.GGGSGGGSGGGS.BtagV7co |
| pET11.Phi29.K131E_Y148I_Y224K_D235E_E239G_V250I_L253A_E375Y_A437G_A484E_Y500F_D510K_K512Y.co.His10co.GGGSGGGSGGGS.BtagV7co |
| pET11.Phi29.K131E_Y148I_Y224K_D235E_E239G_V250I_L253A_E239G_V250I_L253A_E375Y_I378E_A437G_A484E_D510K_K512Y.co.His10co.GGGSGGGSGGGS.BtagV7co |
| pET16.BtagV7co.His10co.Phi29.K131E_Y148I_Q183E_Y224K_E239G_V250I_L253A_E375Y_I378K_A437G_A484E_D510K_K512Y.co.His10co.GGGSGGGSGGGS.BtagV7co |
| pET16.BtagV7co.His10co.Phi29.K131E_Y148I_Q183K_Y224K_E239G_V250I_L253A_Q257E_E375Y_A437G_A484E_D510K_K512Y.co.His10co.GGGSGGGSGGGS.BtagV7co |
| pET11.Phi29.K131E_Y148I_Y224K_D235E_E239G_V250I_L253C_Q257E_E375Y_A437G_A484E_D510K_K512Y.co.His10co.GGGSGGGSGGGS.BtagV7co |
| pET11.Phi29.K131E_Y148I_A190I_Y224K_D235E_E239G_V250I_L253A_E375Y_A437G_A484E_D510K_K512Y.co.His10co.GGGSGGGSGGGS.BtagV7co |
| pET11.Phi29.K131E_Y148I_A190G_Y224K_D235E_E239G_V250I_L253A_E375Y_A437G_A484E_D510K_K512Y.co.His10co.GGGSGGGSGGGS.BtagV7co |
| pET11.Phi29.K131E_Y148I_S194A_Y224K_D235E_E239G_V250I_L253A_E375Y_A437G_A484E_D510K_K512Y_K539Q.co.His10co.GGGSGGGSGGGS.BtagV7co |
| pET11.Phi29.K131E_Y148I_Y224K_D235E_E239G_V250I_L253A_E375Y_A437G_A484E_D510K_K512Y_K536Q_K539Q.co.His10co.GGGSGGGSGGGS.BtagV7co |
| pET11.Phi29.C106S_K131E_Y148I_Y224K_E239G_V250I_L253A_E375Y_A437G_A484E_D510K_K512Y_C448V.co.His10co.GGGSGGGSGGGS.BtagV7co |
| pET11.Phi29.Y148I_Y224K_E239G_V250I_L253A_C290V_E375Y_A437G_A484E_D510K_K512Y.co.His10co.GGGSGGGSGGGS.BtagV7co |
| pET11.Phi29.Y148I_Q183Y_Y224K_E239G_V250I_L253A_I370A_E375Y_A437G_A484E_D510K_K512Y.co.His10co.GGGSGGGSGGGS.BtagV7co |
| pET11.Phi29.Y148I_Q183F_Y224K_E239G_V250I_L253A_I370V_E375Y_A437G_A484E_D510K_K512Y.co.His10co.GGGSGGGSGGGS.BtagV7co |
| pET11.Phi29.Y148I_Q183H_Y224K_E239G_V250I_L253A_I370F_E375Y_A437G_A484E_D510K_K512Y.co.His10co.GGGSGGGSGGGS.BtagV7co |
| pET11.Phi29.Y148I_Q183H_Y224K_E239G_V250I_L253A_I370E_E375Y_A437G_A484E_D510K_K512Y.co.His10co.GGGSGGGSGGGS.BtagV7co |
| pET11.Phi29.Y148I_Q183F_Y224K_E239G_V250I_L253A_I370K_E375Y_A437G_A484E_D510K_K512Y.co.His10co.GGGSGGGSGGGS.BtagV7co |
| pET16.BtagV7co.His10co.Phi29.Y148I_Q183E_Y224K_E239G_V250I_L253A_E375Y_A437G_T441A_A484E_D510K_K512Y.co.His10co.GGGSGGGSGGGGS.BtagV7co |
| pET16.BtagV7co.His10co.Phi29.Y148I_Y224K_E239G_V250I_L253A_E375Y_A437G_T441L_A484E_D510K_K512Y.co.His10co.GGGSGGGSGGGS.BtagV7co |
| pET16.BtagV7co.His10co.Phi29.Y148I_Y224K_E239G_V250I_L253A_E375Y_A437G_T441I_A484E_D510K_K512Y.co.His10co.GGGSGGGSGGGS.BtagV7co |
| pET16.BtagV7co.His10co.Phi29.Y148I_Y224K_E239G_V250S_L253A_E375Y_A437G_A484E_D510K_K512Y_E515Q.co.His10co |
| pET11.Phi29.Y148I_Y224K_D235E_E239G_V250A_L253H_E375Y_A437G_A484E_D510K_K512Y_E515Q.co.His10co |
| pET11.Phi29.Y148I_Y224K_D235E_E239G_V250I_L253H_E375Y_A437G_A484E_D510K_K512Y.co.His10co |
| pET11.Phi29.Y148I_Y224K_D235E_E239G_V250I_L253A_E375Y_A437G_A484E_E508K_D510K_K512Y.co.His10co |
| pET11.K135Q_Y148I_S194A_Y224K_D235E_E239G_V250I_L253A_E375Y_A437G_A484E_D510K_K512Y_E515Q_E515Q.co.His10co.GGGSGGGSGGGS.BtagV7co |

Fig. 7 cont'd

| Construct |
|---|
| pET11.Phi29.K131Q_Y148I_Y224K_E239G_V250I_L253A_E375Y_A437G_A484E_D510K_K512Y_K536Q_K539Q.co.His10co.GGGSGGGSGGGS.BtagV7co |
| pET11.Phi29.K131S_Y148I_Y224K_E239G_V250I_L253A_E375Y_A437G_A484E_D510K_K512Y.co.His10co.GGGSGGGSGGGS.BtagV7co |
| pET11.Phi29.K131E_Y148I_S192A_Y224K_D235E_E239G_V250I_L253A_E375Y_A437G_A484E_D510K_K512Y.co.His10co.GGGSGGGSGGGS.BtagV7co |
| pET11.Phi29.K131E_Y148I_S194A_Y224K_D235E_E239G_V250I_L253A_E375Y_A437G_A484E_D510K_K512Y_E515Q.co.His10co.GGGSGGGSGGGS.BtagV7co |
| pET16.BtagV7co.Phi29.Y148I_Y224K_E239G_V250I_L253A_E375Y_A437G_A444L_W483F_A484E_D510K_K512Y.co.His10co |
| pET16.BtagV7co.Phi29.Y148I_Y224K_E239G_V250I_L253A_E375Y_A437G_A444L_W483V_A484E_D510K_K512Y.co.His10co |
| pET16.BtagV7co.Phi29.Y148I_Y224K_E239G_V250I_L253A_E375Y_A437G_A444L_T440I_A484E_D510K_K512Y.co.His10co |
| pET11.Phi29.K131E_Y148I_Y224K_E239G_V250I_L253A_E375Y_A377S_A437G_A484E_D510K_K512Y.co.His10co.GGGSGGGSGGGS.BtagV7co |
| pET11.Phi29.K131E_Y148I_Y224K_E239G_V250I_L253A_E375Y_A377G_A437G_A484E_D510K_K512Y.co.His10co.GGGSGGGSGGGS.BtagV7co |
| pET11.Phi29.Y148I_Y224K_D235E_E239G_V250I_L253A_E375A_A437G_A484E_D510K_K512Y.co.His10co.GGGSGGGSGGGS.BtagV7co |
| pET11.Phi29.Y148I_Y224K_D235E_E239G_V250I_L253A_K337Q_E375Y_A437G_A484E_D510K_K512Y.co.His10co.GGGSGGGSGGGS.BtagV7co |
| pET11.Phi29.K131E_Y148I_Y224K_D235E_E239G_V250I_L253A_K337Q_E375Y_A437G_A484E_Y405S_D510K_K512Y.co.His10co.GGGSGGGSGGGS.BtagV7co |
| pET11.Phi29.Y148I_Y224K_E239G_V250I_L253H_E375Y_A437G_A484E_D510K_K512Y_E515Q.co.His10co.GGGSGGGSGGGS.BtagV7co |
| pET11.Phi29.K131Q_Y148I_Y224K_E239G_V250I_L253A_Y369R_E375Y_A437G_A484E_D510K_K512Y_E515Q.co.His10co.GGGSGGGSGGGS.BtagV7co |
| pET11.Phi29.K135Q_Y148I_Y224K_E239G_V250I_L253A_Y369R_E375Y_A437G_D469K_A484E_D510K_K512Y_E515Q.co.His10co.GGGSGGGSGGGS.BtagV7co |
| pET11.Phi29.K135Q_Y148I_Y224K_E239G_E241Q_V250I_L253A_E375Y_A437G_D469Y_A484E_D510K_K512Y.co.His10co.GGGSGGGSGGGS.BtagV7co |
| pET16.BtagV7co.His10co.M2.Y145I_E236G_V247I_L250A_S253A_E372Y_A434G_A481E_D507K_K509Y.co.His10co |
| pET16.BtagV7co.His10co.M2.Y145I_E236G_V247I_L250A_S253A_E372Y_A434G_A481E_D507K_K509Y_E512Q.co.His10co |
| pET16.BtagV7co.His10co.M2.Y145I_E236G_V247I_L250H_S253A_E372Y_A434G_A481E_D507K_K509Y_E512Q.co.His10co |
| pET16.BtagV7co.His10co.M2.Y145I_E236G_V247I_L250A_E372Y_A434G_A481E_D507K_K509Y_E512Q.co.His10co |
| pET16.BtagV7co.His10co.M2.Y145I_E236G_V247I_L250A_E372Y_A434G_A481E_D507K_K509Y.co.His10co |
| pET16.BtagV7co.His10co.M2.Y145I_E236G_V247I_L250A_E372Y_A434G_A481E_D507C_K509Y.co.His10co |
| pET11.M2.Y145I_E236G_V247I_L250A_S253A_E372Y_A434G_A481E_D507K_K509Y.co.His10co.GGGSGGGSGGGS.BtagV7co |
| pET11.M2.Y145I_E236G_V247I_L250A_E372Y_A434G_A481E_D507K_K509Y_F523L.co.His10co.GGGSGGGSGGGS.BtagV7co |
| pET11.M2.Y145I_K128E_V247I_L250A_E372Y_A434G_A481E_D507K_K509Y_F523L_F523L.co.His10co.GGGSGGGSGGGS.BtagV7co |
| pET11.M2.Y145I_E236G_V247I_L250A_E372Y_A434G_A481E_D507K_K509Y_E512K_F523L.co.His10co.GGGSGGGSGGGS.BtagV7co |
| pET11.M2.Y145I_E236G_V247I_L250A_E372Y_A434G_A481E_D507K_K509Y_E512P_F523L.co.His10co.GGGSGGGSGGGS.BtagV7co |

Fig. 7 cont'd

| Construct |
|---|
| pET11.Phi29.C106S_Y148I_Y224K_E239G_V250I_L253A_E375Y_A437G_C448V_A484E_D510K_K512Y_E515Q_co.His10co.GGGSGGGSGGGSGGGS.BtagV7co |
| pET11.Phi29.C106S_Y148I_Y224K_E239G_V250I_L253A_C290V_E375Y_A437G_C448V_A484E_D510K_K512Y_E515Q_co.His10co.GGGSGGGSGGGSGGGS.BtagV7co |
| pET11.Phi29.C106S_Y148I_Y224K_E239G_V250I_L253A_C290F_E375Y_A437G_C448V_A484E_D510K_K512Y_E515Q_co.His10co.GGGSGGGSGGGSGGGS.BtagV7co |
| pET11.Phi29.C106S_Y148I_Y224K_E239G_V250I_L253A_C290F_M336I_E375Y_A437G_C448V_A484E_D510K_K512Y_E515Q_co.His10co.GGGSGGGSGGGSGGGS.BtagV7co |
| pET11.Phi29.C106S_Y148I_Y224K_E239G_V250I_L253A_C290F_A324V_M336I_E375Y_A437G_C448V_A484E_D510K_K512Y_E515Q_co.His10co.GGGSGGGSGGGSGGGS.BtagV7co |
| pET11.Phi29.C106S_Y148I_Y224K_E239G_V250I_L253A_C290F_I323P_A324V_M336I_E375Y_A437G_A481E_D507K_K509Y_co.His10co |
| pET16.BtagV7co.His10co.M2_Y145I_E236G_V247I_L250C_E372Y_A434G_A484E_D510K_K512Y_E515Q_co.His10co.GGGSGGGSGGGSGGGS.BtagV7co |
| pET11.Phi29.Y101F_Y148I_Y224K_E239G_V250I_L253A_E375Y_A437G_A484E_D510K_K512Y_E515Q_co.His10co.GGGSGGGSGGGSGGGS.BtagV7co |
| pET11.Phi29.Y101H_Y148I_Y224K_E239G_V250I_L253A_E375Y_A437G_A484E_D510K_K512Y_E515Q_co.His10co.GGGSGGGSGGGSGGGS.BtagV7co |
| pET11.Phi29.K131E_Y148I_Y224K_D235E_E239G_K240E_V250I_L253A_E375Y_A437G_A484E_D510K_K512Y_E515Q_co.His10co.GGGSGGGSGGGSGGGS.BtagV7co |
| pET11.Phi29.K131E_Y148I_Y224K_D235E_E239G_K240E_V250I_L253A_E375Y_A437G_A484E_D510K_K512Y_E515Q_co.His10co.GGGSGGGSGGGSGGGS.BtagV7co |
| pET11.Phi29.K135Q_Y148I_Y224K_D235E_E239G_K240E_V250I_L253A_E375Y_A437G_A484E_D510K_K512Y_K536Q_K539Q_co.His10co.GGGSGGGSGGGSGGGS.BtagV7co |
| pET11.Phi29.K135Q_Y148I_Y224K_D235E_E239G_K240E_V250I_L253A_E375Y_A437G_A484E_D510K_K512Y_K536Q_co.His10co.GGGSGGGSGGGSGGGS.BtagV7co |
| pET11.Phi29.K135Q_Y148I_Y224K_D235E_E239G_V250I_L253A_E375Y_A437G_A484E_D510K_K512Y_K510S_co.His10co.GGGSGGGSGGGSGGGS.BtagV7co |
| pET11.Phi29.K135Q_Y148I_Y224K_D235E_E239G_V250I_L253A_E375Y_A437G_A484E_E508K_D510K_K512Y_E515Q_co.His10co.GGGSGGGSGGGSGGGS.BtagV7co |
| pET11.Phi29.Y148I_Y224K_D235E_E239G_V250I_L253A_E375Y_A437G_K402R_A484E_D510K_K512Y_E515Q_co.His10co.GGGSGGGSGGGSGGGS.BtagV7co |
| pET11.Phi29.Y148I_Y224K_D235E_E239G_V250I_L253A_E375Y_A437G_K402Q_A484E_D510K_K512Y_E515Q_co.His10co.GGGSGGGSGGGSGGGS.BtagV7co |
| pET11.Phi29.Y148I_Y224K_D235E_E239G_V250I_L253A_E375Y_A437G_K402Q_A484E_D510K_K512Y_E515Q_co.His10co.GGGSGGGSGGGSGGGS.BtagV7co |
| pET11.Phi29.Y148I_Y224K_D235E_E239G_V250I_L253A_E375Y_A437G_K392R_A484E_D510K_K512Y_E515Q_co.His10co.GGGSGGGSGGGSGGGS.BtagV7co |
| pET11.Phi29.Y148I_Y224K_D235E_E239G_V250I_L253A_E375Y_A437G_K392Q_A484E_D510K_K512Y_E515Q_co.His10co.GGGSGGGSGGGSGGGS.BtagV7co |
| pET11.Phi29.Y148I_Y224K_D235E_E239G_V250I_L253A_E375Y_A437G_K392A_A484E_D510K_K512Y_E515Q_co.His10co.GGGSGGGSGGGSGGGS.BtagV7co |
| pET11.Phi29.T189S_Y224K_D235E_E239G_V250I_L253A_E375Y_A437G_A484E_R496K_D510K_K512Y_E515Q_co.His10co.GGGSGGGSGGGSGGGS.BtagV7co |
| pET11.Phi29.T189A_Y224K_D235E_E239G_V250I_L253A_E375Y_A437G_A484E_R496Q_D510K_K512Y_E515Q_co.His10co.GGGSGGGSGGGSGGGS.BtagV7co |
| pET11.Phi29.T15V_Y148I_Y224K_D235E_E239G_V250I_L253A_E375Y_A437G_A484E_R496A_D510K_K512Y_E515Q_co.His10co.GGGSGGGSGGGSGGGS.BtagV7co |
| pET11.Phi29.K131E_Y148I_Y224K_D235E_E239G_V250I_L253A_E375Y_L384M_A437G_A484E_K490Q_D510K_K512Y_E515Q_co.His10co.GGGSGGGSGGGSGGGS.BtagV7co |
| pET11.Phi29.K135Q_Y148I_Y224K_D235E_E239G_V250I_L253A_E375Y_L384W_A437G_A484E_K490Q_D510K_K512Y_E515Q_co.His10co.GGGSGGGSGGGSGGGS.BtagV7co |
| pET11.Phi29.Y148I_Y224K_E239G_V250I_L253H_E375Y_A437G_A484E_D510K_K512Y_E515Q_co.His10co.GGGSGGGSGGGSGGGS.BtagV7co |
| pET11.Phi29.K135Q_Y148I_Y224K_E239G_V250I_L253A_E375Y_A437G_A484E_D510K_K512Y_E515Q_co.His10co.GGGSGGGSGGGSGGGS.BtagV7co |

Fig. 7 cont'd

| Construct |
|---|
| pET11.Phi29.Y148I_Q183F_D235E_E239G_L253H_E375Y_A437G_A484E_D510K_K512Y_E515Q.co.His10co.GGGSGGGSGGGS.BtagV7co |
| pET11.Phi29.Y148I_Q183F_D235E_E239G_L253A_E375Y_A437G_A484E_D510K_K512Y_E515Q.co.His10co.GGGSGGGSGGGS.BtagV7co |
| pET11.Phi29.K135Q_Y148I_Q183F_D235E_E239G_L253H_E375Y_A437G_A484E_D510K_K512Y_E515Q.co.His10co.GGGSGGGSGGGS.BtagV7co |
| pET11.Phi29.K135Q_Y148I_Q183F_D235E_E239G_L253A_E375Y_A437G_A484E_D510K_K512Y_E515Q.co.His10co.GGGSGGGSGGGS.BtagV7co |
| pET11.Phi29.K135Q_Y148I_D235E_E239G_L253H_Y369R_E375Y_A437G_A484E_D510K_K512Y_E515Q.co.His10co.GGGSGGGSGGGS.BtagV7co |
| pET11.Phi29.K135Q_Y148I_D235E_E239G_L253A_Y369R_E375Y_A437G_A484E_D510K_K512Y_E515Q.co.His10co.GGGSGGGSGGGS.BtagV7co |
| pET11.Phi29.Y148I_D235E_E239G_L253A_E375Y_A437G_A484E_D510K_K512Y_E515Q.co.His10co.GGGSGGGSGGGS.BtagV7co |
| pET11.Phi29.K135Q_Y148I_Y224K_D235E_E239G_E241Q_L253H_E375Y_A437G_D469K_A484E_D510K_K512Y_E515Q.co.His10co.GGGSGGGSGGGS.BtagV7co |
| pET11.Phi29.K135Q_Y148I_Y224K_D235E_E239G_E241Q_L253A_E375Y_A437G_D469K_A484E_D510K_K512Y_E515Q.co.His10co.GGGSGGGSGGGS.BtagV7co |
| pET11.Phi29.K135Q_Y148I_Y224K_E239G_V250I_L253A_E375Y_A437G_A484E_D510K_K512Y_E515Q.co.His10co.GGGSGGGSGGGS.BtagV7co |
| pET11.Phi29.K131E_Y148I_Y224K_E239G_V250I_L253A_E375Y_A437G_A484E_D510K_K512Y_E515Q.co.His10co.GGGSGGGSGGGS.BtagV7co |
| pET11.Phi29.K131E_Y148I_Y224K_E239G_V250I_L253A_Y369R_E375Y_A437G_A484E_D510K_K512Y_E515Q.co.His10co.GGGSGGGSGGGS.BtagV7co |
| pET11.Phi29.K131E_Y148I_Y224K_E239G_V250I_L253A_E375Y_A437G_T440A_A484E_D510K_K512Y_E515Q.co.His10co.GGGSGGGSGGGS.BtagV7co |
| pET11.Phi29.K131E_Y148I_Y224K_E239G_V250I_L253A_E375Y_A437G_T441A_A484E_D510K_K512Y_E515Q.co.His10co.GGGSGGGSGGGS.BtagV7co |
| pET11.Phi29.K131E_Y148I_Y224K_E239G_V250I_L253A_E375Y_A437G_T441I_A484E_D510K_K512Y_E515Q.co.His10co.GGGSGGGSGGGS.BtagV7co |
| pET11.Phi29.K131E_Y148I_Y224K_D235E_E239G_E241Q_V250I_L253A_E375Y_A437G_A484E_E508R_D510S_K512Y_E515Q.co.His10co.GGGSGGGSGGGS.BtagV7co |
| pET11.Phi29.K131E_Y148I_S194A_Y224K_D235E_E239G_E241Q_V250I_L253A_E375Y_A437G_A484E_D510K_K512Y_E515Q.co.His10co.GGGSGGGSGGGS.BtagV7co |
| pET11.Phi29.K131E_Y148I_S194A_Y224K_D235E_E239G_E241Q_V250I_L253A_E375Y_A437G_D469K_A484E_D510K_K512Y_E515Q.co.His10co.GGGSGGGSGGGS.BtagV7co |
| pET11.M2.Y145I_E236G_V247I_L250A_V247I_L250A_E372Y_A434G_A481E_D507K_K509Y_E512Q.co.His10co.GGGSGGGSGGGS.BtagV7co |
| pET11.M2.Y145I_E236G_V247I_L250A_S253A_E372Y_A434G_A481E_D507K_K509Y_E512Q.co.His10co.GGGSGGGSGGGS.BtagV7co |
| pET11.Phi29.K135Q_Y148I_S194A_Y224K_D235E_E239G_E241Q_V250I_L253A_E375Y_A437G_D469K_A484E_D510K_K512Y_E515Q.co.His10co.GGGSGGGSGGGS.BtagV7co |
| pET11.Phi29.K131E_Y148I_Y224K_D235E_E239G_E241Q_V250I_L253A_E375Y_A437G_D469K_A484E_D510K_K512Y_E515Q.co.His10co.GGGSGGGSGGGS.BtagV7co |
| pET11.Phi29.K131E_Y148I_Y224K_E239G_L253H_Y369R_E375Y_A437G_D469K_A484E_D510K_K512Y_E515Q.co.His10co.GGGSGGGSGGGS.BtagV7co |
| pET11.Phi29.K131E_Y148I_Y224K_E239G_L253A_Y369R_E375Y_A437G_D469K_A484E_D510K_K512Y_E515Q.co.His10co.GGGSGGGSGGGS.BtagV7co |

Fig. 7 cont'd

```
pET11.Phi29.K131E_Y148I_Y224K_D235E_E239G_E241Q_L253A_E375Y_A437G_D469K_A484E_D510K_K512Y_E515Q.co.His10co.GGGSGGGSGGGS.BtagV7co
pET11.Phi29.R96K_Y148I_Y224K_E239G_V250I_L253A_E375Y_A437G_A484E_D510K_K512Y_E515Q.co.His10co.GGGSGGGSGGGS.BtagV7co
pET11.Phi29.R96A_Y148I_Y224K_E239G_V250I_L253A_E375Y_A437G_A484E_D510K_K512Y_E515Q.co.His10co.GGGSGGGSGGGS.BtagV7co
pET11.Phi29.R96F_Y148I_Y224K_E239G_V250I_L253A_E375Y_A437G_A484E_D510K_K512Y_E515Q.co.His10co.GGGSGGGSGGGS.BtagV7co
pET11.Phi29.Y148I_Y224K_E239G_V250I_L253A_E375Y_D398D_A437G_A484E_D510K_K512Y_E515Q.co.His10co.GGGSGGGSGGGS.BtagV7co
pET11.Phi29.Y148I_Y224K_E239G_V250I_L253A_E375Y_D398F_A437G_A484E_D510K_K512Y_E515Q.co.His10co.GGGSGGGSGGGS.BtagV7co
pET11.Phi29.Y148I_Y224K_E239G_V250I_L253A_E375Y_A437G_A484E_D510K_K512Y_E515Q_S527K.co.His10co.GGGSGGGSGGGS.BtagV7co
pET11.Phi29.Y148I_Y224K_E239G_V250I_L253A_E375Y_A437G_A484E_D510K_K512Y_E515Q_S527E.co.His10co.GGGSGGGSGGGS.BtagV7co
pET11.Phi29.Y148I_Y224K_E239G_V250I_L253A_E375Y_A437G_A484E_D510K_K512Y_E515Q_S527N.co.His10co.GGGSGGGSGGGS.BtagV7co
pET11.Phi29.Y148I_Y224K_E239G_V250I_L253A_E375Y_A437G_A484E_D510K_K512Y_E515Q_S517K.co.His10co.GGGSGGGSGGGS.BtagV7co
pET11.Phi29.Y148I_Y224K_E239G_V250I_L253A_E375Y_A437G_A484E_D510K_K512Y_E515Q_S517D.co.His10co.GGGSGGGSGGGS.BtagV7co
pET11.Phi29.Y148I_Y224K_E239G_V250I_L253A_E375Y_A437G_A484E_D510K_K512Y_E515K_S517D.co.His10co.GGGSGGGSGGGS.BtagV7co
pET11.Phi29.Y224K_E239G_V250I_L253A_E375Y_A437G_A484E_D510K_K512Y_E515Q.co.His10co.GGGSGGGSGGGS.BtagV7co
pET11.Phi29.Y224K_E239G_V250I_L253H_E375Y_A437G_A484E_D510K_K512Y.co.His10co.GGGSGGGSGGGS.BtagV7co
pET11.Phi29.E239G_V250I_L253A_E375Y_A437G_A484E_D510K_K512Y.co.His10.GGGSGGGSGGGS.BtagV7co
pET11.Phi29.D235E_E239G_V250I_L253S_E375Y_A437G_A484E_D510K_K512Y_E515Q.co.His10co.GGGSGGGSGGGS.BtagV7co
pET11.Phi29.E239G_V250I_L253G_E375Y_A437G_A484E_D510K_K512Y_E515Q.co.His10co.GGGSGGGSGGGS.BtagV7co
pET11.Phi29.Y148I_Y224K_E239G_V250I_L253A_E375Y_A437G_A484E_D510K_K512Y_E515Q.co.His10co.GGGSGGGSGGGS.BtagV7co
pET11.Phi29.Y148I_Y224K_E239G_V250I_L253A_E375Y_A437G_A484E_D510R_K512Y_E515Q.co.His10co.GGGSGGGSGGGS.BtagV7co
pET11.Phi29.Y148I_Y224K_E239G_V250I_L253A_E375Y_A437G_A484E_D510K_K512Y_E515K.co.His10co.GGGSGGGSGGGS.BtagV7co
pET11.Phi29.Y148I_Y224K_E239G_V250I_L253A_E375Y_A437G_A484E_D510K_K512H_E515Q.co.His10co.GGGSGGGSGGGS.BtagV7co
pET11.Phi29.Y148I_Y224K_E239G_V250I_L253A_E375Y_A437G_A484E_D510K_K512Y_E515P.co.His10co.GGGSGGGSGGGS.BtagV7co
pET11.Phi29.Y148I_Y224K_E239G_V250I_L253A_E375Y_A437G_A484E_D510K_K512Y_E515Q.co.His10co.GGGSGGGSGGGS.BtagV7co
pET11.Phi29.Y148I_Y224K_E239G_V250I_L253A_E375Y_A437G_A484E_D510K_K512Y_E515Q.co.His10co.GGGSGGGSGGGS.BtagV7co
pET11.Phi29.Y148I_Y224K_E239G_V250I_L253A_E375Y_A437G_A484E_D510K_K512Y_E515Q.co.His10co.GGGSGGGSGGGS.BtagV7co
pET11.Phi29.Y148A_Y224K_E239G_V250I_L253A_E375H_A437G_A484E_D510K_K512Y_E515Q.co.His10co.GGGSGGGSGGGS.BtagV7co
pET11.Phi29.Y148H_Y224K_E239G_V250I_L253A_E375Y_A437G_A484E_D510K_K512Y_E515Q.co.His10co.GGGSGGGSGGGS.BtagV7co
pET11.Phi29.D66R_Y148I_Y224K_E239G_V250I_L253A_E375Y_A437G_A484E_D510K_K512Y_E515Q.co.His10co.GGGSGGGSGGGS.BtagV7co
pET11.Phi29.N62D_Y148I_Y224K_E239G_V250I_L253A_E375Y_A437G_A484E_D510K_K512Y_E515Q.co.His10co.GGGSGGGSGGGS.BtagV7co
pET11.Phi29.K143R_Y148I_Y224K_E239G_V250I_L253A_E375Y_A437G_A484E_D510K_K512Y_E515Q.co.His10co.GGGSGGGSGGGS.BtagV7co
pET11.Phi29.K135Q_Y148I_Y224K_D235E_E239G_V250I_L253H_E375Y_A437G_A484E_D510K_K512Y_E515Q.co.His10co.GGGSGGGSGGGS.BtagV7co
pET11.Phi29.K131E_Y148I_Y224K_D235E_E239G_V250I_L253H_E375Y_A437G_A484E_D510K_K512Y_E515Q.co.His10co.GGGSGGGSGGGS.BtagV7co
```

```
pET11.Phi29.K131E_Y148I_Y224K_E239G_V250I_L253A_E375Y_A437G_A484E_E508K_D510K_K512Y.co.His10co.GGGSGGGSGGGS.BtagV7.co
pET11.Phi29.K131E_Y148I_L142K_E239G_V250I_L253A_E375Y_A437G_A484E_E508K_D510K_K512Y_E515Q.co.His10co.GGGSGGGSGGGS.BtagV7.co
pET11.Phi29.K131E_V141K_L142K_Y224K_D235E_E239G_V250I_L253H_E375Y_A437G_A484E_E508K_D510K_K512Y_E515Q.co.His10co.GGGSGGGSGGGS.BtagV7.co
pET11.Phi29.K131E_V141K_Y148I_Y224K_D235E_E239G_V250I_L253H_E375Y_A437G_A484E_E508K_D510K_K512Y_E515Q.co.His10co.GGGSGGGSGGGS.BtagV7.co
pET11.Phi29.K131E_V141K_L142K_Y148I_Y224R_E239G_V250I_L253A_Y369R_E375Y_A437G_A484E_E508R_D510K_K512Y_E515Q.co.His10co.GGGSGGGSGGGS.BtagV7.co
pET11.Phi29.K131K_Y148I_V141K_L142K_Y224K_E239G_V250I_L253A_Y369R_E375Y_A437G_A484E_E508K_E508K_D510K_K512Y_E515Q.co.His10co.GGGSGGGSGGGS.BtagV7.co
pET11.Phi29.C106S_K131E_Y148I_Y224K_E239G_V250I_L253A_C290F_I323P_A324V_M336I_E375Y_A437G_C448L_A484E_D510K_K512Y_E515Q.co.His10co.GGGSGGGSGGGS.BtagV7co
pET11.Phi29.C106S_K131E_Y148I_Y224K_E239G_V250I_L253A_C290F_I323P_A324V_M336I_E375Y_A437G_T441I_C448L_C455A_A484E_D510K_K512Y_E515Q.co.His10co.GGGSGGGSGGGS.BtagV7co
pET11.Phi29.C106S_K131E_Y148I_Y224K_E239G_V250I_L253A_E375A_C290F_A437G_A484V_A484E_D510K_K512Y_E515Q.co.His10co.GGGSGGGSGGGS.BtagV7co
pET11.Phi29.K131E_Y148I_Y224K_E239G_V250I_L253A_E375Y_A437G_A484E_E508Q_D510K_K512Y_E515Q.co.His10co.GGGSGGGSGGGS.BtagV7co
pET11.Phi29.K131E_Y148I_Y224K_E239G_V250I_L253A_E375Y_A437G_A484E_E508Y_D510K_K512Y_E515Q.co.His10co.GGGSGGGSGGGS.BtagV7co
pET11.Phi29.K131E_Y148I_Y224K_E239G_V250I_L253A_E375Y_A437G_A484E_E508F_D510K_K512Y_E515Q.co.His10co.GGGSGGGSGGGS.BtagV7co
pET11.Phi29.K131E_Y148I_Y224K_E239G_V250I_L253A_E375Y_A437G_A484E_D510K_G511K_K512Y_E515Q.co.His10co.GGGSGGGSGGGS.BtagV7co
pET11.Phi29.K131E_Y148I_Y224K_E239G_V250I_L253A_E375Y_A437G_A484E_D510K_K512H_E515Q.co.His10co.GGGSGGGSGGGS.BtagV7co
pET11.Phi29.K131E_Y148I_Y224K_E239G_V250I_L253A_E375Y_A437G_A484E_D510K_K512Q_E515Q.co.His10co.GGGSGGGSGGGS.BtagV7co
pET11.Phi29.K131E_Y148I_Y224K_E239G_V250I_L253A_E375Y_A437G_A484E_D510K_K512Y_L513Y_E515Q.co.His10co.GGGSGGGSGGGS.BtagV7co
pET11.Phi29.K131E_Y148I_Y224K_E239G_V250I_L253A_E375Y_A437G_A484E_D510K_K512Y_E515Y_P518K.co.His10co.GGGSGGGSGGGS.BtagV7co
pET11.Phi29.K131E_Y148I_Y224K_E239G_V250I_L253A_E375Y_A437G_A484E_D510K_K512Y_E515Q_P518D.co.His10co.GGGSGGGSGGGS.BtagV7co
pET11.Phi29.K131E_Y148I_Y224K_E239G_V250I_L253A_E375Y_A437G_A484E_D510K_K512Y_E515Q_P518Q.co.His10co.GGGSGGGSGGGS.BtagV7co
pET11.Phi29.K131E_Y148I_Y224K_E239G_V250I_L253A_E375Y_A437G_A484E_D510K_K512Y_E515Q_D519K.co.His10co.GGGSGGGSGGGS.BtagV7co
pET11.Phi29.K131E_Y148I_Y224K_E239G_V250I_L253A_E375Y_A437G_A484E_D510K_K512Y_E515Q_D519N.co.His10co.GGGSGGGSGGGS.BtagV7co
pET11.Phi29.K131E_Y148I_Y224K_E239G_V250I_L253A_E375Y_A437G_A484E_D510K_K512Y_E515Q_D520K.co.His10co.GGGSGGGSGGGS.BtagV7co
pET11.Phi29.K131E_Y148I_Y224K_E239G_V250I_L253A_E375Y_A437G_A484E_D510K_K512Y_E515Q_D520N.co.His10co.GGGSGGGSGGGS.BtagV7co
pET11.Phi29.K131E_Y148I_Y224K_E239G_V250I_L253A_E375Y_A437G_A484E_D510K_K512Y_E515Q_T522K.co.His10co.GGGSGGGSGGGS.BtagV7co
pET11.Phi29.K131E_Y148I_Y224K_E239G_V250I_L253A_E375Y_A437G_A484E_D510K_K512Y_E515Q_T522S.co.His10co.GGGSGGGSGGGS.BtagV7co
pET11.Phi29.K131E_Y148I_Y224K_E239G_V250I_L253A_E375Y_A437G_A484E_D510K_K512Y_E515T_co.His10co.GGGSGGGSGGGS.BtagV7co
pET11.Phi29.K131E_Y148I_Y224K_E239G_V250I_L253A_E375Y_A437G_A484E_D510K_K512Y_E515Q_V548A.co.His10co.GGGSGGGSGGGS.BtagV7co
pET11.Phi29.K131E_Y148I_Y224K_E239G_V250I_L253A_E375Y_A437G_A484E_D510K_K512Y_E515Q_V548D.co.His10co.GGGSGGGSGGGS.BtagV7co
pET11.Phi29.K131E_Y148I_Y224K_E239G_V250I_L253A_E375Y_A437G_A484E_D510K_K512Y_E515Q_V548K.co.His10co.GGGSGGGSGGGS.BtagV7co
pET11.Phi29.K131E_Y148I_Y224K_E239G_V250I_L253A_E375Y_A437G_A484E_D510K_K512Y_E515Q_V548T.co.His10co.GGGSGGGSGGGS.BtagV7co
```

```
pET11.Phi29.K131E_Y148I_Y224K_E239G_V250I_L253A_E375Y_A437G_A484E_D510K_K512Y_E515R.co.His10co.GGGSGGGSGGGS.BtagV7co
pET11.Phi29.K131E_Y148I_Y224K_E239G_V250I_L253A_E375Y_A437G_A484E_D510K_K512Y_E515S.co.His10co.GGGSGGGSGGGS.BtagV7co
pET11.Phi29.K131E_Y148I_Y224K_E239G_V250I_L253A_E375Y_A437G_A484E_D510K_K512Y_E515T.co.His10co.GGGSGGGSGGGS.BtagV7co
pET11.Phi29.K131E_Y148I_Y224K_E239G_V250I_L253A_E375Y_A437G_A484E_D510K_K512Y_E515V.co.His10co.GGGSGGGSGGGS.BtagV7co
pET11.Phi29.K131E_Y148I_Y224K_E239G_V250I_L253A_E375Y_A437G_A484E_D510K_K512Y_E515W.co.His10co.GGGSGGGSGGGS.BtagV7co
pET11.Phi29.K131E_Y148I_Y224K_E239G_V250I_L253A_E375Y_A437G_A484E_D510K_K512Y_E515Q.co.His10co.GGGSGGGSGGGS.BtagV7co
pET11.Phi29.K131E_Y148I_Y224K_E239G_V250I_L253A_E375Y_A437G_A484E_E508R_D510R_K512Y_E515Q_K536Q.co.His10co.GGGSGGGSGGGS.BtagV7co
pET11.Phi29.D66R_K131E_Y148I_Y224K_E239G_V250I_L253A_E375Y_A437G_A484E_E508R_D510R_K512Y_E515Q_K536Q.co.His10co.GGGSGGGSGGGS.BtagV7co
pET11.Phi29.K131E_Y148I_Y224K_E239G_V250I_L253A_E375Y_A437G_A484E_D510K_K512Y_E515Q.co.His10co.GGGSGGGSGGGS.BtagV7co
pET11.Phi29.K131E_Y148I_Y224K_E239G_V250I_L253A_E375Y_A437G_L480V_A484E_D510K_K512Y_E515Q.co.His10co.GGGSGGGSGGGS.BtagV7co
pET11.Phi29.K131E_Y148I_Y224K_E239G_V250I_L253A_E375Y_A437G_L480V_A484E_D510K_K512Y_E515Q.co.His10co.GGGSGGGSGGGS.BtagV7co
pET11.Phi29.K131E_Y148I_Y224K_E239G_V250I_L253A_E375Y_A437G_L480F_A484E_D510K_K512Y_E515Q.co.His10co.GGGSGGGSGGGS.BtagV7co
pET11.Phi29.K131E_Y148I_Y224K_E239G_V250I_L253A_E375Y_A437G_L480K_A484E_D510K_K512Y_E515Q.co.His10co.GGGSGGGSGGGS.BtagV7co
pET11.Phi29.K131E_Y148I_Y224K_E239G_V250I_L253A_I364V_E375Y_A437G_A484E_D510K_K512Y_E515Q.co.His10co.GGGSGGGSGGGS.BtagV7co
pET11.Phi29.K131E_Y148I_Y224K_E239G_V250I_L253A_I364V_E375Y_A437G_A484E_D510K_K512Y_E515Q.co.His10co.GGGSGGGSGGGS.BtagV7co
pET11.Phi29.K131E_Y148I_Y224K_E239G_V250I_L253A_E375Y_A437G_A484E_D510K_K512Y_E515Q_D523L.co.His10co.GGGSGGGSGGGS.BtagV7co
pET11.Phi29.K131E_Y148I_Y224K_E239G_V250I_L253A_E375Y_A437G_A484E_D510K_K512Y_E515Q_D523N.co.His10co.GGGSGGGSGGGS.BtagV7co
pET11.Phi29.K131E_Y148I_Y224K_E239G_V250I_L253A_E375Y_A437G_A484E_D510K_K512Y_E515Q_D523K.co.His10co.GGGSGGGSGGGS.BtagV7co
pET11.Phi29.K131E_Y148I_Y224K_E239G_V250I_L253A_E375Y_A437G_A484E_D510K_K512Y_E515Q_D523H.co.His10co.GGGSGGGSGGGS.BtagV7co
pET11.Phi29.K131Q_Y148I_Y224K_E239G_V250I_L253A_E375Y_A437G_A484E_E508R_D510R_K512Y_E515Q_K536Q.co.His10co.GGGSGGGSGGGS.BtagV7co
pET11.Phi29.K135Q_Y148I_Y224K_E239G_V250I_L253A_E375Y_A437G_A484E_D510K_K512Y_E515Q.co.His10co.GGGSGGGSGGGS.BtagV7co
pET11.Phi29.K131E_D136A_Y148I_Y224K_E239G_V250I_L253A_E375Y_A437G_A484E_D510K_K512Y_E515Q.co.His10co.GGGSGGGSGGGS.BtagV7co
pET11.Phi29.K131E_A134G_Y148I_Y224K_E239G_V250I_L253A_E375Y_A437G_A484E_D510K_K512Y_E515Q.co.His10co.GGGSGGGSGGGS.BtagV7co
pET11.Phi29.K131E_A134S_Y148I_Y224K_E239G_V250I_L253A_E375Y_A437G_A484E_D510K_K512Y_E515Q.co.His10co.GGGSGGGSGGGS.BtagV7co
pET11.Phi29.K131E_A134T_Y148I_Y224K_E239G_V250I_L253A_A377S_E375Y_A437G_A484E_D510K_K512Y_E515Q.co.His10co.GGGSGGGSGGGS.BtagV7co
pET11.Phi29.K131E_Y148I_Y224K_E239G_V250I_L253A_E375Y_A437G_A484E_D510K_K512Y_E515Q_T571K.co.His10co.GGGSGGGSGGGS.BtagV7co
pET11.Phi29.K131E_Y148I_Y224K_E239G_V250I_L253A_E375Y_A437G_A484E_D510K_K512Y_E515Q_T573S.co.His10co.GGGSGGGSGGGS.BtagV7co
pET11.Phi29.K131E_Y148I_Y224K_E239G_V250I_L253A_E375Y_A437G_A484E_D510K_K512Y_E515Q_T573E.co.His10co.GGGSGGGSGGGS.BtagV7co
pET11.Phi29.K131E_Y148I_Y224K_E239G_V250I_L253A_E375Y_A437G_A484E_D510K_K512Y_E515Q_T573G.co.His10co.GGGSGGGSGGGS.BtagV7co
pET11.Phi29.K131E_Y148I_Y224K_E239G_V250I_L253A_E375Y_A437G_A484E_D510K_K512Y_E515Q_S551K.co.His10co.GGGSGGGSGGGS.BtagV7co
```

Fig. 7 cont'd

- pET11.Phi29.K131E_Y148I_Y224K_E239G_V250I_L253A_E375Y_A437G_A484E_D510K_K512Y_E515Q_S551E.co.His10co.GGGSGGGSGGGSGGGSGGGSGGGS.BtagV7co
- pET11.Phi29.K131E_Y148I_Y224K_E239G_V250I_L253A_E375Y_A437G_A484E_D510K_K512Y_E515Q_S551Q.co.His10co.GGGSGGGSGGGSGGGSGGGSGGGS.BtagV7co
- pET11.Phi29.K131E_Y148I_Y224K_E239G_V250I_L253A_E375Y_A437G_A484E_D510K_K512Y_E515Q_S551Q.co.His10co.GGGSGGGSGGGSGGGSGGGSGGGS.BtagV7co
- pET11.Phi29.K131E_Y148I_Y224K_E239G_V250I_L253A_E375Y_A437G_A484E_D510K_K512Y_E515Q_K575A.co.His10co.GGGSGGGSGGGSGGGSGGGSGGGS.BtagV7co
- pET11.Phi29.K131E_Y148I_Y224K_E239G_V250I_L253A_E375Y_A437G_A484E_D510K_K512Y_E515Q_K575R.co.His10co.GGGSGGGSGGGSGGGSGGGSGGGS.BtagV7co
- pET11.Phi29.K131E_Y148I_Y224K_E239G_V250I_L253A_E375Y_A437G_A484E_D510K_K512Y_E515Q_K575E.co.His10co.GGGSGGGSGGGSGGGSGGGSGGGS.BtagV7co
- pET11.Phi29.K131E_Y148I_Y224K_E239G_V250I_L253A_E375Y_A437G_A484E_D510K_K512Y_E515Q_K575Q.co.His10co.GGGSGGGSGGGSGGGSGGGSGGGS.BtagV7co
- pET11.Phi29.K131E_Y148I_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.K131E_Y148I_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.K131E_Y148I_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.Q99K_K131E_Y148I_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.Q99T_K131E_Y148I_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.Q99S_K131E_Y148I_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.Q99F_K131E_Y148I_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.Q99W_K131E_Y148I_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.Q99A_K131E_Y148I_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.Q99E_K131E_Y148I_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.K124Q_K131E_Y148I_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.K124A_K131E_Y148I_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.K131E_Y148I_A190F_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.K131E_Y148I_A190H_Y224K_E239G_V250I_L253A_E375Y_A437G_A484E_D510K_K512Y_E515Q.co.His10co.GGGSGGGSGGGSGGGSGGGSGGGS.BtagV7co
- pET11.Phi29.V141K_L142K_Y148I_Y224K_E239G_V250I_L253A_E375Y_L384A_A437G_A484E_D510K_K512Y_E515Q.co.His10co.GGGSGGGSGGGSGGGSGGGSGGGS.BtagV7co
- pET11.Phi29.K131E_V141K_L142K_Y148I_Y224K_E239G_V250I_L253A_E375Y_A437G_A484E_E508K_D510K_K512Y_E515Q_K536Q.co.His10co.GGGSGGGSGGGSGGGSGGGSGGGS.BtagV7co

Fig. 7 cont'd

RECOMBINANT POLYMERASES WITH INCREASED PHOTOTOLERANCE

CROSS-REFERENCE TO RELATED APPLICATIONS

This application is a continuation of U.S. patent application Ser. No. 13/756,113, filed Jan. 31, 2013, entitled "RECOMBINANT POLYMERASES WITH INCREASED PHOTOTOLERANCE" by Satwik Kamtekar et al., which is a non-provisional utility patent application claiming priority to and benefit of the following prior provisional patent application: U.S. Ser. No. 61/593,569, filed Feb. 1, 2012, entitled "RECOMBINANT POLYMERASES WITH INCREASED PHOTOTOLERANCE" by Satwik Kamtekar et al. Each of these applications is incorporated herein by reference in its entirety for all purposes.

FIELD OF THE INVENTION

The invention relates to modified DNA polymerases for single molecule sequencing. The polymerases include modified recombinant polymerases that display a reduced susceptibility to photodamage. The invention also relates to methods for amplifying nucleic acids and to methods for determining the sequence of nucleic acid molecules using such polymerases.

BACKGROUND OF THE INVENTION

DNA polymerases replicate the genomes of living organisms. In addition to this central role in biology, DNA polymerases are also ubiquitous tools of biotechnology. They are widely used, e.g., for reverse transcription, amplification, labeling, and sequencing, all central technologies for a variety of applications such as nucleic acid sequencing, nucleic acid amplification, cloning, protein engineering, diagnostics, molecular medicine, and many other technologies.

Because of the importance of DNA polymerases, they have been extensively studied. This study has focused, e.g., on phylogenetic relationships among polymerases, structure of polymerases, structure-function features of polymerases, and the role of polymerases in DNA replication and other basic biological processes, as well as ways of using DNA polymerases in biotechnology. For a review of polymerases, see, e.g., Hübscher et al. (2002) "Eukaryotic DNA Polymerases" Annual Review of Biochemistry Vol. 71: 133-163, Alba (2001) "Protein Family Review: Replicative DNA Polymerases" Genome Biology 2(1): reviews 3002.1-3002.4, Steitz (1999) "DNA polymerases: structural diversity and common mechanisms" J Biol Chem 274:17395-17398, and Burgers et al. (2001) "Eukaryotic DNA polymerases: proposal for a revised nomenclature" J Biol Chem. 276(47): 43487-90. Crystal structures have been solved for many polymerases, which often share a similar architecture. The basic mechanisms of action for many polymerases have been determined.

A fundamental application of DNA technology involves various labeling strategies for labeling a DNA that is produced by a DNA polymerase. This is useful in DNA sequencing, microarray technology, SNP detection, cloning, PCR analysis, and many other applications. Labeling is often performed in various post-synthesis hybridization or chemical labeling schemes, but DNA polymerases have also been used to directly incorporate various labeled nucleotides in a variety of applications, e.g., via nick translation, reverse transcription, random priming, amplification, the polymerase chain reaction, etc. See, e.g., Giller et al. (2003) "Incorporation of reporter molecule-labeled nucleotides by DNA polymerases. I. Chemical synthesis of various reporter group-labeled 2'-deoxyribonucleoside-5'-triphosphates" Nucleic Acids Res. 31(10):2630-2635, Augustin et al. (2001) "Progress towards single-molecule sequencing: enzymatic synthesis of nucleotide-specifically labeled DNA" J. Biotechnol. 86:289-301, Tonon et al. (2000) "Spectral karyotyping combined with locus-specific FISH simultaneously defines genes and chromosomes involved in chromosomal translocations" Genes Chromosom. Cancer 27:418-423, Zhu and Waggoner (1997) "Molecular mechanism controlling the incorporation of fluorescent nucleotides into DNA by PCR" Cytometry, 28:206-211, Yu et al. (1994) "Cyanine dye dUTP analogs for enzymatic labeling of DNA probes" Nucleic Acids Res. 22:3226-3232, Zhu et al. (1994) "Directly labeled DNA probes using fluorescent nucleotides with different length linkers" Nucleic Acids Res. 22:3418-3422, and Reid et al. (1992) "Simultaneous visualization of seven different DNA probes by in situ hybridization using combinatorial fluorescence and digital imaging microscopy" Proc. Natl Acad. Sci. USA, 89:1388-1392.

DNA polymerase mutants have been identified that have a variety of useful properties, including altered nucleotide analog incorporation abilities relative to wild-type counterpart enzymes. For example, Vent$^{A488L}$ DNA polymerase can incorporate certain non-standard nucleotides with a higher efficiency than native Vent DNA polymerase. See Gardner et al. (2004) "Comparative Kinetics of Nucleotide Analog Incorporation by Vent DNA Polymerase" J. Biol. Chem. 279 (12):11834-11842 and Gardner and Jack "Determinants of nucleotide sugar recognition in an archaeon DNA polymerase" Nucleic Acids Research 27(12):2545-2553. The altered residue in this mutant, A488, is predicted to be facing away from the nucleotide binding site of the enzyme. The pattern of relaxed specificity at this position roughly correlates with the size of the substituted amino acid side chain and affects incorporation by the enzyme of a variety of modified nucleotide sugars.

Additional modified polymerases, e.g., modified polymerases that display improved properties useful for single molecule sequencing (SMS) and other polymerase applications (e.g., DNA amplification, sequencing, labeling, detection, cloning, etc.), are desirable. The present invention provides new recombinant DNA polymerases with desirable properties, including increased resistance to photodamage. Other exemplary properties include exonuclease deficiency, altered cofactor selectivity, increased yield, increased thermostability, increased accuracy, increased speed, increased readlength, and the like. Also included are methods of making and using such polymerases, as well as many other features that will become apparent upon a complete review of the following.

SUMMARY OF THE INVENTION

Modified DNA polymerases can find use in such applications as, e.g., single-molecule sequencing (SMS), genotyping analyses such as SNP genotyping using single-base extension methods, sample preparation, and real-time monitoring of amplification, e.g., RT-PCR. Among other aspects, the invention provides compositions comprising recombinant polymerases that comprise mutations which confer properties which can be particularly desirable for these applications. These properties can, e.g., increase enzyme (and therefore assay) robustness, facilitate readout accuracy, or otherwise improve polymerase performance. Also provided by the invention are methods of generating such modified polymerases and methods in which such polymerases can be used to, e.g., sequence a DNA template and/or make a DNA.

One general class of embodiments provides a composition comprising a recombinant Φ29-type DNA polymerase, which recombinant polymerase comprises one or more mutation selected from the group consisting of an amino acid substitution at position 131, an amino acid substitution at position 132, a K135Q substitution, a K135S substitution, an H149D substitution, a Q183F substitution, a G197D substitution, a G197E substitution, an I201E substitution, a K206E substitution, an A437N substitution, and a D510S substitution, wherein identification of positions is relative to wild-type Φ29 polymerase (SEQ ID NO:1). Exemplary mutations at positions 131 and 132 include, e.g., K131E, K131Q, and K132Q. Optionally, the recombinant polymerase is more resistant to photodamage than is a wild-type polymerase or a parental polymerase lacking the one or more mutations.

The polymerase can also include mutations at additional positions. For example, the polymerase can include one or more mutation or combination of mutations selected from the group consisting of an amino acid substitution at position 253, an amino acid substitution at position 375, an amino acid substitution at position 484, an amino acid substitution at position 512, an amino acid substitution at position 510, an amino acid substitution at position 148, an amino acid substitution at position 224, an amino acid substitution at position 239, an amino acid substitution at position 250, an amino acid substitution at position 437, an amino acid substitution at position 235, an amino acid substitution at position 515, an amino acid substitution at position 141, an amino acid substitution at position 142, an amino acid substitution at position 504, an amino acid substitution at position 508, an amino acid substitution at position 513, an amino acid substitution at position 523, an amino acid substitution at position 536, an amino acid substitution at position 539, an amino acid substitution at position 205, an amino acid substitution at position 472, an amino acid substitution at position 437 and an amino acid substitution at position 253, and an amino acid substitution at position 508 and an amino acid substitution at position 510, wherein identification of positions is relative to SEQ ID NO:1.

The polymerase optionally includes one or more mutation or combination of mutations selected from the group consisting of A437G and L253H, A437G and L253C, V250A and L253H, A437G, D235E, E515Q, E515P, E515K, V250A, V250I, Y148I, Y224K, E239G, V141K, L142K, E508K, E508K and D510S, K536Q, K539Q, K205E, K205D, K205A, K472A, E375Y, K512Y, A484E, L253A, L253C, L253S, L253H, and D510K, wherein identification of positions is relative to SEQ ID NO:1. In one class of embodiments, the recombinant polymerase comprises E375Y, A484E, and K512Y substitutions, wherein identification of positions is relative to SEQ ID NO:1.

Optionally, the polymerase comprises mutations at two or more, three or more, four or more, five or more, or even six or more of the indicated positions. Exemplary combinations of mutations include K131E, Y148I, Y224K, E239G, V250I, L253A, E375Y, A437G, A484E, D510K, K512Y, and E515Q; K135Q, Y148I, Y224K, E239G, V250I, L253A, E375Y, A437G, A484E, D510K, K512Y, and E515Q; K131E, Y148I, Y224K, D235E, E239G, V250A, L253H, E375Y, A437G, A484E, D510K, K512Y, and E515Q; Y148I, Y224K, E239G, L253S, E375Y, A437G, A484E, D510K, K512Y, and E515Q; Y148I, Q183F, D235E, E239G, L253H, E375Y, A437G, A484E, D510K, K512Y, and E515Q; Y148I, Y224K, E239G, V250I, L253H, E375Y, A437G, A484E, D510K, and K512Y; Y148I, Y224K, E239G, V250I, L253A, E375Y, A437G, A484E, D510K, K512Y, and E515Q; K131E, Y148I, Y224K, D235E, E239G, L253H, E375Y, A437G, A484E, D510K, K512Y, and E515Q; Y148I, Y224K, E239G, V250I, L253A, E375Y, A437G, A484E, D510K, and K512Y; Y148I, Y224K, E239G, V250I, L253A, E375Y, A437G, A484E, D510K, and K512Y; K131E, Y148I, Y224K, E239G, V250I, L253A, E375Y, A484E, D510K, and K512Y; K135Q, Y148I, Y224K, E239G, V250I, L253A, E375Y, A484E, D510K, and K512Y; Y148I, Y224K, E239G, L253H, E375Y, A437G, A484E, D510K, and K512Y; K131E, K135Q, V141K, L142K, Y148I, Y224K, E239G, V250I, L253A, E375Y, A437G, A484E, E508K, D510K, K512Y, E515Q, and K536Q; K131E, Y148I, Y224K, E239G, V250I, L253A, E375Y, A437G, A484E, E508K, D510K, K512Y, and E515Q; and K131Q, Y148I, Y224K, E239G, V250I, L253A, E375Y, A484E, D510K, and K512Y; wherein identification of positions is relative to SEQ ID NO:1.

Additional exemplary mutations and combinations are described herein or can be formed from those disclosed herein, and polymerases including such combinations are also features of the invention.

The recombinant polymerase can be a modified recombinant Φ29 polymerase. Thus, in one class of embodiments, the recombinant polymerase is at least 70% identical to wild-type Φ29 polymerase (SEQ ID NO:1), for example, at least 80%, at least 85%, at least 90%, at least 95%, at least 98%, or even at least 99% identical to wild-type Φ29 polymerase (SEQ ID NO:1). As another example, the recombinant polymerase can be a modified recombinant M2Y polymerase. Thus, in one class of embodiments, the recombinant polymerase is at least 70% identical to wild-type M2Y polymerase (SEQ ID NO:2), for example, at least 80%, at least 85%, at least 90%, at least 95%, at least 98%, or even at least 99% identical to wild-type M2Y polymerase (SEQ ID NO:2). In other exemplary embodiments, the recombinant polymerase is a recombinant B103, GA-1, PZA, Φ15, BS32, Nf, G1, Cp-1, PRD1, PZE, SFS, Cp-5, Cp-7, PR4, PRS, PR722, or L17 polymerase.

The recombinant polymerase optionally comprises one or more exogenous features, e.g., at the C-terminal and/or N-terminal region of the polymerase, for example, a polyhistidine tag (e.g., a His10 tag) or a biotin ligase recognition sequence. As a few examples, the polymerase can include a C-terminal polyhistidine tag, a C-terminal polyhistidine tag and biotin ligase recognition sequence, or an N-terminal polyhistidine tag and biotin ligase recognition sequence and a C-terminal polyhistidine tag.

A related general class of embodiments provides a composition comprising a recombinant DNA polymerase, which recombinant polymerase comprises an amino acid sequence selected from the group consisting of SEQ ID NOs:27-46 or a conservative or substantially identical variant thereof.

A composition comprising a recombinant polymerase of the invention can also include a nucleotide analog, e.g., a phosphate-labeled nucleotide analog. The analog optionally comprises a fluorophore. The analog can comprise three phosphate groups, or it can comprise four or more phosphate groups, e.g., 4-7 phosphate groups (that is, the analog can be a tetraphosphate, pentaphosphate, hexaphosphate, or heptaphosphate analog). In one class of embodiments, the composition includes a nucleotide analog (e.g., a phosphate-labeled nucleotide analog) and a DNA template, and the polymerase incorporates the nucleotide analog into a copy nucleic acid in response to the DNA template. The composition can be present in a DNA sequencing system, e.g., a zero-mode waveguide (ZMW). The recombinant polymerase can be immobilized on a surface, for example, on a surface of a zero-mode waveguide, preferably in an active form.

In one aspect, the invention provides methods of sequencing a DNA template. In the methods, a reaction mixture that includes the DNA template, a replication initiating moiety that complexes with or is integral to the template, one or more nucleotides and/or nucleotide analogs, and a recombinant polymerase of the invention (e.g., a recombinant Φ29-type DNA polymerase) is provided. The polymerase is capable of replicating at least a portion of the template using the moiety in a template-dependent polymerization reaction. The reaction mixture is subjected to a polymerization reaction in which the recombinant polymerase replicates at least a portion of the template in a template-dependent manner, whereby the one or more nucleotides and/or nucleotide analogs are incorporated into the resulting DNA. A time sequence of incorporation of the one or more nucleotides and/or nucleotide analogs into the resulting DNA is identified.

The nucleotide analogs used in the methods can comprise a first analog and a second analog (and optionally third, fourth, etc. analogs), each of which comprise different fluorescent labels. The different fluorescent labels can optionally be distinguished from one another during the step in which a time sequence of incorporation is identified. Optionally, subjecting the reaction mixture to a polymerization reaction and identifying a time sequence of incorporation are performed in a zero mode waveguide. Essentially all of the features noted for the compositions herein apply to these methods as well, as relevant.

In a related aspect, the invention provides methods of making a DNA. In the methods, a reaction mixture is provided that includes a template, a replication initiating moiety that complexes with or is integral to the template, one or more nucleotides and/or nucleotide analogs, and a recombinant polymerase of the invention (e.g., a recombinant Φ29-type DNA polymerase). The polymerase is capable of replicating at least a portion of the template using the moiety in a template-dependent polymerase reaction. The mixture is reacted such that the polymerase replicates at least a portion of the template in a template-dependent manner, whereby the one or more nucleotides and/or nucleotide analogs are incorporated into the resulting DNA. The reaction mixture is optionally reacted in a zero mode waveguide. The methods optionally include detecting incorporation of at least one of the nucleotides and/or nucleotide analogs. Essentially all of the features noted for the compositions herein apply to these methods as well, as relevant.

In one aspect, the invention provides methods of making a recombinant polymerase. In the methods, a parental polymerase (e.g., a wild-type or other Φ29-type polymerase) is mutated at one or more of the positions described herein (e.g., one or more of positions K131, K132, K135, V141, L142, Y148, H149, Q183, G197, I201, K205, K206, Y224, D235, E239, V250, L253, E375, A437, K472, A484, I504, E508, D510, K512, L513, E515, D523, K536, and K539, where identification of positions is relative to SEQ ID NO:1). Optionally, one or more property of the recombinant polymerase (e.g., resistance to photodamage) is assessed and compared to that for the parental polymerase.

BRIEF DESCRIPTION OF THE DRAWINGS

FIG. 1 presents an alignment between the amino acid sequences of wild-type M2Y polymerase (SEQ ID NO:2) and wild-type Φ29 polymerase (SEQ ID NO:1).

FIG. 7 provides exemplary polymerase mutations and combinations thereof in accordance with the invention. Positions of the mutations are identified relative to a wild-type Φ29 DNA polymerase (SEQ ID NO:1) where the name of the polymerase includes "Phi29" or relative to a wild-type M2Y polymerase (SEQ ID NO:2) where the name of the polymerase includes "M2."

Figure 2:
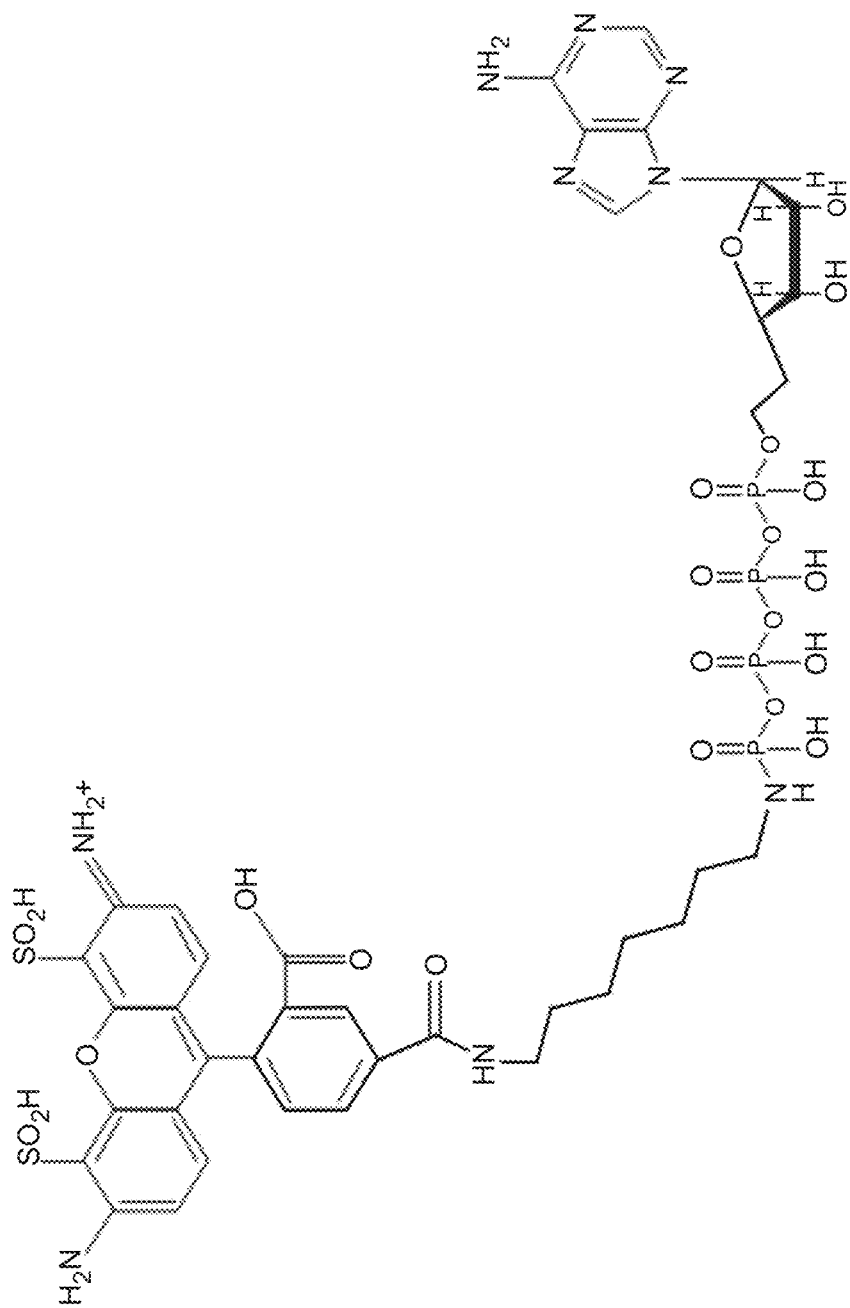
FIG. 2 depicts the structure of A488dA4P.

Schematic figures are not necessarily to scale.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like.

The term "about" as used herein indicates the value of a given quantity varies by +/−10% of the value, or optionally +/−5% of the value, or in some embodiments, by +/−1% of the value so described.

The term "nucleic acid" or "polynucleotide" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA, such as 2'-O-methylated oligonucleotides), and the like. A nucleic acid can be e.g., single-stranded or double-stranded. Unless otherwise indicated, a particular nucleic acid sequence of this invention encompasses complementary sequences, in addition to the sequence explicitly indicated.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation, biotinylation, or the like. The amino acid residues of the polypeptide can be natural or non-natural and can be unsubstituted, unmodified, substituted or modified.

An "amino acid sequence" is a polymer of amino acid residues (a protein, polypeptide, etc.) or a character string representing an amino acid polymer, depending on context.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Numbering of a given amino acid or nucleotide polymer "corresponds to numbering of" or is "relative to" a selected amino acid polymer or nucleic acid when the position of any given polymer component (amino acid residue, incorporated nucleotide, etc.) is designated by reference to the same residue position in the selected amino acid or nucleotide polymer, rather than by the actual position of the component in the given polymer. Similarly, identification of a given position within a given amino acid or nucleotide polymer is "relative to" a selected amino acid or nucleotide polymer when the position of any given polymer component (amino acid residue, incorporated nucleotide, etc.) is designated by reference to the residue name and position in the selected amino acid or nucleotide polymer, rather than by the actual name and position of the component in the given polymer. Correspondence of positions is typically determined by aligning the relevant amino acid or polynucleotide sequences. For example, residue K221 of wild-type M2Y polymerase (SEQ ID NO:2) is identified as position Y224 relative to wild-type Φ29 polymerase (SEQ ID NO:1); see, e.g., the alignment shown in FIG. 1. Similarly, residue L138 of wild-type M2Y polymerase (SEQ ID NO:2) is identified as position V141 relative to wild-type Φ29 polymerase (SEQ ID NO:1), and an L138K substitution in the M2Y polymerase is thus identified as a V141K substitution relative to SEQ ID NO:1 Amino acid positions herein are generally identified relative to SEQ ID NO:1 unless explicitly indicated otherwise.

The term "recombinant" indicates that the material (e.g., a nucleic acid or a protein) has been artificially or synthetically (non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is, e.g., a polypeptide or protein which is produced by expression of a recombinant nucleic acid.

A "Φ29-type DNA polymerase" (or "phi29-type DNA polymerase") is a DNA polymerase from the Φ29 phage or from one of the related phages that, like Φ29, contain a terminal protein used in the initiation of DNA replication. Φ29-type DNA polymerases are homologous to the Φ29 DNA polymerase (e.g., as listed in SEQ ID NO:1); examples include the B103, GA-1, PZA, Φ15, BS32, M2Y (also known as M2), Nf, G1, Cp-1, PRD1, PZE, SF5, Cp-5, Cp-7, PR4, PR5, PR722, L17, and AV-1 DNA polymerases, as well as chimeras thereof. A modified recombinant Φ29-type DNA polymerase includes one or more mutations relative to naturally-occurring wild-type Φ29-type DNA polymerases, for example, one or more mutations that increase phototolerance, alter interaction with and/or incorporation of nucleotide analogs, and/or alter another polymerase property, and may include additional alterations or modifications over the wild-type Φ29-type DNA polymerase, such as one or more deletions, insertions, and/or fusions of additional peptide or protein sequences (e.g., for immobilizing the polymerase on a surface or otherwise tagging the polymerase enzyme).

A variety of additional terms are defined or otherwise characterized herein.

DETAILED DESCRIPTION

One aspect of the invention is generally directed to compositions comprising a recombinant polymerase, e.g., a recombinant Φ29-type DNA polymerase, that includes one or more mutations (e.g., amino acid substitutions, deletions, or insertions) as compared to a reference polymerase, e.g., a wild-type Φ29-type polymerase. Depending on the particular mutation or combination of mutations, the polymerase exhibits one or more properties that find use in, e.g., single molecule sequencing applications or nucleic acid amplification. Exemplary properties exhibited by various polymerases of the invention include increased resistance to photodamage, a reduction in the rate of one or more steps of the polymerase kinetic cycle (resulting from, e.g., enhanced interaction of the polymerase with nucleotide analog, enhanced metal coordination, etc.), increased closed complex stability, an altered branching fraction, reduced or eliminated exonuclease activity, altered cofactor selectivity, and increased processivity, yield, thermostability, accuracy, speed, and/or readlength, as well as other features that will become apparent upon a complete review of the present disclosure. The polymerases can include one or more exogenous or heterologous features, e.g., at the N- and/or C-terminal regions of the polymerase. Such features find use not only for purification of the recombinant polymerase and/or immobilization of the polymerase to a substrate, but can also alter one or more properties of the polymerase.

Among other aspects, the present invention provides new polymerases that incorporate nucleotide analogs, such as dye labeled phosphate labeled analogs, into a growing template copy during DNA amplification. These polymerases are modified such that they have one or more desirable properties, for example, increased resistance to photodamage, decreased branching fraction formation when incorporating the relevant analogs, improved DNA-polymerase stability or processivity, reduced exonuclease activity, increased thermostability and/or yield, altered cofactor selectivity, improved accuracy, speed, and/or readlength, and/or altered kinetic properties as compared to corresponding wild-type or other parental polymerases (e.g., polymerases from which modified recombinant polymerases of the invention were derived, e.g., by mutation). The polymerases of the invention can also include any of the additional features for improved specificity, improved processivity, improved retention time, improved surface stability, affinity tagging, and/or the like noted herein.

These new polymerases are particularly well suited to DNA amplification and/or sequencing applications, particularly sequencing protocols that include detection in real time of the incorporation of labeled analogs into DNA amplicons, since the increased phototolerance can prolong useful life of the polymerase under assay conditions and the altered rates, reduced or eliminated exonuclease activity, decreased branch fraction, improved complex stability, altered metal cofactor selectivity, or the like can facilitate discrimination of nucleotide incorporation events from non-incorporation events such as transient binding of a mismatched nucleotide in the active site of the complex, improve processivity, and/or facilitate detection of incorporation events.

Polymerases of the invention include, for example, a recombinant Φ29-type DNA polymerase that comprises a mutation at one or more positions selected from the group consisting of Q99, K131, K132, K135, V141, L142, Y148, H149, Q183, G197, I201, K205, K206, Y224, D235, E239, V250, L253, C290, R306, R308, K311, E375, A437, T441, C455, K472, A484, I504, E508, D510, K512, L513, E515, D523, K536, and K539, where identification of positions is relative to wild-type Φ29 polymerase (SEQ ID NO:1). Optionally, the polymerase comprises mutations at two or more, three or more, four or more, five or more, or even six or more of these positions. For example, the polymerase can include a mutation at position E375, a mutation at position K512, and a mutation at one or more positions selected from the group consisting of Q99, K131, K132, K135, V141, L142, Y148, H149, Q183, G197, I201, K205, K206, Y224, D235, E239, V250, C290, R306, R308, K311, A437, T441, C455, K472, I504, E508, L513, E515, D523, K536, and K539 (where identification of positions is relative to SEQ ID NO:1), and can optionally also include a mutation at one or more additional positions, e.g., as described herein. Similarly, for example, the polymerase can comprise mutations at positions 375, 512, and 253, positions 375, 512, and 484, positions 253 and 484, positions 375, 512, 253, and 484, or positions 375, 512, 253, 484, and 510, and a mutation at one or more positions selected from the group consisting of Q99, K131, K132, K135, V141, L142, Y148, H149, Q183, G197, I201, K205, K206, Y224, D235, E239, V250, C290, R306, R308, K311, A437, T441, C455, K472, I504, E508, L513, E515, D523, K536, and K539 (where identification of positions is relative to SEQ ID NO:1). A number of exemplary substitutions at these (and other) positions are described herein.

As a few examples, a mutation at E375 can comprise an amino acid substitution selected from the group consisting of E375Y, E375F, E375R, E375Q, E375H, E375L, E375A, E375K, E375S, E375T, E375C, E375G, and E375N; a mutation at position K512 can comprise an amino acid substitution selected from the group consisting of K512Y, K512F, K512I, K512M, K512C, K512E, K512G, K512H, K512N, K512Q, K512R, K512V, and K512H; a mutation at position L253 can comprise an amino acid substitution selected from the group consisting of L253A, L253H, L253S, and L253C; a mutation at position A484 can comprise an A484E substitution; and/or a mutation at position D510 can comprise a D510K or D510S substitution. Other exemplary substitutions include, e.g., Q99W, K131E, K131Q, K135Q, K135S, V141K, L142K, Y148I, H149D, Q183F, G197D, G197E, I201E, K205E, K205D, K205A, K206E, Y224K, D235E, E239G, V250A, V250I, C290F, R306Q, R308L, K311E, A437G, T441I, C455A, K472A, E508K, E515Q, E515P, E515K, and K536Q; additional substitutions are described herein.

The polymerase mutations and mutational strategies noted herein can be combined with each other and with essentially any other available mutations and mutational strategies to confer additional improvements in, e.g., nucleotide analog specificity, enzyme processivity, improved retention time of labeled nucleotides in polymerase-DNA-nucleotide complexes, phototolerance, and the like. For example, the mutations and mutational strategies herein can be combined with those taught in, e.g., WO 2007/076057 POLYMERASES FOR NUCLEOTIDE ANALOGUE INCORPORATION by Hanzel et al., WO 2008/051530 POLYMERASE ENZYMES AND REAGENTS FOR ENHANCED NUCLEIC ACID SEQUENCING by Rank et al., U.S. patent application publication 2010-0075332 ENGINEERING POLYMERASES AND REACTION CONDITIONS FOR MODIFIED INCORPORATION PROPERTIES by Pranav Patel et al., U.S. patent application publication 2010-0093555 ENZYMES RESISTANT TO PHOTODAMAGE by Keith Bjornson et al., U.S. patent application publication 2010-0112645 GENERATION OF MODIFIED POLYMERASES FOR IMPROVED ACCURACY IN SINGLE MOLECULE SEQUENCING by Sonya Clark et al., U.S. patent application publication 2011-0189659 GENERATION OF MODIFIED POLYMERASES FOR IMPROVED ACCURACY IN SINGLE MOLECULE SEQUENCING by Sonya Clark et al., and U.S. patent application publication 2012-0034602 RECOMBINANT POLYMERASES FOR IMPROVED SINGLE MOLECULE SEQUENCING. This combination of mutations/mutational strategies can be used to impart several simultaneous improvements to a polymerase (e.g., increased phototolerance, decreased branch fraction formation, improved specificity, improved processivity, altered rates, improved retention time, improved stability of the closed complex, tolerance for a particular metal cofactor, etc.). In addition, polymerases can be further modified for application-specific reasons, such as to improve activity of the enzyme when bound to a surface, as taught, e.g., in WO 2007/075987 ACTIVE SURFACE COUPLED POLYMERASES by Hanzel et al. and WO 2007/075873 PROTEIN ENGINEERING STRATEGIES TO OPTIMIZE ACTIVITY OF SURFACE ATTACHED PROTEINS by Hanzel et al., or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application publication U.S. 2009-0286245 entitled "Two slow-step polymerase enzyme systems and methods."

Also taught are approaches for modifying polymerases to enhance one or more properties exhibited by the polymerases or to confer an additional property not provided by a starting combination of mutations. For example, provided below are approaches for structure-based design of polymerases with increased resistance to photodamage (increased phototolerance).

DNA Polymerases

DNA polymerases that can be modified to have increased phototolerance and/or other desirable properties as described herein are generally available. DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47): 43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined or can be inferred based upon similarity to solved crystal structures for homologous polymerases. For example, the crystal structure of Φ29, a preferred type of parental enzyme to be modified according to the invention, is available.

Many such polymerases that are suitable for modification are available, e.g., for use in sequencing, labeling, and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich, and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to increase phototolerance, reduce reaction rates, reduce or eliminate exonuclease activity, decrease branching fraction, improve closed complex stability, alter metal cofactor selectivity, and/or alter one or more other property described herein include Taq polymerases, exonuclease deficient Taq polymerases, E. coli DNA Polymerase 1, Klenow fragment, reverse transcriptases, Φ29 related polymerases including wild type Φ29 polymerase and derivatives of such polymerases such as exonuclease deficient forms, T7 DNA polymerase, T5 DNA polymerase, RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Alternately, the modified recombinant DNA polymerase can be homologous to another Φ29-type DNA polymerase, such as B103, GA-1, PZA, Φ15, BS32, M2Y (also known as M2), Nf, G1, Cp-1, PRD1, PZE, SF5, Cp-5, Cp-7, PR4, PR5, PR722, L17, AV-1, Φ21, or the like. For nomenclature, see also, Meijer et al. (2001) "Φ29 Family of Phages" Microbiology and Molecular Biology Reviews, 65(2):261-287. See, e.g., SEQ ID NO:1 for the amino acid sequence of wild-type Φ29 polymerase, SEQ ID NO:2 for the amino acid sequence of wild-type M2Y polymerase, SEQ ID NO:3 for the amino acid sequence of wild-type B103 polymerase, SEQ ID NO:4 for the amino acid sequence of wild-type GA-1 polymerase, SEQ ID NO:5 for the amino acid sequence of wild-type AV-1 polymerase, and SEQ ID NO:6 for the amino acid sequence of wild-type CP-1 polymerase.

In addition to wild-type polymerases, chimeric polymerases made from a mosaic of different sources can be used. For example, Φ29-type polymerases made by taking sequences from more than one parental polymerase into account can be used as a starting point for mutation to produce the polymerases of the invention Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, a M2 polymerase, a B103 polymerase, and a GA-1 polymerase, can be generated. Appropriate mutations to increase phototolerance and/or alter another desirable property as described herein can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branching fraction and translocation (e.g., U.S. patent application publication 2010-0075332 by Pranav Patel et al. entitled "ENGINEERING POLYMERASES AND REACTION CONDITIONS FOR MODIFIED INCORPORATION PROPERTIES"), to increase photostability (e.g., U.S. patent application publication 2010-0093555 ENZYMES RESISTANT TO PHOTODAMAGE by Keith Bjornson et al.), to slow one or more catalytic steps during the polymerase kinetic cycle, increase closed complex stability, decrease branching fraction, alter cofactor selectivity, and increase yield, thermostability, accuracy, speed, and readlength (e.g., U.S. patent application publication 2010-0112645 GENERATION OF MODIFIED POLYMERASES FOR IMPROVED ACCURACY IN SINGLE MOLECULE SEQUENCING by Sonya Clark et al., U.S. patent application publication 2011-0189659 GENERATION OF MODIFIED POLYMERASES FOR IMPROVED ACCURACY IN SINGLE MOLECULE SEQUENCING by Sonya Clark et al., and U.S. patent application publication 2012-0034602 RECOMBINANT POLYMERASES FOR IMPROVED SINGLE MOLECULE SEQUENCING), and to improve surface-immobilized enzyme activities (e.g., WO 2007/075987 ACTIVE SURFACE COUPLED POLYMERASES by Hanzel et al. and WO 2007/075873 PROTEIN ENGINEERING STRATEGIES TO OPTIMIZE ACTIVITY OF SURFACE ATTACHED PROTEINS by Hanzel et al.). Any of these available polymerases can be modified in accordance with the invention.

Nucleotide Analogs

As discussed, various polymerases of the invention can incorporate one or more nucleotide analogs into a growing oligonucleotide chain. Upon incorporation, the analog can leave a residue that is the same as or different than a natural nucleotide in the growing oligonucleotide (the polymerase can incorporate any non-standard moiety of the analog, or can cleave it off during incorporation into the oligonucleotide). A "nucleotide analog" herein is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, i.e., other than A, G, C, T, or U, though upon incorporation into the oligonucleotide, the resulting residue in the oligonucleotide can be the same as (or different from) an A, G, C, T, or U residue.

In one useful aspect of the invention, nucleotide analogs can also be modified to achieve any of the improved properties desired. For example, various linkers or other substituents can be incorporated into analogs that have the effect of reducing branching fraction, improving processivity, or altering rates. Modifications to the analogs can include extending the phosphate chains, e.g., to include a tetra-, penta-, hexa- or heptaphosphate group, and/or adding chemical linkers to extend the distance between the nucleotide base and the dye molecule, e.g., a fluorescent dye molecule. Substitution of one or more non-bridging oxygen in the polyphosphate, for example with S or $BH_3$, can change the polymerase reaction kinetics, e.g., to achieve a system having two slow steps as described hereinbelow. Optionally, one or more, two or more, three or more, or four or more non-bridging oxygen atoms in the polyphosphate group of the analog has an S substituted for an O. While not being bound by theory, it is believed that the properties of the nucleotide, such as the metal chelation properties, electronegativity, or steric properties, can be altered by substitution of the non-bridging oxygen(s).

Many nucleotide analogs are available and can be incorporated by the polymerases of the invention. These include analog structures with core similarity to naturally occurring nucleotides, such as those that comprise one or more substituent on a phosphate, sugar, or base moiety of the nucleoside or nucleotide relative to a naturally occurring nucleoside or nucleotide. In one embodiment, the nucleotide analog includes three phosphate containing groups; for example, the analog can be a labeled nucleoside triphosphate analog and/or an α-thiophosphate nucleotide analog having three phosphate groups. In one embodiment, a nucleotide analog can include one or more extra phosphate containing groups, relative to a nucleoside triphosphate. For example, a variety of nucleotide analogs that comprise, e.g., from 4-6 or more phosphates are described in detail in U.S. patent application publication 2007-0072196, incorporated herein by reference in its entirety for all purposes. Other exemplary useful analogs, including tetraphosphate and pentaphosphate analogs, are described in U.S. Pat. No. 7,041,812, incorporated herein by reference in its entirety for all purposes.

For example, the analog can include a labeled compound of the formula:

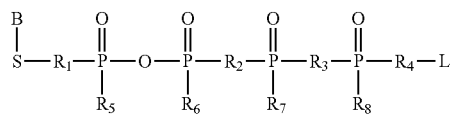

wherein B is a nucleobase (and optionally includes a label); S is selected from a sugar moiety, an acyclic moiety or a carbocyclic moiety (and optionally includes a label); L is an optional detectable label; $R_1$ is selected from O and S; $R_2$, $R_3$ and $R_4$ are independently selected from O, NH, S, methylene, substituted methylene, C(O), $C(CH_2)$, $CNH_2$, $CH_2CH_2$, $C(OH)CH_2R$ where R is 4-pyridine or 1-imidazole, provided that $R_4$ may additionally be selected from

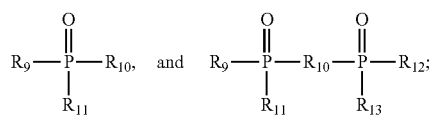

$R_5$, $R_6$, $R_7$, $R_8$, $R_{11}$ and $R_{13}$ are, when present, each independently selected from O, $BH_3$, and S; and $R_9$, $R_{10}$ and $R_{12}$ are independently selected from O, NH, S, methylene, substituted methylene, $CNH_2$, $CH_2CH_2$, and $C(OH)CH_2R$ where R is 4-pyridine or 1-imidazole. In some cases, phosphonate analogs may be employed as the analogs, e.g., where one of $R_2$, $R_3$, $R_4$, $R_9$, $R_{10}$ or $R_{12}$ are not O, e.g., they are methyl etc. See, e.g., U.S. patent application publication 2007-0072196, previously incorporated herein by reference in its entirety for all purposes.

The base moiety incorporated into the analog is generally selected from any of the natural or non-natural nucleobases or nucleobase analogs, including, e.g., purine or pyrimidine bases that are routinely found in nucleic acids and available nucleic acid analogs, including adenine, thymine, guanine, cytidine, uracil, and in some cases, inosine. As noted, the base optionally includes a label moiety. For convenience, nucleotides and nucleotide analogs are generally referred to based upon their relative analogy to naturally occurring nucleotides. As such, an analog that operates, functionally, like adenosine triphosphate may be generally referred to herein by the shorthand letter A. Likewise, the standard abbreviations of T, G, C, U and I may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In the analogs, the S group is optionally a sugar moiety that provides a suitable backbone for a synthesizing nucleic acid strand. For example, the sugar moiety is optionally selected from a D-ribosyl, 2' or 3' D-deoxyribosyl, 2',3'-D-dideoxyribosyl, 2', 3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties can be incorporated as the "S" group in place of a sugar moiety, including, e.g., those described in U.S. Patent Application Publication No. 2003/0124576, which is incorporated herein by reference in its entirety for all purposes.

For most cases, the phosphorus containing chain in the analogs, e.g., a triphosphate in conventional NTPs, is preferably coupled to the 5' hydroxyl group, as in natural nucleoside triphosphates. However, in some cases, the phosphorus containing chain is linked to the S group by the 3' hydroxyl group.

L generally refers to a detectable labeling group that is coupled to the terminal phosphorus atom via the $R_4$ (or $R_{10}$ or $R_{12}$ etc.) group. The labeling groups employed in the analogs of the invention may comprise any of a variety of detectable labels. Detectable labels generally denote a chemical moiety that provides a basis for detection of the analog compound separate and apart from the same compound lacking such a labeling group. Examples of labels include, e.g., optical labels, e.g., labels that impart a detectable optical property to the analog, electrochemical labels, e.g., labels that impart a detectable electrical or electrochemical property to the analog, and physical labels, e.g., labels that impart a different physical or spatial property to the analog, e.g., a mass tag or molecular volume tag. In some cases individual labels or combinations may be used that impart more than one of the aforementioned properties to the analogs of the invention.

Optionally, the labeling groups incorporated into the analogs comprise optically detectable moieties, such as luminescent, chemiluminescent, fluorescent, fluorogenic, chromophoric and/or chromogenic moieties, with fluorescent and/or fluorogenic labels being preferred. A variety of different label moieties are readily employed in nucleotide analogs. Such groups include, e.g., fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen, Inc. and described in 'The Handbook—A Guide to Fluorescent Probes and Labeling Technologies, Eleventh Edition' (2010) (available from Invitrogen, Inc./Molecular Probes). A variety of other fluorescent and fluorogenic labels for use with nucleoside polyphosphates, and which would be applicable to the nucleotide analogs incorporated by the polymerases of the present invention, are described in, e.g., U.S. Patent Application Publication No. 2003/0124576, previously incorporated herein by reference in its entirety for all purposes.

Additional details regarding labels, analogs, and methods of making such analogs can be found in U.S. patent application publication 2007-0072196, WO 2007/041342 Labeled Nucleotide Analogs and Uses Therefor, WO 2009/114182 Labeled Reactants and Their Uses, U.S. patent application publication 2009-0208957 Alternate Labelling Strategies for Single Molecule Sequencing, U.S. patent application Ser. No. 13/218,412 Functionalized Cyanine Dyes, U.S. patent application Ser. No. 13/218,395 Functionalized Cyanine Dyes, U.S. patent application Ser. No. 13/218,428 Cyanine Dyes, and U.S. patent application Ser. No. 13/218,382 Scaffold-Based Polymerase Enzyme Substrates, each of which is incorporated herein by reference in its entirety for all purposes.

Thus, in one illustrative example, the analog can be a phosphate analog (e.g., an analog that has more than the typical number of phosphates found in nucleoside triphosphates) that includes, e.g., an Alexa dye label. For example, an Alexa488 dye can be labeled on a delta phosphate of a tetraphosphate analog (denoted, e.g., A488dC4P or A488dA4P, shown in FIG. 2, for the Alexa488 labeled tetraphosphate analogs of C and A, respectively), or an Alexa568 or Alexa633 dye can be used (e.g., A568dC4P and A633dC4P, respectively, for labeled tetraphosphate analogs of C or A568dT6P for a labeled hexaphosphate analog of T), or an Alexa546 dye can be used (e.g., A546dG4P), or an Alexa594 dye can be used (e.g., A594dT4P). As additional examples, an Alexa555 dye (e.g., A555dC6P or A555dA6P), an Alexa 647 dye (e.g., A647dG6P), an Alexa 568 dye (e.g., A568dT6P), and/or an Alexa660 dye (e.g., A660dA6P or A660dC6P) can be used in, e.g., single molecule sequencing. Similarly, to facilitate color separation, a pair of fluorophores exhibiting FRET (fluorescence resonance energy transfer) can be labeled on a delta phosphate of a tetraphosphate analog (denoted, e.g., FAM-amb-A532dG4P or FAM-amb-A594dT4P).

Applications for Enhanced Nucleic Acid Amplification and Sequencing

Polymerases of the invention, e.g., modified recombinant polymerases, are optionally used in combination with nucleotides and/or nucleotide analogs and nucleic acid templates (e.g., DNA, RNA, or hybrids, analogs, derivatives, or mimetics thereof) to copy the template nucleic acid. That is, a mixture of the polymerase, nucleotides/analogs, and optionally other appropriate reagents, the template and a replication initiating moiety (e.g., primer) is reacted such that the polymerase synthesizes nucleic acid (e.g., extends the primer) in a template-dependent manner. The replication initiating moiety can be a standard oligonucleotide primer, or, alternatively, a component of the template, e.g., the template can be a self-priming single stranded DNA, a nicked double stranded DNA, or the like. Similarly, a terminal protein can serve as an initiating moiety. At least one nucleotide analog can be incorporated into the DNA. The template DNA can be a linear or circular DNA, and in certain applications, is desirably a circular template (e.g., for rolling circle replication or for sequencing of circular templates). Optionally, the composition can be present in an automated DNA replication and/or sequencing system.

Incorporation of labeled nucleotide analogs by the polymerases of the invention is particularly useful in a variety of different nucleic acid analyses, including real-time monitoring of DNA polymerization. The label can itself be incorporated, or more preferably, can be released during incorporation of the analog. For example, analog incorporation can be monitored in real-time by monitoring label release during incorporation of the analog by the polymerase. The portion of the analog that is incorporated can be the same as a natural nucleotide, or can include features of the analog that differ from a natural nucleotide.

In general, label incorporation or release can be used to indicate the presence and composition of a growing nucleic acid strand, e.g., providing evidence of template replication/amplification and/or sequence of the template. Signaling from the incorporation can be the result of detecting labeling groups that are liberated from the incorporated analog, e.g., in a solid phase assay, or can arise upon the incorporation reaction. For example, in the case of FRET labels where a bound label is quenched and a free label is not, release of a label group from the incorporated analog can give rise to a fluorescent signal. Alternatively, the enzyme may be labeled with one member of a FRET pair proximal to the active site, and incorporation of an analog bearing the other member will allow energy transfer upon incorporation. The use of enzyme bound FRET components in nucleic acid sequencing applications is described, e.g., in U.S. Patent Application Publication No. 2003/0044781, incorporated herein by reference.

In one example reaction of interest, a polymerase reaction can be isolated within an extremely small observation volume that effectively results in observation of individual polymerase molecules. As a result, the incorporation event provides observation of an incorporating nucleotide analog that is readily distinguishable from non-incorporated nucleotide analogs. In a preferred aspect, such small observation volumes are provided by immobilizing the polymerase enzyme within an optical confinement, such as a Zero Mode Waveguide (ZMW). For a description of ZMWs and their application in single molecule analyses, and particularly nucleic acid sequencing, see, e.g., U.S. Patent Application Publication No. 2003/0044781 and U.S. Pat. No. 6,917,726, each of which is incorporated herein by reference in its entirety for all purposes. See also Levene et al. (2003) "Zero-mode waveguides for single-molecule analysis at high concentrations" Science 299:682-686, Eid et al. (2009) "Real-time DNA sequencing from single polymerase molecules" Science 323:133-138, and U.S. Pat. Nos. 7,056,676, 7,056,661, 7,052,847, and 7,033,764, the full disclosures of which are incorporated herein by reference in their entirety for all purposes.

In general, a polymerase enzyme is complexed with the template strand in the presence of one or more nucleotides and/or one or more nucleotide analogs. For example, in certain embodiments, labeled analogs are present representing analogous compounds to each of the four natural nucleotides, A, T, G and C, e.g., in separate polymerase reactions, as in classical Sanger sequencing, or multiplexed together, e.g., in a single reaction, as in multiplexed sequencing approaches. When a particular base in the template strand is encountered by the polymerase during the polymerization reaction, it complexes with an available analog that is complementary to such nucleotide, and incorporates that analog into the nascent and growing nucleic acid strand. In one aspect, incorporation can result in a label being released, e.g., in polyphosphate analogs, cleaving between the α and β phosphorus atoms in the analog, and consequently releasing the labeling group (or a portion thereof). The incorporation event is detected, either by virtue of a longer presence of the analog and, thus, the label, in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide. For additional information on single molecule sequencing monitoring incorporation of phosphate-labeled analogs in real time, see, e.g., Eid et al. (2009) "Real-time DNA sequencing from single polymerase molecules" Science 323:133-138.

Figure 3A:
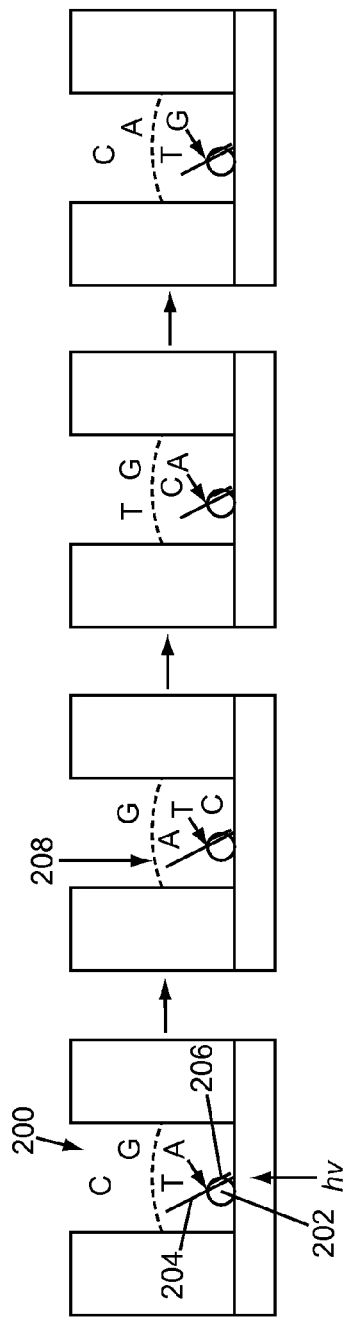
FIGS. 3A-3B schematically illustrate an exemplary single molecule sequencing by incorporation process in which the compositions of the invention provide particular advantages.

In a first exemplary technique, as schematically illustrated in FIG. 3A, a nucleic acid synthesis complex, including a polymerase enzyme 202, a template sequence 204 and a complementary primer sequence 206, is provided immobilized within an observation region 200 that permits illumination (as shown by hv) and observation of a small volume that includes the complex without excessive illumination of the surrounding volume (as illustrated by dashed line 208). By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume.

Figure 3B:
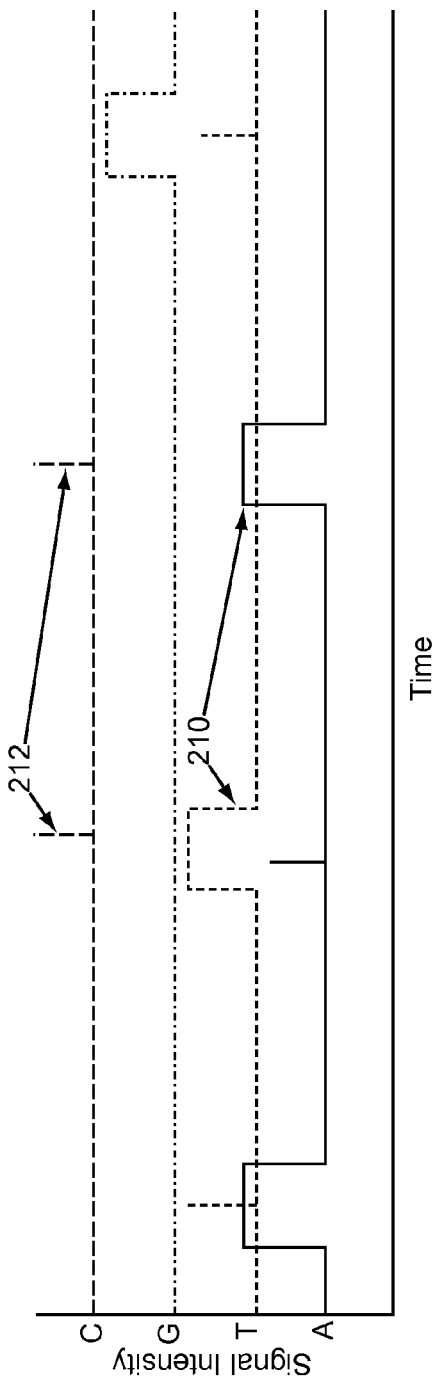

In particular, as shown in FIG. 3B, when a nucleotide, e.g., A, is incorporated into DNA by the polymerase, it is retained within the observation volume for a prolonged period of time, and upon continued illumination yields a prolonged fluorescent signal (shown by peak 210). By comparison, randomly diffusing and not incorporated nucleotides remain within the observation volume for much shorter periods of time, and thus produce only transient signals (such as peak 212), many of which go undetected due to their extremely short duration.

In particularly preferred exemplary systems, the confined illumination volume is provided through the use of arrays of optically confined apertures termed zero mode waveguides (ZMWs), e.g., as shown by confined reaction region 200 (see, e.g., U.S. Pat. No. 6,917,726, which is incorporated herein by reference in its entirety for all purposes). For sequencing applications, the DNA polymerase is typically provided immobilized upon the bottom of the ZMW, although another component of the complex (e.g., a primer or template) is optionally immobilized on the bottom of the ZMW to localize the complex. See, e.g., Korlach et al. (2008) PNAS U.S.A. 105(4):1176-1181 and U.S. patent application publication 2008-0032301, each of which is incorporated herein by reference in its entirety for all purposes.

In operation, the fluorescently labeled nucleotides (shown as A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuse away from the complex following incorporation of the associated nucleotide, nor do such labels interfere with the incorporation event. See, e.g., Korlach et al. (2008) Nucleosides, Nucleotides and Nucleic Acids 27:1072-1083.

Figure 4:
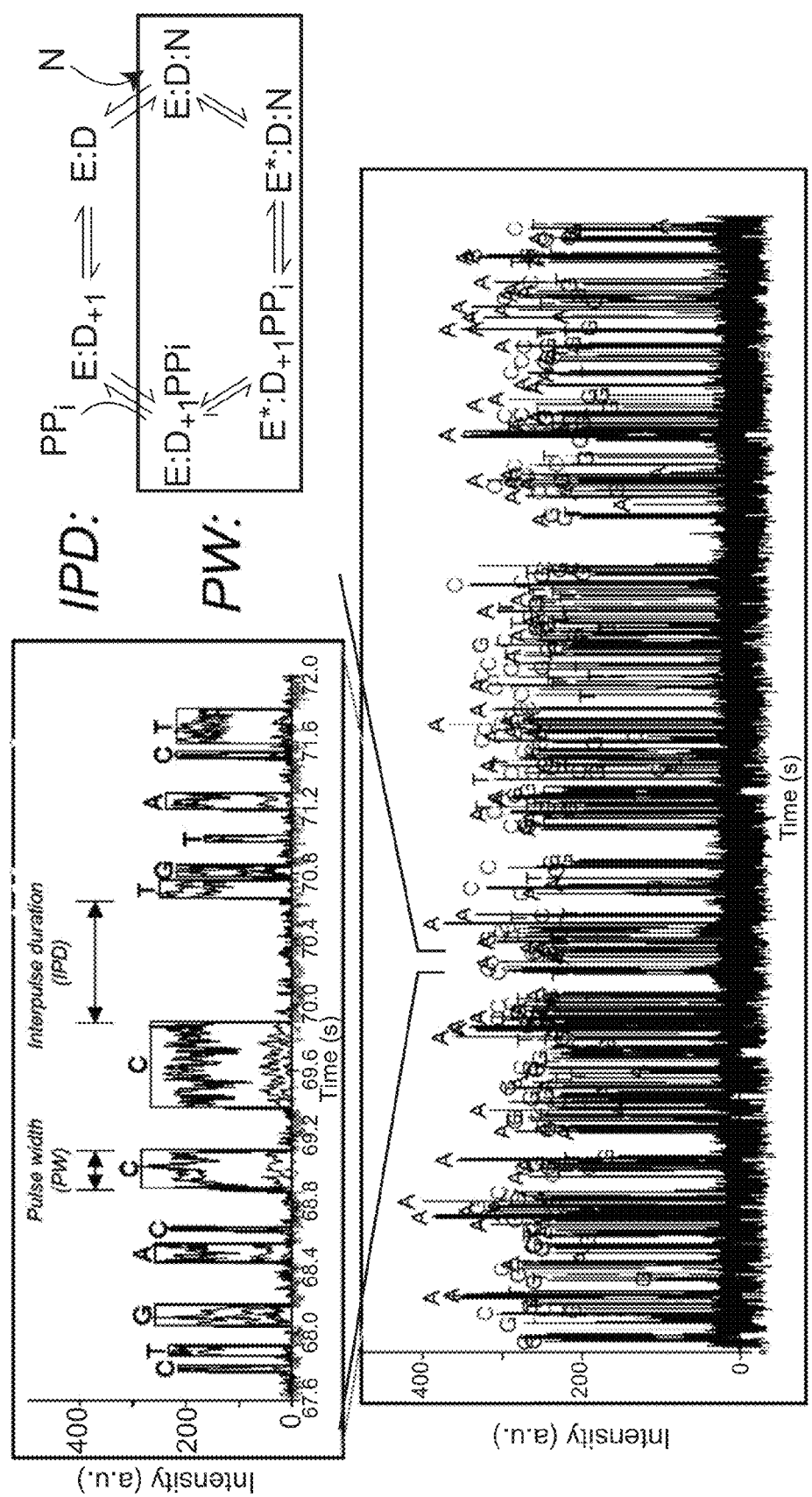
FIG. 4 presents a fluorescence time trace for a ZMW, showing pulses representing incorporation of different nucleotide analogs. The inset schematically illustrates the catalytic cycle for polymerase-mediated extension; the box indicates the portion of the catalytic cycle that corresponds to the pulse when sequencing is performed with phosphate-labeled nucleotide analogs.

A fluorescence time trace for a ZMW, showing pulses (peaks) representing incorporation of different nucleotide analogs, is presented in FIG. 4. A pulse width and interpulse distance are illustrated on the trace. The inset schematically illustrates the catalytic cycle for polymerase-mediated nucleic acid primer extension according to the exemplary reaction scheme described in U.S. patent application publication 2012-0034602; the box indicates the portion of the catalytic cycle that corresponds to the pulse when sequencing is performed with phosphate-labeled nucleotide analogs. The remainder of the cycle corresponds to the interpulse distance.

In a second exemplary technique, the immobilized complex and the nucleotides to be incorporated are each provided with interactive labeling components. Upon incorporation, the nucleotide borne labeling component is brought into sufficient proximity to the complex borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal quenching. Upon incorporation and cleavage of the terminal phosphate groups, e.g., bearing a donor fluorophore, the quenching is removed and the resulting characteristic fluorescent signal of the donor is observable.

In exploiting the foregoing processes, where the incorporation reaction occurs too rapidly, it may result in the incorporation event not being detected, i.e., the event speed exceeds the detection speed of the monitoring system. The missed detection of incorporated nucleotides can lead to an increased rate of errors in sequence determination, as omissions in the real sequence. In order to mitigate the potential for missed pulses due to short reaction or product release times, in one aspect, the current invention can result in increased reaction and/or product release times during incorporation cycles. Similarly, very short interpulse distances can occasionally cause pulse merging. An advantage of employing polymerases with reduced reaction rates, e.g., polymerases exhibiting decreased rates and/or two slow-step kinetics as described in U.S. patent application publications 2009-0286245 and 2010-0112645, is an increased frequency of longer, detectable, binding events. This advantage may also be seen as an increased ratio of longer, detectable pulses to shorter, non-detectable pulses, where the pulses represent binding events.

In addition to their use in sequencing, the polymerases of the invention are also useful in a variety of other genotyping analyses, e.g., SNP genotyping using single base extension methods, real time monitoring of amplification, e.g., RT-PCR methods, and the like. The polymerases of the invention are also useful in amplifying nucleic acids, e.g., DNAs or RNAs, including, for example, in applications such as whole genome amplification. For example, polymerases of the invention that show increased thermostability or resistance to organic solvents (e.g., DMSO), or that otherwise exhibit an improved ability to read through damaged, modified, or other "difficult" stretches of nucleic acid template, can be suitably employed in whole genome amplification. For review of whole genome amplification, see, e.g., Silander and Saarela (2008) "Whole Genome Amplification with Phi29 DNA Polymerase to Enable Genetic or Genomic Analysis of Samples of Low DNA Yield" Methods in Molecular Biology 439:1-18 and Pinard et al. (2006) "Assessment of whole genome amplification-induced bias through high-throughput, massively parallel whole genome sequencing" BMC Genomics 7:216. Further details regarding sequencing and nucleic acid amplification can be found, e.g., in Sambrook, Ausubel, and Innis, all infra.

Recombinant Polymerases with Increased Phototolerance

The compositions of the invention comprise a modified recombinant DNA polymerase which exhibits one or more altered properties desirable in single molecule sequencing applications or other applications involving nucleic acid synthesis. An exemplary property of certain polymerases of the invention is increased phototolerance relative to a wild-type or parental polymerase. Other exemplary properties include altered kinetic behavior (e.g., demonstration of slow catalytic steps), exonuclease deficiency, increased closed complex stability, altered (e.g., reduced) branching fraction, altered cofactor selectivity, increased yield, increased thermostability, increased accuracy, increased speed, and increased readlength.

As will be understood, polymerases of the invention can display one of the aforementioned properties alone or can display two or more of the properties in combination. Moreover, it will be understood that while a polymerase or group of polymerases may be described with respect to a particular property, the polymerase(s) may possess additional modified properties not mentioned in every instance for ease of discussion. It will also be understood that particular properties are observed under certain conditions. For example, a photoprotective mutation can, e.g., confer increased readlength (as compared to a parental polymerase lacking the mutation) when observed with an excitation light source at a constant power or it can confer increased accuracy at a higher power. A single mutation (e.g., a single amino acid substitution, deletion, insertion, or the like) may give rise to the one or more altered properties, or the one or more properties may result from two or more mutations which act in concert to confer the desired activity. The recombinant polymerases, mutations, and altered properties exhibited by the recombinant polymerases are set forth in greater detail below.

Detection of optical labels in an enzymatic reaction generally entails directing excitation radiation at the reaction mixture to excite a labeling group present in the mixture, which is then separately detectable. However, prolonged exposure of chemical and biochemical reactants to radiation (e.g., light) energy during the excitation and detection of optical labels can damage components of the reaction mixture, e.g., enzymes, proteins, substrates, or the like. For example, it has been observed that, in template-directed synthesis of nucleic acids from fluorescently labeled nucleotides or nucleotide analogs, sustained exposure of the DNA polymerase to excitation radiation used in the detection of the relevant label (e.g., fluorophore) reduces the enzyme's processivity and polymerase activity. Although illuminated reactions typically proceed under conditions where the reactants (e.g., enzyme molecules, etc.) are present in excess such that any adverse effects of photodamage on any single enzyme molecule in the reaction mix do not, in general, affect operation of the assay, an increasing number of analyses that entail the use of optical labels are performed with reactants at very low concentrations. For example, polymerases can be used to synthesize DNAs from fluorescently labeled nucleotide analogs in microfluidic or nanofluidic reaction vessels or channels or in optically confined reaction volumes, e.g., in a zero-mode waveguide (ZMW) or ZMW array as described above. Analysis of small, single-analyte reaction volumes is becoming increasingly important in high-throughput applications, e.g., in DNA sequencing. However, in such reactant-limited analyses, any degradation of a critical reagent such as an enzyme molecule due to photodamage can dramatically interfere with the analysis.

Polymerases that exhibit decreased sensitivity to photodamage (increased phototolerance) are thus desirable for use in a variety of single- or low-number enzyme analyses, including, but not limited to, DNA sequencing (e.g., single molecule sequencing), nucleic acid amplification, and others. Exemplary approaches to producing polymerases with increased resistance to photodamage by, e.g., replacing residues susceptible to oxidative damage have been described in U.S. patent application publication 2010-0093555. Additional approaches are described below.

Figure 5:
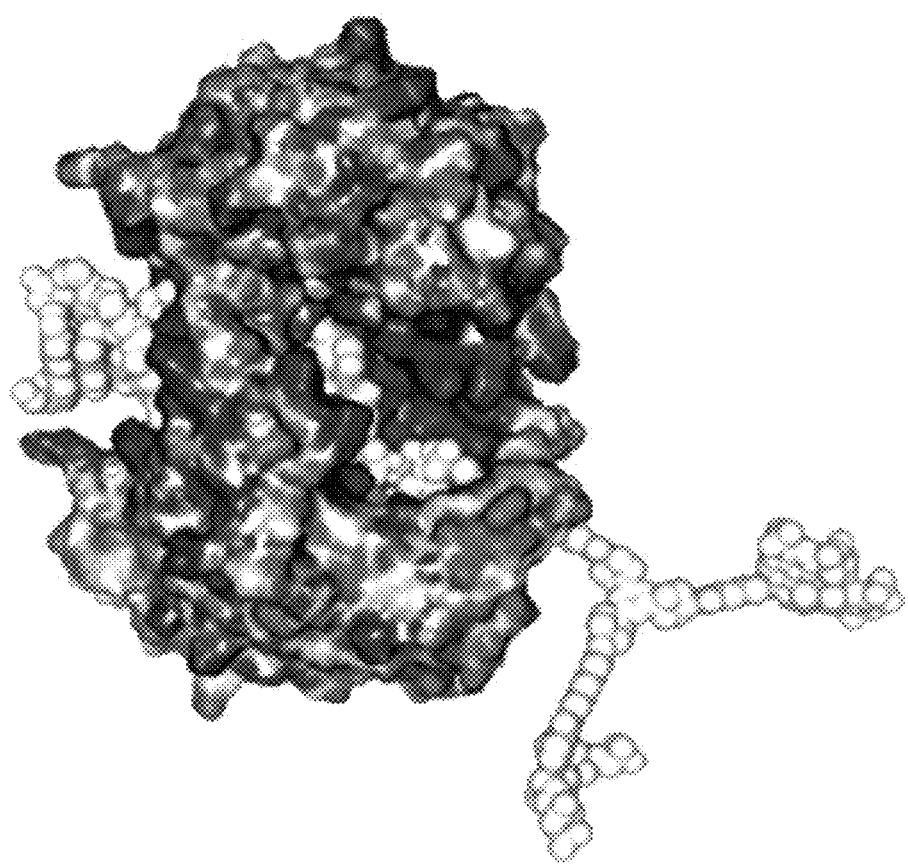
FIG. 5 depicts the electrostatic surface of Φ29 polymerase with a bound phosphate-labeled hexaphosphate analog.
Figure 6:
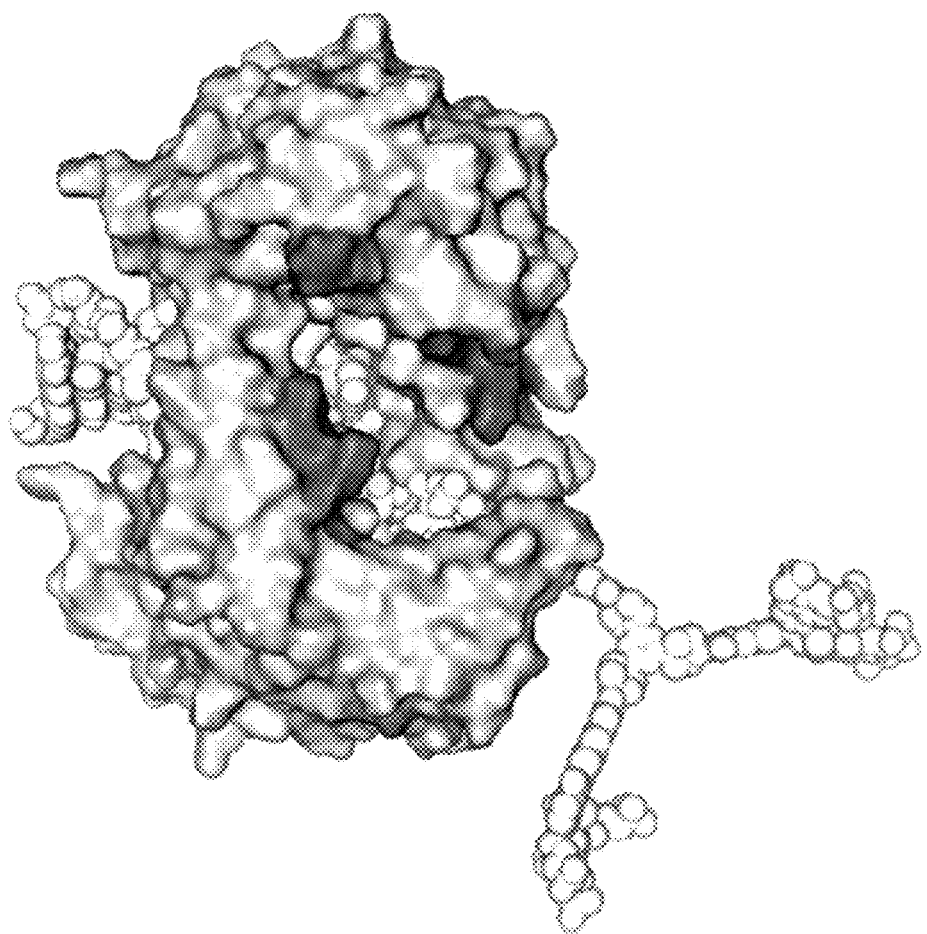
FIG. 6 depicts the location of exemplary residues that can be mutated to reduce positive surface charge of Φ29 polymerase without loss of sequence performance.

Without limitation to any particular mechanism, observation of polymerase performance in single molecule sequencing reactions using labeled nucleotide analogs has revealed that, in many instances, photodamage involves collision of the dye moiety of an analog with the polymerase followed by cros slink formation between the dye and the polymerase. A novel approach to increasing polymerase phototolerance thus involves reducing the frequency of such collisions. In one approach, again without limitation to any particular mechanism, since the nucleotide analog is negatively charged, the frequency of collisions between the polymerase and the label is reduced by introducing negative charges to and/or removing positive charges from the surface of the polymerase that is within reach of the dye moiety. An electrostatic surface representation of Φ29 polymerase with a bound analog is shown in FIG. 5 (dark gray is positively charged surface, and medium gray is negatively charged). It will be evident that residues playing an essential role in nucleotide binding and/or catalysis are not preferred sites for substitution. Exemplary locations where positive surface charge can be reduced without loss of performance in sequencing reactions are shown in dark gray in FIG. 6.

Positions of particular interest include, e.g., K131, K132, K135, H149, G197, I201, K205, K206, K472, K536, and K539, where positions are identified relative to wild-type Φ29 polymerase (SEQ ID NO:1). To produce a polymerase with increased phototolerance, a residue at one (or more) of these positions can be substituted with another residue, preferably a non-positively charged residue (e.g., a negatively charged residue such as Asp or Glu, or an uncharged polar residue, e.g., Asn, Gln, or Ser). Suitable substitutions at these positions include, for example, K131E, K131Q, K131S, K131D, K131A, K131H, K131L, K131Y, K131I, K131N, K131C, K131F, K131G, K131P, K131R, K131T, K131V, K131W, K135Q, K135S, K135N, H149D, G197D, G197E, I201E, K205E, K205D, K205A, K206E, K472A, K536Q, and K539Q.

Decreasing the overall positive surface charge on the polymerase in the vicinity of the analog binding pocket can, however, affect binding rate of the analog, resulting in undesirably lengthened interpulse distances or the like. Increasing positive charge in areas of the polymerase's surface that are less accessible to the dye moiety can compensate for this effect by narrowing interpulse distances and increasing polymerase speed. (It will be evident that such mutations can be employed to increase speed regardless of the presence or absence of mutations that decrease speed while increasing phototolerance.)

Positions of particular interest include, e.g., V141, L142, I504, E508, D510, L513, and D523, where positions are identified relative to wild-type Φ29 polymerase (SEQ ID NO:1). To increase the overall positive surface charge, a residue at one or more of these positions can be substituted with another residue, e.g., with an uncharged residue where the residue was originally negatively charged, or more preferably, with a positively charged residue (e.g., Lys, His, or Arg). Suitable substitutions at these positions include, for example, V141K, L142K, E508K, D510S, and D510K.

As will be appreciated, recombinant polymerases that exhibit increased phototolerance and/or speed can also include additional mutations (e.g., amino acid substitutions, deletions, insertions, exogenous features at the N- and/or C-terminus, and/or the like) which confer one or more additional desirable properties, e.g., reduced or eliminated exonuclease activity, convenient surface immobilization, increased closed complex stability, reduced or increased branching, selectivity for particular metal cofactors, increased yield, increased thermostability, increased accuracy, increased speed, and/or increased readlength.

Design and Characterization of Recombinant Polymerases

In addition to methods of using the polymerases and other compositions herein, the present invention also includes methods of making the polymerases. (Polymerases made by the methods are also a feature of the invention, and it will be evident that, although various design strategies are detailed herein, no limitation of the resulting polymerases to any particular mechanism is thereby intended.) As described, methods of making a recombinant DNA polymerase can include structurally modeling a parental polymerase, e.g., using any available crystal structure and molecular modeling software or system. Based on the modeling, one or more amino acid residue positions in the polymerase are identified as targets for mutation. For example, one or more feature affecting phototolerance, closed complex stability, nucleotide access to or removal from the active site (and, thereby, branching), binding of a DNA or nucleotide analog, product binding, etc. is identified. These residues can be, e.g., in the active site or a binding pocket or in a domain such as the exonuclease, TPR2 or thumb domain (or interface between domains) or proximal to such domains. The DNA polymerase is mutated to include different residues at such positions (e.g., another one of the nineteen other commonly occurring natural amino acids or a non-natural amino acid, e.g., a nonpolar and/or aliphatic residue, a polar uncharged residue, an aromatic residue, a positively charged residue, or a negatively charged residue), and then screened for an activity of interest (e.g., phototolerance, processivity, $k_{off}$, $K_d$, branching fraction, decreased rate constant, balanced rate constants, accuracy, speed, thermostability, yield, cofactor selectivity, etc.). It will be evident that catalytic and/or highly conserved residues are typically (but not necessarily) less preferred targets for mutation.

Further, as noted above, a polymerase of the invention (e.g., a Φ29-type DNA polymerase that includes E375, K512, L253, and/or A484 mutations) can be further modified to enhance the properties of the polymerase. For example, a polymerase comprising a combination of the above mutations can be mutated at one or more additional sites to enhance a property already possessed by the polymerase or to confer a new property not provided by the existing mutations. Details correlating polymerase structure with desirable functionalities that can be added to polymerases of the invention are provided herein. Also provide below are various approaches for modifying/mutating polymerases of the invention, determining kinetic parameters or other properties of the modified polymerases, screening modified polymerases, and adding exogenous features to the N- and/or C-terminal regions of the polymerases.

Structure-Based Design of Recombinant Polymerases

Structural data for a polymerase can be used to conveniently identify amino acid residues as candidates for mutagenesis to create recombinant polymerases, for example, having modified active site regions and/or modified domain interfaces to increase phototolerance, reduce reaction rates, reduce branching, improve complex stability, reduce exonuclease activity, alter cofactor selectivity, increase stability, improve yield, or confer other desirable properties. For example, analysis of the three-dimensional structure of a polymerase such as Φ29 can identify residues that are in the active polymerization site of the enzyme, residues that form part of the nucleotide analog binding pocket, and/or amino acids at an interface between domains.

The three-dimensional structures of a large number of DNA polymerases have been determined by x-ray crystallography and nuclear magnetic resonance (NMR) spectroscopy, including the structures of polymerases with bound templates, nucleotides, and/or nucleotide analogs. Many such structures are freely available for download from the Protein Data Bank, at (www(dot)rcsb(dot)org/pdb. Structures, along with domain and homology information, are also freely available for search and download from the National Center for Biotechnology Information's Molecular Modeling DataBase, at www(dot)ncbi(dot)nlm(dot)nih(dot)gov/Structure/MMDB/mmdb(dot)shtml. The structures of Φ29 polymerase, Φ29 polymerase complexed with terminal protein, and Φ29 polymerase complexed with primer-template DNA in the presence and absence of a nucleoside triphosphate are available; see Kamtekar et al. (2004) "Insights into strand displacement and processivity from the crystal structure of the protein-primed DNA polymerase of bacteriophage Φ29" Mol. Cell 16(4): 609-618), Kamtekar et al. (2006) "The phi29 DNA polymerase:protein-primer structure suggests a model for the initiation to elongation transition" EMBO J. 25(6): 1335-43, and Berman et al. (2007) "Structures of phi29 DNA polymerase complexed with substrate: The mechanism of translocation in B-family polymerases" EMBO J. 26:3494-3505, respectively. The structures of additional polymerases or complexes can be modeled, for example, based on homology of the polymerases with polymerases whose structures have already been determined. Alternatively, the structure of a given polymerase (e.g., a wild-type or modified polymerase), optionally complexed with a DNA (e.g., template and/or primer) and/or nucleotide analog, or the like, can be determined.

Techniques for crystal structure determination are well known. See, for example, McPherson (1999) *Crystallization of Biological Macromolecules* Cold Spring Harbor Laboratory; Bergfors (1999) Protein Crystallization International University Line; Mullin (1993) *Crystallization* Butterwoth-Heinemann; Stout and Jensen (1989) *X-ray structure determination: a practical guide, 2nd Edition* Wiley Publishers, New York; Ladd and Palmer (1993) *Structure determination by X-ray crystallography, 3rd Edition* Plenum Press, NewYork; Blundell and Johnson (1976) *Protein Crystallography* Academic Press, New York; Glusker and Trueblood (1985) *Crystal structure analysis: A primer, 2nd Ed*. Oxford University Press, NewYork; *International Tables for Crystallography, Vol. F. Crystallography of Biological Macromolecules*; McPherson (2002) *Introduction to Macromolecular Crystallography* Wiley-Liss; McRee and David (1999) *Practical Protein Crystallography, Second Edition* Academic Press; Drenth (1999) *Principles of Protein X-Ray Crystallography* (Springer Advanced Texts in Chemistry) Springer-Verlag; Fanchon and Hendrickson (1991) Chapter 15 of *Crystallographic Computing, Volume* 5 IUCr/Oxford University Press; Murthy (1996) Chapter 5 of *Crystallographic Methods and Protocols* Humana Press; Dauter et al. (2000) "Novel approach to phasing proteins: derivatization by short cryosoaking with halides" Acta Cryst.D56:232-237; Dauter (2002) "New approaches to high-throughput phasing" Curr. Opin. Structural Biol. 12:674-678; Chen et al. (1991) "Crystal structure of a bovine neurophysin-II dipeptide complex at 2.8 Å determined from the single-wavelength anomalous scattering signal of an incorporated iodine atom" Proc. Natl Acad. Sci. USA, 88:4240-4244; and Gavira et al. (2002) "Ab initio crystallographic structure determination of insulin from protein to electron density without crystal handling" Acta Cryst.D58:1147-1154.

In addition, a variety of programs to facilitate data collection, phase determination, model building and refinement, and the like are publicly available. Examples include, but are not limited to, the HKL2000 package (Otwinowski and Minor (1997) "Processing of X-ray Diffraction Data Collected in Oscillation Mode" Methods in Enzymology 276: 307-326), the CCP4 package (Collaborative Computational Project (1994) "The CCP4 suite: programs for protein crystallography" Acta Crystallogr D 50:760-763), SOLVE and RESOLVE (Terwilliger and Berendzen (1999) Acta Crystallogr D 55 (Pt 4):849-861), SHELXS and SHELXD (Schneider and Sheldrick (2002) "Substructure solution with SHELXD" Acta Crystallogr D Biol Crystallogr 58:1772-1779), Refmac5 (Murshudov et al. (1997) "Refinement of Macromolecular Structures by the Maximum-Likelihood Method" Acta Crystallogr D 53:240-255), PRODRG (van Aalten et al. (1996) "PRODRG, a program for generating molecular topologies and unique molecular descriptors from coordinates of small molecules" J Comput Aided Mol Des 10:255-262), and Coot (Elmsley et al. (2010) "Features and Development of Coot" Acta Cryst D 66:486-501.

Techniques for structure determination by NMR spectroscopy are similarly well described in the literature. See, e.g., Cavanagh et al. (1995) *Protein NMR Spectroscopy: Principles and Practice*, Academic Press; Levitt (2001) *Spin Dynamics: Basics of Nuclear Magnetic Resonance*, John Wiley & Sons; Evans (1995) *Biomolecular NMR Spectroscopy*, Oxford University Press; Wüthrich (1986) *NMR of Proteins and Nucleic Acids* (Baker Lecture Series), Kurt Wiley-Interscience; Neuhaus and Williamson (2000) *The Nuclear Overhauser Effect in Structural and Conformational Analysis,* 2nd Edition, Wiley-VCH; Macomber (1998) *A Complete Introduction to Modem NMR Spectroscopy*, Wiley-Interscience; Downing (2004) *Protein NMR Techniques* (Methods in Molecular Biology), 2nd edition, Humana Press; Clore and Gronenbom (1994) *NMR of Proteins* (Topics in Molecular and Structural Biology), CRC Press; Reid (1997) *Protein NMR Techniques*, Humana Press; Krishna and Berliner (2003) *Protein NMR for the Millenium* (Biological Magnetic Resonance), Kluwer Academic Publishers; Kiihne and De Groot (2001) *Perspectives on Solid State NMR in Biology* (Focus on Structural Biology, 1), Kluwer Academic Publishers; Jones et al. (1993) *Spectroscopic Methods and Analyses: NMR, Mass Spectrometry, and Related Techniques* (Methods in Molecular Biology, Vol. 17), Humana Press; Goto and Kay (2000) Curr. Opin. Struct. Biol. 10:585; Gardner (1998) Annu. Rev. Biophys. Biomol. Struct. 27:357; Wüthrich (2003) Angew. Chem. Int. Ed. 42:3340; Bax (1994) Curt Opin. Struct. Biol. 4:738; Pervushin et al. (1997) Proc. Natl. Acad. Sci. U.S.A. 94:12366; Fiaux et al. (2002) Nature 418: 207; Fernandez and Wider (2003) Curr. Opin. Struct. Biol. 13:570; Ellman et al. (1992) J. Am. Chem. Soc. 114:7959; Wider (2000) BioTechniques 29:1278-1294; Pellecchia et al. (2002) Nature Rev. Drug Discov. (2002) 1:211-219; Arora and Tamm (2001) Curr. Opin. Struct. Biol. 11:540-547; Flaux et al. (2002) Nature 418:207-211; Pellecchia et al. (2001) J. Am. Chem. Soc. 123:4633-4634; and Pervushin et al. (1997) Proc. Natl. Acad. Sci. USA 94:12366-12371.

The structure of a polymerase or of a polymerase bound to a DNA or with a given nucleotide analog incorporated into the active site can, as noted, be directly determined, e.g., by x-ray crystallography or NMR spectroscopy, or the structure can be modeled based on the structure of the polymerase and/or a structure of a polymerase with a natural nucleotide bound. The active site or other relevant domain of the polymerase can be identified, for example, by homology with other polymerases, examination of polymerase-template or polymerase-nucleotide co-complexes, biochemical analysis of mutant polymerases, and/or the like. The position of a nucleotide analog (as opposed to an available nucleotide structure) in the active site can be modeled, for example, by projecting the location of non-natural features of the analog (e.g., additional phosphate or phosphonate groups in the phosphorus containing chain linked to the nucleotide, e.g., tetra, penta or hexa phosphate groups, detectable labeling groups, e.g., fluorescent dyes, or the like) based on the previously determined location of another nucleotide or nucleotide analog in the active site.

Such modeling of the nucleotide analog or template (or both) in the active site can involve simple visual inspection of a model of the polymerase, for example, using molecular graphics software such as the PyMOL viewer (open source, freely available on the World Wide Web at www(dot)pymol (dot)org), Insight II, or Discovery Studio 2.1 (commercially available from Accelrys at (www (dot) accelrys (dot) com/ products/discovery-studio). Alternatively, modeling of the active site complex of the polymerase or a putative mutant polymerase, for example, can involve computer-assisted docking, molecular dynamics, free energy minimization, and/or like calculations. Such modeling techniques have been well described in the literature; see, e.g., Babine and Abdel-Meguid (eds.) (2004) *Protein Crystallography in Drug Design*, Wiley-VCH, Weinheim; Lyne (2002) "Structure-based virtual screening: An overview" Drug Discov. Today 7:1047-1055; Molecular Modeling for Beginners, at (www (dot) usm (dot) maine (dot) edu/~rhodes/SPVTut/index (dot) html; and Methods for Protein Simulations and Drug Design at (www (dot) dddc (dot) ac (dot) cn/embo04; and references therein. Software to facilitate such modeling is widely available, for example, the CHARMm simulation package, available academically from Harvard University or commercially from Accelrys (at www (dot) accelrys (dot) com), the Discover simulation package (included in Insight II, supra), and Dynama (available at (www(dot) cs (dot) gsu (dot) edu/ ~cscrwh/progs/progs (dot) html). See also an extensive list of modeling software at (www (dot) netsci (dot) org/Resources/ Software/Modeling/MMMD/top (dot) html.

Visual inspection and/or computational analysis of a polymerase model, including optional comparison of models of the polymerase in different states, can identify relevant features of the polymerase, including, for example, residues that can be mutated to increase phototolerance or polymerase speed, as detailed above.

In another example, residues from domains that are in close proximity to one another are mutated to alter inter-domain interactions. In Φ29, Q183 in the exonuclease domain can contact the back of the fingers domain (e.g., Q183 is close to I378, particularly when the fingers are open). Mutating this residue can thus alter the equilibrium between the open and closed conformations of the polymerase. A Q183F substitution, for example, significantly increases mean readlength, although it also reduces accuracy somewhat. This substitution can therefore be of interest in polymerases for applications where readlength is of greater priority than accuracy, e.g., for scaffolding genome assembly. Other substitutions at this position include, e.g., Q183W and Q183T (which also increase readlength), as well as Q183H.

Figure 8:
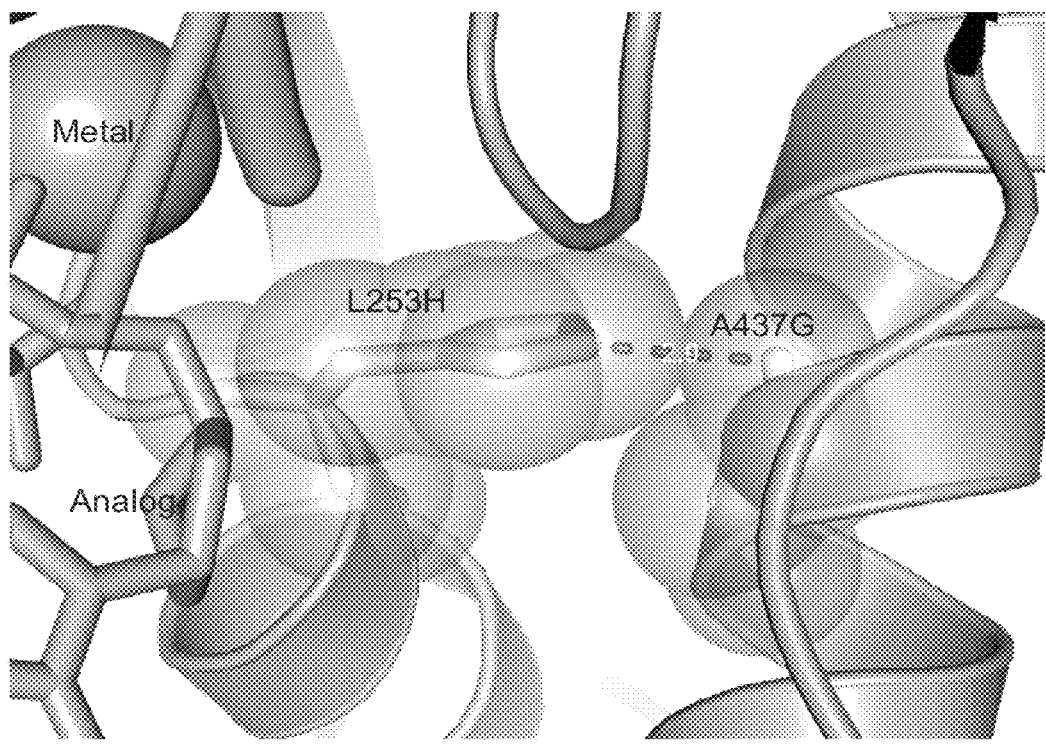
FIG. 8 shows a view in the vicinity of residues 253 and 437 of a recombinant Φ29 polymerase including D12A, D66A, Y224K, E239G, L253H, E375Y, A437G, A484E, D510K, and K512Y substitutions.

As described in U.S. patent application publication 2012-0034602, substitutions at position L253 of Φ29 can affect cofactor selectivity. Introducing an A437G substitution into the polymerase can increase polymerase speed and can also increase the range of useful substitutions at position L253. For example, a combination of L253H and A437G substitutions can reduce pulse width and pausing, increase readlength, and enhance $Mg^{++}$ tolerance. As shown in FIG. 8, examination of a crystal structure of a recombinant Φ29 polymerase including D12A, D66A, Y224K, E239G, L253H, E375Y, A437G, A484E, D510K, and K512Y substitutions reveals that the histidine at position 253 forms a hydrogen bond with the backbone carbonyl of residue 437. Formation of the hydrogen bond is enabled by the A437G substitution.

Substitution of V250 can also increase the range of functional substitutions at position L253. For example, replacement of valine at position 250 with a smaller residue, e.g., alanine, can accommodate a larger side chain at position L253. Exemplary combinations include, e.g., V250A with L253H or L253F. A V250A substitution can also increase readlength.

Amino acid sequence data, e.g., for members of a family of polymerases, can be used in conjunction with structural data to identify particular residues as candidates for mutagenesis. As one example, residues that differ between family members and that are close to the active site can be mutated. For example, as shown in FIG. 1, wild-type Φ29 has an alanine at position 256 while wild-type M2Y has a serine at the corresponding position (position 253 of M2Y, SEQ ID NO:2). Introducing an S253A substitution into M2Y, where positions are numbered with respect to SEQ ID NO:2, can increase readlength and decrease pulse width, improving performance in single molecule sequencing assays. An A256S substitution can be introduced into Φ29, where positions are numbered with respect to SEQ ID NO:1, e.g., to increase pulse width. As another example, wild-type Φ29 has a tyrosine at position 224 while wild-type M2Y has a lysine at the corresponding position (position 221 of M2Y, SEQ ID NO:2). A Y224K substitution can be introduced into Φ29, where positions are numbered with respect to SEQ ID NO:1, or a K221Y substitution can be introduced into M2Y, where positions are numbered with respect to SEQ ID NO:2.

Combining Mutations

As noted repeatedly, the various mutations described herein can be combined in recombinant polymerases of the invention. Combination of mutations can be random, or more desirably, guided by the properties of the particular mutations and the characteristics desired for the resulting polymerase. Additional mutations can also be introduced into a polymerase to compensate for deleterious effects of otherwise desirable mutations.

A large number of exemplary mutations and the properties they confer are described herein, and it will be evident that these mutations can be favorably combined in many different combinations. Exemplary combinations are also provided herein, e.g., in Tables 3 and 4 and FIG. 7, and an example of strategies by which additional favorable combinations are readily derived follows. For the sake of simplicity, a few exemplary combinations using only a few exemplary mutations are discussed, but it will be evident that any of the mutations described herein can be employed in such strategies to produce polymerases with desirable properties.

For example, where a recombinant polymerase is desired to incorporate phosphate-labeled phosphate analogs in a $Mg^{++}$-containing single molecule sequencing reaction, one or more substitutions that enhance analog binding (e.g., E375Y, K512Y, and/or A484E) and one or more substitutions that alter metal cofactor usage (e.g., L253A, L253H, or L253S) can be incorporated. One or more substitutions that increase phototolerance (e.g., K131E, K131Q, and/or K135Q) can be included. Exemplary combinations thus include K131E, L253A and A484E; K131E, L253A, E375Y, and K512Y; K131E, L253A, E375Y, A484E, and K512Y; K135Q, L253A and A484E; K135Q, L253A, E375Y, and K512Y; and K135Q, L253A, E375Y, A484E, and K512Y. Polymerase speed can be enhanced by inclusion of substitutions such as A437G, E508K, V141K, L142K, D510K, and/or V250I, providing combinations such as A437G, L253A, and A484E; A437G, E375Y, and K512Y; K131E, L253A, A484E, and D510K; K135Q, L253A, A484E, and D510K; K131E, Y148I, L253A, and A484E; K135Q, Y148I, L253A, and A484E; K131E, Y148I, L253A, E375Y, A484E, and K512Y; and K135Q, Y148I, L253A, E375Y, A484E, and K512Y. Stability and/or yield can be increased by inclusion of substitutions such as E239G, V250I, and/or Y224K, producing combinations such as K131E, E239G, L253A, A484E, and D510K; K135Q, E239G, L253A, A484E, and D510K; K131E, E239G, L253A, E375Y, A484E, D510K, and K512Y; K135Q, E239G, L253A, E375Y, A484E, D510K, and K512Y; K131E, Y224K, E239G, L253A, E375Y, A484E, D510K, and K512Y; and K135Q, Y224K, E239G, L253A, E375Y, A484E, D510K, and K512Y. Accuracy can be enhanced by inclusion of substitutions such as E515Q, D235E, and/or Y148I, providing combinations such as K131E, Y148I, Y224K, E239G, V250I, L253A, E375Y, A484E, D510K, and K512Y; K131E, Y148I, Y224K, E239G, V250I, L253H, E375Y, A437G, A484E, and K512Y; K135Q, Y148I, Y224K, E239G, V250I, L253H, E375Y, A437G, A484E, and K512Y; K131E, Y148I, Y224K, E239G, V250I, L253A, E375Y, A437G, A484E, D510K, K512Y, and E515Q; K135Q, Y148I, Y224K, E239G, V250I, L253A, E375Y, A437G, A484E, D510K, K512Y, and E515Q; K135Q, Y148I, Y224K, E239G, V250I, L253A, E375Y, A484E, D510K, and K512Y; K131E, Y148I, Y224K, E239G, V250I, L253A, E375Y, A484E, D510K, K512Y, and E515Q; and K135Q, Y148I, Y224K, E239G, V250I, L253A, E375Y, A484E, D510K, K512Y, and E515Q.

Additional exemplary combinations of substitutions that can be present in a polymerase of the invention include, but are not limited to: E239G, L253A, E375Y, A437G, A484E, D510K, K512Y, and E515Q; E239G, V250I, L253A, E375Y, A437G, A484E, D510K, K512Y, and E515Q; E239G, L253A, E375Y, A437N, A484E, D510K, K512Y, and E515Q; E239G, V250I, L253A, E375Y, A437N, A484E, D510K, K512Y, and E515Q; E239G, V250A, L253H, E375Y, A437G, A484E, D510K, K512Y, and E515Q; E239G, V250A, L253H, E375Y, A437N, A484E, D510K, K512Y, and E515Q; Y224K, E239G, L253A, E375Y, A437G, A484E, D510K, K512Y, and E515Q; Y224K, E239G, V250I, L253A, E375Y, A437G, A484E, D510K, K512Y, and E515Q; Y224K, E239G, L253A, E375Y, A437N, A484E, D510K, K512Y, and E515Q; Y224K, E239G, V250I, L253A, E375Y, A437N, A484E, D510K, K512Y, and E515Q; Y224K, E239G, V250A, L253H, E375Y, A437G, A484E, D510K, K512Y, and E515Q; Y224K, E239G, V250A, L253H, E375Y, A437N, A484E, D510K, K512Y, and E515Q; K131E, E239G, L253A, E375Y, A437G, A484E, D510K, K512Y, and E515Q; K131E, E239G, V250I, L253A, E375Y, A437G, A484E, D510K, K512Y, and E515Q; K131E, E239G, L253A, E375Y, A437N, A484E, D510K, K512Y, and E515Q; K131E, E239G, V250I, L253A, E375Y, A437N, A484E, D510K, K512Y, and E515Q; K131E, E239G, V250A, L253H, E375Y, A437G, A484E, D510K, K512Y, and E515Q; K131E, E239G, V250A, L253H, E375Y, A437N, A484E, D510K, K512Y, and E515Q; K131E, Y224K, E239G, L253A, E375Y, A437G, A484E, D510K, K512Y, and E515Q; K131E, Y224K, E239G, V250I, L253A, E375Y, A437G, A484E, D510K, K512Y, and E515Q; K131E, Y224K, E239G, L253A, E375Y, A437N, A484E, D510K, K512Y, and E515Q; K131E, Y224K, E239G, V250I, L253A, E375Y, A437N, A484E, D510K, K512Y, and E515Q; K131E, Y224K, E239G, V250A, L253H, E375Y, A437G, A484E, D510K, K512Y, and E515Q; and K131E, Y224K, E239G, V250A, L253H, E375Y, A437N, A484E, D510K, K512Y, and E515Q.

Many other such recombinant polymerases, including these mutations and/or those described elsewhere herein, will be readily apparent and are features of the invention.

Mutating Polymerases

Various types of mutagenesis are optionally used in the present invention, e.g., to modify polymerases to produce variants, e.g., in accordance with polymerase models and model predictions as discussed above, or using random or semi-random mutational approaches. In general, any available mutagenesis procedure can be used for making polymerase mutants. Such mutagenesis procedures optionally include selection of mutant nucleic acids and polypeptides for one or more activity of interest (e.g., increased phototolerance, reduced reaction rates, decreased exonuclease activity, increased complex stability, decreased branching fraction, altered metal cofactor selectivity, improved processivity, increased thermostability, increased yield, increased accuracy, and/or improved $k_{off}$, $K_m$, $V_{max}$, $k_{cat}$ etc., e.g., for a given nucleotide analog). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting polymerase for mutation can be any of those noted herein, including available polymerase mutants such as those identified e.g., in WO 2007/076057 POLYMERASES FOR NUCLEOTIDE ANALOGUE INCORPORATION by Hanzel et al.; WO 2008/051530 POLYMERASE ENZYMES AND REAGENTS FOR ENHANCED NUCLEIC ACID SEQUENCING; U.S. patent application publication 2010-0075332 ENGINEERING POLYMERASES AND REACTION CONDITIONS FOR MODIFIED INCORPORATION PROPERTIES by Pranav Patel et al.; U.S. patent application publication 2010-0093555 ENZYMES RESISTANT TO PHOTODAMAGE by Keith Bjornson et al.; U.S. patent application publication 2010-0112645 GENERATION OF MODIFIED POLYMERASES FOR IMPROVED ACCURACY IN SINGLE MOLECULE SEQUENCING by Sonya Clark et al.; U.S. patent application publication 2011-0189659 GENERATION OF MODIFIED POLYMERASES FOR IMPROVED ACCURACY IN SINGLE MOLECULE SEQUENCING by Sonya Clark et al.; U.S. patent application publication 2012-0034602 RECOMBINANT POLYMERASES FOR IMPROVED SINGLE MOLECULE SEQUENCING; Hanzel et al. WO 2007/075987 ACTIVE SURFACE COUPLED POLYMERASES; and Hanzel et al. 2007/075873 PROTEIN ENGINEERING STRATEGIES TO OPTIMIZE ACTIVITY OF SURFACE ATTACHED PROTEINS.

Optionally, mutagenesis can be guided by known information from a naturally occurring polymerase molecule, or of a known altered or mutated polymerase (e.g., using an existing mutant polymerase as noted in the preceding references), e.g., sequence, sequence comparisons, physical properties, crystal structure and/or the like as discussed above. However, in another class of embodiments, modification can be essentially random (e.g., as in classical or "family" DNA shuffling, see, e.g., Crameri et al. (1998) "DNA shuffling of a family of genes from diverse species accelerates directed evolution" Nature 391:288-291).

Additional information on mutation formats is found in: Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2012) ("Ausubel")) and *PCR Protocols A Guide to Methods and Applications* (Innis et al. eds) Academic Press Inc. San Diego, Calif. (1990) ("Innis") The following publications and references cited within provide additional detail on mutation formats: Arnold, Protein engineering for unusual environments, Current Opinion in Biotechnology 4:450-455 (1993); Bass et al., Mutant Trp repressors with new DNA-binding specificities, Science 242:240-245 (1988); Bordo and Argos (1991) Suggestions for "Safe" Residue Substitutions in Site-directed Mutagenesis 217:721-729; Botstein & Shortle, Strategies and applications of in vitro mutagenesis, Science 229:1193-1201(1985); Carter et al, Improved oligonucleotide site-directed mutagenesis using M13 vectors, Nucl. Acids Res. 13: 4431-4443 (1985); Carter, Site-directed mutagenesis, Biochem. J. 237:1-7 (1986); Carter, Improved oligonucleotide-directed mutagenesis using M13 vectors, Methods in Enzymol. 154: 382-403 (1987); Dale et al., Oligonucleotide-directed random mutagenesis using the phosphorothioate method, Methods Mol. Biol. 57:369-374 (1996); Eghtedarzadeh & Henikoff, Use of oligonucleotides to generate large deletions, Nucl. Acids Res. 14: 5115 (1986); Fritz et al., Oligonucleotide-directed construction of mutations: a gapped duplex DNA procedure without enzymatic reactions in vitro, Nucl. Acids Res. 16: 6987-6999 (1988); Grundström et al., Oligonucleotide-directed mutagenesis by microscale 'shot-gun' gene synthesis, Nucl. Acids Res. 13: 3305-3316 (1985); Hayes (2002) Combining Computational and Experimental Screening for rapid Optimization of Protein Properties PNAS 99(25) 15926-15931; Kunkel, The efficiency of oligonucleotide directed mutagenesis, in Nucleic Acids & Molecular Biology (Eckstein, F. and Lilley, D. M. J. eds., Springer Verlag, Berlin)) (1987); Kunkel, Rapid and efficient site-specific mutagenesis without phenotypic selection, Proc. Natl. Acad. Sci. USA 82:488-492 (1985); Kunkel et al., Rapid and efficient site-specific mutagenesis without phenotypic selection, Methods in Enzymol. 154, 367-382 (1987); Kramer et al., The gapped duplex DNA approach to oligonucleotide-directed mutation construction, Nucl. Acids Res. 12: 9441-9456 (1984); Kramer & Fritz Oligonucleotide-directed construction of mutations via gapped duplex DNA, Methods in Enzymol. 154:350-367 (1987); Kramer et al., Point Mismatch Repair, Cell 38:879-887 (1984); Kramer et al, Improved enzymatic in vitro reactions in the gapped duplex DNA approach to oligonucleotide-directed construction of mutations, Nucl. Acids Res. 16: 7207 (1988); Ling et al., Approaches to DNA mutagenesis: an overview, Anal Biochem. 254(2): 157-178 (1997); Lorimer and Pastan Nucleic Acids Res. 23, 3067-8 (1995); Mandecki, Oligonucleotide-directed double-strand break repair in plasmids of *Escherichia coli*: a method for site-specific mutagenesis, Proc. Natl. Acad. Sci. USA, 83:7177-7181 (1986); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Nambiar et al., Total synthesis and cloning of a gene coding for the ribonuclease S protein, Science 223: 1299-1301 (1984); Sakamar and Khorana, Total synthesis and expression of a gene for the a-subunit of bovine rod outer segment guanine nucleotide-binding protein (transducin), Nucl. Acids Res. 14: 6361-6372 (1988); Sayers et al., Y-T Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Sieber, et al., Nature Biotechnology, 19:456-460 (2001); Smith, In vitro mutagenesis, Ann. Rev. Genet. 19:423-462(1985); Methods in Enzymol. 100: 468-500 (1983); Methods in Enzymol. 154: 329-350 (1987); Stemmer, Nature 370, 389-91 (1994); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8787 (1985); Wells et al, Importance of hydrogen-bond formation in stabilizing the transition state of subtilisin, Phil. Trans. R. Soc. Lond. A 317: 415-423 (1986); Wells et al., Cassette mutagenesis: an efficient method for generation of multiple mutations at defined sites, Gene 34:315-323 (1985); Zoller & Smith, Oligonucleotide-directed mutagenesis using M13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, Methods in Enzymol. 100:468-500 (1983); Zoller & Smith, Oligonucleotide-directed mutagenesis: a simple method using two oligonucleotide primers and a single-stranded DNA template, Methods in Enzymol. 154:329-350 (1987); Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296. Additional details on many of the above methods can be found in Methods in Enzymology Volume 154, which also describes useful controls for trouble-shooting problems with various mutagenesis methods.

Determining Kinetic Parameters

The polymerases of the invention can be screened or otherwise tested to determine whether the polymerase displays a modified activity for or with a nucleotide analog or template as compared to a parental DNA polymerase (e.g., a corresponding wild-type or available mutant polymerase from which the recombinant polymerase of the invention was derived). For example, branching fraction, a reaction rate constant, $k_{off}$, $k_{cat}$, $K_m$, $V_{max}$, $k_{cat}/K_m$, $V_{max}/K_m$, $k_{pol}$, and/or $K_d$ of the recombinant DNA polymerase for the nucleotide (or analog) or template nucleic acid can be determined. The specificity constant $k_{cat}/K_m$ is also a useful measure, e.g., for assessing branch rate. $k_{cat}/K_m$ is a measure of substrate binding that leads to product formation (and, thus, includes terms defining binding $K_d$ and inversely predicts branching fraction formation).

As is well-known in the art, for enzymes obeying simple Michaelis-Menten kinetics, kinetic parameters are readily derived from rates of catalysis measured at different substrate concentrations. The Michaelis-Menten equation, $V=V_{max}[S]([S]+K_m)^{-1}$, relates the concentration of free substrate ([S], approximated by the total substrate concentration), the maximal rate ($V_{max}$, attained when the enzyme is saturated with substrate), and the Michaelis constant ($K_m$, equal to the substrate concentration at which the reaction rate is half of its maximal value), to the reaction rate (V).

For many enzymes, $K_m$ is equal to the dissociation constant of the enzyme-substrate complex and is thus a measure of the strength of the enzyme-substrate complex. For such an enzyme, in a comparison of $K_m$s, a lower $K_m$ represents a complex with stronger binding, while a higher Km represents a complex with weaker binding. The ratio $k_{cat}/K_m$, sometimes called the specificity constant, can be thought of as the second order rate constant times the probability of that substrate being converted to product once bound. The larger the specificity constant, the more efficient the enzyme is in binding the substrate and converting it to product. The specificity constant is inversely proportional to the branching rate, as branching rate is the rate at which the enzyme binds substrate (e.g., nucleotide) but does not convert it to product (e.g., a DNA polymer).

$k_{cat}$ (also called the turnover number of the enzyme) can be determined if the total enzyme concentration ($[E_T]$, i.e., the concentration of active sites) is known, since $V_{max}=k_{cat}[E_T]$. For situations in which the total enzyme concentration is difficult to measure, the ratio $V_{max}/K_m$ is often used instead as a measure of efficiency. $K_m$ and $V_{max}$ can be determined, for example, from a Lineweaver-Burk plot of $1/V$ against $1/[S]$, where the y intercept represents $1/V_{max}$, the x intercept $-1/K_m$, and the slope $K_m/V_{max}$, or from an Eadie-Hofstee plot of V against V/[S], where the y intercept represents $V_{max}$, the x intercept $V_{max}/K_m$, and the slope $-K_m$. Software packages such as KinetAsyst™ or Enzfit (Biosoft, Cambridge, UK) can facilitate the determination of kinetic parameters from catalytic rate data.

For enzymes such as polymerases that have multiple substrates, varying the concentration of only one substrate while holding the others in suitable excess (e.g., effectively constant) concentration typically yields normal Michaelis-Menten kinetics.

Details regarding $k_{off}$ determination are described, e.g., in U.S. patent application publication 2012-0034602. In general, the dissociation rate can be measured in any manner that detects the polymerase/DNA complex over time. This includes stopped-flow spectroscopy, or even simply taking aliquots over time and testing for polymerase activity on the template of interest. Free polymerase is captured with a polymerase trap after dissociation, e.g., by incubation in the presence of heparin or an excess of competitor DNA (e.g., non-specific salmon sperm DNA, or the like).

In one embodiment, using pre-steady-state kinetics, the nucleotide concentration dependence of the rate constant $k_{obs}$ (the observed first-order rate constant for dNTP incorporation) provides an estimate of the $K_m$ for a ground state binding and the maximum rate of polymerization ($k_{pol}$). The $k_{obs}$ is measured using a burst assay. The results of the assay are fitted with the Burst equation; Product=$A[1-\exp(-k_{obs}*t)]+k_{ss}*t$ where A represents amplitude an estimate of the concentration of the enzyme active sites, $k_{ss}$ is the observed steady-state rate constant and t is the reaction incubation time. The $K_m$ for dNTP binding to the polymerase-DNA complex and the $k_{pol}$ are calculated by fitting the dNTP concentration dependent change in the $k_{obs}$ using the equation $k_{obs}=(k_{pol}*[S])*(K_m+[S])^{-1}$ where [S] is the substrate concentration. Results are optionally obtained from a rapid-quench experiment (also called a quench-flow measurement), for example, based on the methods described in Johnson (1986) "Rapid kinetic analysis of mechanochemical adenosinetriphosphatases" Methods Enzymol. 134:677-705, Patel et al. (1991) "Pre-steady-state kinetic analysis of processive DNA replication including complete characterization of an exonuclease-deficient mutant" Biochemistry 30(2):511-25, and Tsai and Johnson (2006) "A new paradigm for DNA polymerase specificity" Biochemistry 45(32):9675-87.

Parameters such as rate of binding of a nucleotide analog or template by the recombinant polymerase, rate of product release by the recombinant polymerase, or branching rate of the recombinant polymerase can also be determined, and optionally compared to that of a parental polymerase (e.g., a corresponding wild-type polymerase).

For a more thorough discussion of enzyme kinetics, see, e.g., Berg, Tymoczko, and Stryer (2002) *Biochemistry, Fifth Edition*, W. H. Freeman; Creighton (1984) *Proteins: Structures and Molecular Principles*, W. H. Freeman; and Fersht (1985) *Enzyme Structure and Mechanism, Second Edition*, W. H. Freeman.

In one aspect, the improved activity of the enzymes of the invention is compared with a given parental polymerase. For example, in the case of enzymes derived from a Φ29 parental enzyme, where the improvement being sought is an increase in stability of the closed complex, an improved enzyme of the invention would have a lower $k_{off}$ than the parental enzyme, e.g., wild type Φ29. Such comparisons are made under equivalent reaction conditions, e.g., equal concentrations of the parental and modified polymerase, equal substrate concentrations, equivalent solution conditions (pH, salt concentration, presence of divalent cations, etc.), temperature, and the like. In one aspect, the improved activity of the enzymes of the invention is measured with reference to a model analog or analog set and compared with a given parental enzyme. Optionally, the improved activity of the enzymes of the invention is measured under specified reaction conditions. While the foregoing may be used as a characterization tool, it in no way is intended as a specifically limiting reaction of the invention.

Optionally, the polymerase exhibits a $K_m$ for a phosphate-labeled nucleotide analog that is less than a $K_m$ observed for a wild-type polymerase for the analog to facilitate applications in which the polymerase incorporates the analog, e.g., during SMS. For example, the modified recombinant polymerase can exhibit a $K_m$ for the phosphate-labeled nucleotide analog that is less than 75%, less than 50%, or less than 25% than that of wild-type or parental polymerase such as a wild type Φ29. In one specific class of examples, the polymerases of the invention have a $K_m$ of about 10 μM or less for a non-natural nucleotide analog such as a phosphate labeled analog.

Screening Polymerases

Screening or other protocols can be used to determine whether a polymerase displays a modified activity, e.g., for a nucleotide analog, as compared to a parental DNA polymerase. For example, branching fraction, rate constant, $k_{off}$, $k_{cat}$, $K_m$, $V_{max}$, or $k_{cat}/K_m$ of the recombinant DNA polymerase for the template or nucleotide or analog can be determined as discussed above. As another example, activity can be assayed indirectly. Assays for properties such as protein yield, thermostability, and the like are described, e.g., in U.S. patent application publication 2012-0034602. Performance of a recombinant polymerase in a sequencing reaction, e.g., a single molecule sequencing reaction, can be examined to assay properties such as speed, pulse width, interpulse distance, accuracy, readlength, etc. as described herein. Phototolerance can be assessed by monitoring polymerase performance (e.g., in a single molecule sequencing reaction) during or after exposure of the polymerase to light, e.g., excitation light of a specified wavelength at a given intensity for a given time, e.g., as compared to a wild-type or other parental polymerase.

In one desirable aspect, a library of recombinant DNA polymerases can be made and screened for these properties. For example, a plurality of members of the library can be made to include one or more mutation that increases phototolerance, alters (e.g., decreases) reaction rate constants, improves closed complex stability, decreases branching fraction, alters cofactor selectivity, or increases yield, thermostability, accuracy, speed, or readlength and/or randomly generated mutations (e.g., where different members include different mutations or different combinations of mutations), and the library can then be screened for the properties of interest (e.g., increased phototolerance, decreased rate constant, decreased branching fraction, increased closed complex stability, etc.). In general, the library can be screened to identify at least one member comprising a modified activity of interest.

Libraries of polymerases can be either physical or logical in nature. Moreover, any of a wide variety of library formats can be used. For example, polymerases can be fixed to solid surfaces in arrays of proteins. Similarly, liquid phase arrays of polymerases (e.g., in microwell plates) can be constructed for convenient high-throughput fluid manipulations of solutions comprising polymerases. Liquid, emulsion, or gel-phase libraries of cells that express recombinant polymerases can also be constructed, e.g., in microwell plates, or on agar plates. Phage display libraries of polymerases or polymerase domains (e.g., including the active site region or interdomain stability regions) can be produced. Likewise, yeast display libraries can be used. Instructions in making and using libraries can be found, e.g., in Sambrook, Ausubel and Berger, referenced herein.

For the generation of libraries involving fluid transfer to or from microtiter plates, a fluid handling station is optionally used. Several "off the shelf" fluid handling stations for performing such transfers are commercially available, including e.g., the Zymate systems from Caliper Life Sciences (Hopkinton, Mass.) and other stations which utilize automatic pipettors, e.g., in conjunction with the robotics for plate movement (e.g., the ORCA® robot, which is used in a variety of laboratory systems available, e.g., from Beckman Coulter, Inc. (Fullerton, Calif.).

In an alternate embodiment, fluid handling is performed in microchips, e.g., involving transfer of materials from microwell plates or other wells through microchannels on the chips to destination sites (microchannel regions, wells, chambers or the like). Commercially available microfluidic systems include those from Hewlett-Packard/Agilent Technologies (e.g., the HP2100 bioanalyzer) and the Caliper High Throughput Screening System. The Caliper High Throughput Screening System provides one example interface between standard microwell library formats and Labchip technologies. RainDance Technologies' nanodroplet platform provides another method for handling large numbers of spatially separated reactions. Furthermore, the patent and technical literature includes many examples of microfluidic systems which can interface directly with microwell plates for fluid handling.

Tags and Other Optional Polymerase Features

The recombinant DNA polymerase optionally includes additional features exogenous or heterologous to the polymerase. For example, the recombinant polymerase optionally includes one or more tags, e.g., purification, substrate binding, or other tags, such as a polyhistidine tag, a His10 tag, a His6 tag, an alanine tag, an Ala10 tag, an Ala16 tag, a biotin tag, a biotin ligase recognition sequence or other biotin attachment site (e.g., a BiTag or a Btag or variant thereof, e.g., BtagV1-11), a GST tag, an S Tag, a SNAP-tag, an HA tag, a DSB (Sso7D) tag, a lysine tag, a NanoTag, a Cmyc tag, a tag or linker comprising the amino acids glycine and serine, a tag or linker comprising the amino acids glycine, serine, alanine and histidine, a tag or linker comprising the amino acids glycine, arginine, lysine, glutamine and proline, a plurality of polyhistidine tags, a plurality of His10 tags, a plurality of His6 tags, a plurality of alanine tags, a plurality of Ala10 tags, a plurality of Ala16 tags, a plurality of biotin tags, a plurality of GST tags, a plurality of BiTags, a plurality of S Tags, a plurality of SNAP-tags, a plurality of HA tags, a plurality of DSB (Sso7D) tags, a plurality of lysine tags, a plurality of NanoTags, a plurality of Cmyc tags, a plurality of tags or linkers comprising the amino acids glycine and serine, a plurality of tags or linkers comprising the amino acids glycine, serine, alanine and histidine, a plurality of tags or linkers comprising the amino acids glycine, arginine, lysine, glutamine and proline, biotin, avidin, an antibody or antibody domain, antibody fragment, antigen, receptor, receptor domain, receptor fragment, maltose binding protein, ligand, one or more protease site (e.g., Factor Xa, enterokinase, or thrombin site), a dye, an acceptor, a quencher, a DNA binding domain (e.g., a helix-hairpin-helix domain from topoisomerase V), or combination thereof. See, e.g., U.S. patent application publication 2012-0034602 for sequences of a number of suitable tags and linkers, including BtagV1-11. The one or more exogenous or heterologous features can find use not only for purification purposes, immobilization of the polymerase to a substrate, and the like, but can also be useful for altering one or more properties of the polymerase.

The one or more exogenous or heterologous features can be included internal to the polymerase, at the N-terminal region of the polymerase, at the C-terminal region of the polymerase, or at a combination thereof (e.g., at both the N-terminal and C-terminal regions of the polymerase). Where the polymerase includes an exogenous or heterologous feature at both the N-terminal and C-terminal regions, the exogenous or heterologous features can be the same (e.g., a polyhistidine tag, e.g., a His10 tag, at both the N- and C-terminal regions) or different (e.g., a biotin ligase recognition sequence at the N-terminal region and a polyhistidine tag, e.g., His10 tag, at the C-terminal region). Optionally, a terminal region (e.g., the N- or C-terminal region) of a polymerase of the invention can comprise two or more exogenous or heterologous features which can be the same or different (e.g., a biotin ligase recognition sequence and a polyhistidine tag at the N-terminal region, a biotin ligase recognition sequence, a polyhistidine tag, and a Factor Xa recognition site at the N-terminal region, and the like). As a few examples, the polymerase can include a polyhistidine tag at the C-terminal region, a biotin ligase recognition sequence at the N-terminal region and a polyhistidine tag at the C-terminal region, a biotin ligase recognition sequence and a polyhistidine tag at the N-terminal region, a biotin ligase recognition sequence and a polyhistidine tag at the N-terminal region and a polyhistidine tag at the C-terminal region, or a polyhistidine tag and a biotin ligase recognition sequence at the C-terminal region.

For convenience, an exogenous or heterologous feature will often be expressed as a fusion domain of the overall polymerase protein, e.g., as a conventional in-frame fusion of a polypeptide sequence with the active polymerase enzyme (e.g., a polyhistidine tag fused in frame to an active polymerase enzyme sequence). However, features such as tags can be added chemically to the polymerase, e.g., by using an available amino acid residue of the enzyme or by incorporating an amino acid into the protein that provides a suitable attachment site for the coupling domain. Suitable residues of the enzyme can include, e.g., histidine, cysteine, or serine residues (providing for N, S, or O linked coupling reactions). Optionally, one or more cysteines present in the parental polymerase (e.g., up to all of the cysteines present on the polymerase's surface) can be replaced with a different amino acid; either a single reactive surface cysteine can be left unsubstituted or a single reactive surface cysteine can be introduced in place of another residue, for convenient addition of a feature, e.g., for surface immobilization through thiol labeling (e.g., addition of maleimide biotin, or maleimide and an alkyne for click labeling). Unnatural amino acids that comprise unique reactive sites can also be added to the enzyme, e.g., by expressing the enzyme in a system that comprises an orthogonal tRNA and an orthogonal synthetase that loads the unnatural amino acid in response to a selector codon.

The exogenous or heterologous features can find use, e.g., in the context of binding a polymerase in an active form to a surface, e.g., to orient and/or protect the polymerase active site when the polymerase is bound to a surface. In general, surface binding elements and purification tags that can be added to the polymerase (e.g., recombinantly or chemically) include, e.g., biotin attachment sites (e.g., biotin ligase recognition sequences such as Btags or BiTag), polyhistidine tags, His6 tags, His10 tags, biotin, avidin, GST sequences, modified GST sequences, e.g., that are less likely to form dimers, S tags, SNAP-tags, antibodies or antibody domains, antibody fragments, antigens, receptors, receptor domains, receptor fragments, ligands, and combinations thereof.

One aspect of the invention includes DNA polymerases that can be coupled to a surface without substantial loss of activity (e.g., in an active form). DNA polymerases can be coupled to the surface through a single surface coupling domain or through multiple surface coupling domains which act in concert to increase binding affinity of the polymerase for the surface and to orient the polymerase relative to the surface. For example, the active site can be oriented distal to the surface, thereby making it accessible to a polymerase substrate (template, nucleotides, etc.). This orientation also tends to reduce surface denaturation effects in the region of the active site. In a related aspect, activity of the enzyme can be protected by making the coupling domains large, thereby serving to further insulate the active site from surface binding effects. Further details regarding the immobilization of a polymerase to a surface (e.g., the surface of a zero mode waveguide) in an active form are found in WO 2007/075987 ACTIVE SURFACE COUPLED POLYMERASES by Hanzel et al., and WO 2007/075873 PROTEIN ENGINEERING STRATEGIES TO OPTIMIZE ACTIVITY OF SURFACE ATTACHED PROTEINS by Hanzel et al. Further details on attaching tags is available in the art. See, e.g., U.S. Pat. Nos. 5,723,584 and 5,874,239 and U.S. patent application publication 2011/0306096 for additional information on attaching biotinylation peptides to recombinant proteins.

The polymerase immobilized on a surface in an active form can be coupled to the surface through one or a plurality of artificial or recombinant surface coupling domains as discussed above, and typically displays a $k_{cat}/K_m$ (or $V_{max}/K_m$) that is at least about 1%, at least about 10%, at least about 25%, at least about 50%, or at least about 75% as high as a corresponding active polymerase in solution.

Exonuclease-Deficient Recombinant Polymerases

Many native DNA polymerases have a proof-reading exonuclease function which can yield substantial data analysis problems in processes that utilize real time observation of incorporation events as a method of identifying sequence information, e.g., single molecule sequencing applications. Even where exonuclease activity does not introduce such problems in single molecule sequencing, reduction of exonuclease activity can be desirable since it can increase accuracy (in some cases at the expense of readlength).

Accordingly, recombinant polymerases of the invention optionally include one or more mutations (e.g., substitutions, insertions, and/or deletions) relative to the parental polymerase that reduce or eliminate endogenous exonuclease activity. For example, relative to the wild-type Φ29 DNA polymerase of SEQ ID NO:1, one or more of positions N62, D12, E14, T15, H61, D66, D169, K143, Y148, and H149 is optionally mutated to reduce exonuclease activity. Exemplary mutations that can reduce exonuclease activity include, e.g., N62D, N62H, D12A, T15I, E14I, E14A, D66A, K143D, D145A and D169A substitutions, as well as addition of an exogenous feature at the C-terminus (e.g., a polyhistidine tag). Additional exemplary substitutions in the exonuclease domain include N62S, D12N, D12R, D12M, E14Q, H61K, H61D, H61A, D66R, D66N, D66Q, D66K, D66M, D169N, K143R, Y148I, Y148K, Y148A, Y148C, Y148D, Y148E, Y148F, Y148G, Y148H, Y148L, Y148M, Y148N, Y148P, Y148Q, Y148R, Y148S, Y148T, Y148V, Y148W, and H149M. The polymerases of the invention optionally comprise one or more of these mutations. For example, in one aspect, the polymerase is a Φ29-type polymerase that includes one or more mutations in the N-terminal exonuclease domain (residues 5-189 as numbered with respect to wild-type Φ29).

Making and Isolating Recombinant Polymerases

Generally, nucleic acids encoding a polymerase of the invention can be made by cloning, recombination, in vitro synthesis, in vitro amplification and/or other available methods. A variety of recombinant methods can be used for expressing an expression vector that encodes a polymerase of the invention. Methods for making recombinant nucleic acids, expression and isolation of expressed products are well known and described in the art. A number of exemplary mutations and combinations of mutations, as well as strategies for design of desirable mutations, are described herein. Methods for making and selecting mutations in the active site of polymerases, including for modifying steric features in or near the active site to permit improved access by nucleotide analogs are found hereinabove and, e.g., in WO 2007/076057 POLYMERASES FOR NUCLEOTIDE ANALOG INCORPORATION by Hanzel et al. and WO 2008/051530 POLYMERASE ENZYMES AND REAGENTS FOR ENHANCED NUCLEIC ACID SEQUENCING by Rank et al.

Additional useful references for mutation, recombinant and in vitro nucleic acid manipulation methods (including cloning, expression, PCR, and the like) include Berger and Kimmel, *Guide to Molecular Cloning Techniques, Methods in Enzymology volume* 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); and *The Nucleic Acid Protocols Handbook* Ralph Rapley (ed) (2000) Cold Spring Harbor, Humana Press Inc (Rapley); Chen et al. (ed) *PCR Cloning Protocols, Second Edition* (Methods in Molecular Biology, volume 192) Humana Press; and in Viljoen et al. (2005) *Molecular Diagnostic PCR Handbook* Springer, ISBN 1402034032.

In addition, a plethora of kits are commercially available for the purification of plasmids or other relevant nucleic acids from cells, (see, e.g., EasyPrep™, FlexiPrep™ both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Nucleic acids encoding the recombinant polymerases of the invention are also a feature of the invention. A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, nucleic acids of the invention are optionally "codon optimized," meaning that the nucleic acids are synthesized to include codons that are preferred by the particular translation system being employed to express the polymerase. For example, when it is desirable to express the polymerase in a bacterial cell (or even a particular strain of bacteria), the nucleic acid can be synthesized to include codons most frequently found in the genome of that bacterial cell, for efficient expression of the polymerase. A similar strategy can be employed when it is desirable to express the polymerase in a eukaryotic cell, e.g., the nucleic acid can include codons preferred by that eukaryotic cell.

A variety of protein isolation and detection methods are known and can be used to isolate polymerases, e.g., from recombinant cultures of cells expressing the recombinant polymerases of the invention. A variety of protein isolation and detection methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods, 2nd Edition* Wiley-Liss, NY; Walker (1996) *The Protein Protocols Handbook* Humana Press, N.J., Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein purification and detection methods can be found in Satinder Ahuj a ed., *Handbook of Bioseparations*, Academic Press (2000).

Kits

The present invention also features kits that incorporate the polymerases of the invention, optionally with additional useful reagents such as one or more nucleotides and/or nucleotide analogs, e.g., for sequencing, nucleic acid amplification, or the like. Such kits can include the polymerase of the invention packaged in a fashion to enable use of the polymerase (e.g., the polymerase immobilized in a ZMW array), optionally with a set of different nucleotide analogs of the invention, e.g., those that are analogous to A, T, G, and C, e.g., where one or more of the analogs comprise a detectable moiety, to permit identification in the presence of the analogs. Depending upon the desired application, the kits of the invention optionally include additional reagents, such as natural nucleotides, a control template, and other reagents, such as buffer solutions and/or salt solutions, including, e.g., divalent metal ions such as $Ca^{++}$, $Mg^{++}$, $Mn^{++}$ and/or $Fe^{++}$, and standard solutions, e.g., dye standards for detector calibration. Such kits also typically include instructions for use of the compounds and other reagents in accordance with the desired application methods, e.g., nucleic acid sequencing, amplification and the like.

Nucleic Acid and Polypeptide Sequences and Variants

As described herein, the invention also features polynucleotide sequences encoding, e.g., a polymerase as described herein. Examples of polymerase sequences that include features found herein, e.g., as in Tables 3-6, are provided. However, one of skill in the art will immediately appreciate that the invention is not limited to the specifically exemplified sequences. For example, one of skill will appreciate that the invention also provides, e.g., many related sequences with the functions described herein, e.g., polynucleotides and polypeptides encoding conservative variants of a polymerase of Tables 3-6 or FIG. 7 or any other specifically listed polymerase herein. Combinations of any of the mutations noted herein or combinations of any of the mutations herein in combination with those noted in other available references relating to improved polymerases, such as Hanzel et al. WO 2007/076057 POLYMERASES FOR NUCLEOTIDE ANALOGUE INCORPORATION; Rank et al. WO 2008/051530 POLYMERASE ENZYMES AND REAGENTS FOR ENHANCED NUCLEIC ACID SEQUENCING; Hanzel et al. WO 2007/075987 ACTIVE SURFACE COUPLED POLYMERASES; Hanzel et al. WO 2007/075873 PROTEIN ENGINEERING STRATEGIES TO OPTIMIZE ACTIVITY OF SURFACE ATTACHED PROTEINS; U.S. patent application publication 2010-0075332 ENGINEERING POLYMERASES AND REACTION CONDITIONS FOR MODIFIED INCORPORATION PROPERTIES by Pranav Patel et al.; U.S. patent application publication 2010-0093555 ENZYMES RESISTANT TO PHOTODAMAGE by Keith Bjornson et al.; U.S. patent application publication 2010-0112645 GENERATION OF MODIFIED POLYMERASES FOR IMPROVED ACCURACY IN SINGLE MOLECULE SEQUENCING by Sonya Clark et al.; U.S. patent application publication 2011-0189659 GENERATION OF MODIFIED POLYMERASES FOR IMPROVED ACCURACY IN SINGLE MOLECULE SEQUENCING by Sonya Clark et al.; and U.S. patent application publication 2012-0034602 RECOMBINANT POLYMERASES FOR IMPROVED SINGLE MOLECULE SEQUENCING are also features of the invention.

Accordingly, the invention provides a variety of polypeptides (polymerases) and polynucleotides (nucleic acids that encode polymerases). Exemplary polynucleotides of the invention include, e.g., any polynucleotide that encodes a polymerase of Tables 3-6 or FIG. 7 or otherwise described herein. Because of the degeneracy of the genetic code, many polynucleotides equivalently encode a given polymerase sequence. Similarly, an artificial or recombinant nucleic acid that hybridizes to a polynucleotide indicated above under highly stringent conditions over substantially the entire length of the nucleic acid (and is other than a naturally occurring polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention (e.g., that specifically recognizes a feature of the polymerase that confers decreased branching or increased complex stability.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally similar sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence (other than residues noted, e.g., in Tables 3-6 and FIG. 7 or elsewhere herein, as being relevant to a feature or property of interest) are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid, while retaining the relevant mutational feature (for example, the conservative substitution can be of a residue distal to the active site region, or distal to an interdomain stability region). Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional or tagging sequence (introns in the nucleic acid, poly His or similar sequences in the encoded polypeptide, etc.), is a conservative variation of the basic nucleic acid or polypeptide.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

TABLE 1

Conservative amino acid substitutions

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Nucleic Acid Hybridization

Comparative hybridization can be used to identify nucleic acids of the invention, including conservative variations of nucleic acids of the invention. In addition, target nucleic acids which hybridize to a nucleic acid of the invention under high, ultra-high and ultra-ultra high stringency conditions, where the nucleic acids encode mutants corresponding to those noted in Tables 3-6 and FIG. 7 or other listed polymerases, are a feature of the invention. Examples of such nucleic acids include those with one or a few silent or conservative nucleic acid substitutions as compared to a given nucleic acid sequence encoding a polymerase of Tables 3-6 and FIG. 7 (or other exemplified polymerase), where any conservative substitutions are for residues other than those noted in Tables 3-6 and FIG. 7 or elsewhere as being relevant to a feature of interest (increased phototolerance, improved analog binding, etc.).

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5x-10x as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in *Current Protocols in Molecular Biology*, Ausubel et al., eds., *Current Protocols*, a joint venture between Greene Publishing Associates, Inc. and John Wiley & Sons, Inc., (supplemented through 2012); Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2× SSC wash at 65° C. for 15 minutes (see, Sambrook, supra for a description of SSC buffer). Often the high stringency wash is preceded by a low stringency wash to remove background probe signal. An example low stringency wash is 2× SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

Figure 7:
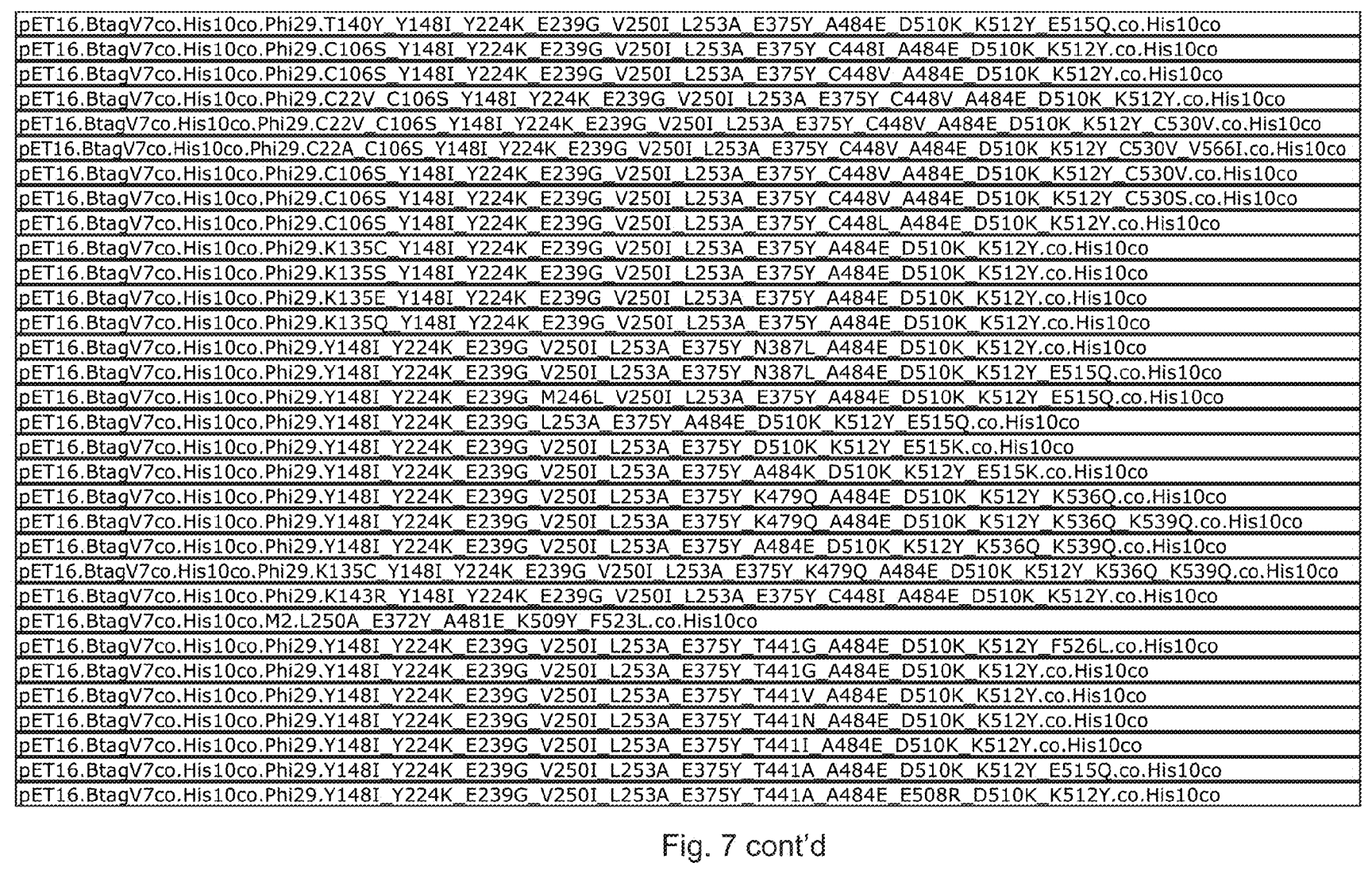
Figure 7:
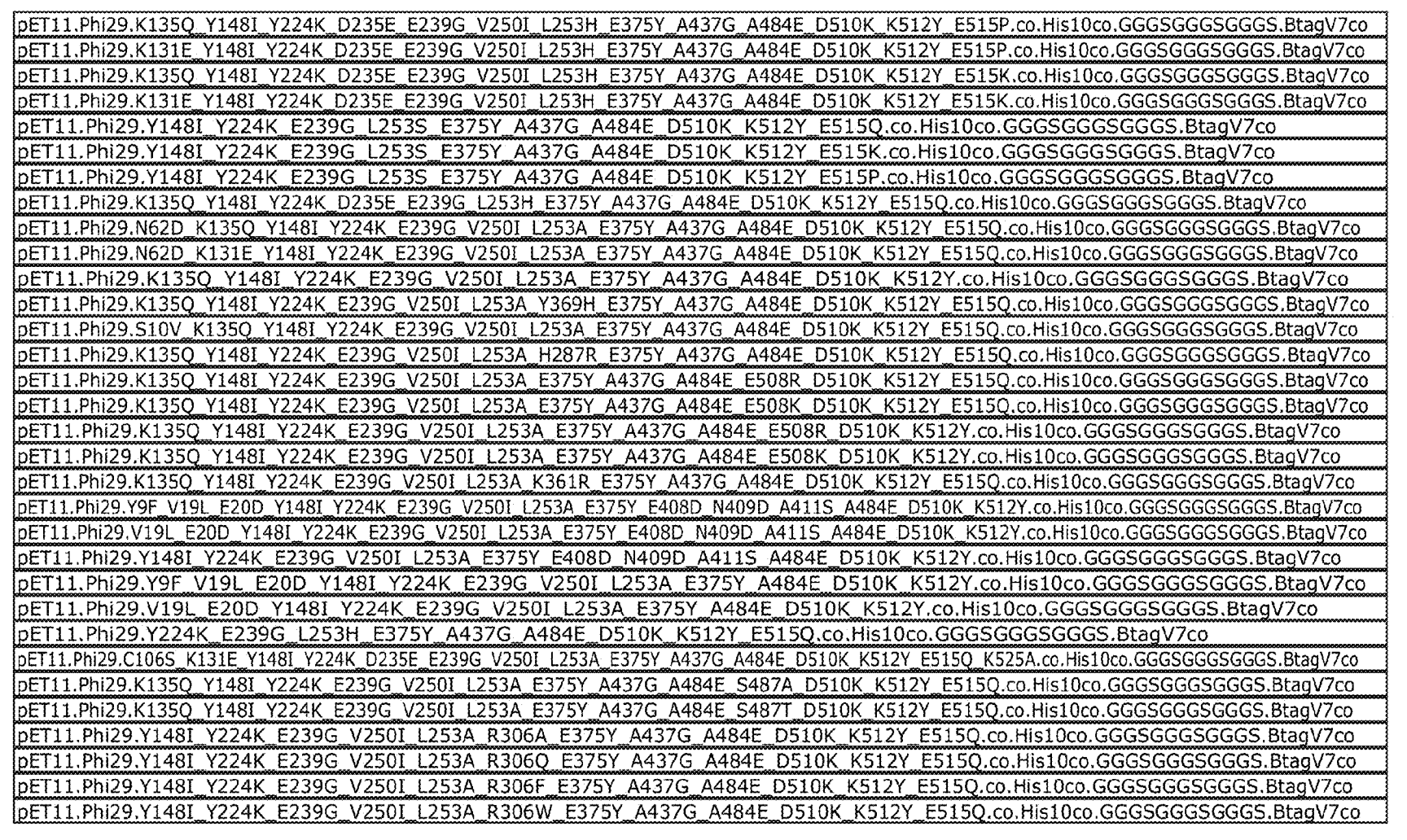
Figure 7:
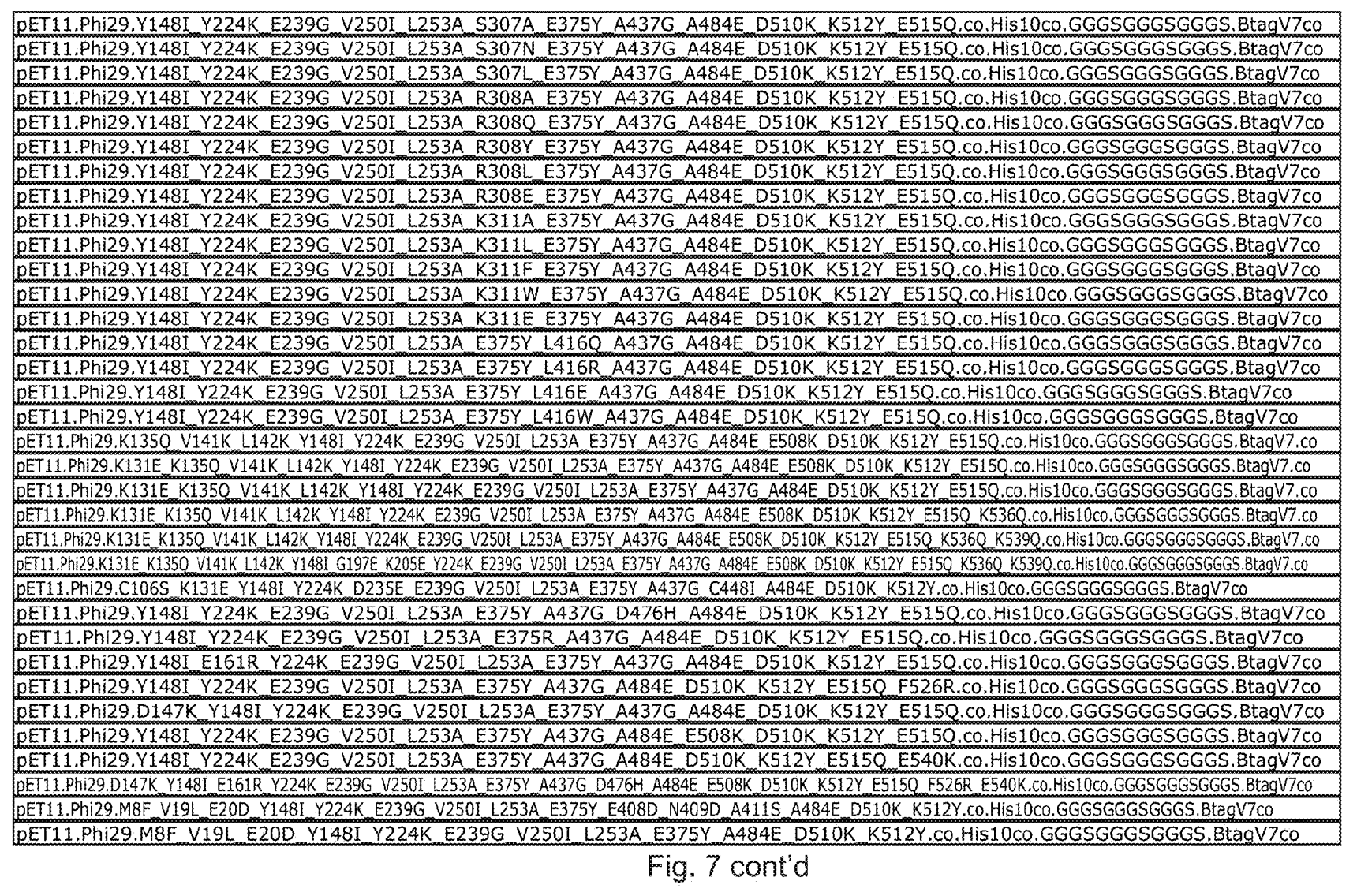
Figure 7:
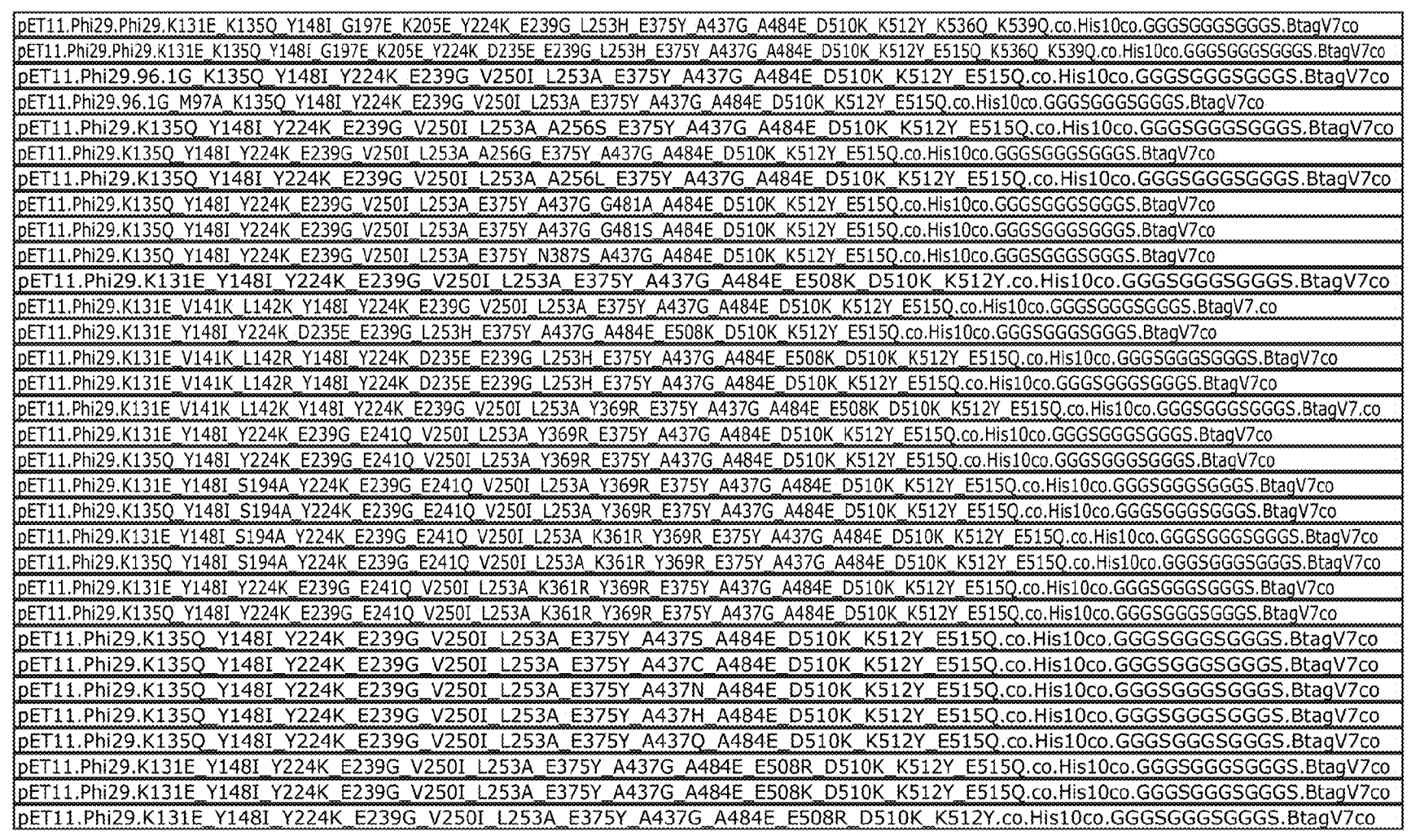
Figure 7:
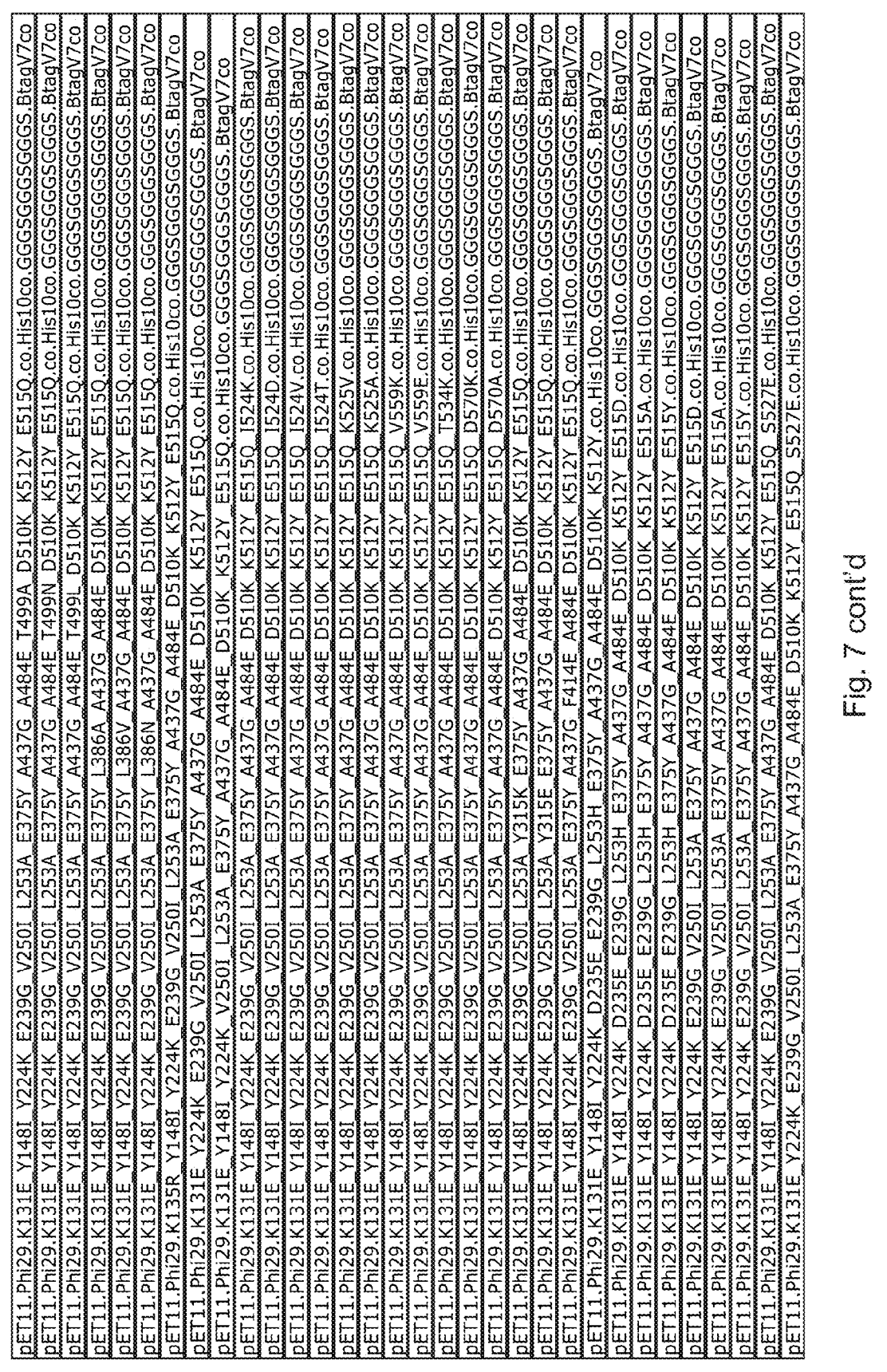
Figure 7:
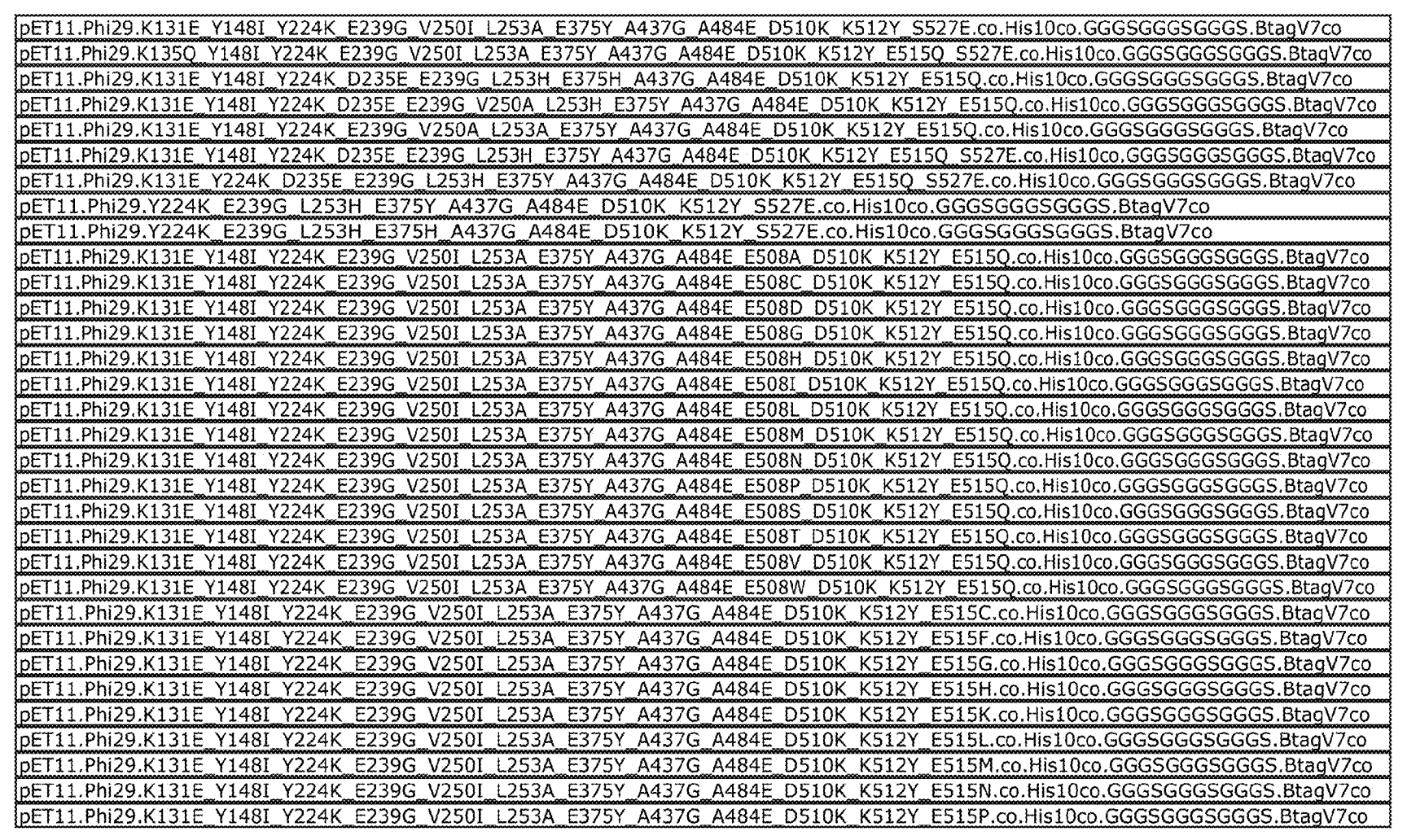

In some aspects, the invention provides a nucleic acid that comprises a unique subsequence in a nucleic acid that encodes a polymerase of Tables 3-6 and FIG. 7 or others described herein. The unique subsequence may be unique as compared to a nucleic acid corresponding to, e.g., a wild type Φ29-type polymerase. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polymerase of Tables 3-6 and FIG. 7 or otherwise detailed herein. Here, the unique subsequence is unique as compared to, e.g., a wild type Φ29-type polymerase or previously characterized mutation thereof.

The invention also provides for target nucleic acids which hybridize under stringent conditions to a unique coding oligonucleotide which encodes a unique subsequence in a polypeptide selected from the modified polymerase sequences of the invention, wherein the unique subsequence is unique as compared to a polypeptide corresponding to a wild type Φ29-type polymerase. Unique sequences are determined as noted above.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a polymerase, or the amino acid sequence of a polymerase) refers to two or more sequences or subsequences that have at least about 60%, about 80%, about 90%, about 95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 75%, 80%, 90%, 95%, 97%, 98%, or 99% or more identity, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2012).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

For reference, the amino acid sequence of a wild-type Φ29 polymerase is presented in Table 2, along with the sequences of several other wild-type Φ29-type polymerases.

TABLE 2

Amino acid sequence of exemplary wild-type Φ29-type polymerases.

| | |
|---|---|
| Φ29<br>SEQ ID NO: 1 | MKHMPRKMYSCDFETTTKVEDCRVWAYGYMNIEDHSEYKIGNSLDEFMA<br>WVLKVQADLYFHNLKFDGAFIINWLERNGFKWSADGLPNTYNTIISRMGQ<br>WYMIDICLGYKGKRKIHTVIYDSLKKLPFPVKKIAKDFKLTVLKGDIDYHKER<br>PVGYKITPEEYAYIKNDIQIIAEALLIQFKQGLDRMTAGSDSLKGFKDIITTKKF<br>KKVFPTLSLGLDKEVRYAYRGGFTWLNDRFKEKEIGEGMVFDVNSLYPAQ<br>MYSRLLPYGEPIVFEGKYVWDEDYPLHIQHIRCEFELKEGYIPTIQIKRSRFY<br>KGNEYLKSSGGEIADLWLSNVDLELMKEHYDLYNVEYISGLKFKATTGLFK<br>DFIDKWTYIKTTSEGAIKQLAKLMLNSLYGKFASNPDVTGKVPYLKENGALG<br>FRLGEEETKDPVYTPMGVFITAWARYTTITAAQACYDRIIYCDTDSIHLTGTE<br>IPDVIKDIVDPKKLGYWAHESTFKRAKYLRQKTYIQDIYMKEVDGKLVEGSP<br>DDYTDIKFSVKCAGMTDKIKKEVTFENFKVGFSRKMKPKPVQVPGGVVLV<br>DDTFTIK |
| M2Y<br>SEQ ID NO: 2 | MSRKMFSCDFETTTKLDDCRVWAYGYMEIGNLDNYKIGNSLDEFMQWVM<br>EIQADLYFHNLKFDGAFIVNWLEQHGFKWSNEGLPNTYNTIISKMGQWYMI<br>DICFGYKGKRKLHTVIYDSLKKLPFPVKKIAKDFQLPLLKGDIDYHTERPVGH<br>EITPEEYEYIKNDIEIIARALDIQFKQGLDRMTAGSDSLKGFKDILSTKKFNKV<br>FPKLSLPMDKEIRKAYRGGFTWLNDKYKEKEIGEGMVFDVNSLYPSQMYS<br>RPLPYGAPIVFQGKYEKDEQYPLYIQRIRFEFELKEGYIPTIQIKKNPFFKGN<br>EYLKNSGVEPVELYLTNVDLELIQEHYELYNVEYIDGFKFREKTGLFKDFIDK<br>WTYVKTHEEGAKKQLAKLMLNSLYGKFASNPDVTGKVPYLKDDGSLGFRV<br>GDEEYKDPVYTPMGVFITAWARFTTITAAQACYDRIIYCDTDSIHLTGTEVP<br>EIIKDIVDPKKLGYWAHESTFKRAKYLRQKTYIQDIYVKEVDGKLKECSPDE<br>ATTTKFSVKCAGMTDTIKKKVTFDNFAVGFSSMGKPKPVQVNGGVVLVDS<br>VFTIK |

TABLE 2-continued

Amino acid sequence of exemplary wild-type Φ29-type polymerases.

| | |
|---|---|
| B103<br>SEQ ID NO: 3 | MPRKMFSCDFETTTKLDDCRVWAYGYMEIGNLDNYKIGNSLDEFMQWVM<br>EIQADLYFHNLKFDGAFIVNWLEHHGFKWSNEGLPNTYNTIISKMGQWYMI<br>DICFGYKGKRKLHTVIYDSLKKLPFPVKKIAKDFQLPLLKGDIDYHAERPVG<br>HEITPEEYEYIKNDIEIIARALDIQFKQGLDRMTAGSDSLKGFKDILSTKKFNK<br>VFPKLSLPMDKEIRRAYRGGFTWLNDKYKEKEIGEGMVFDVNSLYPSQMY<br>SRPLPYGAPIVFQGKYEKDEQYPLYIQRIRFEFELKEGYIPTIQIKKNPFFKG<br>NEYLKNSGAEPVELYLTNVDLELIQEHYEMYNVEYIDGFKFREKTGLFKEFI<br>DKWTYVKTHEKGAKKQLAKLMFDSLYGKFASNPDVTGKVPYLKEDGSLGF<br>RVGDEEYKDPVYTPMGVFITAWARFTTITAAQACYDRIIYCDTDSIHLTGTE<br>VPEIIKDIVDPKKLGYWAHESTFKRAKYLRQKTYIQDIYAKEVDGKLIECSPD<br>EATTTKFSVKCAGMTDTIKKKVTFDNFRVGFSSTGKPKPVQVNGGVVLVD<br>SVFTIK |
| GA-1<br>SEQ ID NO: 4 | MARSVYVCDFETTTDPEDCRLWAWGWMDIYNTDKWSYGEDIDSFMEWA<br>LNSNSDIYFHNLKFDGSFILPWWLRNGYVHTEEDRTNTPKEFTTTISGMGQ<br>WYAVDVCINTRGKNKNHVVFYDSLKKLPFKVEQIAKGFGLPVLKGDIDYKK<br>YRPVGYVMDDNEIEYLKHDLLIVALALRSMFDNDFTSMTVGSDALNTYKEM<br>LGVKQWEKYFPVLSLKVNSEIRKAYKGGFTWVNPKYQGETVYGGMVFDV<br>NSMYPAMMKNKLLPYGEPVMFKGEYKKNVEYPLYIQQVRCFFELKKDKIP<br>CIQIKGNARFGQNEYLSTSGDEYVDLYVTNVDWELIKKHYDIFEEEFIGGFM<br>FKGFIGFFDEYIDRFMEIKNSPDSSAEQSLQAKLMLNSLYGKFATNPDITGK<br>VPYLDENGVLKFRKGELKERDPVYTPMGCFITAYARENILSNAQKLYPRFIY<br>ADTDSIHVEGLGEVDAIKDVIDPKKLGYWDHEATFQRARYVRQKTYFIETT<br>WKENDKGKLVVCEPQDATKVKPKIACAGMSDAIKERIRFNEFKIGYSTHGS<br>LKPKNVLGGVVLMDYPFAIK |
| AV-1<br>SEQ ID NO: 5 | MVRQSTIASPARGGVRRSHKKVPSFCADFETTTDEDDCRVWSWGIIQVGK<br>LQNYVDGISLDGFMSHISERASHIYFHNLAFDGTFILDWLLKHGYRWTKEN<br>PGVKEFTSLISRMGKYYSITVVFETGFRVEFRDSFKKLPMSVSAIAKAFNLH<br>DQKLEIDYEKPRPIGYIPTEQEKRYQRNDVAIVAQALEVQFAEKMTKLTAGS<br>DSLATYKKMTGKLFIRRFPILSPEIDTEIRKAYRGGFTYADPRYAKKLNGKG<br>SVYDVNSLYPSVMRTALLPYGEPIYSEGAPRTNRPLYIASITFTAKLKPNHIP<br>CIQIKKNLSFNPTQYLEEVKEPTTVVATNIDIELWKKHYDFKIYSWNGTFEFR<br>GSHGFFDTYVDHFMEIKKNSTGGLRQIAKLHLNSLYGKFATNPDITGKHPTL<br>KDNRVSLVMNEPETRDPVYTPMGVFITAYARKKTISAAQDNYETFAYADTD<br>SLHLIGPTTPPDSLWVDPVELGAWKHESSFTKSVYIRAKQYAEEIGGKLDV<br>HIAGMPRNVAATLTLEDMLHGGTWNGKLIPVRVPGGTVLKDTTFTLKID |
| CP-1<br>SEQ ID NO: 6 | MTCYYAGDFETTTNEEETEVWLSCFAKVIDYDKLDTFKVNTSLEDFLKSLY<br>LDLDKTYTETGEDEFIIFFHNLKFDGSFLLSFFLNNDIECTYFINDMGVWYSI<br>TLEFPDFTLTFRDSLKILNFSIATMAGLFKMPIAKGTTPLLKHKPEVIKPEWID<br>YIHVDVAILARGIFAMYYEENFTKYTSASEALTEFKRIFRKSKRKFRDFFPILD<br>EKVDDFCRKHIVGAGRLPTLKHRGRTLNQLIDIYDINSMYPATMLQNALPIGI<br>PKRYKGKPKEIKEDHYYIYHIKADFDLKRGYLPTIQIKKKLDALRIGVRTSDY<br>VTTSKNEVIDLYLTNFDLDLFLKHYDATIMYVETLEFQTESDLFDDYITTYRY<br>KKENAQSPAEKQKAKIMLNSLYGKFGAKIISVKKLAYLDDKGILRFKNDDEE<br>EVQPVYAPVALFVTSIARHFIISNAQENYDNFLYADTDSLHLFHSDSLVLDID<br>PSEFGKWAHEGRAVKAKYLRSKLYIEELIQEDGTTHLDVKGAGMTPEIKEKI<br>TFENFVIGATFEGKRASKQIKGGTLIYETTFKIRETDYLV |

Exemplary Mutation Combinations

A list of exemplary polymerase mutation combinations, and optional corresponding exogenous or heterologous features at the N- and/or C-terminal region of the polymerase, is provided in Tables 3 and 4. Positions of amino acid substitutions are identified relative to a wild-type Φ29 DNA polymerase (SEQ ID NO:1) for the recombinant polymerases in Table 3 and relative to a wild-type M2Y DNA polymerase (SEQ ID NO:2) for the recombinant polymerases in Table 4. Polymerases of the invention (including those provided in Tables 3 and 4) can include any exogenous or heterologous feature (or combination of such features), e.g., at the N- and/or C-terminal region. For example, it will be understood that polymerase mutants in Tables 3 and 4 that do not include, e.g., a C-terminal polyhistidine tag can be modified to include a polyhistidine tag at the C-terminal region, alone or in combination with any of the exogenous or heterologous features described herein. Similarly, some or all of the exogenous features listed in Tables 3 and 4 can be omitted, or substituted or combined with any of the other exogenous features described herein, and still result in a polymerase of the invention. As will be appreciated, the numbering of amino acid residues is with respect to a particular reference polymerase, such as the wild-type sequence of the Φ29 polymerase (SEQ ID NO:1); actual position of a mutation within a molecule of the invention may vary based upon the nature of the various modifications that the enzyme includes relative to the wild type Φ29 enzyme, e.g., deletions and/or additions to the molecule, either at the termini or within the molecule itself.

TABLE 3

Exemplary mutations introduced into a Φ29 DNA polymerase.
Positions are identified relative to SEQ ID NO: 1.

| N-terminal region feature(s) | Mutations | C-terminal region feature(s) |
|---|---|---|
| | K131E Y148I Y224K E239G V250I L253A E375Y A437G A484E D510K K512Y E515Q | His10 GGGSGGGSGGGS BtagV7 |
| | K135Q Y148I Y224K E239G V250I L253A E375Y A437G A484E D510K K512Y E515Q | His10 GGGSGGGSGGGS BtagV7 |
| | K131E Y148I Y224K D235E E239G V250A L253H E375Y A437G A484E D510K K512Y E515Q | His10 GGGSGGGSGGGS BtagV7 |
| | Y148I Y224K E239G L253S E375Y A437G A484E D510K K512Y E515Q | His10 GGGSGGGSGGGS BtagV7 |
| | Y148I Q183F D235E E239G L253H E375Y A437G A484E D510K K512Y E515Q | His10 GGGSGGGSGGGS BtagV7 |
| BtagV7 His10 | Y148I Y224K E239G V250I L253H E375Y A437G A484E D510K K512Y | His10 |
| | Y148I Y224K E239G V250I L253A E375Y A437G A484E D510K K512Y E515Q | His10 GGGSGGGSGGGS BtagV7 |
| | K131E Y148I Y224K D235E E239G L253H E375Y A437G A484E D510K K512Y E515Q | His10 GGGSGGGSGGGS BtagV7 |
| | Y148I Y224K D235E E239G L253H E375Y A437G A484E D510K K512Y E515Q | His10co BtagV7 |
| | Y148I Y224K E239G V250I L253A E375Y A437G A484E D510K K512Y | His10 GGGSGGGSGGGS BtagV7 |
| BtagV7 His10 | Y148I Y224K E239G V250I L253A E375Y A437G A484E D510K K512Y | His10 |
| BtagV7 His10 | K131E Y148I Y224K E239G V250I L253A E375Y A484E D510K K512Y | His10 |
| BtagV7 His10 | K135Q Y148I Y224K E239G V250I L253A E375Y A484E D510K K512Y | His10 |
| BtagV7 His10 | Y148I Y224K E239G L253H E375Y A437G A484E D510K K512Y | His10 |
| | K131E K135Q V141K L142K Y148I Y224K E239G V250I L253A E375Y A437G A484E E508K D510K K512Y E515Q K536Q | His10 GGGSGGGSGGGS BtagV7 |
| | K131E Y148I Y224K E239G V250I L253A E375Y A437G A484E E508K D510K K512Y E515Q | His10 GGGSGGGSGGGS BtagV7 |
| BtagV7 His10 | K131Q Y148I Y224K E239G V250I L253A E375Y A484E D510K K512Y | His10 |

TABLE 4

Exemplary mutations introduced into an M2Y DNA polymerase.
Positions are identified relative to SEQ ID NO: 2.

| N-terminal region feature(s) | Mutations | C-terminal region feature(s) |
|---|---|---|
| BtagV7 His10 | L250A S253A E372Y A481E K509Y | His10 |
|  | Y145I E236G V247I L250A S253A E372Y A434G A481E D507K K509Y E512Q | His10 GGGSGGGSGGGS BtagV7 |
| BtagV7 His10 | K132Q Y145I E236G V247I L250A E372Y A434G A481E D507K K509Y E512Q | His10 |

The amino acid sequences of recombinant Φ29 and M2Y polymerases harboring the exemplary mutation combinations of Tables 3 and 4 are provided in Tables 5 and 6. Table 5 includes the polymerase portion of the molecule as well as the one or more exogenous features at the N- and/or C-terminal region of the polymerase, while Table 6 includes the amino acid sequence of the polymerase portion only.

TABLE 5

Amino acid sequences of exemplary recombinant Φ29 and M2Y polymerases including N- and C-terminal exogenous features. Amino acid positions are identified relative to SEQ ID NO: 1 for recombinant Φ29 polymerases (denoted by "Phi29") or relative to SEQ ID NO: 2 for recombinant M2Y polymerases (denoted by "M2").

| SEQ ID NO | Amino Acid Sequence |
|---|---|
| 7 Phi29.K131E_Y148I_Y224K_E239G_V250I_L253A_E375Y_A437G_A484E_D510K_K512Y_E515Q. His10.GGGSGGGSGGGS .BtagV7 | MKHMPRKMYSCDFETTTKVEDCRVWAYGYMNIED HSEYKIGNSLDEEMAWVLKVQADLYFHNLKFDGAFI INWLERNGFKWSADGLPNTYNTIISRMGQWYMIDIC LGYKGKRKIHTVIYDSLKKLPFPVEKIAKDFKLTVLK GDIDIHKERPVGYKITPEEYAYIKNDIQIIAEALLIQFK QGLDRMTAGSDSLKGFKDIITTKKFKKVFPTLSLGLD KEVRKAYRGGFTWLNDRFKGKEIGEGMVFDINSAYP AQMYSRLLPYGEPIVFEGKYVWDEDYPLHIQHIRCEF ELKEGYIPTIQIKRSRFYKGNEYLKSSGGEIADLWLSN VDLELMKEHYDLYNVEYISGLKFKATTGLFKDFIDK WTYIKTTSYGAIKQLAKLMLNSLYGKFASNPDVTGK VPYLKENGALGFRLGEEETKDPVYTPMGVFITAWGR YTTITAAQACYDRIIYCDTDSIHLTGTEIPDVIKDIVDP KKLGYWEHESTFKRAKYLRQKTYIQDIYMKEVKGY LVQGSPDDYTDIKFSVKCAGMTDKIKKEVTFENFKV GFSRKMKPKPVQVPGGVVLVDDTFTIKGHHHHHHH HHHGGGSGGGSGGGSGLNDFFEAQKIEWHE |
| 8 Phi29.K135Q_Y148I_Y224K_E239G_V250I_L253A_E375Y_A437G_A484E_D510K_K512Y_E515Q. His10.GGGSGGGSGGGS .BtagV7 | MKHMPRKMYSCDFETTTKVEDCRVWAYGYMNIED HSEYKIGNSLDEFMAWVLKVQADLYFHNLKFDGAFI INWLERNGFKWSADGLPNTYNTIISRMGQWYMIDIC LGYKGKRKIHTVIYDSLKKLPFPVKKIAQDFKLTVLK GDIDIHKERPVGYKITPEEYAYIKNDIQIIAEALLIQFK QGLDRMTAGSDSLKGFKDIITTKKFKKVFPTLSLGLD KEVRKAYRGGFTWLNDRFKGKEIGEGMVFDINSAYP AQMYSRLLPYGEPIVFEGKYVWDEDYPLHIQHIRCEF ELKEGYIPTIQIKRSRFYKGNEYLKSSGGEIADLWLSN VDLELMKEHYDLYNVEYISGLKFKATTGLFKDFIDK WTYIKTTSYGAIKQLAKLMLNSLYGKFASNPDVTGK VPYLKENGALGFRLGEEETKDPVYTPMGVFITAWGR YTTITAAQACYDRIIYCDTDSIHLTGTEIPDVIKDIVDP KKLGYWEHESTFKRAKYLRQKTYIQDIYMKEVKGY LVQGSPDDYTDIKFSVKCAGMTDKIKKEVTFENFKV GFSRKMKPKPVQVPGGVVLVDDTFTIKGHHHHHHH HHHGGGSGGGSGGGSGLNDFFEAQKIEWHE |
| 9 Phi29.K131E_Y148I_Y224K_D235E_E239G_V250A_L253H_E375Y_A437G_A484E_D510K_K512Y_E515Q.His10.GGGSGGG SGGGS.BtagV7 | MKHMPRKMYSCDFETTTKVEDCRVWAYGYMNIED HSEYKIGNSLDEFMAWVLKVQADLYFHNLKFDGAFI INWLERNGFKWSADGLPNTYNTIISRMGQWYMIDIC LGYKGKRKIHTVIYDSLKKLPFPVEKIAKDFKLTVLK GDIDIHKERPVGYKITPEEYAYIKNDIQIIAEALLIQFK QGLDRMTAGSDSLKGFKDIITTKKFKKVFPTLSLGLD KEVRKAYRGGFTWLNERFKGKEIGEGMVFDANSHY PAQMYSRLLPYGEPIVFEGKYVWDEDYPLHIQHIRCE FELKEGYIPTIQIKRSRFYKGNEYLKSSGGEIADLWLS |

TABLE 5-continued

Amino acid sequences of exemplary recombinant Φ29 and M2Y polymerases including N- and C-terminal exogenous features. Amino acid positions are identified relative to SEQ ID NO: 1 for recombinant Φ29 polymerases (denoted by "Phi29") or relative to SEQ ID NO: 2 for recombinant M2Y polymerases (denoted by "M2").

| SEQ ID NO | Amino Acid Sequence |
|---|---|
| | NVDLELMKEHYDLYNVEYISGLKFKATTGLFKDFID KWTYIKTTSYGAIKQLAKLMLNSLYGKFASNPDVTG KVPYLKENGALGFRLGEEETKDPVYTPMGVFITAWG RYTTITAAQACYDRIIYCDTDSIHLTGTEIPDVIKDIVD PKKLGYWEHESTFKRAKYLRQKTYIQDIYMKEVKG YLVQGSPDDYTDIKFSVKCAGMTDKIKKEVTFENFK VGFSRKMKPKPVQVPGGVVLVDDTFTIKGHHHHHH HHHHGGSGGGSGGGSGLNDFFEAQKIEWHE |
| 10<br>Phi29.Y148I_Y224K_E23 9G_L253S_E375Y_A437 G_A484E_D510K_K512 Y_E515Q.His10.GGGSG GGSGGGS.BtagV7 | MKHMPRKMYSCDFETTTKVEDCRVWAYGYMNIED HSEYKIGNSLDEFMAWVLKVQADLYFHNLKFDGAFI INWLERNGFKWSADGLPNTYNTIISRMGQWYMIDIC LGYKGKRKIHTVIYDSLKKLPFPVKKIAKDFKLTVLK GDIDIHKERPVGYKITPEEYAYIKNDIQIIAEALLIQFK QGLDRMTAGSDSLKGFKDIITTKKFKKVFPTLSLGLD KEVRKAYRGGFTWLNDRFKGKEIGEGMVFDVNSSY PAQMYSRLLPYGEPIVFEGKYVWDEDYPLHIQHIRCE FELKEGYIPTIQIKRSRFYKGNEYLKSSGGEIADLWLS NVDLELMKEHYDLYNVEYISGLKFKATTGLFKDFID KWTYIKTTSYGAIKQLAKLMLNSLYGKFASNPDVTG KVPYLKENGALGFRLGEEETKDPVYTPMGVFITAWG RYTTITAAQACYDRIIYCDTDSIHLTGTEIPDVIKDIVD PKKLGYWEHESTFKRAKYLRQKTYIQDIYMKEVKG YLVQGSPDDYTDIKFSVKCAGMTDKIKKEVTFENFK VGFSRKMKPKPVQVPGGVVLVDDTFTIKGHHHHHH HHHHGGSGGGSGGGSGLNDFFEAQKIEWHE |
| 11<br>Phi29.Y148I_Q183F_D23 5E_E239G_L253E_E375 Y_A437G_A484E_D510 K_K512Y_E515Q.His10. GGGSGGGSGGGS.Btag V7 | MKHMPRKMYSCDFETTTKVEDCRVWAYGYMNIED HSEYKIGNSLDEFMAWVLKVQADLYFHNLKFDGAFI INWLERNGFKWSADGLPNTYNTIISRMGQWYMIDIC LGYKGKRKIHTVIYDSLKKLPFPVKKIAKDFKLTVLK GDIDIHKERPVGYKITPEEYAYIKNDIQIIAEALLIQFK FGLDRMTAGSDSLKGFKDIITTKKFKKVFPTLSLGLD KEVRYAYRGGFTWLNERFKGKEIGEGMVFDVNSHY PAQMYSRLLPYGEPIVFEGKYVWDEDYPLHIQHIRCE FELKEGYIPTIQIKRSRFYKGNEYLKSSGGEIADLWLS NVDLELMKEHYDLYNVEYISGLKFKATTGLFKDFID KWTYIKTTSYGAIKQLAKLMLNSLYGKFASNPDVTG KVPYLKENGALGFRLGEEETKDPVYTPMGVFITAWG RYTTITAAQACYDRIIYCDTDSIHLTGTEIPDVIKDIVD PKKLGYWEHESTFKRAKYLRQKTYIQDIYMKEVKG YLVQGSPDDYTDIKFSVKCAGMTDKIKKEVTFENFK VGFSRKMKPKPVQVPGGVVLVDDTFTIKGHHHHHH HHHHGGSGGGSGGGSGLNDFFEAQKIEWHE |
| 12<br>BtagV7.His10.Phi29.Y148 I_Y224K_E239G_V250I_ L253H_E375Y_A437G_A 484E_D510K_K512Y.His 10 | MSVDGLNDFFEAQKIEWHEAMGHHHHHHHHHHSS GHIEGRHMKHMPRKMYSCDFETTTKVEDCRVWAY GYMNIEDHSEYKIGNSLDEFMAWVLKVQADLYFHN LKFDGAFIINWLERNGFKWSADGLPNTYNTIISRMGQ WYMIDICLGYKGKRKIHTVIYDSLKKLPFPVKKIAKD FKLTVLKGDIDIHKERPVGYKITPEEYAYIKNDIQIIAE ALLIQFKQGLDRMTAGSDSLKGFKDIITTKKFKKVFP TLSLGLDKEVRKAYRGGFTWLNDRFKGKEIGEGMV FDINSHYPAQMYSRLLPYGEPIVFEGKYVWDEDYPL HIQHIRCEFELKEGYIPTIQIKRSRFYKGNEYLKSSGGE IADLWLSNVDLELMKEHYDLYNVEYISGLKFKATTG LFKDFIDKWTYIKTTSYGAIKQLAKLMLNSLYGKFAS NPDVTGKVPYLKENGALGFRLGEEETKDPVYTPMG VFITAWGRYTTITAAQACYDRIIYCDTDSIHLTGTEIP DVIKDIVDPKKLGYWEHESTFKRAKYLRQKTYIQDIY MKEVKGYLVEGSPDDYTDIKFSVKCAGMTDKIKKE VTFENFKVGFSRKMKPKPVQVPGGVVLVDDTFTIKG HHHHHHHHHH |
| 13<br>Phi29.Y148I_Y224K_E23 9G_V250I_L253A_E375 Y_A437G_A484E_D510 K_K512Y_E515Q.His10. GGGSGGGSGGGS.Btag V7 | MKHMPRKMYSCDFETTTKVEDCRVWAYGYMNIED HSEYKIGNSLDEFMAWVLKVQADLYFHNLKFDGAFI INWLERNGFKWSADGLPNTYNTIISRMGQWYMIDIC LGYKGKRKIHTVIYDSLKKLPFPVKKIAKDFKLTVLK GDIDIHKERPVGYKITPEEYAYIKNDIQIIAEALLIQFK QGLDRMTAGSDSLKGFKDIITTKKFKKVFPTLSLGLD KEVRKAYRGGFTWLNDRFKGKEIGEGMVFDINSAYP |

TABLE 5-continued

Amino acid sequences of exemplary recombinant Φ29 and M2Y
polymerases including N- and C-terminal exogenous features.
Amino acid positions are identified relative to SEQ ID
NO: 1 for recombinant Φ29 polymerases (denoted by
"Phi29") or relative to SEQ ID NO: 2 for recombinant
M2Y polymerases (denoted by "M2").

| SEQ ID NO | Amino Acid Sequence |
|---|---|
| | AQMYSRLLPYGEPIVFEGKYVWDEDYPLHIQHIRCEF<br>ELKEGYIPTIQIKRSRFYKGNEYLKSSGGEIADLWLSN<br>VDLELMKEHYDLYNVEYISGLKFKATTGLFKDFIDK<br>WTYIKTTSYGAIKQLAKLMLNSLYGKFASNPDVTGK<br>VPYLKENGALGFRLGEEETKDPVYTPMGVFITAWGR<br>YTTITAAQACYDRIIYCDTDSIHLTGTEIPDVIKDIVDP<br>KKLGYWEHESTFKRAKYLRQKTYIQDIYMKEVKGY<br>LVQGSPDDYTDIKFSVKCAGMTDKIKKEVTFENFKV<br>GFSRKMKPKPVQVPGGVVLVDDTFTIKGHHHHHHH<br>HHHGGGSGGGSGGGSGLNDFFEAQKIEWHE |
| 14<br>Phi29.K131E_Y148I_Y22<br>4K_D235E_E239G_L253<br>H_E375Y_A437G_A484E<br>_D510K_K512Y_E515Q.<br>His10.GGGSGGGSGGGS<br>.BtagV7 | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVEKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNERFKGKEIGEGMVFDVNSHY<br>PAQMYSRLLPYGEPIVFEGKYVWDEDYPLHIQHIRCE<br>FELKEGYIPTIQIKRSRFYKGNEYLKSSGGEIADLWLS<br>NVDLELMKEHYDLYNVEYISGLKFKATTGLFKDFID<br>KWTYIKTTSYGAIKQLAKLMLNSLYGKFASNPDVTG<br>KVPYLKENGALGFRLGEEETKDPVYTPMGVFITAWG<br>RYTTITAAQACYDRIIYCDTDSIHLTGTEIPDVIKDIVD<br>PKKLGYWEHESTFKRAKYLRQKTYIQDIYMKEVKG<br>YLVQGSPDDYTDIKFSVKCAGMTDKIKKEVTFENFK<br>VGFSRKMKPKPVQVPGGVVLVDDTFTIKGHHHHHH<br>HHHHGGGSGGGSGGGSGLNDFFEAQKIEWHE |
| 15<br>Phi29.Y148I_Y224K_D23<br>5E_E239G_L253H_E375<br>Y_A437G_A484E_D510<br>K_K512Y_E515Q.His10.<br>BtagV7 | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVKKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNERFKGKEIGEGMVFDVNSHY<br>PAQMYSRLLPYGEPIVFEGKYVWDEDYPLHIQHIRCE<br>FELKEGYIPTIQIKRSRFYKGNEYLKSSGGEIADLWLS<br>NVDLELMKEHYDLYNVEYISGLKFKATTGLFKDFID<br>KWTYIKTTSYGAIKQLAKLMLNSLYGKFASNPDVTG<br>KVPYLKENGALGERLGEEETKDPVYTPMGVFITAWG<br>RYTTITAAQACYDRIIYCDTDSIHLTGTEIPDVIKDIVD<br>PKKLGYWEHESTFKRAKYLRQKTYIQDIYMKEVKG<br>YLVQGSPDDYTDIKFSVKCAGMTDKIKKEVTFENFK<br>VGFSRKMKPKPVQVPGGVVLVDDTFTIKGHHHHHH<br>HHHHGGGSGGGSGGGSGLNDFFEAQKIEWHE |
| 16<br>Phi29.Y148I_Y224K_E23<br>9G_V250I_L253A_E375<br>Y_A437G_A484E_D510<br>K_K512Y.His10.GGGSG<br>GGSGGGS.BtagV7 | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVKKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNDRFKGKEIGEGMVFDINSAYP<br>AQMYSRLLPYGEPIVFEGKYVWDEDYPLHIQHIRCEF<br>ELKEGYIPTIQIKRSRFYKGNEYLKSSGGEIADLWLSN<br>VDLELMKEHYDLYNVEYISGLKFKATTGLFKDFIDK<br>WTYIKTTSYGAIKQLAKLMLNSLYGKFASNPDVTGK<br>VPYLKENGALGFRLGEEETKDPVYTPMGVFITAWGR<br>YTTITAAQACYDRIIYCDTDSIHLTGTEIPDVIKDIVDP<br>KKLGYWEHESTFKRAKYLRQKTYIQDIYMKEVKGY<br>LVEGSPDDYTDIKFSVKCAGMTDKIKKEVTFENFKV<br>GFSRKMKPKPVQVPGGVVLVDDTFTIKGHHHHHHH<br>HHHGGGSGGGSGGGSGLNDFFEAQKIEWHE |
| 17<br>BtagV7.His10.CTerm_His<br>10.Phi29.Y148I_Y224K_<br>E239G_V250I_L253A_E3<br>75Y_A437G_A484E_D51<br>0K_K512Y | MSVDGLNDFFEAQKIEWHEAMGHHHHHHHHHHSS<br>GHIEGRHMKHMPRKMYSCDFETTTKVEDCRVWAY<br>GYMNIEDHSEYKIGNSLDEFMAWVLKVQADLYFHN<br>LKFDGAFIINWLERNGFKWSADGLPNTYNTIISRMGQ<br>WYMIDICLGYKGKRKIHTVIYDSLKKLPFPVKKIAKD<br>FKLTVLKGDIDIHKERPVGYKITPEEYAYIKNDIQIIAE |

TABLE 5-continued

Amino acid sequences of exemplary recombinant Φ29 and M2Y polymerases including N- and C-terminal exogenous features. Amino acid positions are identified relative to SEQ ID NO: 1 for recombinant Φ29 polymerases (denoted by "Phi29") or relative to SEQ ID NO: 2 for recombinant M2Y polymerases (denoted by "M2").

| SEQ ID NO | Amino Acid Sequence |
|---|---|
| | ALLIQFKQGLDRMTAGSDSLKGFKDIITTKKFKKVFP<br>TLSLGLDKEVRKAYRGGFTWLNDRFKGKEIGEGMV<br>FDINSAYPAQMYSRLLPYGEPIVFEGKYVWDEDYPL<br>HIQHIRCEFELKEGYIPTIQIKRSRFYKGNEYLKSSGGE<br>IADLWLSNVDLELMKEHYDLYNVEYISGLKFKATTG<br>LFKDFIDKWTYIKTTSYGAIKQLAKLMLNSLYGKFAS<br>NPDVTGKVPYLKENGALGFRLGEEETKDPVYTPMG<br>VFITAWGRYTTITAAQACYDRIIYCDTDSIHLTGTEIP<br>DVIKDIVDPKKLGYWEHESTFKRAKYLRQKTYIQDIY<br>MKEVKGYLVEGSPDDYTDIKFSVKCAGMTDKIKKE<br>VTFENFKVGFSRKMKPKPVQVPGGVVLVDDTFTIKG<br>HHHHHHHHHH |
| 18<br>BtagV7.His10.CTerm_His<br>10.Phi29.K131E_Y148I_<br>Y224K_E239G_V250I_L<br>253A_E375Y_A484E_D5<br>10K_K512Y | MSVDGLNDFFEAQKIEWHEAMGHHHHHHHHHHSS<br>GHIEGRHMKHMPRKMYSCDFETTTKVEDCRVWAY<br>GYMNIEDHSEYKIGNSLDEFMAWVLKVQADLYFHN<br>LKFDGAFIINWLERNGFKWSADGLPNTYNTIISRMGQ<br>WYMIDICLGYKGKRKIHTVIYDSLKKLPFPVEKIAKD<br>FKLTVLKGDIDIHKERPVGYKITPEEYAYIKNDIQIIAE<br>ALLIQFKQGLDRMTAGSDSLKGFKDIITTKKFKKVFP<br>TLSLGLDKEVRKAYRGGFTWLNDRFKGKEIGEGMV<br>FDINSAYPAQMYSRLLPYGEPIVFEGKYVWDEDYPL<br>HIQHIRCEFELKEGYIPTIQIKRSRFYKGNEYLKSSGGE<br>IADLWLSNVDLELMKEHYDLYNVEYISGLKFKATTG<br>LFKDFIDKWTYIKTTSYGAIKQLAKLMLNSLYGKFAS<br>NPDVTGKVPYLKENGALGFRLGEEETKDPVYTPMG<br>VFITAWARYTTITAAQACYDRIIYCDTDSIHLTGTEIP<br>DVIKDIVDPKKLGYWEHESTFKRAKYLRQKTYIQDIY<br>MKEVKGYLVEGSPDDYTDIKFSVKCAGMTDKIKKE<br>VTFENFKVGFSRKMKPKPVQVPGGVVLVDDTFTIKG<br>HHHHHHHHHH |
| 19<br>BtagV7.His10.CTerm_His<br>10.Phi29.K135Q_Y148I_<br>Y224K_E239G_V250I_L<br>253A_E375Y_A484E_D5<br>10K_K512Y | MSVDGLNDFFEAQKIEWHEAMGHHHHHHHHHHSS<br>GHIEGRHMKHMPRKMYSCDFETTTKVEDCRVWAY<br>GYMNIEDHSEYKIGNSLDEFMAWVLKVQADLYFHN<br>LKFDGAFIINWLERNGFKWSADGLPNTYNTIISRMGQ<br>WYMIDICLGYKGKRKIHTVIYDSLKKLPFPVKKIAQD<br>FKLTVLKGDIDIHKERPVGYKITPEEYAYIKNDIQIIAE<br>ALLIQFKQGLDRMTAGSDSLKGFKDIITTKKFKKVFP<br>TLSLGLDKEVRKAYRGGFTWLNDRFKGKEIGEGMV<br>FDINSAYPAQMYSRLLPYGEPIVFEGKYVWDEDYPL<br>HIQHIRCEFELKEGYIPTIQIKRSRFYKGNEYLKSSGGE<br>IADLWLSNVDLELMKEHYDLYNVEYISGLKFKATTG<br>LFKDFIDKWTYIKTTSYGAIKQLAKLMLNSLYGKFAS<br>NPDVTGKVPYLKENGALGFRLGEEETKDPVYTPMG<br>VFITAWARYTTITAAQACYDRIIYCDTDSIHLTGTEIP<br>DVIKDIVDPKKLGYWEHESTFKRAKYLRQKTYIQDIY<br>MKEVKGYLVEGSPDDYTDIKFSVKCAGMTDKIKKE<br>VTFENFKVGFSRKMKPKPVQVPGGVVLVDDTFTIKG<br>HHHHHHHHHH |
| 20<br>BtagV7.His10.CTerm_His<br>10.M2.L250A_S253A_E3<br>72Y_A481E_K509Y | MSVDGLNDFFEAQKIEWHEAMGHHHHHHHHHHSS<br>GHIEGRHMSRKMFSCDFETTTKLDDCRVWAYGYME<br>IGNLDNYKIGNSLDEFMQWVMEIQADLYFHNLKFDG<br>AFIVNWLEQHGFKWSNEGLPNTYNTIISKMGQWYMI<br>DICFGYKGKRKLHTVIYDSLKKLPFPVKKIAKDFQLP<br>LLKGDIDYHTERPVGHEITPEEYEYIKNDIEIIARALDI<br>QFKQGLDRMTAGSDSLKGFKDILSTKKFNKVFPKLS<br>LPMDKEIRKAYRGGFTWLNDKYKEKEIGEGMVFDV<br>NSAYPAQMYSRPLPYGAPIVFQGKYEKDEQYPLYIQ<br>RIRFEFELKEGYIPTIQIKKNPFFKGNEYLKNSGVEPV<br>ELYLTNVDLELIQEHYELYNVEYIDGFKFREKTGLFK<br>DFIDKWTYVKTHEYGAKKQLAKLMLNSLYGKFASN<br>PDVTGKVPYLKDDGSLGFRVGDEEYKDPVYTPMGV<br>FITAWARFTTITAAQACYDRIYCDTDSIHLTGTEVPEI<br>IKDIVDPKKLGYWEHESTFKRAKYLRQKTYIQDIYVK<br>EVDGYLKECSPDEATTTKFSVKCAGMTDTIKKKVTF<br>DNFAVGFSSMGKPKPVQVNGGVVLVDSVFTIKGHH<br>HHHHHHHH |

TABLE 5-continued

Amino acid sequences of exemplary recombinant Φ29 and M2Y polymerases including N- and C-terminal exogenous features. Amino acid positions are identified relative to SEQ ID NO: 1 for recombinant Φ29 polymerases (denoted by "Phi29") or relative to SEQ ID NO: 2 for recombinant M2Y polymerases (denoted by "M2").

| SEQ ID NO | Amino Acid Sequence |
|---|---|
| 21 BtagV7.His10.CTerm_His 10.Phi29.Y148I_Y224K_ E239G_L253H_E375Y_A 437G_A484E_D510K_K5 12Y | MSVDGLNDFFEAQKIEWHEAMGHHHHHHHHHSS GHIEGRHMKHMPRKMYSCDFETTTKVEDCRVWAY GYMNIEDHSEYKIGNSLDEFMAWVLKVQADLYFHN LKFDGAFIINWLERNGFKWSADGLPNTYNTIISRMGQ WYMIDICLGYKGKRKIHTVIYDSLKKLPFPVKKIAKD FKLTVLKGDIDIHKERPVGYKITPEEYAYIKNDIQIIAE ALLIQFKQGLDRMTAGSDSLKGFKDIITTKKFKKVFP TLSLGLDKEVRKAYRGGFTWLNDRFKGKEIGEGMV FDVNSHYPAQMYSRLLPYGEPIVFEGKYVWDEDYPL HIQHIRCEFELKEGYIPTIQIKRSRFYKGNEYLKSSGGE IADLWLSNVDLELMKEHYDLYNVEYISGLKFKATTG LFKDFIDKWTYIKTTSYGAIKQLAKLMLNSLYGKFAS NPDVTGKVPYLKENGALGFRLGEEETKDPVYTPMG VFITAWGRYTTITAAQACYDRIIYCDTDSIHLTGTEIP DVIKDIVDPKKLGYWEHESTFKRAKYLRQKTYIQDIY MKEVKGYLVEGSPDDYTDIKFSVKCAGMTDKIKKE VTFENFKVGFSRKMKPKPVQVPGGVVLVDDTFTIKG HHHHHHHHHH |
| 22 M2.Y145I_E236G_V247I _L250A_S253A_E372Y_ A434G_A481E_D507K_ K509Y_E512Q.His10.GG GSGGGSGGGS.BtagV7 | MSRKMFSCDFETTTKLDDCRVWAYGYMEIGNLDNY KIGNSLDEFMQWVMEIQADLYFHNLKFDGAFIVNWL EQHGFKWSNEGLPNTYNTIISKMGQWYMIDICFGYK GKRKLHTVIYDSLKKLPFPVKKIAKDFQLPLLKGDIDI HTERPVGHEITPEEYEYIKNDIEIIARALDIQFKQGLDR MTAGSDSLKGFKDILSTKKFNKVFPKLSLPMDKEIRK AYRGGFTWLNDKYKGKEIGEGMVFDINSAYPAQMY SRPLPYGAPIVFQGKYEKDEQYPLYIQRIRFEFELKEG YIPTIQIKKNPFFKGNEYLKNSGVEPVELYLTNVDLEL IQEHYELYNVEYIDGFKFREKTGLFKDFIDKWTYVKT HEYGAKKQLAKLMLNSLYGKFASNPDVTGKVPYLK DDGSLGFRVGDEEYKDPVYTPMGVFITAWGRFTTIT AAQACYDRIIYCDTDSIHLTGTEVPEIIKDIVDPKKLG YWEHESTFKRAKYLRQKTYIQDIYVKEVKGYLKQCS PDEATTTKFSVKCAGMTDTIKKKVTFDNFAVGFSSM GKPKPVQVNGGVVLVDSVFTIKGHHHHHHHHHHGG GSGGGSGGGSGLNDFFEAQKIEWHE |
| 23 BtagV7.His10.M2.K132Q Y145I_E236G_V247I_L 250A_E372Y_A434G_A4 81E_D507K_K509Y_E51 2Q.His10 | MSVDGLNDFFEAQKIEWHEAMGHHHHHHHHHSS GHIEGRHMSRKMFSCDFETTTKLDDCRVWAYGYME IGNLDNYKIGNSLDEFMQWVMEIQADLYFHNLKFDG AFIVNWLEQHGFKWSNEGLPNTYNTIISKMGQWYMI DICFGYKGKRKLHTVIYDSLKKLPFPVKKIAQDFQLP LLKGDIDIHTERPVGHEITPEEYEYIKNDIEIIARALDIQ FKQGLDRMTAGSDSLKGFKDILSTKKFNKVFPKLSLP MDKEIRKAYRGGFTWLNDKYKGKEIGEGMVFDINS AYPSQMYSRPLPYGAPIVFQGKYEKDEQYPLYIQRIR FEFELKEGYIPTIQIKKNPFFKGNEYLKNSGVEPVELY LTNVDLELIQEHYELYNVEYIDGFKFREKTGLFKDFI DKWTYVKTHEYGAKKQLAKLMLNSLYGKFASNPD VTGKVPYLKDDGSLGFRVGDEEYKDPVYTPMGVFIT AWGRFTTITAAQACYDRIIYCDTDSIHLTGTEVPEIIK DIVDPKKLGYWEHESTFKRAKYLRQKTYIQDIYVKE VKGYLKQCSPDEATTTKFSVKCAGMTDTIKKKVTFD NFAVGFSSMGKPKPVQVNGGVVLVDSVFTIKGHHH HHHHHHH |
| 24 Phi29.K131E_K135Q_V1 41K_L142K_Y148I_Y224 K_E239G_V250I_L253A _E375Y_A437G_A484E_ E508K_D510K_K512Y_E 515Q_K536Q.His10.GGG SGGGSGGGS.BtagV7 | MKHMPRKMYSCDFETTTKVEDCRVWAYGYMNIED HSEYKIGNSLDEFMAWVLKVQADLYFHNLKFDGAFI INWLERNGFKWSADGLPNTYNTIISRMGQWYMIDIC LGYKGKRKIHTVIYDSLKKLPFPVEKIAQDFKLTKKK GDIDIHKERPVGYKITPEEYAYIKNDIQIIAEALLIQFK QGLDRMTAGSDSLKGFKDIITTKKFKKVFPTLSLGLD KEVRKAYRGGFTWLNDRFKGKEIGEGMVFDINSAYP AQMYSRLLPYGEPIVFEGKYVWDEDYPLHIQHIRCEF ELKEGYIPTIQIKRSRFYKGNEYLKSSGGEIADLWLSN VDLELMKEHYDLYNVEYISGLKFKATTGLFKDFIDK WTYIKTTSYGAIKQLAKLMLNSLYGKFASNPDVTGK VPYLKENGALGFRLGEEETKDPVYTPMGVFITAWGR YTTITAAQACYDRIIYCDTDSIHLTGTEIPDVIKDIVDP KKLGYWEHESTFKRAKYLRQKTYIQDIYMKKVKGY |

TABLE 5-continued

Amino acid sequences of exemplary recombinant Φ29 and M2Y polymerases including N- and C-terminal exogenous features. Amino acid positions are identified relative to SEQ ID NO: 1 for recombinant Φ29 polymerases (denoted by "Phi29") or relative to SEQ ID NO: 2 for recombinant M2Y polymerases (denoted by "M2").

| SEQ ID NO | Amino Acid Sequence |
|---|---|
| | LVQGSPDDYTDIKFSVKCAGMTDQIKKEVTFENFKV GFSRKMKPKPVQVPGGVVLVDDTFTIKGHHHHHHH HHHGGGSGGGSGGGSGLNDFFEAQKIEWHE |
| 25 Phi29.K131E_Y148I_Y224K_E239G_V250I_L253A_E375Y_A437G_A484E_E508K_D510K_K512Y_E515Q.His10.GGGSGGGSGGGS.BtagV7 | MKHMPRKMYSCDFETTTKVEDCRVWAYGYMNIED HSEYKIGNSLDEFMAWVLKVQADLYFHNLKFDGAFI INWLERNGFKWSADGLPNTYNTIISRMGQWYMIDIC LGYKGKRKIHTVIYDSLKKLPFPVEKIAKDFKLTVLK GDIDIHKERPVGYKITPEEYAYIKNDIQIIAEALLIQFK QGLDRMTAGSDSLKGFKDIITTKKFKKVFPTLSLGLD KEVRKAYRGGFTWLNDRFKGKEIGEGMVFDINSAYP AQMYSRLLPYGEPIVFEGKYVWDEDYPLHIQHIRCEF ELKEGYIPTIQIKRSRFYKGNEYLKSSGGEIADLWLSN VDLELMKEHYDLYNVEYISGLKFKATTGLFKDFIDK WTYIKTTSYGAIKQLAKLMLNSLYGKFASNPDVTGK VPYLKENGALGFRLGEEETKDPVYTPMGVFITAWGR YTTITAAQACYDRIIYCDTDSIHLTGTEIPDVIKDIVDP KKLGYWEHESTFKRAKYLRQKTYIQDIYMKKVKGY LVQGSPDDYTDIKFSVKCAGMTDKIKKEVTFENFKV GFSRKMKPKPVQVPGGVVLVDDTFTIKGHHHHHHH HHHGGGSGGGSGGGSGLNDFFEAQKIEWHE |
| 26 BtagV7.His10.Phi29.K131Q_Y148I_Y224K_E239G_V250I_L253A_E375Y_A484E_D510K_K512Y.His10 | MSVDGLNDFFEAQKIEWHEAMGHHHHHHHHHHSS GHIEGRHMKHMPRKMYSCDFETTTKVEDCRVWAY GYMNIEDHSEYKIGNSLDEFMAWVLKVQADLYFHN LKFDGAFIINWLERNGFKWSADGLPNTYNTIISRMGQ WYMIDICLGYKGKRKIHTVIYDSLKKLPFPVQKIAKD FKLTVLKGDIDIHKERPVGYKITPEEYAYIKNDIQIIAE ALLIQFKQGLDRMTAGSDSLKGFKDIITTKKFKKVFP TLSLGLDKEVRKAYRGGFTWLNDRFKGKEIGEGMV FDINSAYPAQMYSRLLPYGEPIVFEGKYVWDEDYPL HIQHIRCEFELKEGYIPTIQIKRSRFYKGNEYLKSSGGE IADLWLSNVDLELMKEHYDLYNVEYISGLKFKATTG LFKDFIDKWTYIKTTSYGAIKQLAKLMLNSLYGKFAS NPDVTGKVPYLKENGALGFRLGEEETKDPVYTPMG VFITAWARYTTITAAQACYDRIIYCDTDSIHLTGTEIP DVIKDIVDPKKLGYWEHESTFKRAKYLRQKTYIQDIY MKEVKGYLVEGSPDDYTDIKFSVKCAGMTDKIKKE VTFENFKVGFSRKMKPKPVQVPGGVVLVDDTFTIKG HHHHHHHHHH |

TABLE 6

Amino acid sequences of exemplary recombinant Φ29 and M2Y polymerases. Amino acid positions are identified relative to SEQ ID NO: 1 for recombinant Φ29 polymerases (denoted by "Phi29") or relative to SEQ ID NO: 2 for recombinant M2Y polymerases (denoted by "M2").

| SEQ ID NO | Amino Acid Sequence |
|---|---|
| 27 Phi29.K131E_Y148I_Y224K_E239G_V250I_L253A_E375Y_A437G_A484E_D510K_K512Y_E515Q | MKHMPRKMYSCDFETTTKVEDCRVWAYGYMNIED HSEYKIGNSLDEEMAWVLKVQADLYFHNLKFDGAFI INWLERNGFKWSADGLPNTYNTIISRMGQWYMIDIC LGYKGKRKIHTVIYDSLKKLPFPVEKIAKDFKLTVLK GDIDIHKERPVGYKITPEEYAYIKNDIQIIAEALLIQFK QGLDRMTAGSDSLKGFKDIITTKKFKKVFPTLSLGLD KEVRKAYRGGFTWLNDRFKGKEIGEGMVFDINSAYP AQMYSRLLPYGEPIVFEGKYVWDEDYPLHIQHIRCEF ELKEGYIPTIQIKRSRFYKGNEYLKSSGGEIADLWLSN VDLELMKEHYDLYNVEYISGLKFKATTGLFKDFIDK WTYIKTTSYGAIKQLAKLMLNSLYGKFASNPDVTGK VPYLKENGALGFRLGEEETKDPVYTPMGVFITAWGR YTTITAAQACYDRIIYCDTDSIHLTGTEIPDVIKDIVDP KKLGYWEHESTFKRAKYLRQKTYIQDIYMKEVKGY LVQGSPDDYTDIKFSVKCAGMTDKIKKEVTFENFKV GFSRKMKPKPVQVPGGVVLVDDTFTIK |

TABLE 6-continued

Amino acid sequences of exemplary recombinant Φ29 and M2Y polymerases. Amino acid positions are identified relative to SEQ ID NO: 1 for recombinant Φ29 polymerases (denoted by "Phi29") or relative to SEQ ID NO: 2 for recombinant M2Y polymerases (denoted by "M2").

| SEQ ID NO | Amino Acid Sequence |
|---|---|
| 28<br>Phi29.K135Q_Y148I_Y224K_E239G_V250I_L253A_E375Y_A437G_A484E_D510K_K512Y_E515Q | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFFVKKIAQDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNDRFKGKEIGEGMVFDINSAYP<br>AQMYSRLLPYGEPIVFEGKYVWDEDYPLHIQHIRCEF<br>ELKEGYIPTIQIKRSRFYKGNEYLKSSGGEIADLWLSN<br>VDLELMKEHYDLYNVEYISGLKFKATTGLFKDFIDK<br>WTYIKTTSYGAIKQLAKLMLNSLYGKFASNPDVTGK<br>VPYLKENGALGFRLGEEETKDPVYTPMGVFITAWGR<br>YTTITAAQACYDRIIYCDTDSIHLTGTEIPDVIKDIVDP<br>KKLGYWEHESTFKRAKYLRQKTYIQDIYMKEVKGY<br>LVQGSPDDYTDIKFSVKCAGMTDKIKKEVTFENFKV<br>GFSRKMKPKPVQVPGGVVLVDDTFTIK |
| 29<br>Phi29.K131E_Y148I_Y224K_D235E_E239G_V250A_L253H_E375Y_A437G_A484E_D510K_K512Y_E515Q | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVEKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNERFKGKEIGEGMVFDANSHY<br>PAQMYSRLLPYGEPIVFEGKYVWDEDYPLHIQHIRCE<br>FELKEGYIPTIQIKRSRFYKGNEYLKSSGGEIADLWLS<br>NVDLELMKEHYDLYNVEYISGLKFKATTGLFKDFID<br>KWTYIKTTSYGAIKQLAKLMLNSLYGKFASNPDVTG<br>KVPYLKENGALGFRLGEEETKDPVYTPMGVFITAWG<br>RYTTITAAQACYDRIIYCDTDSIHLTGTEIPDVIKDIVD<br>PKKLGYWEHESTFKRAKYLRQKTYIQDIYMKEVKG<br>YLVQGSPDDYTDIKFSVKCAGMTDKIKKEVTFENFK<br>VGFSRKMKPKPVQVPGGVVLVDDTFTIK |
| 30<br>Phi29.Y148I_Y224K_E239G_L253S_E375Y_A437G_A484E_D510K_K512Y_E515Q | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVKKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNDRFKGKEIGEGMVFDNSSY<br>PAQMYSRLLPYGEPIVFEGKYVWDEDYPLHIQHIRCE<br>FELKEGYIPTIQIKRSRFYKGNEYLKSSGGEIADLWLS<br>NVDLELMKEHYDLYNVEYISGLKFKATTGLFKDFID<br>KWTYIKTTSYGAIKQLAKLMLNSLYGKFASNPDVTG<br>KVPYLKENGALGFRLGEEETKDPVYTPMGVFITAWG<br>RYTTITAAQACYDRIIYCDTDSIHLTGTEIPDVIKDIVD<br>PKKLGYWEHESTFKRAKYLRQKTYIQDIYMKEVKG<br>YLVQGSPDDYTDIKFSVKCAGMTDKIKKEVTFENFK<br>VGFSRKMKPKPVQVPGGVVLVDDTFTIK |
| 31<br>Phi29.Y148I_Q183F_D235E_E239G_L253H_E375Y_A437G_A484E_D510K_K512Y_E515Q | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVKKIAKDFKLTVLK<br>GDIDIHKERPVGYKITPEEYAYIKNDIQIIAEALLIQFK<br>FGLDRMTAGSDSLKGFKDIITTKKFKKVFPTLSLGLD<br>KEVRYAYRGGFTWLNERFKGKEIGEGMVFDNSHY<br>PAQMYSRLLPYGEPIVFEGKYVWDEDYPLHIQHIRCE<br>FELKEGYIPTIQIKRSRFYKGNEYLKSSGGEIADLWLS<br>NVDLELMKEHYDLYNVEYISGLKFKATTGLFKDFID<br>KWTYIKTTSYGAIKQLAKLMLNSLYGKFASNPDVTG<br>KVPYLKENGALGFRLGEEETKDPVYTPMGVFITAWG<br>RYTTITAAQACYDRIIYCDTDSIHLTGTEIPDVIKDIVD<br>PKKLGYWEHESTFKRAKYLRQKTYIQDIYMKEVKG<br>YLVQGSPDDYTDIKFSVKCAGMTDKIKKEVTFENFK<br>VGFSRKMKPKPVQVPGGVVLVDDTFTIK |

TABLE 6-continued

Amino acid sequences of exemplary recombinant Φ29 and M2Y polymerases. Amino acid positions are identified relative to SEQ ID NO: 1 for recombinant Φ29 polymerases (denoted by "Phi29") or relative to SEQ ID NO: 2 for recombinant M2Y polymerases (denoted by "M2").

| SEQ ID NO | Amino Acid Sequence |
|---|---|
| 32<br>Phi29.Y148I_Y224K_E239G_V250I_L253H_E375Y_A437G_A484E_D510K_K512Y | MKHMPRKMYSCDFETTTKVEDCRVWAYGYMNIED<br>HSEYKIGNSLDEFMAWVLKVQADLYHNLKFDGAFI<br>INWLERNGFKWSADGLPNTYNTIISRMGQWYMIDIC<br>LGYKGKRKIHTVIYDSLKKLPFPVKKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNDRFKGKEIGEGMVFDINSHYP<br>AQMYSRLLPYGEPIVFEGKYVWDEDYPLHIQHIRCEF<br>ELKEGYIPTIQIKRSRFYKGNEYLKSSGGEIADLWLSN<br>VDLELMKEHYDLYNVEYISGLKFKATTGLFKDFIDK<br>WTYIKTTSYGAIKQLAKLMLNSLYGKFASNPDVTGK<br>VPYLKENGALGFRLGEEETKDPVYTPMGVFITAWGR<br>YTTITAAQACYDRIIYCDTDSIHLTGTEIPDVIKDIVDP<br>KKLGYWEHESTFKRAKYLRQKTYIQDIYMKEVKGY<br>LVEGSPDDYTDIKFSVKCAGMTDKIKKEVTFENFKV<br>GFSRKMKPKPVQVPGGVVLVDDTFTIK |
| 33<br>Phi29.Y148I_Y224K_E239G_V250I_L253A_E375Y_A437G_A484E_D510K_K512Y_E515Q | MKHMPRKMYSCDFETTTKVEDCRVWAYGYMNIED<br>HSEYKIGNSLDEFMAWVLKVQADLYHNLKFDGAFI<br>INWLERNGFKWSADGLPNTYNTIISRMGQWYMIDIC<br>LGYKGKRKIHTVIYDSLKKLPFPVKKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNDRFKGKEIGEGMVFDINSAYP<br>AQMYSRLLPYGEPIVFEGKYVWDEDYPLHIQHIRCEF<br>ELKEGYIPTIQIKRSRFYKGNEYLKSSGGEIADLWLSN<br>VDLELMKEHYDLYNVEYISGLKFKATTGLFKDFIDK<br>WTYIKTTSYGAIKQLAKLMLNSLYGKFASNPDVTGK<br>VPYLKENGALGFRLGEEETKDPVYTPMGVFITAWGR<br>YTTITAAQACYDRIIYCDTDSIHLTGTEIPDVIKDIVDP<br>KKLGYWEHESTFKRAKYLRQKTYIQDIYMKEVKGY<br>LVQGSPDDYTDIKFSVKCAGMTDKIKKEVTFENFKV<br>GFSRKMKPKPVQVPGGVVLVDDTFTIK |
| 34<br>Phi29.K131E_Y148I_Y224K_D235E_E239G_L253H_E375Y_A437G_A484E_D510K_K512Y_E515Q | MKHMPRKMYSCDFETTTKVEDCRVWAYGYMNIED<br>HSEYKIGNSLDEFMAWVLKVQADLYHNLKFDGAFI<br>INWLERNGFKWSADGLPNTYNTIISRMGQWYMIDIC<br>LGYKGKRKIHTVIYDSLKKLPFPVEKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNERFKGKEIGEGMVFDVNSHY<br>PAQMYSRLLPYGEPIVFEGKYVWDEDYPLHIQHIRCE<br>FELKEGYIPTIQIKRSRFYKGNEYLKSSGGEIADLWLS<br>NVDLELMKEHYDLYNVEYISGLKFKATTGLFKDFID<br>KWTYIKTTSYGAIKQLAKLMLNSLYGKFASNPDVTG<br>KVPYLKENGALGFRLGEEETKDPVYTPMGVFITAWG<br>RYTTITAAQACYDRIIYCDTDSIHLTGTEIPDVIKDIVD<br>PKKLGYWEHESTFKRAKYLRQKTYIQDIYMKEVKG<br>YLVQGSPDDYTDIKFSVKCAGMTDKIKKEVTFENFK<br>VGFSRKMKPKPVQVPGGVVLVDDTFTIK |
| 35<br>Phi29.Y148I_Y224K_D235E_E239G_L253H_E375Y_A437G_A484E_D510K_K512Y_E515Q | MKHMPRKMYSCDFETTTKVEDCRVWAYGYMNIED<br>HSEYKIGNSLDEFMAWVLKVQADLYHNLKFDGAFI<br>INWLERNGFKWSADGLPNTYNTIISRMGQWYMIDIC<br>LGYKGKRKIHTVIYDSLKKLPFPVKKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNERFKGKEIGEGMVFDVNSHY<br>PAQMYSRLLPYGEPIVFEGKYVWDEDYPLHIQHIRCE<br>FELKEGYIPTIQIKRSRFYKGNEYLKSSGGEIADLWLS<br>NVDLELMKEHYDLYNVEYISGLKFKATTGLFKDFID<br>KWTYIKTTSYGAIKQLAKLMLNSLYGKFASNPDVTG<br>KVPYLKENGALGFRLGEEETKDPVYTPMGVFITAWG<br>RYTTITAAQACYDRIIYCDTDSIHLTGTEIPDVIKDIVD<br>PKKLGYWEHESTFKRAKYLRQKTYIQDIYMKEVKG<br>YLVQGSPDDYTDIKFSVKCAGMTDKIKKEVTFENFK<br>VGFSRKMKPKPVQVPGGVVLVDDTFTIK |

TABLE 6-continued

Amino acid sequences of exemplary recombinant Φ29 and M2Y polymerases. Amino acid positions are identified relative to SEQ ID NO: 1 for recombinant Φ29 polymerases (denoted by "Phi29") or relative to SEQ ID NO: 2 for recombinant M2Y polymerases (denoted by "M2").

| SEQ ID NO | Amino Acid Sequence |
| --- | --- |
| 36<br>Phi29.Y148I_Y224K_E239G_V250I_L253A_E375Y_A437G_A484E_D510K_K512Y | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVKKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNDRFKGKEIGEGMVFDINSAYP<br>AQMYSRLLPYGEPIVFEGKYVWDEDYPLHIQHIRCEF<br>ELKEGYIPTIQIKRSRFYKGNEYLKSSGGEIADLWLSN<br>VDLELMKEHYDLYNVEYISGLKFKATTGLFKDFIDK<br>WTYIKTTSYGAIKQLAKLMLNSLYGKFASNPDVTGK<br>VPYLKENGALGFRLGEEETKDPVYTPMGVFITAWGR<br>YTTITAAQACYDRIIYCDTDSIHLTGTEIPDVIKDIVDP<br>KKLGYWEHESTFKRAKYLRQKTYIQDIYMKEVKGY<br>LVEGSPDDYTDIKFSVKCAGMTDKIKKEVTFENFKV<br>GFSRKMKPKPVQVPGGVVLVDDTFTIK |
| 37<br>Phi29.Y148I_Y224K_E239G_V250I_L253A_E375Y_A437G_A484E_D510K_K512Y | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVKKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNDRFKGKEIGEGMVFDINSAYP<br>AQMYSRLLPYGEPIVFEGKYVWDEDYPLHIQHIRCEF<br>ELKEGYIPTIQIKRSRFYKGNEYLKSSGGEIADLWLSN<br>VDLELMKEHYDLYNVEYISGLKFKATTGLFKDFIDK<br>WTYIKTTSYGAIKQLAKLMLNSLYGKFASNPDVTGK<br>VPYLKENGALGFRLGEEETKDPVYTPMGVFITAWGR<br>YTTITAAQACYDRIIYCDTDSIHLTGTEIPDVIKDIVDP<br>KKLGYWEHESTFKRAKYLRQKTYIQDIYMKEVKGY<br>LVEGSPDDYTDIKFSVKCAGMTDKIKKEVTFENFKV<br>GFSRKMKPKPVQVPGGVVLVDDTFTIK |
| 38<br>Phi29.K131E_Y148I_Y224K_E239G_V250I_L253A_E375Y_A484E_D510K_K512Y | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVEKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNDRFKGKEIGEGMVFDINSAYP<br>AQMYSRLLPYGEPIVFEGKYVWDEDYPLHIQHIRCEF<br>ELKEGYIPTIQIKRSRFYKGNEYLKSSGGEIADLWLSN<br>VDLELMKEHYDLYNVEYISGLKFKATTGLFKDFIDK<br>WTYIKTTSYGAIKQLAKLMLNSLYGKFASNPDVTGK<br>VPYLKENGALGFRLGEEETKDPVYTPMGVFITAWAR<br>YTTITAAQACYDRIIYCDTDSIHLTGTEIPDVIKDIVDP<br>KKLGYWEHESTFKRAKYLRQKTYIQDIYMKEVKGY<br>LVEGSPDDYTDIKFSVKCAGMTDKIKKEVTFENFKV<br>GFSRKMKPKPVQVPGGVVLVDDTFTIK |
| 39<br>Phi29.K135Q_Y148I_Y224K_E239G_V250I_L253A_E375Y_A484E_D510K_K512Y | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVKKIAQDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNDRFKGKEIGEGMVFDINSAYP<br>AQMYSRLLPYGEPIVFEGKYVWDEDYPLHIQHIRCEF<br>ELKEGYIPTIQIKRSRFYKGNEYLKSSGGEIADLWLSN<br>VDLELMKEHYDLYNVEYISGLKFKATTGLFKDFIDK<br>WTYIKTTSYGAIKQLAKLMLNSLYGKFASNPDVTGK<br>VPYLKENGALGFRLGEEETKDPVYTPMGVFITAWAR<br>YTTITAAQACYDRIIYCDTDSIHLTGTEIPDVIKDIVDP<br>KKLGYWEHESTFKRAKYLRQKTYIQDIYMKEVKGY<br>LVEGSPDDYTDIKFSVKCAGMTDKIKKEVTFENFKV<br>GFSRKMKPKPVQVPGGVVLVDDTFTIK |

TABLE 6-continued

Amino acid sequences of exemplary recombinant Φ29 and M2Y polymerases. Amino acid positions are identified relative to SEQ ID NO: 1 for recombinant Φ29 polymerases (denoted by "Phi29") or relative to SEQ ID NO: 2 for recombinant M2Y polymerases (denoted by "M2").

| SEQ ID NO | Amino Acid Sequence |
|---|---|
| 40<br>M2.L250A_S253A_E372Y_A481E_K509Y | MSRKMFSCDFETTTKLDDCRVWAYGYMEIGNLDNY<br>KIGNSLDEFMQWVMEIQADLYFHNLKFDGAFIVNWL<br>EQHGFKWSNEGLPNTYNTIISKMGQWYMIDICFGYK<br>GKRKLHTVIYDSLKKLPFPVKKIAKDFQLPLLKGDID<br>YHTERPVGHEITPEEYEYIKNDIEIIARALDIQFKQGLD<br>RMTAGSDSLKGFKDILSTKKFNKVFPKLSLPMDKEIR<br>KAYRGGFTWLNDKYKEKEIGEGMVFDVNSAYPAQ<br>MYSRPLPYGAPIVFQGKYEKDEQYPLYIQRIRFEFEL<br>KEGYIPTIQIKKNPFFKGNEYLKNSGVEPVELYLTNV<br>DLELIQEHYELYNVEYIDGFKFREKTGLFKDFIDKWT<br>YVKTHEYGAKKQLAKLMLNSLYGKFASNPDVTGKV<br>PYLKDDGSLGFRVGDEEYKDPVYTPMGVFITAWARF<br>TTITAAQACYDRIIYCDTDSIHLTGTEVPEIIKDIVDPK<br>KLGYWEHESTFKRAKYLRQKTYIQDIYVKEVDGYLK<br>ECSPDEATTTKFSVKCAGMTDTIKKKVTFDNFAVGF<br>SSMGKPKPVQVNGGVVLVDSVFTIK |
| 41<br>Phi29.Y148I_Y224K_E239G_L253H_E375Y_A437G_A484E_D510K_K512Y | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVKKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNDRFKGKEIGEGMVFDVNSHY<br>PAQMYSRLLPYGEPIVFEGKYVWDEDYPLHIQHIRCE<br>FELKEGYIPTIQIKRSRFYKGNEYLKSSGGEIADLWLS<br>NVDLELMKEHYDLYNVEYISGLKFKATTGLFKDFID<br>KWTYIKTTSYGAIKQLAKLMLNSLYGKFASNPDVTG<br>KVPYLKENGALGFRLGEEETKDPVYTPMGVFITAWG<br>RYTTITAAQACYDRIIYCDTDSIHLTGTEIPDVIKDIVD<br>PKKLGYWEHESTFKRAKYLRQKTYIQDIYMKEVKG<br>YLVEGSPDDYTDIKFSVKCAGMTDKIKKEVTFENFK<br>VGFSRKMKPKPVQVPGGVVLVDDTFTIK |
| 42<br>M2.Y145I_E236G_V247I_L250A_S253A_E372Y_A434G_A481E_D507K_K509Y_E512Q | MSRKMFSCDFETTTKLDDCRVWAYGYMEIGNLDNY<br>KIGNSLDEFMQWVMEIQADLYFHNLKFDGAFIVNWL<br>EQHGFKWSNEGLPNTYNTIISKMGQWYMIDICFGYK<br>GKRKLHTVIYDSLKKLPFPVKKIAKDFQLPLLKGDIDI<br>HTERPVGHEITPEEYEYIKNDIEIIARALDIQFKQGLDR<br>MTAGSDSLKGFKDILSTKKFNKVFPKLSLPMDKEIRK<br>AYRGGFTWLNDKYKGKEIGEGMVFDINSAYPAQMY<br>SRPLPYGAPIVFQGKYEKDEQYPLYIQRIRFEFELKEG<br>YIPTIQIKKNPFFKGNEYLKNSGVEPVELYLTNVDLEL<br>IQEHYELYNVEYIDGFKFREKTGLFKDFIDKWTYVKT<br>HEYGAKKQLAKLMLNSLYGKFASNPDVTGKVPYLK<br>DDGSLGFRVGDEEYKDPVYTPMGVFITAWGRFTTIT<br>AAQACYDRIIYCDTDSIHLTGTEVPEIIKDIVDPKKLG<br>YWEHESTFKRAKYLRQKTYIQDIYVKEVKGYLKQCS<br>PDEATTTKFSVKCAGMTDTIKKKVTFDNFAVGFSSM<br>GKPKPVQVNGGVVLVDSVFTIK |
| 43<br>M2.K132Q_Y145I_E236G_V247I_L250A_E372Y_A434G_A481E_D507K_K509Y_E512Q | MSRKMFSCDFETTTKLDDCRVWAYGYMEIGNLDNY<br>KIGNSLDEFMQWVMEIQADLYFHNLKFDGAFIVNWL<br>EQHGFKWSNEGLPNTYNTIISKMGQWYMIDICFGYK<br>GKRKLHTVIYDSLKKLPFPVKKIAQDFQLPLLKGDIDI<br>HTERPVGHEITPEEYEYIKNDIEIIARALDIQFKQGLDR<br>MTAGSDSLKGFKDILSTKKFNKVFPKLSLPMDKEIRK<br>AYRGGFTWLNDKYKGKEIGEGMVFDINSAYPSQMY<br>SRPLPYGAPIVFQGKYEKDEQYPLYIQRIRFEFELKEG<br>YIPTIQIKKNPFFKGNEYLKNSGVEPVELYLTNVDLEL<br>IQEHYELYNVEYIDGFKFREKTGLFKDFIDKWTYVKT<br>HEYGAKKQLAKLMLNSLYGKFASNPDVTGKVPYLK<br>DDGSLGFRVGDEEYKDPVYTPMGVFITAWGRFTTIT<br>AAQACYDRIIYCDTDSIHLTGTEVPEIIKDIVDPKKLG<br>YWEHESTFKRAKYLRQKTYIQDIYVKEVKGYLKQCS<br>PDEATTTKFSVKCAGMTDTIKKKVTFDNFAVGFSSM<br>GKPKPVQVNGGVVLVDSVFTIK |

TABLE 6-continued

Amino acid sequences of exemplary recombinant Φ29 and M2Y polymerases. Amino acid positions are identified relative to SEQ ID NO: 1 for recombinant Φ29 polymerases (denoted by "Phi29") or relative to SEQ ID NO: 2 for recombinant M2Y polymerases (denoted by "M2").

| SEQ ID NO | Amino Acid Sequence |
|---|---|
| 44<br>Phi29.K131E_K135Q_V1<br>41K_L142K_Y148I_Y224<br>K_E239G_V250I_L253A<br>_E375Y_A437G_A484E_<br>E508K_D510K_K512Y_E<br>515Q_K536Q | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVEKIAQDFKLTKKK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNDRFKGKEIGEGMVFDINSAYP<br>AQMYSRLLPYGEPIVFEGKYVWDEDYPLHIQHIRCEF<br>ELKEGYIPTIQIKRSRFYKGNEYLKSSGGEIADLWLSN<br>VDLELMKEHYDLYNVEYISGLKFKATTGLFKDFIDK<br>WTYIKTTSYGAIKQLAKLMLNSLYGKFASNPDVTGK<br>VPYLKENGALGFRLGEEETKDPVYTPMGVFITAWGR<br>YTTITAAQACYDRIIYCDTDSIHLTGTEIPDVIKDIVDP<br>KKLGYWEHESTFKRAKYLRQKTYIQDIYMKKVKGY<br>LVQGSPDDYTDIKFSVKCAGMTDQIKKEVTFENFKV<br>GFSRKMKPKPVQVPGGVVLVDDTFTIK |
| 45<br>Phi29.K131E_Y148I_Y22<br>4K_E239G_V250I_L253<br>A_E375Y_A437G_A484E<br>E508K_D510K_K512Y_<br>E515Q | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVEKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNDRFKGKEIGEGMVFDINSAYP<br>AQMYSRLLPYGEPIVFEGKYVWDEDYPLHIQHIRCEF<br>ELKEGYIPTIQIKRSRFYKGNEYLKSSGGEIADLWLSN<br>VDLELMKEHYDLYNVEYISGLKFKATTGLFKDFIDK<br>WTYIKTTSYGAIKQLAKLMLNSLYGKFASNPDVTGK<br>VPYLKENGALGFRLGEEETKDPVYTPMGVFITAWGR<br>YTTITAAQACYDRIIYCDTDSIHLTGTEIPDVIKDIVDP<br>KKLGYWEHESTFKRAKYLRQKTYIQDIYMKKVKGY<br>LVQGSPDDYTDIKFSVKCAGMTDKIKKEVTFENFKV<br>GFSRKMKPKPVQVPGGVVLVDDTFTIK |
| 46<br>Phi29.K131Q_Y148I_Y22<br>4K_E239G_V250I_L253<br>A_E375Y_A484E_D510K<br>_K512Y | MKHMPRKMYSCDFETTTKVEDCRVWAYGYMNIED<br>HSEYKIGNSLDEFMAWVLKVQADLYFHNLKFDGAFI<br>INWLERNGFKWSADGLPNTYNTIISRMGQWYMIDIC<br>LGYKGKRKIHTVIYDSLKKLPFPVQKIAKDFKLTVLK<br>GDIDIHKERPVGYKITPEEYAYIKNDIQIIAEALLIQFK<br>QGLDRMTAGSDSLKGFKDIITTKKFKKVFPTLSLGLD<br>KEVRKAYRGGFTWLNDRFKGKEIGEGMVFDINSAYP<br>AQMYSRLLPYGEPIVFEGKYVWDEDYPLHIQHIRCEF<br>ELKEGYIPTIQIKRSRFYKGNEYLKSSGGEIADLWLSN<br>VDLELMKEHYDLYNVEYISGLKFKATTGLFKDFIDK<br>WTYIKTTSYGAIKQLAKLMLNSLYGKFASNPDVTGK<br>VPYLKENGALGFRLGEEETKDPVYTPMGVFITAWAR<br>YTTITAAQACYDRIIYCDTDSIHLTGTEIPDVIKDIVDP<br>KKLGYWEHESTFKRAKYLRQKTYIQDIYMKEVKGY<br>LVEGSPDDYTDIKFSVKCAGMTDKIKKEVTFENFKV<br>GFSRKMKPKPVQVPGGVVLVDDTFTIK |

Additional exemplary polymerase mutations and/or combinations thereof are provided in FIG. 7. In FIG. 7, positions of the mutations are identified relative to a wild-type Φ29 DNA polymerase (SEQ ID NO:1) where the name of the polymerase includes "Phi29," and where the name of the polymerase includes "M2" positions are identified relative to a wild-type M2Y polymerase (SEQ ID NO:2). Where the feature "topo V fusion" is listed, it indicates that the polymerase includes a fusion as described in de Vega et al. (2010) "Improvement of φ29 DNA polymerase amplification performance by fusion of DNA binding motifs" Proc Natl Acad Sci USA 107:16506-16511. Where the feature "Maltose Binding Fusion Protein" is listed, it indicates that the polymerase includes a fusion with maltose binding protein as known in the art. The notation "pET16.BtagV7co.His10co," where the tags are listing in the N-terminal position, indicates that the polymerase includes N-terminal biotin and His10 tags. The feature "Cterm_His10co" is the same as listing the His10 in the C terminal position; both terms indicate that the polymerase includes a C-terminal His10 tag. "pET16" or "pET11" refers to a vector used to produce a recombinant Φ29 polymerase comprising the indicated mutations, and "co" indicates that the polynucleotide sequence encoding certain features (e.g., a His10 tag or BtagV7) has been codon optimized; neither notation is relevant to the structure of the polymerase.

The mutations or combinations of mutations shown in FIG. 7 are not limited to use in a Φ29 or M2Y polymerase. Essentially any of these mutations, any combination of these mutations, and/or any combination of these mutations with the other mutations disclosed or referenced herein can be introduced into a polymerase (e.g., a Φ29-type polymerase) to produce a modified recombinant polymerase in accordance with the invention. Similarly, polymerases of the invention including the mutations or mutation combinations provided in FIG. 7 can include any exogenous or heterologous feature (or combination of such features), e.g., at the N- and/or C-terminal region. Similarly, some or all of the exogenous features listed in FIG. 7 can be omitted, or substituted or combined with any of the other exogenous features described herein, and still result in a polymerase of the invention. As will be appreciated, the numbering of amino acid residues is with respect to a particular reference polymerase, such as the wild-type sequence of the Φ29 polymerase (SEQ ID NO:1) or M2Y polymerase (SEQ ID NO:2); actual position of a mutation within a molecule of the invention may vary based upon the nature of the various modifications that the enzyme includes relative to the wild type Φ29 enzyme, e.g., deletions and/or additions to the molecule, either at the termini or within the molecule itself.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

Characterization of Exemplary Recombinant Polymerases in Single Molecule Sequencing Reactions Recombinant polymerases based on Φ29 or M2Y polymerase and including various combinations of mutations were expressed and purified as described below. The polymerases were characterized by use in single molecule sequencing. Single molecule sequencing data was obtained with recombinant Φ29 and M2Y polymerases including the mutation combinations listed in FIG. 7. Exemplary data are presented in Table 7. Data for each polymerase is presented along with data for a control polymerase, acquired from the same chip for comparison. nReads represents the number of ZMWs from which single molecule sequencing data was obtained. Accuracy and readlength are determined using data for those reads meeting selected performance criteria.

TABLE 7

Single molecule sequencing with the exemplary recombinant Φ29 and M2Y polymerases listed in Tables 3-5.

| Pol.[a] | nReads | Read length[b] | Accuracy (%) | Control Pol.[c] | Control nReads | Control Readlength | Control Accuracy |
|---|---|---|---|---|---|---|---|
| 7 | 2696 | 1893 | 85.5 | 13 | 3089 | 1677 | 84.9 |
| 8 | 1958 | 1907 | 83.5 | 13 | 1927 | 1628 | 83.1 |
| 9 | 2324 | 2655 | 81.9 | 14 | 2623 | 2358 | 81.7 |
| 10 | 1782 | 1805 | 82 | 22 | 1434 | 1587 | 82.1 |
| 11 | 2278 | 3111 | 81.7 | 15 | 2481 | 2284 | 83.1 |
| 12 | 1347 | 1815 | 80.4 | C1 | 2701 | 1207 | 83.8 |
| 13 | 2570 | 1744 | 85 | 17 | 2479 | 1823 | 83.4 |
| 14 | 1802 | 2089 | 83.5 | 15 | 4921 | 1915 | 83.1 |
| 15 | 2585 | 1617 | 83.6 | C1 | 1886 | 1029 | 83.8 |
| 16 | 1264 | 2076 | 84.5 | 17 | 1400 | 1981 | 83.7 |
| 17 | 2123 | 1507 | 84.9 | C1 | 1715 | 1145 | 85.1 |
| 18 | 2134 | 1289 | 84.3 | C1 | 2282 | 1145 | 84.3 |
| 19 | 3001 | 1450 | 84.9 | C1 | 2072 | 1261 | 84.8 |
| 20 | 868 | 976 | 82.8 | C2 | 2231 | 908 | 83.8 |
| 21 | 2540 | 1470 | 81.2 | C1 | 972 | 878 | 83.3 |
| 22 | 2119 | 2063 | 82.7 | 13 | 1802 | 2180 | 83.5 |
| 23 | 1772 | 996 | 82.8 | C3 | 817 | 870 | 82.5 |
| 24 | 2330 | 2020 | 83 | 7 | 1376 | 2063 | 83.1 |
| 25 | 2644 | 1847 | 83 | 7 | 1427 | 1747 | 83.7 |
| 26 | 2098 | 1333 | 83.4 | C1 | 2080 | 1197 | 83.4 |

[a]SEQ ID NO of exemplary polymerase (see Table 5).
[b]Readlength in nucleotides.
[c]SEQ ID NO of control polymerase (see Table 5). Additional control polymerases are C1: Φ29 BtagV7 His10 Y148I Y224K E239G V250I L253A E375Y A484E D510K K512Y His10, C2: D29 BtagV7 His10 L253A E375Y A484E K512Y His10, and C3: M2Y BtagV7 His10 Y145I E236G V247I L250A E372Y A434G A481E D507K K509Y E512Q His10, where positions are identified relative to SEQ ID NO: 1 for C1 and C2 and relative to SEQ ID NO: 2 for C3.

Materials and Methods
Molecular Cloning
The phi29 and M2Y polymerase genes were cloned into either pET16 or pET11 (Novagen). Primers for specified mutations are designed and introduced into the gene using the Phusion Hot Start DNA Polymerase Kit (New England Biolabs). A PCR reaction is performed to incorporate mutations and product is purified using ZR-96 DNA Clean and Concentration Kits (Zymo Research). PCR products are digested with NdeI/BamHI and ligated into the vector. Plasmids are transformed into TOP10 E. coli competent cells, plated on selective media and incubated at 37° C. overnight. Colonies are selected and plasmid is purified using Qiagen miniprep kits. Plasmids are then sequenced (Sequetech).

Protein Purification
Plasmid containing the recombinant polymerase gene is transformed into BL21 Star21 CDE3+Biotin Ligase cells (Invitrogen) using heat shock. Transformed cells are grown in selective media overnight at 37° C. 200 μL of the overnight culture are diluted into 4 mL of Overnight Express Instant TB Medium (EMD Chemicals) and grown at 37° C. until controls reach O.D. value of 4-6. Cultures are then incubated at 18° C. for 16 hours. Following this incubation, cells are harvested, resuspended in buffer, and frozen at −80° C. Cells are thawed. The resulting lysate is centrifuged and supernatant is collected. Polymerase is purified over nickel followed by heparin columns. The resulting proteins are run on gels and quantified by SYPRO® staining.

Single Molecule Sequencing

Enzymes are characterized by single molecule sequencing basically as described in Eid et al. (2009) Science 323:133-138 (including supplemental information), using reagents similar to those commercially available in SMRT™ sequencing kits (Pacific Biosciences of California, Inc.). Each enzyme is initially screened with a single 5-7 minute movie, followed by secondary screening with 30 minute replicates where applicable. Data presented in Table 7 are from 30 minute movies. Enzymes are evaluated, e.g., based on readlength and accuracy compared to control enzymes.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

---

What is claimed is:

1. A composition comprising a φ29-type (phi29-type) recombinant DNA polymerase, which recombinant polymerase comprises an amino acid sequence that is at least 80% identical to SEQ ID NO:1, and which recombinant polymerase comprises one or more mutation selected from the group consisting of an amino acid substitution at position E20, an amino acid substitution at position R308, a Q99W substitution, a K131S substitution, an R261Q substitution, a C290F substitution, an R306Q substitution, a C455A substitution, an E466K substitution, an E466R substitution, and an E508Q substitution, wherein identification of positions is relative to SEQ ID NO:1, and wherein said polymerase exhibits polymerase activity.

2. The composition of claim 1, wherein the recombinant polymerase comprises an E20D substitution or an R308L substitution, wherein identification of positions is relative to SEQ ID NO:1.

3. The composition of claim 1, wherein the recombinant polymerase comprises one or more mutation or combination of mutations selected from the group consisting of an amino acid substitution at position 253, an amino acid substitution at position 375, an amino acid substitution at position 484, an amino acid substitution at position 512, an amino acid substitution at position 510, an amino acid substitution at position 148, an amino acid substitution at position 224, an amino acid substitution at position 239, an amino acid substitution at position 250, an amino acid substitution at position 437, an amino acid substitution at position 235, an amino acid substitution at position 515, an amino acid substitution at position 141, an amino acid substitution at position 142, an amino acid substitution at position 504, an amino acid substitution at position 508, an amino acid substitution at position 513, an amino acid substitution at position 523, an amino acid substitution at position 536, an amino acid substitution at position 539, an amino acid substitution at position 205, an amino acid substitution at position 472, an amino acid substitution at position 437 and an amino acid substitution at position 253, an amino acid substitution at position 508 and an amino acid substitution at position 510, an A437G substitution and an L253H substitution, an A437G substitution and an L253C substitution, a V250A substitution and an L253H substitution, an A437G substitution, a D235E substitution, an E515Q substitution, an E515P substitution, an E515K substitution, a V250A substitution, a V250I substitution, a Y148I substitution, a Y224K substitution, an E239G substitution, a V141K substitution, an L142K substitution, an E508K substitution, an E508K substitution and a D510S substitution, a K536Q substitution, a K539Q substitution, a K205E substitution, a K205D substitution, a K205A substitution, a K472A substitution, an E375Y substitution, a K512Y substitution, an A484E substitution, an L253A substitution, an L253C substitution, an L253S substitution, an L253H substitution, and a D510K substitution, wherein identification of positions is relative to SEQ ID NO:1.

4. The composition of claim 1, wherein the recombinant polymerase comprises E375Y, A484E, and K512Y substitutions, wherein identification of positions is relative to SEQ ID NO:1.

5. The composition of claim 1, where the recombinant polymerase comprises an amino acid sequence that is at least 90% identical to SEQ ID NO:1.

6. The composition of claim 1, wherein the recombinant polymerase comprises one or more exogenous features at the C-terminal and/or N-terminal region of the polymerase.

7. The composition of claim 6, wherein the recombinant polymerase comprises a biotin ligase recognition sequence and a polyhistidine tag.

8. The composition of claim 6, wherein the C-terminal region of the recombinant polymerase comprises a His10 tag.

9. The composition of claim 1, comprising a phosphate-labeled nucleotide analog.

10. The composition of claim 9, wherein the nucleotide analog comprises a fluorophore.

11. The composition of claim 1, comprising a phosphate-labeled nucleotide analog and a DNA template, wherein the recombinant polymerase incorporates the nucleotide analog into a copy nucleic acid in response to the DNA template.

12. The composition of claim 1, wherein the composition is present in a DNA sequencing system.

13. The composition of claim 12, wherein the sequencing system comprises a zero-mode waveguide.

14. The composition of claim 13, wherein the recombinant polymerase is immobilized on a surface of the zero-mode waveguide in an active form.

15. A method of sequencing a DNA template, the method comprising:
   a) providing a reaction mixture comprising:
      the DNA template,
      a replication initiating moiety that complexes with or is integral to the template,
      the recombinant polymerase of claim 1, wherein the polymerase is capable of replicating at least a portion of the template using the moiety in a template-dependent polymerization reaction, and
      one or more nucleotides and/or nucleotide analogs;
   b) subjecting the reaction mixture to a polymerization reaction in which the modified recombinant polymerase replicates at least a portion of the template in a template-dependent manner, whereby the one or more nucleotides and/or nucleotide analogs are incorporated into the resulting DNA; and
   c) identifying a time sequence of incorporation of the one or more nucleotides and/or nucleotide analogs into the resulting DNA.

16. The method of claim 15, wherein the subjecting and identifying steps are performed in a zero mode waveguide.

17. A method of making a DNA, the method comprising:
   (a) providing a reaction mixture comprising:
      a template,
      a replication initiating moiety that complexes with or is integral to the template,
      the recombinant polymerase of claim 1, which polymerase is capable of replicating at least a portion of the template using the moiety in a template-dependent polymerase reaction, and
      one or more nucleotides and/or nucleotide analogs; and
   (b) reacting the mixture such that the polymerase replicates at least a portion of the template in a template-dependent manner, whereby the one or more nucleotides and/or nucleotide analogs are incorporated into the resulting DNA.

18. The method of claim 17, wherein the mixture is reacted in a zero mode waveguide.

19. The method of claim 17, the method comprising detecting incorporation of at least one of the nucleotides and/or nucleotide analogs.

* * * * *

SEQUENCE LISTING

```
<160> NUMBER OF SEQ ID NOS: 46

<210> SEQ ID NO 1
<211> LENGTH: 575
<212> TYPE: PRT
<213> ORGANISM: Bacteriophage phi-29

<400> SEQUENCE: 1

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285
```

```
Arg Cys Glu Phe Glu Leu Lys Glu Gly Tyr Ile Pro Thr Ile Gln Ile
    290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Thr
        355                 360                 365
Tyr Ile Lys Thr Thr Ser Glu Gly Ala Ile Lys Gln Leu Ala Lys Leu
    370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
        435                 440                 445
Tyr Asp Arg Ile Ile Tyr Cys Asp Thr Asp Ser Ile His Leu Thr Gly
    450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Gln Lys Thr Tyr Ile Gln Asp Ile Tyr Met Lys Glu Val Asp Gly Lys
            500                 505                 510
Leu Val Glu Gly Ser Pro Asp Asp Tyr Thr Asp Ile Lys Phe Ser Val
        515                 520                 525
Lys Cys Ala Gly Met Thr Asp Lys Ile Lys Lys Glu Val Thr Phe Glu
    530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys
                565                 570                 575

<210> SEQ ID NO 2
<211> LENGTH: 572
<212> TYPE: PRT
<213> ORGANISM: Bacteriophage M2Y

<400> SEQUENCE: 2

Met Ser Arg Lys Met Phe Ser Cys Asp Phe Glu Thr Thr Thr Lys Leu
1               5                   10                  15
Asp Asp Cys Arg Val Trp Ala Tyr Gly Tyr Met Glu Ile Gly Asn Leu
            20                  25                  30
Asp Asn Tyr Lys Ile Gly Asn Ser Leu Asp Glu Phe Met Gln Trp Val
        35                  40                  45
Met Glu Ile Gln Ala Asp Leu Tyr Phe His Asn Leu Lys Phe Asp Gly
    50                  55                  60
Ala Phe Ile Val Asn Trp Leu Glu Gln His Gly Phe Lys Trp Ser Asn
65                  70                  75                  80
Glu Gly Leu Pro Asn Thr Tyr Asn Thr Ile Ile Ser Lys Met Gly Gln
```

-continued

```
                85                  90                  95
Trp Tyr Met Ile Asp Ile Cys Phe Gly Tyr Lys Gly Lys Arg Lys Leu
                100                 105                 110
His Thr Val Ile Tyr Asp Ser Leu Lys Lys Leu Pro Phe Pro Val Lys
                115                 120                 125
Lys Ile Ala Lys Asp Phe Gln Leu Pro Leu Leu Lys Gly Asp Ile Asp
            130                 135                 140
Tyr His Thr Glu Arg Pro Val Gly His Glu Ile Thr Pro Glu Glu Tyr
145                 150                 155                 160
Glu Tyr Ile Lys Asn Asp Ile Glu Ile Ala Arg Ala Leu Asp Ile
                165                 170                 175
Gln Phe Lys Gln Gly Leu Asp Arg Met Thr Ala Gly Ser Asp Ser Leu
                180                 185                 190
Lys Gly Phe Lys Asp Ile Leu Ser Thr Lys Phe Asn Lys Val Phe
                195                 200                 205
Pro Lys Leu Ser Leu Pro Met Asp Lys Glu Ile Arg Lys Ala Tyr Arg
            210                 215                 220
Gly Gly Phe Thr Trp Leu Asn Asp Lys Tyr Lys Glu Lys Glu Ile Gly
225                 230                 235                 240
Glu Gly Met Val Phe Asp Val Asn Ser Leu Tyr Pro Ser Gln Met Tyr
                245                 250                 255
Ser Arg Pro Leu Pro Tyr Gly Ala Pro Ile Val Phe Gln Gly Lys Tyr
            260                 265                 270
Glu Lys Asp Glu Gln Tyr Pro Leu Tyr Ile Gln Arg Ile Arg Phe Glu
            275                 280                 285
Phe Glu Leu Lys Glu Gly Tyr Ile Pro Thr Ile Gln Ile Lys Lys Asn
            290                 295                 300
Pro Phe Phe Lys Gly Asn Glu Tyr Leu Lys Asn Ser Gly Val Glu Pro
305                 310                 315                 320
Val Glu Leu Tyr Leu Thr Asn Val Asp Leu Glu Leu Ile Gln Glu His
                325                 330                 335
Tyr Glu Leu Tyr Asn Val Glu Tyr Ile Asp Gly Phe Lys Phe Arg Glu
            340                 345                 350
Lys Thr Gly Leu Phe Lys Asp Phe Ile Asp Lys Trp Thr Tyr Val Lys
            355                 360                 365
Thr His Glu Glu Gly Ala Lys Lys Gln Leu Ala Lys Leu Met Leu Asn
        370                 375                 380
Ser Leu Tyr Gly Lys Phe Ala Ser Asn Pro Asp Val Thr Gly Lys Val
385                 390                 395                 400
Pro Tyr Leu Lys Asp Asp Gly Ser Leu Gly Phe Arg Val Gly Asp Glu
                405                 410                 415
Glu Tyr Lys Asp Pro Val Tyr Thr Pro Met Gly Val Phe Ile Thr Ala
            420                 425                 430
Trp Ala Arg Phe Thr Thr Ile Thr Ala Ala Gln Ala Cys Tyr Asp Arg
            435                 440                 445
Ile Ile Tyr Cys Asp Thr Asp Ser Ile His Leu Thr Gly Thr Glu Val
        450                 455                 460
Pro Glu Ile Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
            485                 490                 495
Tyr Ile Gln Asp Ile Tyr Val Lys Glu Val Asp Gly Lys Leu Lys Glu
            500                 505                 510
```

```
Cys Ser Pro Asp Glu Ala Thr Thr Thr Lys Phe Ser Val Lys Cys Ala
            515                 520                 525
Gly Met Thr Asp Thr Ile Lys Lys Val Thr Phe Asp Asn Phe Ala
        530                 535                 540
Val Gly Phe Ser Ser Met Gly Lys Pro Lys Pro Val Gln Val Asn Gly
545                 550                 555                 560
Gly Val Val Leu Val Asp Ser Val Phe Thr Ile Lys
                565                 570

<210> SEQ ID NO 3
<211> LENGTH: 572
<212> TYPE: PRT
<213> ORGANISM: Bacteriophage B103

<400> SEQUENCE: 3

Met Pro Arg Lys Met Phe Ser Cys Asp Phe Glu Thr Thr Thr Lys Leu
1               5                   10                  15
Asp Asp Cys Arg Val Trp Ala Tyr Gly Tyr Met Glu Ile Gly Asn Leu
                20                  25                  30
Asp Asn Tyr Lys Ile Gly Asn Ser Leu Asp Glu Phe Met Gln Trp Val
            35                  40                  45
Met Glu Ile Gln Ala Asp Leu Tyr Phe His Asn Leu Lys Phe Asp Gly
    50                  55                  60
Ala Phe Ile Val Asn Trp Leu Glu His His Gly Phe Lys Trp Ser Asn
65                  70                  75                  80
Glu Gly Leu Pro Asn Thr Tyr Asn Thr Ile Ile Ser Lys Met Gly Gln
                85                  90                  95
Trp Tyr Met Ile Asp Ile Cys Phe Gly Tyr Lys Gly Lys Arg Lys Leu
                100                 105                 110
His Thr Val Ile Tyr Asp Ser Leu Lys Lys Leu Pro Phe Pro Val Lys
            115                 120                 125
Lys Ile Ala Lys Asp Phe Gln Leu Pro Leu Leu Lys Gly Asp Ile Asp
    130                 135                 140
Tyr His Ala Glu Arg Pro Val Gly His Glu Ile Thr Pro Glu Glu Tyr
145                 150                 155                 160
Glu Tyr Ile Lys Asn Asp Ile Glu Ile Ile Ala Arg Ala Leu Asp Ile
                165                 170                 175
Gln Phe Lys Gln Gly Leu Asp Arg Met Thr Ala Gly Ser Asp Ser Leu
            180                 185                 190
Lys Gly Phe Lys Asp Ile Leu Ser Thr Lys Lys Phe Asn Lys Val Phe
    195                 200                 205
Pro Lys Leu Ser Leu Pro Met Asp Lys Glu Ile Arg Arg Ala Tyr Arg
210                 215                 220
Gly Gly Phe Thr Trp Leu Asn Asp Lys Tyr Lys Glu Lys Glu Ile Gly
225                 230                 235                 240
Glu Gly Met Val Phe Asp Val Asn Ser Leu Tyr Pro Ser Gln Met Tyr
                245                 250                 255
Ser Arg Pro Leu Pro Tyr Gly Ala Pro Ile Val Phe Gln Gly Lys Tyr
            260                 265                 270
Glu Lys Asp Glu Gln Tyr Pro Leu Tyr Ile Gln Arg Ile Arg Phe Glu
    275                 280                 285
Phe Glu Leu Lys Glu Gly Tyr Ile Pro Thr Ile Gln Ile Lys Lys Asn
290                 295                 300
Pro Phe Phe Lys Gly Asn Glu Tyr Leu Lys Asn Ser Gly Ala Glu Pro
```

305                 310                 315                 320

Val Glu Leu Tyr Leu Thr Asn Val Asp Leu Glu Leu Ile Gln Glu His
                        325                 330                 335

Tyr Glu Met Tyr Asn Val Glu Tyr Ile Asp Gly Phe Lys Phe Arg Glu
                        340                 345                 350

Lys Thr Gly Leu Phe Lys Glu Phe Ile Asp Lys Trp Thr Tyr Val Lys
                        355                 360                 365

Thr His Glu Lys Gly Ala Lys Lys Gln Leu Ala Lys Leu Met Phe Asp
                        370                 375                 380

Ser Leu Tyr Gly Lys Phe Ala Ser Asn Pro Asp Val Thr Gly Lys Val
        385                 390                 395                 400

Pro Tyr Leu Lys Glu Asp Gly Ser Leu Gly Phe Arg Val Gly Asp Glu
                        405                 410                 415

Glu Tyr Lys Asp Pro Val Tyr Thr Pro Met Gly Val Phe Ile Thr Ala
                        420                 425                 430

Trp Ala Arg Phe Thr Thr Ile Thr Ala Ala Gln Ala Cys Tyr Asp Arg
                        435                 440                 445

Ile Ile Tyr Cys Asp Thr Asp Ser Ile His Leu Thr Gly Thr Glu Val
                        450                 455                 460

Pro Glu Ile Ile Lys Asp Ile Val Asp Pro Lys Lys Leu Gly Tyr Trp
        465                 470                 475                 480

Ala His Glu Ser Thr Phe Lys Arg Ala Lys Tyr Leu Arg Gln Lys Thr
                        485                 490                 495

Tyr Ile Gln Asp Ile Tyr Ala Lys Glu Val Asp Gly Lys Leu Ile Glu
                        500                 505                 510

Cys Ser Pro Asp Glu Ala Thr Thr Lys Phe Ser Val Lys Cys Ala
                        515                 520                 525

Gly Met Thr Asp Thr Ile Lys Lys Val Thr Phe Asp Asn Phe Arg
                        530                 535                 540

Val Gly Phe Ser Ser Thr Gly Lys Pro Lys Pro Val Gln Val Asn Gly
        545                 550                 555                 560

Gly Val Val Leu Val Asp Ser Val Phe Thr Ile Lys
                        565                 570

<210> SEQ ID NO 4
<211> LENGTH: 578
<212> TYPE: PRT
<213> ORGANISM: Bacteriophage GA-1

<400> SEQUENCE: 4

Met Ala Arg Ser Val Tyr Val Cys Asp Phe Glu Thr Thr Thr Asp Pro
        1               5                   10                  15

Glu Asp Cys Arg Leu Trp Ala Trp Gly Trp Met Asp Ile Tyr Asn Thr
                        20                  25                  30

Asp Lys Trp Ser Tyr Gly Glu Asp Ile Asp Ser Phe Met Glu Trp Ala
                        35                  40                  45

Leu Asn Ser Asn Ser Asp Ile Tyr Phe His Asn Leu Lys Phe Asp Gly
                        50                  55                  60

Ser Phe Ile Leu Pro Trp Trp Leu Arg Asn Gly Tyr Val His Thr Glu
        65                  70                  75                  80

Glu Asp Arg Thr Asn Thr Pro Lys Glu Phe Thr Thr Ile Ser Gly
                        85                  90                  95

Met Gly Gln Trp Tyr Ala Val Asp Val Cys Ile Asn Thr Arg Gly Lys
                        100                 105                 110

-continued

```
Asn Lys Asn His Val Val Phe Tyr Asp Ser Leu Lys Lys Leu Pro Phe
            115                 120                 125

Lys Val Glu Gln Ile Ala Lys Gly Phe Gly Leu Pro Val Leu Lys Gly
        130                 135                 140

Asp Ile Asp Tyr Lys Lys Tyr Arg Pro Val Gly Tyr Val Met Asp Asp
145                 150                 155                 160

Asn Glu Ile Glu Tyr Leu Lys His Asp Leu Leu Ile Val Ala Leu Ala
                165                 170                 175

Leu Arg Ser Met Phe Asp Asn Asp Phe Thr Ser Met Thr Val Gly Ser
            180                 185                 190

Asp Ala Leu Asn Thr Tyr Lys Glu Met Leu Gly Val Lys Gln Trp Glu
        195                 200                 205

Lys Tyr Phe Pro Val Leu Ser Leu Lys Val Asn Ser Glu Ile Arg Lys
    210                 215                 220

Ala Tyr Lys Gly Gly Phe Thr Trp Val Asn Pro Lys Tyr Gln Gly Glu
225                 230                 235                 240

Thr Val Tyr Gly Gly Met Val Phe Asp Val Asn Ser Met Tyr Pro Ala
                245                 250                 255

Met Met Lys Asn Lys Leu Leu Pro Tyr Gly Glu Pro Val Met Phe Lys
            260                 265                 270

Gly Glu Tyr Lys Lys Asn Val Glu Tyr Pro Leu Tyr Ile Gln Gln Val
        275                 280                 285

Arg Cys Phe Phe Glu Leu Lys Lys Asp Lys Ile Pro Cys Ile Gln Ile
    290                 295                 300

Lys Gly Asn Ala Arg Phe Gly Gln Asn Glu Tyr Leu Ser Thr Ser Gly
305                 310                 315                 320

Asp Glu Tyr Val Asp Leu Tyr Val Thr Asn Val Asp Trp Glu Leu Ile
                325                 330                 335

Lys Lys His Tyr Asp Ile Phe Glu Glu Glu Phe Ile Gly Gly Phe Met
            340                 345                 350

Phe Lys Gly Phe Ile Gly Phe Asp Glu Tyr Ile Asp Arg Phe Met
        355                 360                 365

Glu Ile Lys Asn Ser Pro Asp Ser Ser Ala Glu Gln Ser Leu Gln Ala
    370                 375                 380

Lys Leu Met Leu Asn Ser Leu Tyr Gly Lys Phe Ala Thr Asn Pro Asp
385                 390                 395                 400

Ile Thr Gly Lys Val Pro Tyr Leu Asp Glu Asn Gly Val Leu Lys Phe
                405                 410                 415

Arg Lys Gly Glu Leu Lys Glu Arg Asp Pro Val Tyr Thr Pro Met Gly
            420                 425                 430

Cys Phe Ile Thr Ala Tyr Ala Arg Glu Asn Ile Leu Ser Asn Ala Gln
        435                 440                 445

Lys Leu Tyr Pro Arg Phe Ile Tyr Ala Asp Thr Asp Ser Ile His Val
    450                 455                 460

Glu Gly Leu Gly Glu Val Asp Ala Ile Lys Asp Val Ile Asp Pro Lys
465                 470                 475                 480

Lys Leu Gly Tyr Trp Asp His Glu Ala Thr Phe Gln Arg Ala Arg Tyr
                485                 490                 495

Val Arg Gln Lys Thr Tyr Phe Ile Glu Thr Thr Trp Lys Glu Asn Asp
            500                 505                 510

Lys Gly Lys Leu Val Val Cys Glu Pro Gln Asp Ala Thr Lys Val Lys
        515                 520                 525

Pro Lys Ile Ala Cys Ala Gly Met Ser Asp Ala Ile Lys Glu Arg Ile
```

```
            530                 535                 540
Arg Phe Asn Glu Phe Lys Ile Gly Tyr Ser Thr His Gly Ser Leu Lys
545                 550                 555                 560

Pro Lys Asn Val Leu Gly Gly Val Val Leu Met Asp Tyr Pro Phe Ala
                565                 570                 575

Ile Lys

<210> SEQ ID NO 5
<211> LENGTH: 566
<212> TYPE: PRT
<213> ORGANISM: Bacteriophage AV-1

<400> SEQUENCE: 5

Met Val Arg Gln Ser Thr Ile Ala Ser Pro Ala Arg Gly Gly Val Arg
1               5                   10                  15

Arg Ser His Lys Lys Val Pro Ser Phe Cys Ala Asp Phe Glu Thr Thr
                20                  25                  30

Thr Asp Glu Asp Asp Cys Arg Val Trp Ser Trp Gly Ile Ile Gln Val
            35                  40                  45

Gly Lys Leu Gln Asn Tyr Val Asp Gly Ile Ser Leu Asp Gly Phe Met
        50                  55                  60

Ser His Ile Ser Glu Arg Ala Ser His Ile Tyr Phe His Asn Leu Ala
65                  70                  75                  80

Phe Asp Gly Thr Phe Ile Leu Asp Trp Leu Leu Lys His Gly Tyr Arg
                85                  90                  95

Trp Thr Lys Glu Asn Pro Gly Val Lys Glu Phe Thr Ser Leu Ile Ser
                100                 105                 110

Arg Met Gly Lys Tyr Tyr Ser Ile Thr Val Val Phe Glu Thr Gly Phe
            115                 120                 125

Arg Val Glu Phe Arg Asp Ser Phe Lys Lys Leu Pro Met Ser Val Ser
130                 135                 140

Ala Ile Ala Lys Ala Phe Asn Leu His Asp Gln Lys Leu Glu Ile Asp
145                 150                 155                 160

Tyr Glu Lys Pro Arg Pro Ile Gly Tyr Ile Pro Thr Glu Gln Glu Lys
                165                 170                 175

Arg Tyr Gln Arg Asn Asp Val Ala Ile Val Ala Gln Ala Leu Glu Val
            180                 185                 190

Gln Phe Ala Glu Lys Met Thr Lys Leu Thr Ala Gly Ser Asp Ser Leu
        195                 200                 205

Ala Thr Tyr Lys Lys Met Thr Gly Lys Leu Phe Ile Arg Arg Phe Pro
210                 215                 220

Ile Leu Ser Pro Glu Ile Asp Thr Glu Ile Arg Lys Ala Tyr Arg Gly
225                 230                 235                 240

Gly Phe Thr Tyr Ala Asp Pro Arg Tyr Ala Lys Lys Leu Asn Gly Lys
                245                 250                 255

Gly Ser Val Tyr Asp Val Asn Ser Leu Tyr Pro Ser Val Met Arg Thr
            260                 265                 270

Ala Leu Leu Pro Tyr Gly Glu Pro Ile Tyr Ser Glu Gly Ala Pro Arg
        275                 280                 285

Thr Asn Arg Pro Leu Tyr Ile Ala Ser Ile Thr Phe Thr Ala Lys Leu
290                 295                 300

Lys Pro Asn His Ile Pro Cys Ile Gln Ile Lys Lys Asn Leu Ser Phe
305                 310                 315                 320

Asn Pro Thr Gln Tyr Leu Glu Glu Val Lys Glu Pro Thr Thr Val Val
```

-continued

```
                325                 330                 335
Ala Thr Asn Ile Asp Ile Glu Leu Trp Lys Lys His Tyr Asp Phe Lys
            340                 345                 350
Ile Tyr Ser Trp Asn Gly Thr Phe Glu Phe Arg Gly Ser His Gly Phe
            355                 360                 365
Phe Asp Thr Tyr Val Asp His Phe Met Glu Ile Lys Lys Asn Ser Thr
        370                 375                 380
Gly Gly Leu Arg Gln Ile Ala Lys Leu His Leu Asn Ser Leu Tyr Gly
385                 390                 395                 400
Lys Phe Ala Thr Asn Pro Asp Ile Thr Gly Lys His Pro Thr Leu Lys
                405                 410                 415
Asp Asn Arg Val Ser Leu Val Met Asn Glu Pro Glu Thr Arg Asp Pro
                420                 425                 430
Val Tyr Thr Pro Met Gly Val Phe Ile Thr Ala Tyr Ala Arg Lys Lys
                435                 440                 445
Thr Ile Ser Ala Ala Gln Asp Asn Tyr Glu Thr Phe Ala Tyr Ala Asp
            450                 455                 460
Thr Asp Ser Leu His Leu Ile Gly Pro Thr Thr Pro Pro Asp Ser Leu
465                 470                 475                 480
Trp Val Asp Pro Val Glu Leu Gly Ala Trp Lys His Glu Ser Ser Phe
                485                 490                 495
Thr Lys Ser Val Tyr Ile Arg Ala Lys Gln Tyr Ala Glu Glu Ile Gly
                500                 505                 510
Gly Lys Leu Asp Val His Ile Ala Gly Met Pro Arg Asn Val Ala Ala
                515                 520                 525
Thr Leu Thr Leu Glu Asp Met Leu His Gly Gly Thr Trp Asn Gly Lys
        530                 535                 540
Leu Ile Pro Val Arg Val Pro Gly Gly Thr Val Leu Lys Asp Thr Thr
545                 550                 555                 560
Phe Thr Leu Lys Ile Asp
                565

<210> SEQ ID NO 6
<211> LENGTH: 568
<212> TYPE: PRT
<213> ORGANISM: Bacteriophage CP-1

<400> SEQUENCE: 6

Met Thr Cys Tyr Tyr Ala Gly Asp Phe Glu Thr Thr Asn Glu Glu
1               5                   10                  15
Glu Thr Glu Val Trp Leu Ser Cys Phe Ala Lys Val Ile Asp Tyr Asp
                20                  25                  30
Lys Leu Asp Thr Phe Lys Val Asn Thr Ser Leu Glu Asp Phe Leu Lys
            35                  40                  45
Ser Leu Tyr Leu Asp Leu Asp Lys Thr Tyr Thr Glu Thr Gly Glu Asp
        50                  55                  60
Glu Phe Ile Ile Phe Phe His Asn Leu Lys Phe Asp Gly Ser Phe Leu
65                  70                  75                  80
Leu Ser Phe Phe Leu Asn Asn Asp Ile Glu Cys Thr Tyr Phe Ile Asn
                85                  90                  95
Asp Met Gly Val Trp Tyr Ser Ile Thr Leu Glu Phe Pro Asp Phe Thr
            100                 105                 110
Leu Thr Phe Arg Asp Ser Leu Lys Ile Leu Asn Phe Ser Ile Ala Thr
        115                 120                 125
```

```
Met Ala Gly Leu Phe Lys Met Pro Ile Ala Lys Gly Thr Thr Pro Leu
    130                 135                 140

Leu Lys His Lys Pro Glu Val Ile Lys Pro Glu Trp Ile Asp Tyr Ile
145                 150                 155                 160

His Val Asp Val Ala Ile Leu Ala Arg Gly Ile Phe Ala Met Tyr Tyr
                165                 170                 175

Glu Glu Asn Phe Thr Lys Tyr Thr Ser Ala Ser Glu Ala Leu Thr Glu
            180                 185                 190

Phe Lys Arg Ile Phe Arg Lys Ser Lys Arg Lys Phe Arg Asp Phe Phe
        195                 200                 205

Pro Ile Leu Asp Glu Lys Val Asp Asp Phe Cys Arg Lys His Ile Val
    210                 215                 220

Gly Ala Gly Arg Leu Pro Thr Leu Lys His Arg Gly Arg Thr Leu Asn
225                 230                 235                 240

Gln Leu Ile Asp Ile Tyr Asp Ile Asn Ser Met Tyr Pro Ala Thr Met
                245                 250                 255

Leu Gln Asn Ala Leu Pro Ile Gly Ile Pro Lys Arg Tyr Lys Gly Lys
            260                 265                 270

Pro Lys Glu Ile Lys Glu Asp His Tyr Tyr Ile Tyr His Ile Lys Ala
        275                 280                 285

Asp Phe Asp Leu Lys Arg Gly Tyr Leu Pro Thr Ile Gln Ile Lys Lys
    290                 295                 300

Lys Leu Asp Ala Leu Arg Ile Gly Val Arg Thr Ser Asp Tyr Val Thr
305                 310                 315                 320

Thr Ser Lys Asn Glu Val Ile Asp Leu Tyr Leu Thr Asn Phe Asp Leu
                325                 330                 335

Asp Leu Phe Leu Lys His Tyr Asp Ala Thr Ile Met Tyr Val Glu Thr
            340                 345                 350

Leu Glu Phe Gln Thr Glu Ser Asp Leu Phe Asp Asp Tyr Ile Thr Thr
        355                 360                 365

Tyr Arg Tyr Lys Lys Glu Asn Ala Gln Ser Pro Ala Glu Lys Gln Lys
    370                 375                 380

Ala Lys Ile Met Leu Asn Ser Leu Tyr Gly Lys Phe Gly Ala Lys Ile
385                 390                 395                 400

Ile Ser Val Lys Lys Leu Ala Tyr Leu Asp Asp Lys Gly Ile Leu Arg
                405                 410                 415

Phe Lys Asn Asp Asp Glu Glu Val Gln Pro Val Tyr Ala Pro Val
        420                 425                 430

Ala Leu Phe Val Thr Ser Ile Ala Arg His Phe Ile Ile Ser Asn Ala
    435                 440                 445

Gln Glu Asn Tyr Asp Asn Phe Leu Tyr Ala Asp Thr Asp Ser Leu His
450                 455                 460

Leu Phe His Ser Asp Ser Leu Val Leu Asp Ile Asp Pro Ser Glu Phe
465                 470                 475                 480

Gly Lys Trp Ala His Glu Gly Arg Ala Val Lys Ala Lys Tyr Leu Arg
                485                 490                 495

Ser Lys Leu Tyr Ile Glu Glu Leu Ile Gln Glu Asp Gly Thr Thr His
            500                 505                 510

Leu Asp Val Lys Gly Ala Gly Met Thr Pro Glu Ile Lys Glu Lys Ile
        515                 520                 525

Thr Phe Glu Asn Phe Val Ile Gly Ala Thr Phe Glu Gly Lys Arg Ala
    530                 535                 540

Ser Lys Gln Ile Lys Gly Gly Thr Leu Ile Tyr Glu Thr Thr Phe Lys
```

Ile Arg Glu Thr Asp Tyr Leu Val
            565

<210> SEQ ID NO 7
<211> LENGTH: 613
<212> TYPE: PRT
<213> ORGANISM: Artificial
<220> FEATURE:
<223> OTHER INFORMATION: mutant recombinant phi29-type DNA polymerase

<400> SEQUENCE: 7

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Glu Lys Ile Ala Lys Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys

```
                340             345             350
Phe Lys Ala Thr Thr Gly Leu Phe Lys Asp Phe Ile Asp Lys Trp Thr
            355                 360                 365

Tyr Ile Lys Thr Thr Ser Tyr Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Gly Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
            500                 505                 510

Leu Val Gln Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Gly
                565                 570                 575

His His His His His His His His Gly Gly Gly Ser Gly Gly
            580                 585                 590

Gly Ser Gly Gly Gly Ser Gly Leu Asn Asp Phe Phe Glu Ala Gln Lys
        595                 600                 605

Ile Glu Trp His Glu
    610

<210> SEQ ID NO 8
<211> LENGTH: 613
<212> TYPE: PRT
<213> ORGANISM: Artificial
<220> FEATURE:
<223> OTHER INFORMATION: mutant recombinant phi29-type DNA polymerase

<400> SEQUENCE: 8

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
```

```
                  85                  90                  95
Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
                115                 120                 125

Pro Val Lys Lys Ile Ala Gln Asp Phe Lys Leu Thr Val Leu Lys Gly
            130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Ile Thr Thr Lys Lys Phe Lys
                195                 200                 205

Lys Val Phe Pro Thr Leu Ser Leu Gly Leu Asp Lys Glu Val Arg Lys
            210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
                275                 280                 285

Arg Cys Glu Phe Glu Leu Lys Glu Gly Tyr Ile Pro Thr Ile Gln Ile
            290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
            355                 360                 365

Tyr Ile Lys Thr Thr Ser Tyr Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
                420                 425                 430

Ile Thr Ala Trp Gly Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
            450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
            500                 505                 510
```

Leu Val Gln Gly Ser Pro Asp Tyr Thr Asp Ile Lys Phe Ser Val
         515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Thr Phe Thr Ile Lys Gly
             565                 570                 575

His His His His His His His His Gly Gly Gly Ser Gly Gly
                 580                 585                 590

Gly Ser Gly Gly Ser Gly Leu Asn Asp Phe Phe Glu Ala Gln Lys
             595                 600                 605

Ile Glu Trp His Glu
         610

<210> SEQ ID NO 9
<211> LENGTH: 613
<212> TYPE: PRT
<213> ORGANISM: Artificial
<220> FEATURE:
<223> OTHER INFORMATION: mutant recombinant phi29-type DNA polymerase

<400> SEQUENCE: 9

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Glu Lys Ile Ala Lys Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Glu Arg Phe Lys Gly Lys
225                 230                 235                 240

Glu Ile Gly Glu Gly Met Val Phe Asp Ala Asn Ser His Tyr Pro Ala
                245                 250                 255

```
Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Tyr Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Gly Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
            500                 505                 510

Leu Val Gln Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Gly
                565                 570                 575

His His His His His His His His His Gly Gly Gly Ser Gly Gly
            580                 585                 590

Gly Ser Gly Gly Gly Ser Gly Leu Asn Asp Phe Phe Glu Ala Gln Lys
        595                 600                 605

Ile Glu Trp His Glu
    610

<210> SEQ ID NO 10
<211> LENGTH: 613
<212> TYPE: PRT
<213> ORGANISM: Artificial
<220> FEATURE:
<223> OTHER INFORMATION: mutant recombinant phi29-type DNA polymerase

<400> SEQUENCE: 10
```

-continued

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Lys
210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Val Asn Ser Ser Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Tyr Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415
```

```
Gly Glu Glu Glu Thr Lys Asp Pro Val Tyr Thr Pro Met Gly Val Phe
            420                 425                 430

Ile Thr Ala Trp Gly Arg Tyr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
            500                 505                 510

Leu Val Gln Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Gly
                565                 570                 575

His His His His His His His His Gly Gly Ser Gly Gly
            580                 585                 590

Gly Ser Gly Gly Ser Gly Leu Asn Asp Phe Phe Glu Ala Gln Lys
        595                 600                 605

Ile Glu Trp His Glu
        610

<210> SEQ ID NO 11
<211> LENGTH: 613
<212> TYPE: PRT
<213> ORGANISM: Artificial
<220> FEATURE:
<223> OTHER INFORMATION: mutant recombinant phi29-type DNA polymerase

<400> SEQUENCE: 11

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160
```

-continued

Glu Glu Tyr Ala Tyr Ile Lys Asn Asp Ile Gln Ile Ala Glu Ala
            165                 170                 175

Leu Leu Ile Gln Phe Lys Phe Gly Leu Asp Arg Met Thr Ala Gly Ser
        180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Tyr
        210                 215                 220

Ala Tyr Arg Gly Gly Phe Thr Trp Leu Asn Glu Arg Phe Lys Gly Lys
225                 230                 235                 240

Glu Ile Gly Glu Gly Met Val Phe Asp Val Asn Ser His Tyr Pro Ala
            245                 250                 255

Gln Met Tyr Ser Arg Leu Leu Pro Tyr Gly Glu Pro Ile Val Phe Glu
        260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
        340                 345                 350

Phe Lys Ala Thr Thr Gly Leu Phe Lys Asp Phe Ile Asp Lys Trp Thr
        355                 360                 365

Tyr Ile Lys Thr Thr Ser Tyr Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
        420                 425                 430

Ile Thr Ala Trp Gly Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
            485                 490                 495

Gln Lys Thr Tyr Ile Gln Asp Ile Tyr Met Lys Glu Val Lys Gly Tyr
        500                 505                 510

Leu Val Gln Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Gly
            565                 570                 575

His His His His His His His His His Gly Gly Gly Ser Gly Gly

-continued

```
                580                 585                 590
Gly Ser Gly Gly Gly Ser Gly Leu Asn Asp Phe Phe Glu Ala Gln Lys
            595                 600                 605

Ile Glu Trp His Glu
    610

<210> SEQ ID NO 12
<211> LENGTH: 627
<212> TYPE: PRT
<213> ORGANISM: Artificial
<220> FEATURE:
<223> OTHER INFORMATION: mutant recombinant phi29-type DNA polymerase

<400> SEQUENCE: 12

Met Ser Val Asp Gly Leu Asn Asp Phe Phe Glu Ala Gln Lys Ile Glu
1               5                   10                  15

Trp His Glu Ala Met Gly His His His His His His His His His His
            20                  25                  30

Ser Ser Gly His Ile Glu Gly Arg His Met Lys His Met Pro Arg Lys
        35                  40                  45

Met Tyr Ser Cys Asp Phe Glu Thr Thr Thr Lys Val Glu Asp Cys Arg
    50                  55                  60

Val Trp Ala Tyr Gly Tyr Met Asn Ile Glu Asp His Ser Glu Tyr Lys
65                  70                  75                  80

Ile Gly Asn Ser Leu Asp Glu Phe Met Ala Trp Val Leu Lys Val Gln
                85                  90                  95

Ala Asp Leu Tyr Phe His Asn Leu Lys Phe Asp Gly Ala Phe Ile Ile
            100                 105                 110

Asn Trp Leu Glu Arg Asn Gly Phe Lys Trp Ser Ala Asp Gly Leu Pro
        115                 120                 125

Asn Thr Tyr Asn Thr Ile Ile Ser Arg Met Gly Gln Trp Tyr Met Ile
    130                 135                 140

Asp Ile Cys Leu Gly Tyr Lys Gly Lys Arg Lys Ile His Thr Val Ile
145                 150                 155                 160

Tyr Asp Ser Leu Lys Lys Leu Pro Phe Pro Val Lys Lys Ile Ala Lys
                165                 170                 175

Asp Phe Lys Leu Thr Val Leu Lys Gly Asp Ile Asp Ile His Lys Glu
            180                 185                 190

Arg Pro Val Gly Tyr Lys Ile Thr Pro Glu Glu Tyr Ala Tyr Ile Lys
        195                 200                 205

Asn Asp Ile Gln Ile Ile Ala Glu Ala Leu Leu Ile Gln Phe Lys Gln
    210                 215                 220

Gly Leu Asp Arg Met Thr Ala Gly Ser Asp Ser Leu Lys Gly Phe Lys
225                 230                 235                 240

Asp Ile Ile Thr Thr Lys Lys Phe Lys Lys Val Phe Pro Thr Leu Ser
                245                 250                 255

Leu Gly Leu Asp Lys Glu Val Arg Lys Ala Tyr Arg Gly Gly Phe Thr
            260                 265                 270

Trp Leu Asn Asp Arg Phe Lys Gly Lys Glu Ile Gly Glu Gly Met Val
        275                 280                 285

Phe Asp Ile Asn Ser His Tyr Pro Ala Gln Met Tyr Ser Arg Leu Leu
    290                 295                 300

Pro Tyr Gly Glu Pro Ile Val Phe Glu Gly Lys Tyr Val Trp Asp Glu
305                 310                 315                 320

Asp Tyr Pro Leu His Ile Gln His Ile Arg Cys Glu Phe Glu Leu Lys
```

```
                    325                 330                 335
Glu Gly Tyr Ile Pro Thr Ile Gln Ile Lys Arg Ser Arg Phe Tyr Lys
                340                 345                 350
Gly Asn Glu Tyr Leu Lys Ser Ser Gly Gly Glu Ile Ala Asp Leu Trp
            355                 360                 365
Leu Ser Asn Val Asp Leu Glu Leu Met Lys Glu His Tyr Asp Leu Tyr
        370                 375                 380
Asn Val Glu Tyr Ile Ser Gly Leu Lys Phe Lys Ala Thr Thr Gly Leu
385                 390                 395                 400
Phe Lys Asp Phe Ile Asp Lys Trp Thr Tyr Ile Lys Thr Thr Ser Tyr
                405                 410                 415
Gly Ala Ile Lys Gln Leu Ala Lys Leu Met Leu Asn Ser Leu Tyr Gly
                420                 425                 430
Lys Phe Ala Ser Asn Pro Asp Val Thr Gly Lys Val Pro Tyr Leu Lys
            435                 440                 445
Glu Asn Gly Ala Leu Gly Phe Arg Leu Gly Glu Glu Thr Lys Asp
        450                 455                 460
Pro Val Tyr Thr Pro Met Gly Val Phe Ile Thr Ala Trp Gly Arg Tyr
465                 470                 475                 480
Thr Thr Ile Thr Ala Ala Gln Ala Cys Tyr Asp Arg Ile Ile Tyr Cys
                485                 490                 495
Asp Thr Asp Ser Ile His Leu Thr Gly Thr Glu Ile Pro Asp Val Ile
                500                 505                 510
Lys Asp Ile Val Asp Pro Lys Lys Leu Gly Tyr Trp Glu His Glu Ser
            515                 520                 525
Thr Phe Lys Arg Ala Lys Tyr Leu Arg Gln Lys Thr Tyr Ile Gln Asp
        530                 535                 540
Ile Tyr Met Lys Glu Val Lys Gly Tyr Leu Val Glu Gly Ser Pro Asp
545                 550                 555                 560
Asp Tyr Thr Asp Ile Lys Phe Ser Val Lys Cys Ala Gly Met Thr Asp
                565                 570                 575
Lys Ile Lys Lys Glu Val Thr Phe Glu Asn Phe Lys Val Gly Phe Ser
            580                 585                 590
Arg Lys Met Lys Pro Lys Pro Val Gln Val Pro Gly Gly Val Val Leu
        595                 600                 605
Val Asp Asp Thr Phe Thr Ile Lys Gly His His His His His His
    610                 615                 620
His His His
625

<210> SEQ ID NO 13
<211> LENGTH: 613
<212> TYPE: PRT
<213> ORGANISM: Artificial
<220> FEATURE:
<223> OTHER INFORMATION: mutant recombinant phi29-type DNA polymerase

<400> SEQUENCE: 13

Met Lys His Met Pro Arg Lys Met Tyr Ser Cys Asp Phe Glu Thr Thr
1               5                   10                  15
Thr Lys Val Glu Asp Cys Arg Val Trp Ala Tyr Gly Tyr Met Asn Ile
            20                  25                  30
Glu Asp His Ser Glu Tyr Lys Ile Gly Asn Ser Leu Asp Glu Phe Met
        35                  40                  45
Ala Trp Val Leu Lys Val Gln Ala Asp Leu Tyr Phe His Asn Leu Lys
```

-continued

```
               50                  55                  60

Phe Asp Gly Ala Phe Ile Ile Asn Trp Leu Glu Arg Asn Gly Phe Lys
 65                  70                  75                  80

Trp Ser Ala Asp Gly Leu Pro Asn Thr Tyr Asn Thr Ile Ile Ser Arg
                     85                  90                  95

Met Gly Gln Trp Tyr Met Ile Asp Ile Cys Leu Gly Tyr Lys Gly Lys
                    100                 105                 110

Arg Lys Ile His Thr Val Ile Tyr Asp Ser Leu Lys Lys Leu Pro Phe
                115                 120                 125

Pro Val Lys Lys Ile Ala Lys Asp Phe Lys Leu Thr Val Leu Lys Gly
            130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Tyr Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Gly Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480
```

```
Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
            500                 505                 510

Leu Val Gln Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Gly
                565                 570                 575

His His His His His His His His Gly Gly Gly Ser Gly Gly
                580                 585                 590

Gly Ser Gly Gly Gly Ser Gly Leu Asn Asp Phe Phe Glu Ala Gln Lys
        595                 600                 605

Ile Glu Trp His Glu
    610

<210> SEQ ID NO 14
<211> LENGTH: 613
<212> TYPE: PRT
<213> ORGANISM: Artificial
<220> FEATURE:
<223> OTHER INFORMATION: mutant recombinant phi29-type DNA polymerase

<400> SEQUENCE: 14

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Glu Lys Ile Ala Lys Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220
```

```
Ala Tyr Arg Gly Gly Phe Thr Trp Leu Asn Glu Arg Phe Lys Gly Lys
225                 230                 235                 240

Glu Ile Gly Glu Gly Met Val Phe Asp Val Asn Ser His Tyr Pro Ala
            245                 250                 255

Gln Met Tyr Ser Arg Leu Leu Pro Tyr Gly Glu Pro Ile Val Phe Glu
        260                 265                 270

Gly Lys Tyr Val Trp Asp Glu Asp Tyr Pro Leu His Ile Gln His Ile
    275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
        340                 345                 350

Phe Lys Ala Thr Thr Gly Leu Phe Lys Asp Phe Ile Asp Lys Trp Thr
    355                 360                 365

Tyr Ile Lys Thr Thr Ser Tyr Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
        420                 425                 430

Ile Thr Ala Trp Gly Arg Tyr Thr Thr Ile Thr Ala Ala Gln Ala Cys
    435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
            485                 490                 495

Gln Lys Thr Tyr Ile Gln Asp Ile Tyr Met Lys Glu Val Lys Gly Tyr
        500                 505                 510

Leu Val Gln Gly Ser Pro Asp Asp Tyr Thr Asp Ile Lys Phe Ser Val
    515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Gly
            565                 570                 575

His His His His His His His His Gly Gly Ser Gly Gly
        580                 585                 590

Gly Ser Gly Gly Gly Ser Gly Leu Asn Asp Phe Phe Glu Ala Gln Lys
    595                 600                 605

Ile Glu Trp His Glu
    610

<210> SEQ ID NO 15
<211> LENGTH: 613
```

```
<212> TYPE: PRT
<213> ORGANISM: Artificial
<220> FEATURE:
<223> OTHER INFORMATION: mutant recombinant phi29-type DNA polymerase

<400> SEQUENCE: 15
```

| | | | | | | | | | | | | | | |
|---|---|---|---|---|---|---|---|---|---|---|---|---|---|---|
| Met | Lys | His | Met | Pro | Arg | Lys | Met | Tyr | Ser | Cys | Asp | Phe | Glu | Thr | Thr |
| 1 | | | | 5 | | | | | 10 | | | | | 15 | |

| | | | | | | | | | | | | | |
|---|---|---|---|---|---|---|---|---|---|---|---|---|---|
| Thr | Lys | Val | Glu | Asp | Cys | Arg | Val | Trp | Ala | Tyr | Gly | Tyr | Met | Asn | Ile |
| | | | 20 | | | | | 25 | | | | | 30 | | |

| Glu | Asp | His | Ser | Glu | Tyr | Lys | Ile | Gly | Asn | Ser | Leu | Asp | Glu | Phe | Met |
| | | | 35 | | | | | 40 | | | | | 45 | | |

| Ala | Trp | Val | Leu | Lys | Val | Gln | Ala | Asp | Leu | Tyr | Phe | His | Asn | Leu | Lys |
| | 50 | | | | | 55 | | | | | 60 | | | | |

| Phe | Asp | Gly | Ala | Phe | Ile | Ile | Asn | Trp | Leu | Glu | Arg | Asn | Gly | Phe | Lys |
| 65 | | | | | 70 | | | | | 75 | | | | | 80 |

| Trp | Ser | Ala | Asp | Gly | Leu | Pro | Asn | Thr | Tyr | Asn | Thr | Ile | Ile | Ser | Arg |
| | | | | 85 | | | | | 90 | | | | | 95 | |

| Met | Gly | Gln | Trp | Tyr | Met | Ile | Asp | Ile | Cys | Leu | Gly | Tyr | Lys | Gly | Lys |
| | | | 100 | | | | | 105 | | | | | 110 | | |

| Arg | Lys | Ile | His | Thr | Val | Ile | Tyr | Asp | Ser | Leu | Lys | Lys | Leu | Pro | Phe |
| | | | 115 | | | | | 120 | | | | | 125 | | |

| Pro | Val | Lys | Lys | Ile | Ala | Lys | Asp | Phe | Lys | Leu | Thr | Val | Leu | Lys | Gly |
| | 130 | | | | | 135 | | | | | 140 | | | | |

| Asp | Ile | Asp | Ile | His | Lys | Glu | Arg | Pro | Val | Gly | Tyr | Lys | Ile | Thr | Pro |
| 145 | | | | | 150 | | | | | 155 | | | | | 160 |

| Glu | Glu | Tyr | Ala | Tyr | Ile | Lys | Asn | Asp | Ile | Gln | Ile | Ile | Ala | Glu | Ala |
| | | | | 165 | | | | | 170 | | | | | 175 | |

| Leu | Leu | Ile | Gln | Phe | Lys | Gln | Gly | Leu | Asp | Arg | Met | Thr | Ala | Gly | Ser |
| | | | 180 | | | | | 185 | | | | | 190 | | |

| Asp | Ser | Leu | Lys | Gly | Phe | Lys | Asp | Ile | Ile | Thr | Thr | Lys | Lys | Phe | Lys |
| | | | 195 | | | | | 200 | | | | | 205 | | |

| Lys | Val | Phe | Pro | Thr | Leu | Ser | Leu | Gly | Leu | Asp | Lys | Glu | Val | Arg | Lys |
| | 210 | | | | | 215 | | | | | 220 | | | | |

| Ala | Tyr | Arg | Gly | Gly | Phe | Thr | Trp | Leu | Asn | Glu | Arg | Phe | Lys | Gly | Lys |
| 225 | | | | | 230 | | | | | 235 | | | | | 240 |

| Glu | Ile | Gly | Glu | Gly | Met | Val | Phe | Asp | Val | Asn | Ser | His | Tyr | Pro | Ala |
| | | | | 245 | | | | | 250 | | | | | 255 | |

| Gln | Met | Tyr | Ser | Arg | Leu | Leu | Pro | Tyr | Gly | Glu | Pro | Ile | Val | Phe | Glu |
| | | | 260 | | | | | 265 | | | | | 270 | | |

| Gly | Lys | Tyr | Val | Trp | Asp | Glu | Asp | Tyr | Pro | Leu | His | Ile | Gln | His | Ile |
| | | | 275 | | | | | 280 | | | | | 285 | | |

| Arg | Cys | Glu | Phe | Glu | Leu | Lys | Glu | Gly | Tyr | Ile | Pro | Thr | Ile | Gln | Ile |
| | 290 | | | | | 295 | | | | | 300 | | | | |

| Lys | Arg | Ser | Arg | Phe | Tyr | Lys | Gly | Asn | Glu | Tyr | Leu | Lys | Ser | Ser | Gly |
| 305 | | | | | 310 | | | | | 315 | | | | | 320 |

| Gly | Glu | Ile | Ala | Asp | Leu | Trp | Leu | Ser | Asn | Val | Asp | Leu | Glu | Leu | Met |
| | | | | 325 | | | | | 330 | | | | | 335 | |

| Lys | Glu | His | Tyr | Asp | Leu | Tyr | Asn | Val | Glu | Tyr | Ile | Ser | Gly | Leu | Lys |
| | | | 340 | | | | | 345 | | | | | 350 | | |

| Phe | Lys | Ala | Thr | Thr | Gly | Leu | Phe | Lys | Asp | Phe | Ile | Asp | Lys | Trp | Thr |
| | | | 355 | | | | | 360 | | | | | 365 | | |

| Tyr | Ile | Lys | Thr | Thr | Ser | Tyr | Gly | Ala | Ile | Lys | Gln | Leu | Ala | Lys | Leu |
| | 370 | | | | | 375 | | | | | 380 | | | | |

```
Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Thr Lys Asp Pro Val Tyr Thr Pro Met Gly Val Phe
        420                 425                 430

Ile Thr Ala Trp Gly Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
            485                 490                 495

Gln Lys Thr Tyr Ile Gln Asp Ile Tyr Met Lys Glu Val Lys Gly Tyr
        500                 505                 510

Leu Val Gln Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Gly
            565                 570                 575

His His His His His His His His Gly Gly Gly Ser Gly Gly
        580                 585                 590

Gly Ser Gly Gly Gly Ser Gly Leu Asn Asp Phe Phe Glu Ala Gln Lys
        595                 600                 605

Ile Glu Trp His Glu
        610

<210> SEQ ID NO 16
<211> LENGTH: 613
<212> TYPE: PRT
<213> ORGANISM: Artificial
<220> FEATURE:
<223> OTHER INFORMATION: mutant recombinant phi29-type DNA polymerase

<400> SEQUENCE: 16

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
            85                  90                  95

Met Gly Gln Trp Tyr Met Ile Asp Ile Cys Leu Gly Tyr Lys Gly Lys
        100                 105                 110

Arg Lys Ile His Thr Val Ile Tyr Asp Ser Leu Lys Lys Leu Pro Phe
        115                 120                 125
```

```
Pro Val Lys Lys Ile Ala Lys Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Lys
210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
            355                 360                 365

Tyr Ile Lys Thr Thr Ser Tyr Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
                420                 425                 430

Ile Thr Ala Trp Gly Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
                500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
```

```
545                 550                 555                 560
Val Pro Gly Gly Val Leu Val Asp Asp Thr Phe Thr Ile Lys Gly
                565                 570                 575

His His His His His His His His Gly Gly Gly Ser Gly Gly
                580                 585                 590

Gly Ser Gly Gly Ser Gly Leu Asn Asp Phe Phe Glu Ala Gln Lys
                595                 600                 605

Ile Glu Trp His Glu
                610

<210> SEQ ID NO 17
<211> LENGTH: 627
<212> TYPE: PRT
<213> ORGANISM: Artificial
<220> FEATURE:
<223> OTHER INFORMATION: mutant recombinant phi29-type DNA polymerase

<400> SEQUENCE: 17

Met Ser Val Asp Gly Leu Asn Asp Phe Phe Glu Ala Gln Lys Ile Glu
1               5                   10                  15

Trp His Glu Ala Met Gly His His His His His His His His
                20                  25                  30

Ser Ser Gly His Ile Glu Gly Arg His Met Lys His Met Pro Arg Lys
            35                  40                  45

Met Tyr Ser Cys Asp Phe Glu Thr Thr Thr Lys Val Glu Asp Cys Arg
        50                  55                  60

Val Trp Ala Tyr Gly Tyr Met Asn Ile Glu Asp His Ser Glu Tyr Lys
65                  70                  75                  80

Ile Gly Asn Ser Leu Asp Glu Phe Met Ala Trp Val Leu Lys Val Gln
                85                  90                  95

Ala Asp Leu Tyr Phe His Asn Leu Lys Phe Asp Gly Ala Phe Ile Ile
            100                 105                 110

Asn Trp Leu Glu Arg Asn Gly Phe Lys Trp Ser Ala Asp Gly Leu Pro
        115                 120                 125

Asn Thr Tyr Asn Thr Ile Ile Ser Arg Met Gly Gln Trp Tyr Met Ile
    130                 135                 140

Asp Ile Cys Leu Gly Tyr Lys Gly Lys Arg Lys Ile His Thr Val Ile
145                 150                 155                 160

Tyr Asp Ser Leu Lys Lys Leu Pro Phe Pro Val Lys Lys Ile Ala Lys
                165                 170                 175

Asp Phe Lys Leu Thr Val Leu Lys Gly Asp Ile Asp Ile His Lys Glu
            180                 185                 190

Arg Pro Val Gly Tyr Lys Ile Thr Pro Glu Glu Tyr Ala Tyr Ile Lys
        195                 200                 205

Asn Asp Ile Gln Ile Ile Ala Glu Ala Leu Leu Ile Gln Phe Lys Gln
    210                 215                 220

Gly Leu Asp Arg Met Thr Ala Gly Ser Asp Ser Leu Lys Gly Phe Lys
225                 230                 235                 240

Asp Ile Ile Thr Thr Lys Lys Phe Lys Lys Val Phe Pro Thr Leu Ser
                245                 250                 255

Leu Gly Leu Asp Lys Glu Val Arg Lys Ala Tyr Arg Gly Gly Phe Thr
            260                 265                 270

Trp Leu Asn Asp Arg Phe Lys Gly Lys Glu Ile Gly Glu Gly Met Val
        275                 280                 285

Phe Asp Ile Asn Ser Ala Tyr Pro Ala Gln Met Tyr Ser Arg Leu Leu
```

```
                    290                 295                 300
Pro Tyr Gly Glu Pro Ile Val Phe Glu Gly Lys Tyr Val Trp Asp Glu
305                 310                 315                 320

Asp Tyr Pro Leu His Ile Gln His Ile Arg Cys Glu Phe Glu Leu Lys
                325                 330                 335

Glu Gly Tyr Ile Pro Thr Ile Gln Ile Lys Arg Ser Arg Phe Tyr Lys
            340                 345                 350

Gly Asn Glu Tyr Leu Lys Ser Ser Gly Gly Glu Ile Ala Asp Leu Trp
        355                 360                 365

Leu Ser Asn Val Asp Leu Glu Leu Met Lys Glu His Tyr Asp Leu Tyr
    370                 375                 380

Asn Val Glu Tyr Ile Ser Gly Leu Lys Phe Lys Ala Thr Thr Gly Leu
385                 390                 395                 400

Phe Lys Asp Phe Ile Asp Lys Trp Thr Tyr Ile Lys Thr Thr Ser Tyr
                405                 410                 415

Gly Ala Ile Lys Gln Leu Ala Lys Leu Met Leu Asn Ser Leu Tyr Gly
            420                 425                 430

Lys Phe Ala Ser Asn Pro Asp Val Thr Gly Lys Val Pro Tyr Leu Lys
        435                 440                 445

Glu Asn Gly Ala Leu Gly Phe Arg Leu Gly Glu Glu Thr Lys Asp
    450                 455                 460

Pro Val Tyr Thr Pro Met Gly Val Phe Ile Thr Ala Trp Gly Arg Tyr
465                 470                 475                 480

Thr Thr Ile Thr Ala Ala Gln Ala Cys Tyr Asp Arg Ile Ile Tyr Cys
                485                 490                 495

Asp Thr Asp Ser Ile His Leu Thr Gly Thr Glu Ile Pro Asp Val Ile
            500                 505                 510

Lys Asp Ile Val Asp Pro Lys Lys Leu Gly Tyr Trp Glu His Glu Ser
        515                 520                 525

Thr Phe Lys Arg Ala Lys Tyr Leu Arg Gln Lys Thr Tyr Ile Gln Asp
    530                 535                 540

Ile Tyr Met Lys Glu Val Lys Gly Tyr Leu Val Glu Gly Ser Pro Asp
545                 550                 555                 560

Asp Tyr Thr Asp Ile Lys Phe Ser Val Lys Cys Ala Gly Met Thr Asp
                565                 570                 575

Lys Ile Lys Lys Glu Val Thr Phe Glu Asn Phe Lys Val Gly Phe Ser
            580                 585                 590

Arg Lys Met Lys Pro Lys Pro Val Gln Val Pro Gly Gly Val Val Leu
        595                 600                 605

Val Asp Asp Thr Phe Thr Ile Lys Gly His His His His His His
    610                 615                 620

His His His
625

<210> SEQ ID NO 18
<211> LENGTH: 627
<212> TYPE: PRT
<213> ORGANISM: Artificial
<220> FEATURE:
<223> OTHER INFORMATION: mutant recombinant phi29-type DNA polymerase

<400> SEQUENCE: 18

Met Ser Val Asp Gly Leu Asn Asp Phe Phe Glu Ala Gln Lys Ile Glu
1               5                   10                  15

Trp His Glu Ala Met Gly His His His His His His His His His
```

```
                    20                  25                  30
        Ser Ser Gly His Ile Glu Gly Arg His Met Lys His Met Pro Arg Lys
                35                  40                  45
        Met Tyr Ser Cys Asp Phe Glu Thr Thr Thr Lys Val Glu Asp Cys Arg
                50                  55                  60
        Val Trp Ala Tyr Gly Tyr Met Asn Ile Glu Asp His Ser Glu Tyr Lys
        65                  70                  75                  80
        Ile Gly Asn Ser Leu Asp Glu Phe Met Ala Trp Val Leu Lys Val Gln
                        85                  90                  95
        Ala Asp Leu Tyr Phe His Asn Leu Lys Phe Asp Gly Ala Phe Ile Ile
                        100                 105                 110
        Asn Trp Leu Glu Arg Asn Gly Phe Lys Trp Ser Ala Asp Gly Leu Pro
                        115                 120                 125
        Asn Thr Tyr Asn Thr Ile Ile Ser Arg Met Gly Gln Trp Tyr Met Ile
                        130                 135                 140
        Asp Ile Cys Leu Gly Tyr Lys Gly Lys Arg Lys Ile His Thr Val Ile
        145                 150                 155                 160
        Tyr Asp Ser Leu Lys Lys Leu Pro Phe Pro Val Glu Lys Ile Ala Lys
                        165                 170                 175
        Asp Phe Lys Leu Thr Val Leu Lys Gly Asp Ile Asp Ile His Lys Glu
                        180                 185                 190
        Arg Pro Val Gly Tyr Lys Ile Thr Pro Glu Glu Tyr Ala Tyr Ile Lys
                        195                 200                 205
        Asn Asp Ile Gln Ile Ile Ala Glu Ala Leu Leu Ile Gln Phe Lys Gln
                        210                 215                 220
        Gly Leu Asp Arg Met Thr Ala Gly Ser Asp Ser Leu Lys Gly Phe Lys
        225                 230                 235                 240
        Asp Ile Ile Thr Thr Lys Lys Phe Lys Lys Val Phe Pro Thr Leu Ser
                        245                 250                 255
        Leu Gly Leu Asp Lys Glu Val Arg Lys Ala Tyr Arg Gly Gly Phe Thr
                        260                 265                 270
        Trp Leu Asn Asp Arg Phe Lys Gly Lys Glu Ile Gly Glu Gly Met Val
                        275                 280                 285
        Phe Asp Ile Asn Ser Ala Tyr Pro Ala Gln Met Tyr Ser Arg Leu Leu
        290                 295                 300
        Pro Tyr Gly Glu Pro Ile Val Phe Glu Gly Lys Tyr Val Trp Asp Glu
        305                 310                 315                 320
        Asp Tyr Pro Leu His Ile Gln His Ile Arg Cys Glu Phe Glu Leu Lys
                        325                 330                 335
        Glu Gly Tyr Ile Pro Thr Ile Gln Ile Lys Arg Ser Arg Phe Tyr Lys
                        340                 345                 350
        Gly Asn Glu Tyr Leu Lys Ser Ser Gly Gly Glu Ile Ala Asp Leu Trp
                        355                 360                 365
        Leu Ser Asn Val Asp Leu Glu Leu Met Lys Glu His Tyr Asp Leu Tyr
                        370                 375                 380
        Asn Val Glu Tyr Ile Ser Gly Leu Lys Phe Lys Ala Thr Thr Gly Leu
        385                 390                 395                 400
        Phe Lys Asp Phe Ile Asp Lys Trp Thr Tyr Ile Lys Thr Thr Ser Tyr
                        405                 410                 415
        Gly Ala Ile Lys Gln Leu Ala Lys Leu Met Leu Asn Ser Leu Tyr Gly
                        420                 425                 430
        Lys Phe Ala Ser Asn Pro Asp Val Thr Gly Lys Val Pro Tyr Leu Lys
                        435                 440                 445
```

-continued

```
Glu Asn Gly Ala Leu Gly Phe Arg Leu Gly Glu Glu Thr Lys Asp
    450                 455                 460
Pro Val Tyr Thr Pro Met Gly Val Phe Ile Thr Ala Trp Ala Arg Tyr
465                 470                 475                 480
Thr Thr Ile Thr Ala Ala Gln Ala Cys Tyr Asp Arg Ile Ile Tyr Cys
                485                 490                 495
Asp Thr Asp Ser Ile His Leu Thr Gly Thr Glu Ile Pro Asp Val Ile
                500                 505                 510
Lys Asp Ile Val Asp Pro Lys Lys Leu Gly Tyr Trp Glu His Glu Ser
            515                 520                 525
Thr Phe Lys Arg Ala Lys Tyr Leu Arg Gln Lys Thr Tyr Ile Gln Asp
        530                 535                 540
Ile Tyr Met Lys Glu Val Lys Gly Tyr Leu Val Glu Gly Ser Pro Asp
545                 550                 555                 560
Asp Tyr Thr Asp Ile Lys Phe Ser Val Lys Cys Ala Gly Met Thr Asp
                565                 570                 575
Lys Ile Lys Lys Glu Val Thr Phe Glu Asn Phe Lys Val Gly Phe Ser
                580                 585                 590
Arg Lys Met Lys Pro Lys Pro Val Gln Val Pro Gly Gly Val Val Leu
            595                 600                 605
Val Asp Asp Thr Phe Thr Ile Lys Gly His His His His His His
610                 615                 620
His His His
625

<210> SEQ ID NO 19
<211> LENGTH: 627
<212> TYPE: PRT
<213> ORGANISM: Artificial
<220> FEATURE:
<223> OTHER INFORMATION: mutant recombinant phi29-type DNA polymerase

<400> SEQUENCE: 19

Met Ser Val Asp Gly Leu Asn Asp Phe Phe Glu Ala Gln Lys Ile Glu
1               5                   10                  15
Trp His Glu Ala Met Gly His His His His His His His His His
            20                  25                  30
Ser Ser Gly His Ile Glu Gly Arg His Met Lys His Met Pro Arg Lys
        35                  40                  45
Met Tyr Ser Cys Asp Phe Glu Thr Thr Thr Lys Val Glu Asp Cys Arg
    50                  55                  60
Val Trp Ala Tyr Gly Tyr Met Asn Ile Glu Asp His Ser Glu Tyr Lys
65                  70                  75                  80
Ile Gly Asn Ser Leu Asp Glu Phe Met Ala Trp Val Leu Lys Val Gln
                85                  90                  95
Ala Asp Leu Tyr Phe His Asn Leu Lys Phe Asp Gly Ala Phe Ile Ile
                100                 105                 110
Asn Trp Leu Glu Arg Asn Gly Phe Lys Trp Ser Ala Asp Gly Leu Pro
            115                 120                 125
Asn Thr Tyr Asn Thr Ile Ile Ser Arg Met Gly Gln Trp Tyr Met Ile
        130                 135                 140
Asp Ile Cys Leu Gly Tyr Lys Gly Lys Arg Lys Ile His Thr Val Ile
145                 150                 155                 160
Tyr Asp Ser Leu Lys Lys Leu Pro Phe Pro Val Lys Lys Ile Ala Gln
                165                 170                 175
```

```
Asp Phe Lys Leu Thr Val Leu Lys Gly Asp Ile Asp Ile His Lys Glu
            180                 185                 190

Arg Pro Val Gly Tyr Lys Ile Thr Pro Glu Glu Tyr Ala Tyr Ile Lys
            195                 200                 205

Asn Asp Ile Gln Ile Ile Ala Glu Ala Leu Leu Ile Gln Phe Lys Gln
            210                 215                 220

Gly Leu Asp Arg Met Thr Ala Gly Ser Asp Ser Leu Lys Gly Phe Lys
225                 230                 235                 240

Asp Ile Ile Thr Thr Lys Lys Phe Lys Lys Val Phe Pro Thr Leu Ser
                245                 250                 255

Leu Gly Leu Asp Lys Glu Val Arg Lys Ala Tyr Arg Gly Gly Phe Thr
            260                 265                 270

Trp Leu Asn Asp Arg Phe Lys Gly Lys Glu Ile Gly Glu Gly Met Val
            275                 280                 285

Phe Asp Ile Asn Ser Ala Tyr Pro Ala Gln Met Tyr Ser Arg Leu Leu
            290                 295                 300

Pro Tyr Gly Glu Pro Ile Val Phe Glu Gly Lys Tyr Val Trp Asp Glu
305                 310                 315                 320

Asp Tyr Pro Leu His Ile Gln His Ile Arg Cys Glu Phe Glu Leu Lys
                325                 330                 335

Glu Gly Tyr Ile Pro Thr Ile Gln Ile Lys Arg Ser Arg Phe Tyr Lys
            340                 345                 350

Gly Asn Glu Tyr Leu Lys Ser Ser Gly Gly Glu Ile Ala Asp Leu Trp
            355                 360                 365

Leu Ser Asn Val Asp Leu Glu Leu Met Lys Glu His Tyr Asp Leu Tyr
            370                 375                 380

Asn Val Glu Tyr Ile Ser Gly Leu Lys Phe Lys Ala Thr Thr Gly Leu
385                 390                 395                 400

Phe Lys Asp Phe Ile Asp Lys Trp Thr Tyr Ile Lys Thr Thr Ser Tyr
                405                 410                 415

Gly Ala Ile Lys Gln Leu Ala Lys Leu Met Leu Asn Ser Leu Tyr Gly
            420                 425                 430

Lys Phe Ala Ser Asn Pro Asp Val Thr Gly Lys Val Pro Tyr Leu Lys
            435                 440                 445

Glu Asn Gly Ala Leu Gly Phe Arg Leu Gly Glu Glu Thr Lys Asp
            450                 455                 460

Pro Val Tyr Thr Pro Met Gly Val Phe Ile Thr Ala Trp Ala Arg Tyr
465                 470                 475                 480

Thr Thr Ile Thr Ala Ala Gln Ala Cys Tyr Asp Arg Ile Ile Tyr Cys
                485                 490                 495

Asp Thr Asp Ser Ile His Leu Thr Gly Thr Glu Ile Pro Asp Val Ile
            500                 505                 510

Lys Asp Ile Val Asp Pro Lys Lys Leu Gly Tyr Trp Glu His Glu Ser
            515                 520                 525

Thr Phe Lys Arg Ala Lys Tyr Leu Arg Gln Lys Thr Tyr Ile Gln Asp
            530                 535                 540

Ile Tyr Met Lys Glu Val Lys Gly Tyr Leu Val Glu Gly Ser Pro Asp
545                 550                 555                 560

Asp Tyr Thr Asp Ile Lys Phe Ser Val Lys Cys Ala Gly Met Thr Asp
                565                 570                 575

Lys Ile Lys Lys Glu Val Thr Phe Glu Asn Phe Lys Val Gly Phe Ser
            580                 585                 590
```

-continued

```
Arg Lys Met Lys Pro Lys Pro Val Gln Val Pro Gly Gly Val Val Leu
        595             600             605

Val Asp Asp Thr Phe Thr Ile Lys Gly His His His His His His
610             615             620

His His His
625

<210> SEQ ID NO 20
<211> LENGTH: 624
<212> TYPE: PRT
<213> ORGANISM: Artificial
<220> FEATURE:
<223> OTHER INFORMATION: mutant recombinant phi29-type DNA polymerase

<400> SEQUENCE: 20

Met Ser Val Asp Gly Leu Asn Asp Phe Phe Glu Ala Gln Lys Ile Glu
1               5                   10                  15

Trp His Glu Ala Met Gly His His His His His His His His
            20                  25                  30

Ser Ser Gly His Ile Glu Gly Arg His Met Ser Arg Lys Met Phe Ser
            35                  40                  45

Cys Asp Phe Glu Thr Thr Thr Lys Leu Asp Asp Cys Arg Val Trp Ala
50                  55                  60

Tyr Gly Tyr Met Glu Ile Gly Asn Leu Asp Asn Tyr Lys Ile Gly Asn
65                  70                  75                  80

Ser Leu Asp Glu Phe Met Gln Trp Val Met Glu Ile Gln Ala Asp Leu
                85                  90                  95

Tyr Phe His Asn Leu Lys Phe Asp Gly Ala Phe Ile Val Asn Trp Leu
            100                 105                 110

Glu Gln His Gly Phe Lys Trp Ser Asn Glu Gly Leu Pro Asn Thr Tyr
            115                 120                 125

Asn Thr Ile Ile Ser Lys Met Gly Gln Trp Tyr Met Ile Asp Ile Cys
130                 135                 140

Phe Gly Tyr Lys Gly Lys Arg Lys Leu His Thr Val Ile Tyr Asp Ser
145                 150                 155                 160

Leu Lys Lys Leu Pro Phe Pro Val Lys Lys Ile Ala Lys Asp Phe Gln
                165                 170                 175

Leu Pro Leu Leu Lys Gly Asp Ile Asp Tyr His Thr Glu Arg Pro Val
            180                 185                 190

Gly His Glu Ile Thr Pro Glu Glu Tyr Glu Tyr Ile Lys Asn Asp Ile
            195                 200                 205

Glu Ile Ile Ala Arg Ala Leu Asp Ile Gln Phe Lys Gln Gly Leu Asp
            210                 215                 220

Arg Met Thr Ala Gly Ser Asp Ser Leu Lys Gly Phe Lys Asp Ile Leu
225                 230                 235                 240

Ser Thr Lys Lys Phe Asn Lys Val Phe Pro Lys Leu Ser Leu Pro Met
                245                 250                 255

Asp Lys Glu Ile Arg Lys Ala Tyr Arg Gly Gly Phe Thr Trp Leu Asn
            260                 265                 270

Asp Lys Tyr Lys Glu Lys Glu Ile Gly Glu Gly Met Val Phe Asp Val
            275                 280                 285

Asn Ser Ala Tyr Pro Ala Gln Met Tyr Ser Arg Pro Leu Pro Tyr Gly
            290                 295                 300

Ala Pro Ile Val Phe Gln Gly Lys Tyr Glu Lys Asp Glu Gln Tyr Pro
305                 310                 315                 320
```

```
Leu Tyr Ile Gln Arg Ile Arg Phe Glu Phe Glu Leu Lys Glu Gly Tyr
            325                 330                 335

Ile Pro Thr Ile Gln Ile Lys Lys Asn Pro Phe Phe Lys Gly Asn Glu
        340                 345                 350

Tyr Leu Lys Asn Ser Gly Val Glu Pro Val Glu Leu Tyr Leu Thr Asn
            355                 360                 365

Val Asp Leu Glu Leu Ile Gln Glu His Tyr Glu Leu Tyr Asn Val Glu
    370                 375                 380

Tyr Ile Asp Gly Phe Lys Phe Arg Glu Lys Thr Gly Leu Phe Lys Asp
385                 390                 395                 400

Phe Ile Asp Lys Trp Thr Tyr Val Lys Thr His Glu Tyr Gly Ala Lys
                405                 410                 415

Lys Gln Leu Ala Lys Leu Met Leu Asn Ser Leu Tyr Gly Lys Phe Ala
            420                 425                 430

Ser Asn Pro Asp Val Thr Gly Lys Val Pro Tyr Leu Lys Asp Asp Gly
        435                 440                 445

Ser Leu Gly Phe Arg Val Gly Asp Glu Glu Tyr Lys Asp Pro Val Tyr
            450                 455                 460

Thr Pro Met Gly Val Phe Ile Thr Ala Trp Ala Arg Phe Thr Thr Ile
465                 470                 475                 480

Thr Ala Ala Gln Ala Cys Tyr Asp Arg Ile Ile Tyr Cys Asp Thr Asp
                485                 490                 495

Ser Ile His Leu Thr Gly Thr Glu Val Pro Glu Ile Ile Lys Asp Ile
            500                 505                 510

Val Asp Pro Lys Lys Leu Gly Tyr Trp Glu His Glu Ser Thr Phe Lys
        515                 520                 525

Arg Ala Lys Tyr Leu Arg Gln Lys Thr Tyr Ile Gln Asp Ile Tyr Val
            530                 535                 540

Lys Glu Val Asp Gly Tyr Leu Lys Glu Cys Ser Pro Asp Glu Ala Thr
545                 550                 555                 560

Thr Thr Lys Phe Ser Val Lys Cys Ala Gly Met Thr Asp Thr Ile Lys
                565                 570                 575

Lys Lys Val Thr Phe Asp Asn Phe Ala Val Gly Phe Ser Ser Met Gly
            580                 585                 590

Lys Pro Lys Pro Val Gln Val Asn Gly Gly Val Val Leu Val Asp Ser
        595                 600                 605

Val Phe Thr Ile Lys Gly His His His His His His His His
    610                 615                 620
```

<210> SEQ ID NO 21
<211> LENGTH: 627
<212> TYPE: PRT
<213> ORGANISM: Artificial
<220> FEATURE:
<223> OTHER INFORMATION: mutant recombinant phi29-type DNA polymerase

<400> SEQUENCE: 21

```
Met Ser Val Asp Gly Leu Asn Asp Phe Phe Glu Ala Gln Lys Ile Glu
1               5                   10                  15

Trp His Glu Ala Met Gly His His His His His His His His
            20                  25                  30

Ser Ser Gly His Ile Glu Gly Arg His Met Lys His Met Pro Arg Lys
        35                  40                  45

Met Tyr Ser Cys Asp Phe Glu Thr Thr Thr Lys Val Glu Asp Cys Arg
    50                  55                  60
```

-continued

Val Trp Ala Tyr Gly Tyr Met Asn Ile Glu Asp His Ser Glu Tyr Lys
 65                  70                  75                  80

Ile Gly Asn Ser Leu Asp Glu Phe Met Ala Trp Val Leu Lys Val Gln
                 85                  90                  95

Ala Asp Leu Tyr Phe His Asn Leu Lys Phe Asp Gly Ala Phe Ile Ile
            100                 105                 110

Asn Trp Leu Glu Arg Asn Gly Phe Lys Trp Ser Ala Asp Gly Leu Pro
        115                 120                 125

Asn Thr Tyr Asn Thr Ile Ile Ser Arg Met Gly Gln Trp Tyr Met Ile
    130                 135                 140

Asp Ile Cys Leu Gly Tyr Lys Gly Lys Arg Lys Ile His Thr Val Ile
145                 150                 155                 160

Tyr Asp Ser Leu Lys Lys Leu Pro Phe Pro Val Lys Lys Ile Ala Lys
                165                 170                 175

Asp Phe Lys Leu Thr Val Leu Lys Gly Asp Ile Asp Ile His Lys Glu
            180                 185                 190

Arg Pro Val Gly Tyr Lys Ile Thr Pro Glu Glu Tyr Ala Tyr Ile Lys
        195                 200                 205

Asn Asp Ile Gln Ile Ile Ala Glu Ala Leu Leu Ile Gln Phe Lys Gln
    210                 215                 220

Gly Leu Asp Arg Met Thr Ala Gly Ser Asp Ser Leu Lys Gly Phe Lys
225                 230                 235                 240

Asp Ile Ile Thr Thr Lys Lys Phe Lys Lys Val Phe Pro Thr Leu Ser
                245                 250                 255

Leu Gly Leu Asp Lys Glu Val Arg Lys Ala Tyr Arg Gly Gly Phe Thr
            260                 265                 270

Trp Leu Asn Asp Arg Phe Lys Gly Lys Glu Ile Gly Glu Gly Met Val
        275                 280                 285

Phe Asp Val Asn Ser His Tyr Pro Ala Gln Met Tyr Ser Arg Leu Leu
    290                 295                 300

Pro Tyr Gly Glu Pro Ile Val Phe Glu Gly Lys Tyr Val Trp Asp Glu
305                 310                 315                 320

Asp Tyr Pro Leu His Ile Gln His Ile Arg Cys Glu Phe Glu Leu Lys
                325                 330                 335

Glu Gly Tyr Ile Pro Thr Ile Gln Ile Lys Arg Ser Arg Phe Tyr Lys
            340                 345                 350

Gly Asn Glu Tyr Leu Lys Ser Ser Gly Gly Glu Ile Ala Asp Leu Trp
        355                 360                 365

Leu Ser Asn Val Asp Leu Glu Leu Met Lys Glu His Tyr Asp Leu Tyr
    370                 375                 380

Asn Val Glu Tyr Ile Ser Gly Leu Lys Phe Lys Ala Thr Thr Gly Leu
385                 390                 395                 400

Phe Lys Asp Phe Ile Asp Lys Trp Thr Tyr Ile Lys Thr Thr Ser Tyr
                405                 410                 415

Gly Ala Ile Lys Gln Leu Ala Lys Leu Met Leu Asn Ser Leu Tyr Gly
            420                 425                 430

Lys Phe Ala Ser Asn Pro Asp Val Thr Gly Lys Val Pro Tyr Leu Lys
        435                 440                 445

Glu Asn Gly Ala Leu Gly Phe Arg Leu Gly Glu Glu Thr Lys Asp
    450                 455                 460

Pro Val Tyr Thr Pro Met Gly Val Phe Ile Thr Ala Trp Gly Arg Tyr
465                 470                 475                 480

Thr Thr Ile Thr Ala Ala Gln Ala Cys Tyr Asp Arg Ile Ile Tyr Cys

```
                    485                 490                 495
Asp Thr Asp Ser Ile His Leu Thr Gly Thr Glu Ile Pro Asp Val Ile
                500                 505                 510

Lys Asp Ile Val Asp Pro Lys Lys Leu Gly Tyr Trp Glu His Glu Ser
            515                 520                 525

Thr Phe Lys Arg Ala Lys Tyr Leu Arg Gln Lys Thr Tyr Ile Gln Asp
        530                 535                 540

Ile Tyr Met Lys Glu Val Lys Gly Tyr Leu Val Glu Gly Ser Pro Asp
545                 550                 555                 560

Asp Tyr Thr Asp Ile Lys Phe Ser Val Lys Cys Ala Gly Met Thr Asp
                565                 570                 575

Lys Ile Lys Lys Glu Val Thr Phe Glu Asn Phe Lys Val Gly Phe Ser
            580                 585                 590

Arg Lys Met Lys Pro Lys Pro Val Gln Val Pro Gly Gly Val Val Leu
        595                 600                 605

Val Asp Asp Thr Phe Thr Ile Lys Gly His His His His His His
    610                 615                 620

His His His
625

<210> SEQ ID NO 22
<211> LENGTH: 610
<212> TYPE: PRT
<213> ORGANISM: Artificial
<220> FEATURE:
<223> OTHER INFORMATION: mutant recombinant phi29-type DNA polymerase

<400> SEQUENCE: 22

Met Ser Arg Lys Met Phe Ser Cys Asp Phe Glu Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
        50                  55                  60

Ala Phe Ile Val Asn Trp Leu Glu Gln His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
130                 135                 140

Ile His Thr Glu Arg Pro Val Gly His Glu Ile Thr Pro Glu Glu Tyr
                145                 150                 155                 160

Glu Tyr Ile Lys Asn Asp Ile Glu Ile Ile Ala Arg Ala Leu Asp Ile
            165                 170                 175

Gln Phe Lys Gln Gly Leu Asp Arg Met Thr Ala Gly Ser Asp Ser Leu
        180                 185                 190

Lys Gly Phe Lys Asp Ile Leu Ser Thr Lys Lys Phe Asn Lys Val Phe
    195                 200                 205

Pro Lys Leu Ser Leu Pro Met Asp Lys Glu Ile Arg Lys Ala Tyr Arg
```

```
            210                 215                 220
Gly Gly Phe Thr Trp Leu Asn Asp Lys Tyr Lys Gly Lys Glu Ile Gly
225                 230                 235                 240

Glu Gly Met Val Phe Asp Ile Asn Ser Ala Tyr Pro Ala Gln Met Tyr
                245                 250                 255

Ser Arg Pro Leu Pro Tyr Gly Ala Pro Ile Val Phe Gln Gly Lys Tyr
                    260                 265                 270

Glu Lys Asp Glu Gln Tyr Pro Leu Tyr Ile Gln Arg Ile Arg Phe Glu
                275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Val Glu Pro
305                 310                 315                 320

Val Glu Leu Tyr Leu Thr Asn Val Asp Leu Glu Leu Ile Gln Glu His
                325                 330                 335

Tyr Glu Leu Tyr Asn Val Glu Tyr Ile Asp Gly Phe Lys Phe Arg Glu
                340                 345                 350

Lys Thr Gly Leu Phe Lys Asp Phe Ile Asp Lys Trp Thr Tyr Val Lys
                355                 360                 365

Thr His Glu Tyr Gly Ala Lys Lys Gln Leu Ala Lys Leu Met Leu Asn
                370                 375                 380

Ser Leu Tyr Gly Lys Phe Ala Ser Asn Pro Asp Val Thr Gly Lys Val
385                 390                 395                 400

Pro Tyr Leu Lys Asp Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
                420                 425                 430

Trp Gly Arg Phe Thr Thr Ile Thr Ala Ala Gln Ala Cys Tyr Asp Arg
                435                 440                 445

Ile Ile Tyr Cys Asp Thr Asp Ser Ile His Leu Thr Gly Thr Glu Val
                450                 455                 460

Pro Glu Ile Ile Lys Asp Ile Val Asp Pro Lys Lys Leu Gly Tyr Trp
465                 470                 475                 480

Glu His Glu Ser Thr Phe Lys Arg Ala Lys Tyr Leu Arg Gln Lys Thr
                485                 490                 495

Tyr Ile Gln Asp Ile Tyr Val Lys Glu Val Lys Gly Tyr Leu Lys Gln
                500                 505                 510

Cys Ser Pro Asp Glu Ala Thr Thr Thr Lys Phe Ser Val Lys Cys Ala
                515                 520                 525

Gly Met Thr Asp Thr Ile Lys Lys Lys Val Thr Phe Asp Asn Phe Ala
                530                 535                 540

Val Gly Phe Ser Ser Met Gly Lys Pro Lys Pro Val Gln Val Asn Gly
545                 550                 555                 560

Gly Val Val Leu Val Asp Ser Val Phe Thr Ile Lys Gly His His His
                565                 570                 575

His His His His His His Gly Gly Gly Ser Gly Gly Gly Ser Gly
                580                 585                 590

Gly Gly Ser Gly Leu Asn Asp Phe Phe Glu Ala Gln Lys Ile Glu Trp
                595                 600                 605

His Glu
610

<210> SEQ ID NO 23
```

<211> LENGTH: 624
<212> TYPE: PRT
<213> ORGANISM: Artificial
<220> FEATURE:
<223> OTHER INFORMATION: mutant recombinant phi29-type DNA polymerase

<400> SEQUENCE: 23

```
Met Ser Val Asp Gly Leu Asn Asp Phe Phe Glu Ala Gln Lys Ile Glu
1               5                   10                  15

Trp His Glu Ala Met Gly His His His His His His His His
            20                  25                  30

Ser Ser Gly His Ile Glu Gly Arg His Met Ser Arg Lys Met Phe Ser
        35                  40                  45

Cys Asp Phe Glu Thr Thr Thr Lys Leu Asp Asp Cys Arg Val Trp Ala
    50                  55                  60

Tyr Gly Tyr Met Glu Ile Gly Asn Leu Asp Asn Tyr Lys Ile Gly Asn
65                  70                  75                  80

Ser Leu Asp Glu Phe Met Gln Trp Val Met Glu Ile Gln Ala Asp Leu
                85                  90                  95

Tyr Phe His Asn Leu Lys Phe Asp Gly Ala Phe Ile Val Asn Trp Leu
            100                 105                 110

Glu Gln His Gly Phe Lys Trp Ser Asn Glu Gly Leu Pro Asn Thr Tyr
        115                 120                 125

Asn Thr Ile Ile Ser Lys Met Gly Gln Trp Tyr Met Ile Asp Ile Cys
    130                 135                 140

Phe Gly Tyr Lys Gly Lys Arg Lys Leu His Thr Val Ile Tyr Asp Ser
145                 150                 155                 160

Leu Lys Lys Leu Pro Phe Pro Val Lys Lys Ile Ala Gln Asp Phe Gln
                165                 170                 175

Leu Pro Leu Leu Lys Gly Asp Ile Asp Ile His Thr Glu Arg Pro Val
            180                 185                 190

Gly His Glu Ile Thr Pro Glu Glu Tyr Glu Tyr Ile Lys Asn Asp Ile
        195                 200                 205

Glu Ile Ile Ala Arg Ala Leu Asp Ile Gln Phe Lys Gln Gly Leu Asp
    210                 215                 220

Arg Met Thr Ala Gly Ser Asp Ser Leu Lys Gly Phe Lys Asp Ile Leu
225                 230                 235                 240

Ser Thr Lys Lys Phe Asn Lys Val Phe Pro Lys Leu Ser Leu Pro Met
                245                 250                 255

Asp Lys Glu Ile Arg Lys Ala Tyr Arg Gly Gly Phe Thr Trp Leu Asn
            260                 265                 270

Asp Lys Tyr Lys Gly Lys Glu Ile Gly Glu Gly Met Val Phe Asp Ile
        275                 280                 285

Asn Ser Ala Tyr Pro Ser Gln Met Tyr Ser Arg Pro Leu Pro Tyr Gly
    290                 295                 300

Ala Pro Ile Val Phe Gln Gly Lys Tyr Glu Lys Asp Glu Gln Tyr Pro
305                 310                 315                 320

Leu Tyr Ile Gln Arg Ile Arg Phe Glu Phe Glu Leu Lys Glu Gly Tyr
                325                 330                 335

Ile Pro Thr Ile Gln Ile Lys Lys Asn Pro Phe Phe Lys Gly Asn Glu
            340                 345                 350

Tyr Leu Lys Asn Ser Gly Val Glu Pro Val Glu Leu Tyr Leu Thr Asn
        355                 360                 365

Val Asp Leu Glu Leu Ile Gln Glu His Tyr Glu Leu Tyr Asn Val Glu
    370                 375                 380
```

```
Tyr Ile Asp Gly Phe Lys Phe Arg Glu Lys Thr Gly Leu Phe Lys Asp
385                 390                 395                 400

Phe Ile Asp Lys Trp Thr Tyr Val Lys Thr His Glu Tyr Gly Ala Lys
                405                 410                 415

Lys Gln Leu Ala Lys Leu Met Leu Asn Ser Leu Tyr Gly Lys Phe Ala
            420                 425                 430

Ser Asn Pro Asp Val Thr Gly Lys Val Pro Tyr Leu Lys Asp Asp Gly
        435                 440                 445

Ser Leu Gly Phe Arg Val Gly Asp Glu Glu Tyr Lys Asp Pro Val Tyr
    450                 455                 460

Thr Pro Met Gly Val Phe Ile Thr Ala Trp Gly Arg Phe Thr Thr Ile
465                 470                 475                 480

Thr Ala Ala Gln Ala Cys Tyr Asp Arg Ile Ile Tyr Cys Asp Thr Asp
                485                 490                 495

Ser Ile His Leu Thr Gly Thr Glu Val Pro Glu Ile Ile Lys Asp Ile
            500                 505                 510

Val Asp Pro Lys Lys Leu Gly Tyr Trp Glu His Glu Ser Thr Phe Lys
        515                 520                 525

Arg Ala Lys Tyr Leu Arg Gln Lys Thr Tyr Ile Gln Asp Ile Tyr Val
    530                 535                 540

Lys Glu Val Lys Gly Tyr Leu Lys Gln Cys Ser Pro Asp Glu Ala Thr
545                 550                 555                 560

Thr Thr Lys Phe Ser Val Lys Cys Ala Gly Met Thr Asp Thr Ile Lys
                565                 570                 575

Lys Lys Val Thr Phe Asp Asn Phe Ala Val Gly Phe Ser Ser Met Gly
            580                 585                 590

Lys Pro Lys Pro Val Gln Val Asn Gly Gly Val Val Leu Val Asp Ser
        595                 600                 605

Val Phe Thr Ile Lys Gly His His His His His His His His
    610                 615                 620

<210> SEQ ID NO 24
<211> LENGTH: 613
<212> TYPE: PRT
<213> ORGANISM: Artificial
<220> FEATURE:
<223> OTHER INFORMATION: mutant recombinant phi29-type DNA polymerase

<400> SEQUENCE: 24

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125
```

-continued

```
Pro Val Glu Lys Ile Ala Gln Asp Phe Lys Leu Thr Lys Lys Gly
    130                 135                 140
Asp Ile Asp Ile His Lys Glu Arg Pro Val Gly Tyr Lys Ile Thr Pro
145                 150                 155                 160
Glu Glu Tyr Ala Tyr Ile Lys Asn Asp Ile Gln Ile Ala Glu Ala
                165                 170                 175
Leu Leu Ile Gln Phe Lys Gln Gly Leu Asp Arg Met Thr Ala Gly Ser
                180                 185                 190
Asp Ser Leu Lys Gly Phe Lys Asp Ile Ile Thr Thr Lys Lys Phe Lys
            195                 200                 205
Lys Val Phe Pro Thr Leu Ser Leu Gly Leu Asp Lys Glu Val Arg Lys
    210                 215                 220
Ala Tyr Arg Gly Gly Phe Thr Trp Leu Asn Asp Arg Phe Lys Gly Lys
225                 230                 235                 240
Glu Ile Gly Glu Gly Met Val Phe Asp Ile Asn Ser Ala Tyr Pro Ala
                245                 250                 255
Gln Met Tyr Ser Arg Leu Leu Pro Tyr Gly Glu Pro Ile Val Phe Glu
            260                 265                 270
Gly Lys Tyr Val Trp Asp Glu Asp Tyr Pro Leu His Ile Gln His Ile
    275                 280                 285
Arg Cys Glu Phe Glu Leu Lys Glu Gly Tyr Ile Pro Thr Ile Gln Ile
290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Thr
    355                 360                 365
Tyr Ile Lys Thr Thr Ser Tyr Gly Ala Ile Lys Gln Leu Ala Lys Leu
370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
            420                 425                 430
Ile Thr Ala Trp Gly Arg Tyr Thr Thr Ile Thr Ala Ala Gln Ala Cys
    435                 440                 445
Tyr Asp Arg Ile Ile Tyr Cys Asp Thr Asp Ser Ile His Leu Thr Gly
450                 455                 460
Thr Glu Ile Pro Asp Val Ile Lys Asp Ile Val Asp Pro Lys Lys Leu
465                 470                 475                 480
Gly Tyr Trp Glu His Glu Ser Thr Phe Lys Arg Ala Lys Tyr Leu Arg
                485                 490                 495
Gln Lys Thr Tyr Ile Gln Asp Ile Tyr Met Lys Lys Val Lys Gly Tyr
            500                 505                 510
Leu Val Gln Gly Ser Pro Asp Asp Tyr Thr Asp Ile Lys Phe Ser Val
    515                 520                 525
Lys Cys Ala Gly Met Thr Asp Gln Ile Lys Lys Glu Val Thr Phe Glu
530                 535                 540
```

```
Asn Phe Lys Val Gly Phe Ser Arg Lys Met Lys Pro Lys Pro Val Gln
545                 550                 555                 560

Val Pro Gly Gly Val Leu Val Asp Asp Thr Phe Thr Ile Lys Gly
            565                 570                 575

His His His His His His His His Gly Gly Gly Ser Gly Gly
            580                 585                 590

Gly Ser Gly Gly Ser Gly Leu Asn Asp Phe Phe Glu Ala Gln Lys
        595                 600                 605

Ile Glu Trp His Glu
    610

<210> SEQ ID NO 25
<211> LENGTH: 613
<212> TYPE: PRT
<213> ORGANISM: Artificial
<220> FEATURE:
<223> OTHER INFORMATION: mutant recombinant phi29-type DNA polymerase

<400> SEQUENCE: 25

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Glu Lys Ile Ala Lys Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285
```

```
Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Tyr Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
            420                 425                 430

Ile Thr Ala Trp Gly Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
            485                 490                 495

Gln Lys Thr Tyr Ile Gln Asp Ile Tyr Met Lys Lys Val Lys Gly Tyr
            500                 505                 510

Leu Val Gln Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Gly
            565                 570                 575

His His His His His His His His His Gly Gly Ser Gly Gly
            580                 585                 590

Gly Ser Gly Gly Ser Gly Leu Asn Asp Phe Phe Glu Ala Gln Lys
        595                 600                 605

Ile Glu Trp His Glu
    610

<210> SEQ ID NO 26
<211> LENGTH: 627
<212> TYPE: PRT
<213> ORGANISM: Artificial
<220> FEATURE:
<223> OTHER INFORMATION: mutant recombinant phi29-type DNA polymerase

<400> SEQUENCE: 26

Met Ser Val Asp Gly Leu Asn Asp Phe Phe Glu Ala Gln Lys Ile Glu
1               5                   10                  15

Trp His Glu Ala Met Gly His His His His His His His His
            20                  25                  30
```

```
Ser Ser Gly His Ile Glu Gly Arg His Met Lys His Met Pro Arg Lys
         35                  40                  45

Met Tyr Ser Cys Asp Phe Glu Thr Thr Thr Lys Val Glu Asp Cys Arg
 50                  55                  60

Val Trp Ala Tyr Gly Tyr Met Asn Ile Glu Asp His Ser Glu Tyr Lys
 65                  70                  75                  80

Ile Gly Asn Ser Leu Asp Glu Phe Met Ala Trp Val Leu Lys Val Gln
                 85                  90                  95

Ala Asp Leu Tyr Phe His Asn Leu Lys Phe Asp Gly Ala Phe Ile Ile
            100                 105                 110

Asn Trp Leu Glu Arg Asn Gly Phe Lys Trp Ser Ala Asp Gly Leu Pro
        115                 120                 125

Asn Thr Tyr Asn Thr Ile Ile Ser Arg Met Gly Gln Trp Tyr Met Ile
    130                 135                 140

Asp Ile Cys Leu Gly Tyr Lys Gly Lys Arg Lys Ile His Thr Val Ile
145                 150                 155                 160

Tyr Asp Ser Leu Lys Lys Leu Pro Phe Pro Val Gln Lys Ile Ala Lys
                165                 170                 175

Asp Phe Lys Leu Thr Val Leu Lys Gly Asp Ile Asp Ile His Lys Glu
            180                 185                 190

Arg Pro Val Gly Tyr Lys Ile Thr Pro Glu Glu Tyr Ala Tyr Ile Lys
        195                 200                 205

Asn Asp Ile Gln Ile Ile Ala Glu Ala Leu Leu Ile Gln Phe Lys Gln
    210                 215                 220

Gly Leu Asp Arg Met Thr Ala Gly Ser Asp Ser Leu Lys Gly Phe Lys
225                 230                 235                 240

Asp Ile Ile Thr Thr Lys Lys Phe Lys Lys Val Phe Pro Thr Leu Ser
                245                 250                 255

Leu Gly Leu Asp Lys Glu Val Arg Lys Ala Tyr Arg Gly Gly Phe Thr
            260                 265                 270

Trp Leu Asn Asp Arg Phe Lys Gly Lys Glu Ile Gly Glu Gly Met Val
        275                 280                 285

Phe Asp Ile Asn Ser Ala Tyr Pro Ala Gln Met Tyr Ser Arg Leu Leu
    290                 295                 300

Pro Tyr Gly Glu Pro Ile Val Phe Glu Gly Lys Tyr Val Trp Asp Glu
305                 310                 315                 320

Asp Tyr Pro Leu His Ile Gln His Ile Arg Cys Glu Phe Glu Leu Lys
                325                 330                 335

Glu Gly Tyr Ile Pro Thr Ile Gln Ile Lys Arg Ser Arg Phe Tyr Lys
            340                 345                 350

Gly Asn Glu Tyr Leu Lys Ser Ser Gly Gly Glu Ile Ala Asp Leu Trp
        355                 360                 365

Leu Ser Asn Val Asp Leu Glu Leu Met Lys Glu His Tyr Asp Leu Tyr
    370                 375                 380

Asn Val Glu Tyr Ile Ser Gly Leu Lys Phe Lys Ala Thr Thr Gly Leu
385                 390                 395                 400

Phe Lys Asp Phe Ile Asp Lys Trp Thr Tyr Ile Lys Thr Thr Ser Tyr
                405                 410                 415

Gly Ala Ile Lys Gln Leu Ala Lys Leu Met Leu Asn Ser Leu Tyr Gly
            420                 425                 430

Lys Phe Ala Ser Asn Pro Asp Val Thr Gly Lys Val Pro Tyr Leu Lys
        435                 440                 445

Glu Asn Gly Ala Leu Gly Phe Arg Leu Gly Glu Glu Thr Lys Asp
```

```
            450                 455                 460
Pro Val Tyr Thr Pro Met Gly Val Phe Ile Thr Ala Trp Ala Arg Tyr
465                 470                 475                 480

Thr Thr Ile Thr Ala Ala Gln Ala Cys Tyr Asp Arg Ile Ile Tyr Cys
                485                 490                 495

Asp Thr Asp Ser Ile His Leu Thr Gly Thr Glu Ile Pro Asp Val Ile
                500                 505                 510

Lys Asp Ile Val Asp Pro Lys Lys Leu Gly Tyr Trp Glu His Glu Ser
            515                 520                 525

Thr Phe Lys Arg Ala Lys Tyr Leu Arg Gln Lys Thr Tyr Ile Gln Asp
        530                 535                 540

Ile Tyr Met Lys Glu Val Lys Gly Tyr Leu Val Glu Gly Ser Pro Asp
545                 550                 555                 560

Asp Tyr Thr Asp Ile Lys Phe Ser Val Lys Cys Ala Gly Met Thr Asp
                565                 570                 575

Lys Ile Lys Lys Glu Val Thr Phe Glu Asn Phe Lys Val Gly Phe Ser
                580                 585                 590

Arg Lys Met Lys Pro Lys Pro Val Gln Val Pro Gly Gly Val Val Leu
            595                 600                 605

Val Asp Asp Thr Phe Thr Ile Lys Gly His His His His His His
610                 615                 620

His His His
625

<210> SEQ ID NO 27
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 27

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Glu Lys Ile Ala Lys Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
```

```
                180                 185                 190
Asp Ser Leu Lys Gly Phe Lys Asp Ile Thr Thr Lys Phe Lys
        195                 200                 205

Lys Val Phe Pro Thr Leu Ser Leu Gly Leu Asp Lys Glu Val Arg Lys
210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
                275                 280                 285

Arg Cys Glu Phe Glu Leu Lys Glu Gly Tyr Ile Pro Thr Ile Gln Ile
                290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
                355                 360                 365

Tyr Ile Lys Thr Thr Ser Tyr Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
                420                 425                 430

Ile Thr Ala Trp Gly Arg Tyr Thr Thr Ile Thr Ala Ala Gln Ala Cys
                435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
                500                 505                 510

Leu Val Gln Gly Ser Pro Asp Asp Tyr Thr Asp Ile Lys Phe Ser Val
                515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 28
<211> LENGTH: 575
<212> TYPE: PRT
<213> ORGANISM: Artificial
```

<220> FEATURE:
<223> OTHER INFORMATION: mutant recombinant phi29-type DNA polymerase

<400> SEQUENCE: 28

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Gln Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Tyr Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400
```

```
Gly Lys Val Pro Tyr Leu Lys Glu Asn Gly Ala Leu Gly Phe Arg Leu
            405                 410                 415
Gly Glu Glu Glu Thr Lys Asp Pro Val Tyr Thr Pro Met Gly Val Phe
            420                 425                 430
Ile Thr Ala Trp Gly Arg Tyr Thr Ile Thr Ala Ala Gln Ala Cys
            435                 440                 445
Tyr Asp Arg Ile Ile Tyr Cys Asp Thr Asp Ser Ile His Leu Thr Gly
450                 455                 460
Thr Glu Ile Pro Asp Val Ile Lys Asp Ile Val Asp Pro Lys Lys Leu
465                 470                 475                 480
Gly Tyr Trp Glu His Glu Ser Thr Phe Lys Arg Ala Lys Tyr Leu Arg
            485                 490                 495
Gln Lys Thr Tyr Ile Gln Asp Ile Tyr Met Lys Glu Val Lys Gly Tyr
            500                 505                 510
Leu Val Gln Gly Ser Pro Asp Asp Tyr Thr Asp Ile Lys Phe Ser Val
            515                 520                 525
Lys Cys Ala Gly Met Thr Asp Lys Ile Lys Lys Glu Val Thr Phe Glu
            530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys
            565                 570                 575

<210> SEQ ID NO 29
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 29

Met Lys His Met Pro Arg Lys Met Tyr Ser Cys Asp Phe Glu Thr Thr
1               5                   10                  15
Thr Lys Val Glu Asp Cys Arg Val Trp Ala Tyr Gly Tyr Met Asn Ile
            20                  25                  30
Glu Asp His Ser Glu Tyr Lys Ile Gly Asn Ser Leu Asp Glu Phe Met
            35                  40                  45
Ala Trp Val Leu Lys Val Gln Ala Asp Leu Tyr Phe His Asn Leu Lys
        50                  55                  60
Phe Asp Gly Ala Phe Ile Ile Asn Trp Leu Glu Arg Asn Gly Phe Lys
65                  70                  75                  80
Trp Ser Ala Asp Gly Leu Pro Asn Thr Tyr Asn Thr Ile Ile Ser Arg
            85                  90                  95
Met Gly Gln Trp Tyr Met Ile Asp Ile Cys Leu Gly Tyr Lys Gly Lys
            100                 105                 110
Arg Lys Ile His Thr Val Ile Tyr Asp Ser Leu Lys Lys Leu Pro Phe
            115                 120                 125
Pro Val Glu Lys Ile Ala Lys Asp Phe Lys Leu Thr Val Leu Lys Gly
            130                 135                 140
Asp Ile Asp Ile His Lys Glu Arg Pro Val Gly Tyr Lys Ile Thr Pro
145                 150                 155                 160
Glu Glu Tyr Ala Tyr Ile Lys Asn Asp Ile Gln Ile Ile Ala Glu Ala
            165                 170                 175
Leu Leu Ile Gln Phe Lys Gln Gly Leu Asp Arg Met Thr Ala Gly Ser
            180                 185                 190
```

```
Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
210                 215                 220

Ala Tyr Arg Gly Gly Phe Thr Trp Leu Asn Glu Arg Phe Lys Gly Lys
225                 230                 235                 240

Glu Ile Gly Glu Gly Met Val Phe Asp Ala Asn Ser His Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Tyr Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Gly Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
            500                 505                 510

Leu Val Gln Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 30
<211> LENGTH: 575
<212> TYPE: PRT
<213> ORGANISM: Artificial
<220> FEATURE:
```

<223> OTHER INFORMATION: mutant recombinant phi29-type DNA polymerase

<400> SEQUENCE: 30

```
Met Lys His Met Pro Arg Lys Met Tyr Ser Cys Asp Phe Glu Thr Thr
1               5                   10                  15
Thr Lys Val Glu Asp Cys Arg Val Trp Ala Tyr Gly Tyr Met Asn Ile
            20                  25                  30
Glu Asp His Ser Glu Tyr Lys Ile Gly Asn Ser Leu Asp Glu Phe Met
        35                  40                  45
Ala Trp Val Leu Lys Val Gln Ala Asp Leu Tyr Phe His Asn Leu Lys
    50                  55                  60
Phe Asp Gly Ala Phe Ile Ile Asn Trp Leu Glu Arg Asn Gly Phe Lys
65                  70                  75                  80
Trp Ser Ala Asp Gly Leu Pro Asn Thr Tyr Asn Thr Ile Ile Ser Arg
                85                  90                  95
Met Gly Gln Trp Tyr Met Ile Asp Ile Cys Leu Gly Tyr Lys Gly Lys
            100                 105                 110
Arg Lys Ile His Thr Val Ile Tyr Asp Ser Leu Lys Lys Leu Pro Phe
        115                 120                 125
Pro Val Lys Lys Ile Ala Lys Asp Phe Lys Leu Thr Val Leu Lys Gly
    130                 135                 140
Asp Ile Asp Ile His Lys Glu Arg Pro Val Gly Tyr Lys Ile Thr Pro
145                 150                 155                 160
Glu Glu Tyr Ala Tyr Ile Lys Asn Asp Ile Gln Ile Ile Ala Glu Ala
                165                 170                 175
Leu Leu Ile Gln Phe Lys Gln Gly Leu Asp Arg Met Thr Ala Gly Ser
            180                 185                 190
Asp Ser Leu Lys Gly Phe Lys Asp Ile Ile Thr Thr Lys Lys Phe Lys
        195                 200                 205
Lys Val Phe Pro Thr Leu Ser Leu Gly Leu Asp Lys Glu Val Arg Lys
    210                 215                 220
Ala Tyr Arg Gly Gly Phe Thr Trp Leu Asn Asp Arg Phe Lys Gly Lys
225                 230                 235                 240
Glu Ile Gly Glu Gly Met Val Phe Asp Val Asn Ser Ser Tyr Pro Ala
                245                 250                 255
Gln Met Tyr Ser Arg Leu Leu Pro Tyr Gly Glu Pro Ile Val Phe Glu
            260                 265                 270
Gly Lys Tyr Val Trp Asp Glu Asp Tyr Pro Leu His Ile Gln His Ile
        275                 280                 285
Arg Cys Glu Phe Glu Leu Lys Glu Gly Tyr Ile Pro Thr Ile Gln Ile
    290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Thr
        355                 360                 365
Tyr Ile Lys Thr Thr Ser Tyr Gly Ala Ile Lys Gln Leu Ala Lys Leu
    370                 375                 380
Met Leu Asn Ser Leu Tyr Gly Lys Phe Ala Ser Asn Pro Asp Val Thr
385                 390                 395                 400
```

Gly Lys Val Pro Tyr Leu Lys Glu Asn Gly Ala Leu Gly Phe Arg Leu
            405                 410                 415

Gly Glu Glu Thr Lys Asp Pro Val Tyr Thr Pro Met Gly Val Phe
        420                 425                 430

Ile Thr Ala Trp Gly Arg Tyr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
            500                 505                 510

Leu Val Gln Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 31
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 31

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
        130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Phe Gly Leu Asp Arg Met Thr Ala Gly Ser
            180                 185                 190

-continued

```
Asp Ser Leu Lys Gly Phe Lys Asp Ile Ile Thr Thr Lys Phe Lys
            195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Glu Arg Phe Lys Gly Lys
225                 230                 235                 240

Glu Ile Gly Glu Gly Met Val Phe Asp Val Asn Ser His Tyr Pro Ala
                245                 250                 255

Gln Met Tyr Ser Arg Leu Leu Pro Tyr Gly Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Tyr Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Gly Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
            500                 505                 510

Leu Val Gln Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575
```

<210> SEQ ID NO 32
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 32

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser His Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Tyr Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
```

```
                405                 410                 415
Gly Glu Glu Glu Thr Lys Asp Pro Val Tyr Thr Pro Met Gly Val Phe
            420                 425                 430
Ile Thr Ala Trp Gly Arg Tyr Thr Ile Thr Ala Ala Gln Ala Cys
        435                 440                 445
Tyr Asp Arg Ile Ile Tyr Cys Asp Thr Asp Ser Ile His Leu Thr Gly
    450                 455                 460
Thr Glu Ile Pro Asp Val Ile Lys Asp Ile Val Asp Pro Lys Lys Leu
465                 470                 475                 480
Gly Tyr Trp Glu His Glu Ser Thr Phe Lys Arg Ala Lys Tyr Leu Arg
                485                 490                 495
Gln Lys Thr Tyr Ile Gln Asp Ile Tyr Met Lys Glu Val Lys Gly Tyr
            500                 505                 510
Leu Val Glu Gly Ser Pro Asp Asp Tyr Thr Asp Ile Lys Phe Ser Val
        515                 520                 525
Lys Cys Ala Gly Met Thr Asp Lys Ile Lys Glu Val Thr Phe Glu
    530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys
                565                 570                 575

<210> SEQ ID NO 33
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 33

Met Lys His Met Pro Arg Lys Met Tyr Ser Cys Asp Phe Glu Thr Thr
1               5                   10                  15
Thr Lys Val Glu Asp Cys Arg Val Trp Ala Tyr Gly Tyr Met Asn Ile
            20                  25                  30
Glu Asp His Ser Glu Tyr Lys Ile Gly Asn Ser Leu Asp Glu Phe Met
        35                  40                  45
Ala Trp Val Leu Lys Val Gln Ala Asp Leu Tyr Phe His Asn Leu Lys
    50                  55                  60
Phe Asp Gly Ala Phe Ile Ile Asn Trp Leu Glu Arg Asn Gly Phe Lys
65                  70                  75                  80
Trp Ser Ala Asp Gly Leu Pro Asn Thr Tyr Asn Thr Ile Ile Ser Arg
                85                  90                  95
Met Gly Gln Trp Tyr Met Ile Asp Ile Cys Leu Gly Tyr Lys Gly Lys
            100                 105                 110
Arg Lys Ile His Thr Val Ile Tyr Asp Ser Leu Lys Lys Leu Pro Phe
        115                 120                 125
Pro Val Lys Lys Ile Ala Lys Asp Phe Lys Leu Thr Val Leu Lys Gly
    130                 135                 140
Asp Ile Asp Ile His Lys Glu Arg Pro Val Gly Tyr Lys Ile Thr Pro
145                 150                 155                 160
Glu Glu Tyr Ala Tyr Ile Lys Asn Asp Ile Gln Ile Ile Ala Glu Ala
                165                 170                 175
Leu Leu Ile Gln Phe Lys Gln Gly Leu Asp Arg Met Thr Ala Gly Ser
            180                 185                 190
Asp Ser Leu Lys Gly Phe Lys Asp Ile Ile Thr Thr Lys Lys Phe Lys
```

```
            195                 200                 205
Lys Val Phe Pro Thr Leu Ser Leu Gly Leu Asp Lys Glu Val Arg Lys
210                 215                 220
Ala Tyr Arg Gly Gly Phe Thr Trp Leu Asn Asp Arg Phe Lys Gly Lys
225                 230                 235                 240
Glu Ile Gly Glu Gly Met Val Phe Asp Ile Asn Ser Ala Tyr Pro Ala
                245                 250                 255
Gln Met Tyr Ser Arg Leu Leu Pro Tyr Gly Pro Ile Val Phe Glu
                260                 265                 270
Gly Lys Tyr Val Trp Asp Glu Asp Tyr Pro Leu His Ile Gln His Ile
                275                 280                 285
Arg Cys Glu Phe Glu Leu Lys Glu Gly Tyr Ile Pro Thr Ile Gln Ile
                290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
                340                 345                 350
Phe Lys Ala Thr Thr Gly Leu Phe Lys Asp Phe Ile Asp Lys Trp Thr
                355                 360                 365
Tyr Ile Lys Thr Thr Ser Tyr Gly Ala Ile Lys Gln Leu Ala Lys Leu
370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
                420                 425                 430
Ile Thr Ala Trp Gly Arg Tyr Thr Thr Ile Thr Ala Ala Gln Ala Cys
                435                 440                 445
Tyr Asp Arg Ile Ile Tyr Cys Asp Thr Asp Ser Ile His Leu Thr Gly
450                 455                 460
Thr Glu Ile Pro Asp Val Ile Lys Asp Ile Val Asp Pro Lys Lys Leu
465                 470                 475                 480
Gly Tyr Trp Glu His Glu Ser Thr Phe Lys Arg Ala Lys Tyr Leu Arg
                485                 490                 495
Gln Lys Thr Tyr Ile Gln Asp Ile Tyr Met Lys Glu Val Lys Gly Tyr
                500                 505                 510
Leu Val Gln Gly Ser Pro Asp Asp Tyr Thr Asp Ile Lys Phe Ser Val
                515                 520                 525
Lys Cys Ala Gly Met Thr Asp Lys Ile Lys Lys Glu Val Thr Phe Glu
                530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys
                565                 570                 575

<210> SEQ ID NO 34
<211> LENGTH: 575
<212> TYPE: PRT
<213> ORGANISM: Artificial
<220> FEATURE:
<223> OTHER INFORMATION: mutant recombinant phi29-type DNA polymerase
```

<400> SEQUENCE: 34

```
Met Lys His Met Pro Arg Lys Met Tyr Ser Cys Asp Phe Glu Thr Thr
1               5                   10                  15
Thr Lys Val Glu Asp Cys Arg Val Trp Ala Tyr Gly Tyr Met Asn Ile
            20                  25                  30
Glu Asp His Ser Glu Tyr Lys Ile Gly Asn Ser Leu Asp Glu Phe Met
        35                  40                  45
Ala Trp Val Leu Lys Val Gln Ala Asp Leu Tyr Phe His Asn Leu Lys
    50                  55                  60
Phe Asp Gly Ala Phe Ile Ile Asn Trp Leu Glu Arg Asn Gly Phe Lys
65                  70                  75                  80
Trp Ser Ala Asp Gly Leu Pro Asn Thr Tyr Asn Thr Ile Ile Ser Arg
                85                  90                  95
Met Gly Gln Trp Tyr Met Ile Asp Ile Cys Leu Gly Tyr Lys Gly Lys
            100                 105                 110
Arg Lys Ile His Thr Val Ile Tyr Asp Ser Leu Lys Lys Leu Pro Phe
        115                 120                 125
Pro Val Glu Lys Ile Ala Lys Asp Phe Lys Leu Thr Val Leu Lys Gly
    130                 135                 140
Asp Ile Asp Ile His Lys Glu Arg Pro Val Gly Tyr Lys Ile Thr Pro
145                 150                 155                 160
Glu Glu Tyr Ala Tyr Ile Lys Asn Asp Ile Gln Ile Ala Glu Ala
                165                 170                 175
Leu Leu Ile Gln Phe Lys Gln Gly Leu Asp Arg Met Thr Ala Gly Ser
            180                 185                 190
Asp Ser Leu Lys Gly Phe Lys Asp Ile Ile Thr Thr Lys Lys Phe Lys
        195                 200                 205
Lys Val Phe Pro Thr Leu Ser Leu Gly Leu Asp Lys Glu Val Arg Lys
    210                 215                 220
Ala Tyr Arg Gly Gly Phe Thr Trp Leu Asn Glu Arg Phe Lys Gly Lys
225                 230                 235                 240
Glu Ile Gly Glu Gly Met Val Phe Asp Val Asn Ser His Tyr Pro Ala
                245                 250                 255
Gln Met Tyr Ser Arg Leu Leu Pro Tyr Gly Glu Pro Ile Val Phe Glu
            260                 265                 270
Gly Lys Tyr Val Trp Asp Glu Asp Tyr Pro Leu His Ile Gln His Ile
        275                 280                 285
Arg Cys Glu Phe Glu Leu Lys Glu Gly Tyr Ile Pro Thr Ile Gln Ile
    290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Thr
        355                 360                 365
Tyr Ile Lys Thr Thr Ser Tyr Gly Ala Ile Lys Gln Leu Ala Lys Leu
    370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
```

```
Gly Glu Glu Glu Thr Lys Asp Pro Val Tyr Thr Pro Met Gly Val Phe
            420                 425                 430

Ile Thr Ala Trp Gly Arg Tyr Thr Ile Thr Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
            500                 505                 510

Leu Val Gln Gly Ser Pro Asp Asp Tyr Thr Asp Ile Lys Phe Ser Val
            515                 520                 525

Lys Cys Ala Gly Met Thr Asp Lys Ile Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 35
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 35

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205
```

Lys Val Phe Pro Thr Leu Ser Leu Gly Leu Asp Lys Glu Val Arg Lys
210                 215                 220

Ala Tyr Arg Gly Gly Phe Thr Trp Leu Asn Glu Arg Phe Lys Gly Lys
225                 230                 235                 240

Glu Ile Gly Glu Gly Met Val Phe Asp Val Asn Ser His Tyr Pro Ala
            245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Tyr Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
            420                 425                 430

Ile Thr Ala Trp Gly Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
            485                 490                 495

Gln Lys Thr Tyr Ile Gln Asp Ile Tyr Met Lys Glu Val Lys Gly Tyr
                500                 505                 510

Leu Val Gln Gly Ser Pro Asp Asp Tyr Thr Asp Ile Lys Phe Ser Val
            515                 520                 525

Lys Cys Ala Gly Met Thr Asp Lys Ile Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
            565                 570                 575

<210> SEQ ID NO 36
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 36

-continued

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
        130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Tyr Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415
```

```
Gly Glu Glu Glu Thr Lys Asp Pro Val Tyr Thr Pro Met Gly Val Phe
                420                 425                 430

Ile Thr Ala Trp Gly Arg Tyr Thr Ile Thr Ala Ala Gln Ala Cys
    435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
                500                 505                 510

Leu Val Glu Gly Ser Pro Asp Asp Tyr Thr Asp Ile Lys Phe Ser Val
                515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 37
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 37

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Ile Thr Thr Lys Lys Phe Lys
            195                 200                 205
```

```
Lys Val Phe Pro Thr Leu Ser Leu Gly Leu Asp Lys Glu Val Arg Lys
            210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
                275                 280                 285

Arg Cys Glu Phe Glu Leu Lys Glu Gly Tyr Ile Pro Thr Ile Gln Ile
            290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
                355                 360                 365

Tyr Ile Lys Thr Thr Ser Tyr Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
                420                 425                 430

Ile Thr Ala Trp Gly Arg Tyr Thr Thr Ile Thr Ala Ala Gln Ala Cys
                435                 440                 445

Tyr Asp Arg Ile Ile Tyr Cys Asp Thr Asp Ser Ile His Leu Thr Gly
            450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
                500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 38
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 38
```

-continued

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
        115                 120                 125

Pro Val Glu Lys Ile Ala Lys Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
                290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
            355                 360                 365

Tyr Ile Lys Thr Thr Ser Tyr Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
```

```
            420                 425                 430
Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
            450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                    485                 490                 495

Gln Lys Thr Tyr Ile Gln Asp Ile Tyr Met Lys Glu Val Lys Gly Tyr
            500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                    565                 570                 575

<210> SEQ ID NO 39
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 39

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Gln Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
```

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
            245                 250                 255

Gln Met Tyr Ser Arg Leu Leu Pro Tyr Gly Glu Pro Ile Val Phe Glu
        260                 265                 270

Gly Lys Tyr Val Trp Asp Glu Asp Tyr Pro Leu His Ile Gln His Ile
    275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Tyr Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Glu Val Lys Gly Tyr
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 40
<211> LENGTH: 572
<212> TYPE: PRT
<213> ORGANISM: Artificial
<220> FEATURE:
<223> OTHER INFORMATION: mutant recombinant phi29-type DNA polymerase

<400> SEQUENCE: 40

Met Ser Arg Lys Met Phe Ser Cys Asp Phe Glu Thr Thr Thr Lys Leu

```
1               5                    10                   15
Asp Asp Cys Arg Val Trp Ala Tyr Gly Tyr Met Glu Ile Gly Asn Leu
                20                  25                  30
Asp Asn Tyr Lys Ile Gly Asn Ser Leu Asp Glu Phe Met Gln Trp Val
                35                  40                  45
Met Glu Ile Gln Ala Asp Leu Tyr Phe His Asn Leu Lys Phe Asp Gly
                50                  55                  60
Ala Phe Ile Val Asn Trp Leu Glu Gln His Gly Phe Lys Trp Ser Asn
65                  70                  75                  80
Glu Gly Leu Pro Asn Thr Tyr Asn Thr Ile Ile Ser Lys Met Gly Gln
                85                  90                  95
Trp Tyr Met Ile Asp Ile Cys Phe Gly Tyr Lys Gly Lys Arg Lys Leu
                100                 105                 110
His Thr Val Ile Tyr Asp Ser Leu Lys Lys Leu Pro Phe Pro Val Lys
                115                 120                 125
Lys Ile Ala Lys Asp Phe Gln Leu Pro Leu Lys Gly Asp Ile Asp
130                 135                 140
Tyr His Thr Glu Arg Pro Val Gly His Glu Ile Thr Pro Glu Glu Tyr
145                 150                 155                 160
Glu Tyr Ile Lys Asn Asp Ile Glu Ile Ala Arg Ala Leu Asp Ile
                165                 170                 175
Gln Phe Lys Gln Gly Leu Asp Arg Met Thr Ala Gly Ser Asp Ser Leu
                180                 185                 190
Lys Gly Phe Lys Asp Ile Leu Ser Thr Lys Lys Phe Asn Lys Val Phe
                195                 200                 205
Pro Lys Leu Ser Leu Pro Met Asp Lys Glu Ile Arg Lys Ala Tyr Arg
                210                 215                 220
Gly Gly Phe Thr Trp Leu Asn Asp Lys Tyr Lys Glu Lys Glu Ile Gly
225                 230                 235                 240
Glu Gly Met Val Phe Asp Val Asn Ser Ala Tyr Pro Ala Gln Met Tyr
                245                 250                 255
Ser Arg Pro Leu Pro Tyr Gly Ala Pro Ile Val Phe Gln Gly Lys Tyr
                260                 265                 270
Glu Lys Asp Glu Gln Tyr Pro Leu Tyr Ile Gln Arg Ile Arg Phe Glu
                275                 280                 285
Phe Glu Leu Lys Glu Gly Tyr Ile Pro Thr Ile Gln Ile Lys Lys Asn
                290                 295                 300
Pro Phe Phe Lys Gly Asn Glu Tyr Leu Lys Asn Ser Gly Val Glu Pro
305                 310                 315                 320
Val Glu Leu Tyr Leu Thr Asn Val Asp Leu Glu Leu Ile Gln Glu His
                325                 330                 335
Tyr Glu Leu Tyr Asn Val Glu Tyr Ile Asp Gly Phe Lys Phe Arg Glu
                340                 345                 350
Lys Thr Gly Leu Phe Lys Asp Phe Ile Asp Lys Trp Thr Tyr Val Lys
                355                 360                 365
Thr His Glu Tyr Gly Ala Lys Lys Gln Leu Ala Lys Leu Met Leu Asn
                370                 375                 380
Ser Leu Tyr Gly Lys Phe Ala Ser Asn Pro Asp Val Thr Gly Lys Val
385                 390                 395                 400
Pro Tyr Leu Lys Asp Asp Gly Ser Leu Gly Phe Arg Val Gly Asp Glu
                405                 410                 415
Glu Tyr Lys Asp Pro Val Tyr Thr Pro Met Gly Val Phe Ile Thr Ala
                420                 425                 430
```

```
Trp Ala Arg Phe Thr Thr Ile Thr Ala Ala Gln Ala Cys Tyr Asp Arg
        435                 440                 445
Ile Ile Tyr Cys Asp Thr Asp Ser Ile His Leu Thr Gly Thr Glu Val
450                 455                 460
Pro Glu Ile Ile Lys Asp Ile Val Asp Pro Lys Lys Leu Gly Tyr Trp
465                 470                 475                 480
Glu His Glu Ser Thr Phe Lys Arg Ala Lys Tyr Leu Arg Gln Lys Thr
                485                 490                 495
Tyr Ile Gln Asp Ile Tyr Val Lys Glu Val Asp Gly Tyr Leu Lys Glu
            500                 505                 510
Cys Ser Pro Asp Glu Ala Thr Thr Thr Lys Phe Ser Val Lys Cys Ala
        515                 520                 525
Gly Met Thr Asp Thr Ile Lys Lys Lys Val Thr Phe Asp Asn Phe Ala
530                 535                 540
Val Gly Phe Ser Ser Met Gly Lys Pro Lys Pro Val Gln Val Asn Gly
545                 550                 555                 560
Gly Val Val Leu Val Asp Ser Val Phe Thr Ile Lys
                565                 570

<210> SEQ ID NO 41
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 41

Met Lys His Met Pro Arg Lys Met Tyr Ser Cys Asp Phe Glu Thr Thr
1               5                   10                  15
Thr Lys Val Glu Asp Cys Arg Val Trp Ala Tyr Gly Tyr Met Asn Ile
                20                  25                  30
Glu Asp His Ser Glu Tyr Lys Ile Gly Asn Ser Leu Asp Glu Phe Met
            35                  40                  45
Ala Trp Val Leu Lys Val Gln Ala Asp Leu Tyr Phe His Asn Leu Lys
        50                  55                  60
Phe Asp Gly Ala Phe Ile Ile Asn Trp Leu Glu Arg Asn Gly Phe Lys
65                  70                  75                  80
Trp Ser Ala Asp Gly Leu Pro Asn Thr Tyr Asn Thr Ile Ile Ser Arg
                85                  90                  95
Met Gly Gln Trp Tyr Met Ile Asp Ile Cys Leu Gly Tyr Lys Gly Lys
            100                 105                 110
Arg Lys Ile His Thr Val Ile Tyr Asp Ser Leu Lys Lys Leu Pro Phe
        115                 120                 125
Pro Val Lys Lys Ile Ala Lys Asp Phe Lys Leu Thr Val Leu Lys Gly
    130                 135                 140
Asp Ile Asp Ile His Lys Glu Arg Pro Val Gly Tyr Lys Ile Thr Pro
145                 150                 155                 160
Glu Glu Tyr Ala Tyr Ile Lys Asn Asp Ile Gln Ile Ile Ala Glu Ala
                165                 170                 175
Leu Leu Ile Gln Phe Lys Gln Gly Leu Asp Arg Met Thr Ala Gly Ser
            180                 185                 190
Asp Ser Leu Lys Gly Phe Lys Asp Ile Ile Thr Thr Lys Lys Phe Lys
        195                 200                 205
Lys Val Phe Pro Thr Leu Ser Leu Gly Leu Asp Lys Glu Val Arg Lys
    210                 215                 220
```

```
Ala Tyr Arg Gly Gly Phe Thr Trp Leu Asn Asp Arg Phe Lys Gly Lys
225                 230                 235                 240

Glu Ile Gly Glu Gly Met Val Phe Asp Val Asn Ser His Tyr Pro Ala
            245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Tyr Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
            420                 425                 430

Ile Thr Ala Trp Gly Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
            485                 490                 495

Gln Lys Thr Tyr Ile Gln Asp Ile Tyr Met Lys Glu Val Lys Gly Tyr
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
        530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
            565                 570                 575

<210> SEQ ID NO 42
<211> LENGTH: 572
<212> TYPE: PRT
<213> ORGANISM: Artificial
<220> FEATURE:
<223> OTHER INFORMATION: mutant recombinant phi29-type DNA polymerase

<400> SEQUENCE: 42

Met Ser Arg Lys Met Phe Ser Cys Asp Phe Glu Thr Thr Thr Lys Leu
1               5                   10                  15
```

```
Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu Gln His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Lys Gly Asp Ile Asp
130                 135                 140

Ile His Thr Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Phe Asn Lys Val Phe
        195                 200                 205

Pro Lys Leu Ser Leu Pro Met Asp Lys Glu Ile Arg Lys Ala Tyr Arg
    210                 215                 220

Gly Gly Phe Thr Trp Leu Asn Asp Lys Tyr Lys Gly Lys Glu Ile Gly
225                 230                 235                 240

Glu Gly Met Val Phe Asp Ile Asn Ser Ala Tyr Pro Ala Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Val Glu Pro
305                 310                 315                 320

Val Glu Leu Tyr Leu Thr Asn Val Asp Leu Glu Leu Ile Gln Glu His
                325                 330                 335

Tyr Glu Leu Tyr Asn Val Glu Tyr Ile Asp Gly Phe Lys Phe Arg Glu
            340                 345                 350

Lys Thr Gly Leu Phe Lys Asp Phe Ile Asp Lys Trp Thr Tyr Val Lys
        355                 360                 365

Thr His Glu Tyr Gly Ala Lys Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Asp Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430
```

```
Trp Gly Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Glu His Glu Ser Thr Phe Lys Arg Ala Lys Tyr Leu Arg Gln Lys Thr
                485                 490                 495

Tyr Ile Gln Asp Ile Tyr Val Lys Glu Val Lys Gly Tyr Leu Lys Gln
            500                 505                 510

Cys Ser Pro Asp Glu Ala Thr Thr Thr Lys Phe Ser Val Lys Cys Ala
        515                 520                 525

Gly Met Thr Asp Thr Ile Lys Lys Lys Val Thr Phe Asp Asn Phe Ala
    530                 535                 540

Val Gly Phe Ser Ser Met Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 43
<211> LENGTH: 572
<212> TYPE: PRT
<213> ORGANISM: Artificial
<220> FEATURE:
<223> OTHER INFORMATION: mutant recombinant phi29-type DNA polymerase

<400> SEQUENCE: 43

Met Ser Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
        50                  55                  60

Ala Phe Ile Val Asn Trp Leu Glu Gln His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Gln Asp Phe Gln Leu Pro Leu Leu Lys Gly Asp Ile Asp
    130                 135                 140

Ile His Thr Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Lys Ala Tyr Arg
    210                 215                 220
```

```
Gly Gly Phe Thr Trp Leu Asn Asp Lys Tyr Lys Gly Lys Glu Ile Gly
225                 230                 235                 240

Glu Gly Met Val Phe Asp Ile Asn Ser Ala Tyr Pro Ser Gln Met Tyr
            245                 250                 255

Ser Arg Pro Leu Pro Tyr Gly Ala Pro Ile Val Phe Gln Gly Lys Tyr
        260                 265                 270

Glu Lys Asp Glu Gln Tyr Pro Leu Tyr Ile Gln Arg Ile Arg Phe Glu
    275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Val Glu Pro
305                 310                 315                 320

Val Glu Leu Tyr Leu Thr Asn Val Asp Leu Glu Leu Ile Gln Glu His
            325                 330                 335

Tyr Glu Leu Tyr Asn Val Glu Tyr Ile Asp Gly Phe Lys Phe Arg Glu
        340                 345                 350

Lys Thr Gly Leu Phe Lys Asp Phe Ile Asp Lys Trp Thr Tyr Val Lys
    355                 360                 365

Thr His Glu Tyr Gly Ala Lys Lys Gln Leu Ala Lys Leu Met Leu Asn
370                 375                 380

Ser Leu Tyr Gly Lys Phe Ala Ser Asn Pro Asp Val Thr Gly Lys Val
385                 390                 395                 400

Pro Tyr Leu Lys Asp Asp Gly Ser Leu Gly Phe Arg Val Gly Asp Glu
            405                 410                 415

Glu Tyr Lys Asp Pro Val Tyr Thr Pro Met Gly Val Phe Ile Thr Ala
        420                 425                 430

Trp Gly Arg Phe Thr Thr Ile Thr Ala Ala Gln Ala Cys Tyr Asp Arg
    435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Glu His Glu Ser Thr Phe Lys Arg Ala Lys Tyr Leu Arg Gln Lys Thr
            485                 490                 495

Tyr Ile Gln Asp Ile Tyr Val Lys Glu Val Lys Gly Tyr Leu Lys Gln
        500                 505                 510

Cys Ser Pro Asp Glu Ala Thr Thr Thr Lys Phe Ser Val Lys Cys Ala
    515                 520                 525

Gly Met Thr Asp Thr Ile Lys Lys Lys Val Thr Phe Asp Asn Phe Ala
530                 535                 540

Val Gly Phe Ser Ser Met Gly Lys Pro Lys Pro Val Gln Val Asn Gly
545                 550                 555                 560

Gly Val Val Leu Val Asp Ser Val Phe Thr Ile Lys
            565                 570

<210> SEQ ID NO 44
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 44

Met Lys His Met Pro Arg Lys Met Tyr Ser Cys Asp Phe Glu Thr Thr
1               5                   10                  15
```

-continued

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Glu Lys Ile Ala Gln Asp Phe Lys Leu Thr Lys Lys Lys Gly
        130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Lys
210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
            355                 360                 365

Tyr Ile Lys Thr Thr Ser Tyr Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
                420                 425                 430

Ile Thr Ala Trp Gly Arg Tyr Thr Thr Ile Thr Ala Ala Gln Ala Cys

```
                    435                 440                 445
Tyr Asp Arg Ile Ile Tyr Cys Asp Thr Asp Ser Ile His Leu Thr Gly
            450                 455                 460

Thr Glu Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Lys Val Lys Gly Tyr
            500                 505                 510

Leu Val Gln Gly Ser Pro Asp Asp Tyr Thr Asp Ile Lys Phe Ser Val
                515                 520                 525

Lys Cys Ala Gly Met Thr Asp Gln Ile Lys Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 45
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 45

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
        50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Glu Lys Ile Ala Lys Asp Phe Lys Leu Thr Val Leu Lys Gly
    130                 135                 140

Asp Ile Asp Ile His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
```

```
            225                 230                 235                 240

Glu Ile Gly Glu Gly Met Val Phe Asp Ile Asn Ser Ala Tyr Pro Ala
                    245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
                275                 280                 285

Arg Cys Glu Phe Glu Leu Lys Glu Gly Tyr Ile Pro Thr Ile Gln Ile
                290                 295                 300

Lys Arg Ser Arg Phe Tyr Lys Gly Asn Glu Tyr Leu Lys Ser Ser Gly
    305                 310                 315                 320

Gly Glu Ile Ala Asp Leu Trp Leu Ser Asn Val Asp Leu Glu Leu Met
                    325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
                355                 360                 365

Tyr Ile Lys Thr Thr Ser Tyr Gly Ala Ile Lys Gln Leu Ala Lys Leu
                370                 375                 380

Met Leu Asn Ser Leu Tyr Gly Lys Phe Ala Ser Asn Pro Asp Val Thr
    385                 390                 395                 400

Gly Lys Val Pro Tyr Leu Lys Glu Asn Gly Ala Leu Gly Phe Arg Leu
                    405                 410                 415

Gly Glu Glu Glu Thr Lys Asp Pro Val Tyr Thr Pro Met Gly Val Phe
                420                 425                 430

Ile Thr Ala Trp Gly Arg Tyr Thr Thr Ile Thr Ala Ala Gln Ala Cys
                435                 440                 445

Tyr Asp Arg Ile Ile Tyr Cys Asp Thr Asp Ser Ile His Leu Thr Gly
                450                 455                 460

Thr Glu Ile Pro Asp Val Ile Lys Asp Ile Val Asp Pro Lys Lys Leu
    465                 470                 475                 480

Gly Tyr Trp Glu His Glu Ser Thr Phe Lys Arg Ala Lys Tyr Leu Arg
                    485                 490                 495

Gln Lys Thr Tyr Ile Gln Asp Ile Tyr Met Lys Lys Val Lys Gly Tyr
                500                 505                 510

Leu Val Gln Gly Ser Pro Asp Asp Tyr Thr Asp Ile Lys Phe Ser Val
                515                 520                 525

Lys Cys Ala Gly Met Thr Asp Lys Ile Lys Lys Glu Val Thr Phe Glu
                530                 535                 540

Asn Phe Lys Val Gly Phe Ser Arg Lys Met Lys Pro Lys Pro Val Gln
    545                 550                 555                 560

Val Pro Gly Gly Val Val Leu Val Asp Asp Thr Phe Thr Ile Lys
                    565                 570                 575

<210> SEQ ID NO 46
<211> LENGTH: 575
<212> TYPE: PRT
<213> ORGANISM: Artificial
<220> FEATURE:
<223> OTHER INFORMATION: mutant recombinant phi29-type DNA polymerase

<400> SEQUENCE: 46

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
```

-continued

```
                 20                  25                  30
Glu Asp His Ser Glu Tyr Lys Ile Gly Asn Ser Leu Asp Glu Phe Met
             35                  40                  45
Ala Trp Val Leu Lys Val Gln Ala Asp Leu Tyr Phe His Asn Leu Lys
 50                  55                  60
Phe Asp Gly Ala Phe Ile Ile Asn Trp Leu Glu Arg Asn Gly Phe Lys
 65                  70                  75                  80
Trp Ser Ala Asp Gly Leu Pro Asn Thr Tyr Asn Thr Ile Ile Ser Arg
                 85                  90                  95
Met Gly Gln Trp Tyr Met Ile Asp Ile Cys Leu Gly Tyr Lys Gly Lys
                100                 105                 110
Arg Lys Ile His Thr Val Ile Tyr Asp Ser Leu Lys Lys Leu Pro Phe
                115                 120                 125
Pro Val Gln Lys Ile Ala Lys Asp Phe Lys Leu Thr Val Leu Lys Gly
                130                 135                 140
Asp Ile Asp Ile His Lys Glu Arg Pro Val Gly Tyr Lys Ile Thr Pro
145                 150                 155                 160
Glu Glu Tyr Ala Tyr Ile Lys Asn Asp Ile Gln Ile Ala Glu Ala
                165                 170                 175
Leu Leu Ile Gln Phe Lys Gln Gly Leu Asp Arg Met Thr Ala Gly Ser
                180                 185                 190
Asp Ser Leu Lys Gly Phe Lys Asp Ile Thr Thr Lys Lys Phe Lys
                195                 200                 205
Lys Val Phe Pro Thr Leu Ser Leu Gly Leu Asp Lys Glu Val Arg Lys
                210                 215                 220
Ala Tyr Arg Gly Gly Phe Thr Trp Leu Asn Asp Arg Phe Lys Gly Lys
225                 230                 235                 240
Glu Ile Gly Glu Gly Met Val Phe Asp Ile Asn Ser Ala Tyr Pro Ala
                245                 250                 255
Gln Met Tyr Ser Arg Leu Leu Pro Tyr Gly Glu Pro Ile Val Phe Glu
                260                 265                 270
Gly Lys Tyr Val Trp Asp Glu Asp Tyr Pro Leu His Ile Gln His Ile
                275                 280                 285
Arg Cys Glu Phe Glu Leu Lys Glu Gly Tyr Ile Pro Thr Ile Gln Ile
                290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
                340                 345                 350
Phe Lys Ala Thr Thr Gly Leu Phe Lys Asp Phe Ile Asp Lys Trp Thr
                355                 360                 365
Tyr Ile Lys Thr Thr Ser Tyr Gly Ala Ile Lys Gln Leu Ala Lys Leu
                370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
                420                 425                 430
Ile Thr Ala Trp Ala Arg Tyr Thr Thr Ile Thr Ala Ala Gln Ala Cys
                435                 440                 445
```

```
Tyr Asp Arg Ile Ile Tyr Cys Asp Thr Asp Ser Ile His Leu Thr Gly
        450             455             460

Thr Glu Ile Pro Asp Val Ile Lys Asp Ile Val Asp Pro Lys Lys Leu
465             470             475                     480

Gly Tyr Trp Glu His Glu Ser Thr Phe Lys Arg Ala Lys Tyr Leu Arg
                485             490                 495

Gln Lys Thr Tyr Ile Gln Asp Ile Tyr Met Lys Glu Val Lys Gly Tyr
            500             505                 510

Leu Val Glu Gly Ser Pro Asp Asp Tyr Thr Asp Ile Lys Phe Ser Val
        515             520                 525

Lys Cys Ala Gly Met Thr Asp Lys Ile Lys Lys Glu Val Thr Phe Glu
    530             535             540

Asn Phe Lys Val Gly Phe Ser Arg Lys Met Lys Pro Lys Pro Val Gln
545             550             555                     560

Val Pro Gly Gly Val Val Leu Val Asp Asp Thr Phe Thr Ile Lys
            565             570             575
```